United States Patent
Lichter et al.

(10) Patent No.: US 10,092,580 B2
(45) Date of Patent: Oct. 9, 2018

(54) CONTROLLED-RELEASE OTIC STRUCTURE MODULATING AND INNATE IMMUNE SYSTEM MODULATING COMPOSITIONS AND METHODS FOR THE TREATMENT OF OTIC DISORDERS

(75) Inventors: Jay Lichter, Rancho Santa Fe, CA (US); Benedikt Vollrath, San Diego, CA (US); Sergio G. Duron, San Diego, CA (US); Carl Lebel, Malibu, CA (US); Fabrice Piu, San Diego, CA (US); Qiang Ye, San Diego, CA (US); Luis A. Dellamary, San Marcos, CA (US); Andrew M. Trammel, Olathe, KS (US); Michael Christopher Scaife, Los Altos, CA (US); Jeffrey P. Harris, La Jolla, CA (US)

(73) Assignees: OTONOMY, INC., San Diego, CA (US); THE REGENTS OF THE UNIVERSITY OF CALIFORNIA, Oakland, CA (US)

( * ) Notice: Subject to any disclaimer, the term of this patent is extended or adjusted under 35 U.S.C. 154(b) by 491 days.

(21) Appl. No.: 12/506,091

(22) Filed: Jul. 20, 2009

(65) Prior Publication Data
US 2010/0021416 A1    Jan. 28, 2010

Related U.S. Application Data

(60) Provisional application No. 61/082,450, filed on Jul. 21, 2008, provisional application No. 61/091,205, (Continued)

(51) Int. Cl.
*A61K 31/663* (2006.01)
*A61K 47/34* (2017.01)
(Continued)

(52) U.S. Cl.
CPC .......... *A61K 31/663* (2013.01); *A61K 9/0046* (2013.01); *A61K 31/5513* (2013.01);
(Continued)

(58) Field of Classification Search
CPC .... A61K 9/0046; A61K 31/663; A61K 47/34; A61K 47/10; Y10S 514/944
See application file for complete search history.

(56) References Cited

U.S. PATENT DOCUMENTS 3,737,337 A    6/1973    Schnoring et al.
3,773,919 A   11/1973    Boswell et al.
(Continued)

FOREIGN PATENT DOCUMENTS

EP    0551626 A1    7/1993
JP    2006-509791    3/2006
(Continued)

OTHER PUBLICATIONS

Coulson et al., "Collagen and a Thermally Reversibly Polo9xamer Deliver Demineralized Bone Matrix (DBM) and Biologically Active Proteins to Sites of Bone Regeneration," Portland Bone Symposium (1999) pp. 1-8.*
(Continued)

*Primary Examiner* — Kevin S Orwig
*Assistant Examiner* — Barbara S Frazier
(74) *Attorney, Agent, or Firm* — Wilson Sonsini Goodrich & Rosati

(57) ABSTRACT

Disclosed herein are compositions and methods for the treatment of otic disorders with otic structure modulating compositions administered locally to an individual afflicted with an otic disorder, through direct application of these compositions and compositions onto or via perfusion into the targeted auris structure(s).

3 Claims, 5 Drawing Sheets

Related U.S. Application Data filed on Aug. 22, 2008, provisional application No. 61/094,384, filed on Sep. 4, 2008, provisional application No. 61/101,112, filed on Sep. 29, 2008, provisional application No. 61/108,845, filed on Oct. 27, 2008, provisional application No. 61/140,033, filed on Dec. 22, 2008, provisional application No. 61/156,771, filed on Mar. 2, 2008, provisional application No. 61/091,200, filed on Aug. 22, 2008.

(51) Int. Cl.
*A61K 9/00* (2006.01)
*A61K 31/5513* (2006.01)
*A61K 38/17* (2006.01)
*A61K 38/29* (2006.01)
*A61K 38/39* (2006.01)
*A61K 38/47* (2006.01)
*A61K 38/48* (2006.01)
*A61K 31/66* (2006.01)

(52) U.S. Cl.
CPC .......... *A61K 31/66* (2013.01); *A61K 38/1748* (2013.01); *A61K 38/29* (2013.01); *A61K 38/39* (2013.01); *A61K 38/47* (2013.01); *A61K 38/4886* (2013.01); *A61K 47/34* (2013.01)

(56) References Cited

U.S. PATENT DOCUMENTS

| | | |
|---|---|---|
| 4,389,330 A | 6/1983 | Tice et al. |
| 4,474,572 A | 10/1984 | McNaughton et al. |
| 4,478,822 A | 10/1984 | Haslam et al. |
| 4,530,840 A | 7/1985 | Tice et al. |
| 4,675,189 A | 6/1987 | Kent et al. |
| 4,758,435 A | 7/1988 | Schaaf |
| 4,900,552 A | 2/1990 | Sanvordeker et al. |
| 4,938,763 A | 7/1990 | Dunn et al. |
| 5,033,252 A | 7/1991 | Carter |
| 5,052,558 A | 10/1991 | Carter |
| 5,292,516 A | 3/1994 | Viegas et al. |
| 5,323,907 A | 6/1994 | Kalvelage |
| 5,324,519 A | 6/1994 | Dunn et al. |
| 5,421,818 A | 6/1995 | Arenberg |
| 5,451,399 A | 9/1995 | Gimbrone, Jr. et al. |
| 5,474,529 A | 12/1995 | Arenberg |
| 5,476,446 A | 12/1995 | Arenberg |
| 5,503,848 A | 4/1996 | Perbellini et al. |
| 5,527,832 A * | 6/1996 | Chi et al. ............ 514/772.4 |
| 5,578,709 A | 11/1996 | Woiszwillo |
| 5,702,716 A | 12/1997 | Dunn et al. |
| 5,714,167 A | 2/1998 | Milstein et al. |
| 5,744,153 A | 4/1998 | Yewey et al. |
| 5,814,330 A | 9/1998 | Putteman et al. |
| 5,861,174 A | 1/1999 | Stratton et al. |
| 5,945,126 A | 8/1999 | Thanoo et al. |
| 5,981,719 A | 11/1999 | Woiszwillo et al. |
| 5,990,194 A | 11/1999 | Dunn et al. |
| 6,004,573 A | 12/1999 | Rathi et al. |
| 6,036,978 A | 3/2000 | Gombotz et al. |
| 6,045,528 A | 4/2000 | Arenberg et al. |
| 6,083,534 A | 7/2000 | Wallach et al. |
| 6,090,925 A | 7/2000 | Woiszwillo et al. |
| 6,117,949 A | 9/2000 | Rathi et al. |
| 6,139,870 A | 10/2000 | Verrecchia |
| 6,177,434 B1 | 1/2001 | Kopke et al. |
| 6,201,072 B1 | 3/2001 | Rathi et al. |
| 6,221,367 B1 | 4/2001 | Milstein et al. |
| 6,268,053 B1 | 7/2001 | Woiszwillo et al. |
| 6,270,802 B1 | 8/2001 | Thanoo et al. |
| 6,287,588 B1 | 9/2001 | Shih et al. |
| 6,306,789 B1 | 10/2001 | Dettmar et al. |
| 6,316,011 B1 | 11/2001 | Ron et al. |
| 6,319,513 B1 | 11/2001 | Dobrozsi |
| 6,348,502 B1 | 2/2002 | Gardiner et al. |
| 6,361,798 B1 | 3/2002 | Thanoo et al. |
| 6,392,036 B1 | 5/2002 | Karlsson et al. |
| 6,458,387 B1 | 10/2002 | Scott et al. |
| 6,509,028 B2 | 1/2003 | Williams et al. |
| 6,562,363 B1 | 5/2003 | Mantelle et al. |
| 6,589,549 B2 | 7/2003 | Shih et al. |
| 6,638,521 B2 | 10/2003 | Dobrozsi |
| 6,649,621 B2 | 11/2003 | Kopke et al. |
| 6,740,664 B2 | 5/2004 | Cagle et al. |
| 7,001,615 B1 | 2/2006 | Singh et al. |
| 7,018,645 B1 | 3/2006 | Piao et al. |
| 7,151,191 B2 | 12/2006 | Boyd et al. |
| 7,279,499 B2 | 10/2007 | Durst et al. |
| 7,524,834 B2 | 4/2009 | Karlsson et al. |
| 8,030,297 B2 | 10/2011 | Lichter et al. |
| 2002/0033144 A1 * | 3/2002 | Thompson .................... 119/651 |
| 2003/0044445 A1 * | 3/2003 | Kay et al. .................... 424/423 |
| 2003/0092776 A1 | 5/2003 | Ron et al. |
| 2003/0229333 A1 | 12/2003 | Ashton |
| 2004/0082509 A1 | 4/2004 | Bonny |
| 2004/0101560 A1 | 5/2004 | Sawchuk et al. |
| 2004/0185047 A1 | 9/2004 | Giles-Komar et al. |
| 2005/0123541 A1 | 6/2005 | Heavner et al. |
| 2005/0147585 A1 * | 7/2005 | Schwarz .................... 424/78.38 |
| 2005/0153984 A1 | 7/2005 | Chen et al. |
| 2005/0214338 A1 | 9/2005 | Guitton et al. |
| 2005/0215572 A1 | 9/2005 | Kelly et al. |
| 2005/0227986 A1 | 10/2005 | Bo et al. |
| 2005/0260272 A1 * | 11/2005 | Figueiredo et al. .......... 424/489 |
| 2005/0272931 A1 | 12/2005 | Bo et al. |
| 2005/0277643 A1 | 12/2005 | Kelly et al. |
| 2005/0277646 A1 | 12/2005 | Doherty et al. |
| 2006/0013858 A1 | 1/2006 | Trune |
| 2006/0030618 A1 | 2/2006 | Bo et al. |
| 2006/0034889 A1 | 2/2006 | Jo et al. |
| 2006/0046970 A1 | 3/2006 | Bowman et al. |
| 2006/0063802 A1 | 3/2006 | Guitton et al. |
| 2006/0100490 A1 | 5/2006 | Wang et al. |
| 2006/0105967 A1 | 5/2006 | Hsu et al. |
| 2006/0172971 A1 | 8/2006 | Nicotera et al. |
| 2006/0194801 A1 | 8/2006 | Kelly et al. |
| 2006/0205773 A1 | 9/2006 | Kelly et al. |
| 2006/0205789 A1 | 9/2006 | Sawchuk et al. |
| 2006/0205980 A1 | 9/2006 | Hanazawa et al. |
| 2006/0210639 A1 * | 9/2006 | Liversidge et al. .......... 424/489 |
| 2006/0211741 A1 | 9/2006 | Hanazawa et al. |
| 2006/0264897 A1 | 11/2006 | Lobl et al. |
| 2006/0269602 A1 * | 11/2006 | Dasch et al. .................... 424/468 |
| 2006/0270682 A1 | 11/2006 | Inoue et al. |
| 2007/0110788 A1 | 5/2007 | Hissong et al. |
| 2007/0128177 A1 | 6/2007 | Burstein et al. |
| 2007/0167918 A1 | 7/2007 | Reed et al. |
| 2007/0178051 A1 | 8/2007 | Pruitt et al. |
| 2007/0249538 A1 | 10/2007 | Sazani et al. |
| 2008/0015183 A1 | 1/2008 | Bakthavatchalam et al. |
| 2008/0031847 A1 * | 2/2008 | Cohn .................... A61K 31/74 424/78.06 |
| 2008/0085901 A1 | 4/2008 | Caldwell et al. |
| 2008/0088713 A1 | 4/2008 | Jung et al. |
| 2008/0089883 A1 | 4/2008 | Kandimalla et al. |
| 2008/0103118 A1 | 5/2008 | Clement et al. |
| 2008/0153857 A1 | 6/2008 | Bakthavatchalam et al. |
| 2008/0175794 A1 | 7/2008 | Caldwell et al. |
| 2011/0166060 A1 | 7/2011 | Simons et al. |

FOREIGN PATENT DOCUMENTS

| | | |
|---|---|---|
| WO | WO 1997/038698 | 10/1997 |
| WO | WO 1999/024051 | 5/1999 |
| WO | WO-0061111 A1 | 10/2000 |
| WO | WO-2002-056890 A1 | 7/2002 |
| WO | WO 2003/034979 | 5/2003 |
| WO | WO 2003/017990 | 6/2003 |
| WO | WO 2003/071986 | 9/2003 |
| WO | WO-2003-071986 A2 | 9/2003 |
| WO | WO 2006/099325 | 9/2006 |
| WO | WO 2006102117 A1 * | 9/2006 |
| WO | WO 2007/031098 | 3/2007 |

(56) References Cited

FOREIGN PATENT DOCUMENTS

| WO | WO 2007/031280 | 3/2007 |
|---|---|---|
| WO | WO 2007/037874 | 4/2007 |
| WO | WO 2007/037886 | 4/2007 |
| WO | WO 2007/038949 | 4/2007 |
| WO | WO 2007/089490 | 8/2007 |
| WO | WO 2007/150016 | 12/2007 |
| WO | WO 2008/027880 | 3/2008 |
| WO | WO 2008/076556 | 6/2008 |

OTHER PUBLICATIONS

USP Pharmacists' Pharmacopeia, The United States Pharmacopeial Convention pp. S2/ii and S2/10 (2008).*
Cao et al., Methods in Molecular Medicine, 18: 75-83 (1999).*
Escobar-Chavez et al., Journal of Pharmacy and Pharmaceutical Sciences, 9: 339-358 (2006).*
Masaki et al. (Acta Otolaryngol (Stockh) 108: 113-121 (1989).*
Ricci et al., European Journal of Pharmaceutical Sciences, 17: 161-167 (2002).*
Ganem-Quintanar et al., Drug Development and Industrial Pharmacy, 26(8): 809-820 (2000).*
Remington's Pharmaceutical Sciences, Gennaro, Ed.,17th Ed., Mack Publishing Co. (1985) Front matter, pp. 207 and 271-273 only.*
Miyazaki et al., Journal of Pharmaceutical Sciences, vol. 76, No. 11, Abstract N 04-W-49 (1987).*
Dourmishev et al., "Waardenburg syndrome," Intl J Dermatol 39:656-663 (1999).
Hall et al., "Anti-Pneumocystis Activities of Aromatic Diamidoxine Prodrugs," Antimicrobial Agents & Chemotherapy, 1998, American Society for Microbiology 42(4):666-674 (1998).
McCarthy et al., "Alport syndrome: a review," Clinical Eye and Vision Care 12:139-150 (2000).
Nance et al., "The Genetics of Deafness," Mental Retardation and Developmental Disabilities, 2003, Wiley-Liss, vol. 9, pp. 109-119.
Salt et al., "Local Inner Ear Drug Delivery and Pharmacokinetics," Drug Discovery Today 10(19):1299-1306 (2005).
U.S. Appl. No. 12/466,310 Office Action dated Jan. 12, 2011.
Karolewicz and Pluta, "Thermosensitive polymers in drug form technology II. Possibilities of use of thermosensitive polymers as active substance carriers," Polimery W Medycynie 38(1):15-26, 2008 (English language abstract).
PCT/US2009/051165 International Search Report dated Mar. 12, 2010.
PCT/US2009/067552 international search report dated Aug. 18, 2010.
Ahn et al., "Lipoic acid rescues DBA mice from early-onset age-related hearing impairment," Neuroreport 19(13):1265-9, 2008.
Arnold et al., "Novel slow- and fast-type drug release round-window microimplants for local drug application to the cochlea: an experimental study in guinea pigs," Audiol Neurootol 10(1):53-63, 2005.
Auris Medical, press release reporting initiating of phase I/II clinical trial with AM-101, Feb. 22, 2007.
Auris Medical, press release reporting results of phase I/II clinical trial with AM-111, Jun. 21, 2006.
Battaglia et al., "Combination therapy (intratympanic dexamethasone + high-dose prednisone taper) for the treatment of idiopathic sudden sensorineural hearing loss," Otol Neurotol 29(4):453-60, 2008.
Campbell et al., "Oral-D-methionine (MRX-1024) significantly protects against cisplatin-induced hearing loss: a phase II study in humans," Abst 32$^{nd}$ Ann MidWinter Res Meeting, ARO Abstracts 32:7, Feb. 14-19, 2009.
Chen and Nathans, "Estrogen-related receptor beta/NR3B2 controls epithelial cell fate and endolymph production by the stria vascularis," Dev Cell 13(3):325-37, 2007.
Chen et al., "Design and preparation of thermosensitive in situ gel of dexamethasone sodium phosphate," J Guangdong Coll Pharm 23(5):518-21, 2007 (English abstract).

Chen et al., "Evaluation of thermosensitive in situ gel using dynamic rheological experiment," Chin Pharm J 43(6):444-447, 2008 (English abstract).
Chen et al., "In vivo distribution and pharmacokinetics of dexamethasone sodium phosphate thermosensitive in situ gel following intratympanic injection," Sichuan Da Xue Xue Bao Yi Xue Ban 37(3):456-9, 2006 (English translation).
Chen et al., "Preparation and characterization of dexamethasone acetate-loaded solid lipid nanoparticles," Chinese J Pharm 39(4):261-264, 2008 (English abstract).
Chen et al., "Study on dexamethasone thermosensitive in situ gel for treating deafness," Chin Pharm J 41(9):685-688, 2006 (English abstract).
Ciprodex, product label, 2009.
Derin et al., "The effects of L-carnitine on presbyacusis in the rat model," Clin Otolaryngol Allied Sci 29(3):238-41, 2004.
Endo et al., "Novel strategy for treatment of inner ears using a biodegradable gel," Laryngoscope 115(11):2016-20, 2005.
Feng et al., "Effect of poloxamer 407 on the middle ear and inner ear after regional perfusion in guinea pigs," Zhonghua Er Bi Yan Hou Tou Jing Wai Ke Za Zhi 42(6):443-6, 2007 (English translation).
Feng et al., "In vitro and in vivo biodegradation of sustained-release vehicle poloxamer 407 in situ gel," Lin Chung Er Bi Yan Hou Tou Jing Wai Ke Za Zhi 22(1):28-31, 2008 (English translation).
Fernandez et al., "Self-curing controlled release systems for steroids. Application of prednisolone-based polymeric systems to ear diseases," Biomaterials 26(16):3311-8, 2005.
Friedman et al., "GRM7 variants confer susceptibility to age-related hearing impairment," Hum Mol Genet 18(4):785-96, 2009.
Garduno-Anaya et al., "Dexamethasone inner ear perfusion by intratympanic injection in unilateral Ménière's disease: a two-year prospective, placebo-controlled, double-blind, randomized trial," Otolaryngol Head Neck Surg 133(2):285-94, 2005.
Gubbels et al., "Functional auditory hair cells produced in the mammalian cochlea by in utero gene transfer," Nature 455(7212):537-41, 2008.
Guyot et al., "Intratympanic application of an antiviral agent for the treatment of Ménière's disease," ORL J Otorhinolaryngol Relat Spec 70(1):21-6; discussion 26-7, 2008.
Hargunani et al., "Intratympanic injection of dexamethasone: time course of inner ear distribution and conversion to its active form," Otol Neurotol 27(4):564-9, 2006.
Harris et al., "Prevention of noise-induced hearing loss with Src-PTK inhibitors," Hear Res 208(1-2):14-25, 2005.
Harris et al., "Treatment of corticosteroid-responsive autoimmune inner ear disease with methotrexate: a randomized controlled trial," JAMA 290(14):1875-83, 2003.
Hill et al., "Cisplatin-induced ototoxicity: effect of intratympanic dexamethasone injections," Otol Neurotol 29:1005-11, 2008.
Hoffer et al., "Transtympanic management of tinnitus," Otolaryngol Clin North Am 36(2):353-8, 2003.
Hoshino et al., "The non-steroidal anti-inflammatory drugs protect mouse cochlea against acoustic injury," Tohoku J Exp Med 216(1):53-9, 2008.
Inaoka et al., "Local application of hepatocyte growth factor using gelatin hydrogels attenuates noise-induced hearing loss in guinea pigs," Acta Otolaryngol 129(4):453-7, 2009.
Jia et al., "Intratympanic dexamethasone for refractory sudden deafness," Lin Chung Er Bi Yan Hou Tou Jing Wai Ke Za Zhi 22(7):309-11, 2008 (English translation).
Kazama et al., "Lithium effectively complements vasopressin V2 receptor antagonist in the treatment of hyponatraemia of SIADH rats," Nephrol Dial Transplant 22(1):68-76, 2007.
Keithley et al., "GDNF protects the cochlea against noise damage," Neuroreport 9(10):2183-7, 1998.
Kim et al., "Effects of tumor necrosis factor alpha antagonist, platelet activating factor antagonist, and nitric oxide synthase inhibitor on experimental otitis media with effusion," Ann Otol Rhinol Laryngol 115(8):617-23, 2006.
Kitahara et al., "Up-regulation of cochlear aquaporin-3 mRNA expression after intra-endolymphatic sac application of dexamethasone," Neurol Res. 25(8):865-70, 2003.

(56) References Cited

OTHER PUBLICATIONS

Lamm and Arnold, "The effect of prednisolone and non-steroidal anti-inflammatory agents on the normal and noise-damaged guinea pig inner ear," Hear Res 115(1-2):149-61, 1998.
Lavreysen and Dautzenberg, "Therapeutic potential of group III metabotropic glutamate receptors," Curr Med Chem 15(7):671-84, 2008.
Lee et al., "Novel therapy for hearing loss: delivery of insulin-like growth factor 1 to the cochlea using gelatin hydrogel," Otol Neurotol 28(7):976-81, 2007.
Lee et al., "Regional delivery of vancomycin using pluronic F-127 to inhibit methicillin resistant *Staphylococcus aureus* (MRSA) growth in chronic otitis media in vitro and in vivo," J Control Release 96(1):1-7, 2004.
Liu et al., "Permeability of different Dexamethasone drugs through round window membrane," Zhonghua Er Bi Yan Hou Tou Jing Wai Ke Za Zhi 41(3):211-5, 2006 (English abstract).
McGuinness and Shepherd, "Exogenous BDNF rescues rat spiral ganglion neurons in vivo," Otol Neurotol 26(5):1064-72, 2005.
Meltser et al., "Estrogen receptor beta protects against acoustic trauma in mice," J Clin Invest 118(4):1563-70, 2008.
Miceli et al., "Molecular pharmacology and therapeutic potential of neuronal Kv7-modulating drugs," Curr Opin Pharmacol 8(1):65-74, 2008.
Mitsukawa et al., "A selective metabotropic glutamate receptor 7 agonist: activation of receptor signaling via an allosteric site modulates stress parameters in vivo," Proc Natl Acad Sci U S A 102(51):18712-7, 2005.
Nakagawa and Ito, "Local drug delivery to inner ear for treatment of hearing loss," Curr Drug Ther 3:143-147, 2008.
Nishimaki et al., "Reduction of metabotropic glutamate receptor-mediated heterosynaptic inhibition of developing MNTB-LSO inhibitory synapses," Eur J Neurosci 26(2):323-30, 2007.
Nouvian et al., "Degeneration of sensory outer hair cells following pharmacological blockade of cochlear KCNQ channels in the adult guinea pig," Eur J Neurosci 17(12):2553-62, 2003.
Park et al., "Effect of inhibitor of tumor necrosis factor-alpha and oxatomide on immune mediated otitis media," Laryngoscope 116(9):1642-6, 2006.
Parnes et al., "Corticosteroid pharmacokinetics in the inner ear fluids: an animal study followed by clinical application," Laryngoscope 109(7 Pt 2 Supplement No. 91):1-17, 1999.
Paulson et al., "A novel controlled local drug delivery system for inner ear disease," Laryngoscope 118(4):706-11, 2008.
Peng et al., "Clinical investigation of different routes of administration of dexamethasone on sudden deafness," Lin Chung Er Bi Yan Hou Tou Jing Wai Ke Za Zhi 22(10):442-5, 2008 (English translation).
Plontke et al., "Rapid clearance of methylprednisolone after intratympanic application in humans. Comment on: Bird PA, Begg EJ, Zhang M, et al. Intratympanic versus intravenous delivery of methylprednisolone to cochlear perilymph. Otol Neurotol 2007; 28:1124-30," Otol Neurotol 29(5):732-3, 2008.
Pondugula et al., "Glucocorticoid regulation of genes in the amiloride-sensitive sodium transport pathway by semicircular canal duct epithelium of neonatal rat," Physiol Genomics 24(2):114-23, 2006.
Pondugula et al., "Glucocorticoids stimulate cation absorption by semicircular canal duct epithelium via epithelial sodium channel," Am J Physiol Renal Physiol 286(6):F1127-35, 2004.
Psillas et al., "Potential efficacy of early treatment of acute acoustic trauma with steroids and piracetam after gunshot noise," Eur Arch Otorhinolaryngol 265(12):1465-9, 2008.
Puel, "Chemical synaptic transmission in the cochlea," Prog Neurobiol 47(6):449-76, 1995.
Satoh et al., "Tumor necrosis factor-alpha, an initiator, and etanercept, an inhibitor of cochlear inflammation," Laryngoscope 112(9):1627-34, 2002.
Schoepp et al., "Pharmacological agents acting at subtypes of metabotropic glutamate receptors," Neuropharmacology 38(10):1431-76, 1999.
Seidman et al., "Anti-intercellular adhesion molecule-1 antibody's effect on noise damage," Laryngoscope 119(4):707-12, 2009.
She et al., "A short term study on the efficacies of intratympanic prednisolone and dexamethasone injection for subjective tinnitus," Lin Chung Er Bi Yan Hou Tou ling Wai Ke Za Zhi 22(19):871-3, 2008 (English translation).
Shepherd et al., "Neurotrophins and electrical stimulation for protection and repair of spiral ganglion neurons following sensorineural hearing loss," Hear Res 242(1-2):100-9, 2008.
Shinohara et al., "Neurotrophic factor intervention restores auditory function in deafened animals," Proc Natl Acad Sci U S A 99(3):1657-60, 2002.
Sun et al., "In vitro permeability of round window membrane to transforming dexamethasone with delivery vehicles—a dosage estimation," Chin Med J (Engl) 120(24):2284-9, 2007.
Synphora AB, website printout for JB004/A, 2009.
Tabuchi et al., "Hearing impairment in TRPV4 knockout mice," Neurosci Lett 382(3):304-8, 2005.
Taguchi et al., "Expressions of aquaporin-2, vasopressin type 2 receptor, transient receptor potential channel vanilloid (TRPV)1, and TRPV4 in the human endolymphatic sac," Laryngoscope 117(4):695-8, 2007.
Tahera et al., "NF-kB mediated glucocorticoid response in the inner ear after acoustic trauma," J Neurosci Res 1;83(6):1066-76, 2006.
Takeda and Taguchi, "Aquaporins as potential drug targets for Meniere's disease and its related diseases," Handb Exp Pharmacol 190:171-84, 2009.
Takeda et al., "Decompression effects of erythritol on endolymphatic hydrops," Auris Nasus Larynx 36(2):146-51, 2009.
Takeda et al., "The effects of V2 antagonist (OPC-31260) on endolymphatic hydrops," Hear Res 182(1-2):9-18, 2003.
Takemura et al., "Direct inner ear infusion of dexamethasone attenuates noise-induced trauma in guinea pig," Hear Res 196(1-2):58-68, 2004.
Takumida and Anniko, "Nitric oxide in the inner ear,"Cur Opin Neurol 15(1):11-5, 2002.
Tang et al., "COUP-TFI controls Notch regulation of hair cell and support cell differentiation," Development 133(18):3683-93, 2006.
The Royal National Institute for Deaf People (RNID), advertisement in Nature 8(5):339-431, 2009.
Thorne et al., "Potential role of purinergic signalling in cochlear pathology," Audiol Neurootol 7(3):180-4, 2002.
Van Wijk et al., "Local perfusion of the tumor necrosis factor alpha blocker infliximab to the inner ear improves autoimmune neurosensory hearing loss," Audiol Neurootol 11(6):357-65, 2006.
Wang et al., "A novel dual inhibitor of calpains and lipid peroxidation (BN82270) rescues the cochlea from sound trauma," Neuropharmacology 52(6):1426-37, 2007.
Wang et al., "Over-expression of X-linked inhibitor of apoptosis protein slows presbycusis in C57BL/6J mice," Neurobiol Aging Aug. 26, 2008 [Epub ahead of print].
Watanabe et al., "Inhibition of inducible nitric oxide synthase lowers the cochlear damage by lipopolysaccharide in guinea pigs," Free Radic Res 32(4):363-70, 2000.
Watanabe et al., "Nitric oxide synthase inhibitor reduces the apoptotic change in the cisplatin-treated cochlea of guinea pigs," Anticancer Drugs 11(9):731-5, 2000.
Watanabe et al., "Nitric oxide synthase inhibitor suppresses the ototoxic side effect of cisplatin in guinea pigs," Anticancer Drugs 11(5):401-6, 2000.
Yamamoto et al., "Inhibition of Notch/RBP-J signaling induces hair cell formation in neonate mouse cochleas," J Mol Med 84(1):37-45, 2006.
Yang et al., "Intratympanic immunosuppressives for prevention of immune-mediated sensorineural hearing loss," Am J Otol 21(4):499-504, 2000.
Yildirim et al., "Effect of intratympanic dexamethasone on noise-induced temporary threshold shift," Laryngoscope 115(7):1219-22, 2005.
Zheng et al., "Vanilloid receptors in hearing: altered cochlear sensitivity by vanilloids and expression of TRPV1 in the organ of corti," J Neurophysiol 90(1):444-55, 2003.

(56) References Cited

OTHER PUBLICATIONS

Zhou et al., "Intratympanic administration of methylprednisolone reduces impact of experimental intensive impulse noise trauma on hearing," Acta Oto-Laryngologica 129:602-607, 2009.
Combined search and examination report in UK Patent Application No. GB0823378.5 dated Feb. 27, 2009.
Combined search and examination report in UK Patent Application No. GB0912650.9 dated Oct. 23, 2009.
Combined search and examination report in UK Patent Application No. GB0907065.7 dated Nov. 16, 2009.
Examination report in UK Patent Application No. GB0823378.5 dated Oct. 23, 2009.
PCT/US2008/061330 International Search Report dated Jul. 31, 2008.
Lichter et al., U.S. Appl. No. 12/466,310, filed May 14, 2009.
Lichter et al., U.S. Appl. No. 12/472,034, filed May 26, 2009.
Lichter et al., U.S. Appl. No. 12/493,611, filed Jun. 29, 2009.
Lichter et al., U.S. Appl. No. 12/427,663, filed Apr. 21, 2009.
Lichter et al., U.S. Appl. No. 12/486,697, filed Jun. 17, 2009.
Lichter et al., U.S. Appl. No. 12/500,486, filed Jul. 9, 2009.
Lichter et al., U.S. Appl. No. 12/494,156, filed Jun. 29, 2009.
Lichter et al., U.S. Appl. No. 12/506,127, filed Jul. 20, 2009.
Lichter et al., U.S. Appl. No. 12/504,553, filed Jul. 16, 2009.
Lichter et al., U.S. Appl. No. 12/506,616, filed Jul. 21, 2009.
Lichter et al., U.S. Appl. No. 12/506,664, filed Jul. 21, 2009.
Lichter et al., U.S. Appl. No. 12/506,573, filed Jul. 21, 2009.
Friedman et al., U.S. Appl. No. 12/597,054, filed Oct. 22, 2009.
Feng et al., Zhonghua er Bi Yan Hon Tou Jing Wai Ke Za Zhi, Jun. 2007;42(6):443-6 (English Abstract).
Feng et al., Zhonghua Yi Xue Za Zhi, Aug. 28, 2007;87(32):2289-91 (English Translation).
U.S. Appl. No. 12/504,553 Office Action dated Feb. 14, 2012.
EP09800849.3 Extended Search Report dated Oct. 3, 2012.
Amoils et al. An animal model of chronic tympanic membrane perforation. Otolaryngol Head Neck Surg. (1992), 106:47-55.
Bartfai et al. A low molecular weight mimic of the Toll/IL-1 receptor/resistance domain inhibits IL-1 receptor-mediated responses. PNAS, Jun. 24, 2003. 100(13):7971-7976.
Beitz et al. Aquaporin-Mediated Fluid Regulation in the Inner Ear. Cellular and Molecular Neurobiology (2003) 23(3):315-29.
Caggiano. WAY-VNA-932. Drugs of the Future. 2002. 27(3):248-253.
Carfrae et al. 3 Tesla delayed contrast magnetic resonance imaging evaluation of Ménière's disease. Laryngoscope 118:501-505 (Mar. 2008).
Chi et al. The quantification of endolymphatic hydrops in an experimental animal model with guinea pigs, J. Oto-Rhino-Larynol. (2004) 66:56-61.
Gloddek et al. Role of Lymphokines in the Immune response of the Inner Ear. Acta Otolaryngol. (1989) 108:68-75.
Gross et al. The treatment of hyponatraemia using vasopressin antagonists. Exp. Physiol. (2000) 85S:253S-257S.
Hansen et al. Determination of the Regime of Rapid Reacting Systems in Stopped-and Steady-Flow Investigations by the Velocity Probe Method. J Phys Chem. 92:2189-96. 1988.
Harris. 1983. Immunology of the inner ear: Response of the inner ear to antigen challenge. Otorhinolaryngology Head and Neck Surgery. 91:18-32.
Harris et al. Spiral Modiolar Vein: Its Importance in Inner Ear Inflammation. Acta Otolaryngol. (1990) 110:357-365.
Hashimoto et al. Innate Immunity Contributes to Cochlear Adaptive Immune.Responses. Audiol. Neurootol. (2005) 10: 35-43.
Inoue et al. Therapeutic and diagnostic potential of a vasopressin-2 antagonist for impaired water handling in cirrhosis. Clin. Pharm. Therap. (1998) 63(5):561.
Jeong et al. Thermosensitive sol-gel reversible hydrogels. Adv. Drug Delivery Rev. (2002), 54:37-51.
Jeong et al. Drug release from biodegradable injectable thermosensitive hydrogel of PEG-PLGA-PEG triblock copolymers . . . J. Control. Release (2000), 63:155-63.

Jeong et al. Biodegradable block copolymers as injectable drug-delivery systems. Nature. (1997) 388:860-2.
Johns et al. Broad Applicability of a Continuous Formation Process. Drug Delivery Technology vol. 4 (Jan./Feb. 2004).
Karin et al. The IKK NF-kappa B system: a treasure trove for drug development. Nature Reviews Drug Discovery (2004) 3:17-26.
Kim et al. Oral administration of collagen conjugated with cholera toxin induces tolerance to type II collagen and suppresses chondritis in an animal model of autoimmune ear disease. Ann. Otol. Rhinol. Larynogol. (2001) 110:646-654.
Kitano et al. Vasopressin and oxytocin receptor mRNAs are expressed in the rat inner ear. Neuroreport (1997) 8:2289-92.
Kondo et al. Novel design of nonpeptide AVP V(2) receptor agonists: structural requirements for an agonist having 1-(4-aminobenzoyl)-2,3,4, 5-tetrahydro-1H-1-benzazepine as a template. J. Med. Chem. (2000) 43:4388-4397.
Li et al. Characteristics of poloxamer thermosensitive in situ gel of dexamethasone sodium phosphate. Acta Pharmaceutica Sinica 2008. 43(2):208-203 (English Abstract).
Luetje et al. Plasmapheresis in autoimmune inner ear disease: long-term follow-up. Am. J. Otol. (1997) 18:572-576.
Luzzi Microencapsulation. J. Pharm. Psy. 59:1367 (1970).
Majithiya et al. Thermoreversible-mucoadhesive gel for nasal delivery of sumatriptan. AAPS PharmSciTech (2006), 7(3):Article 67 E1-E6.
Martin et al. Selective V2-receptor vasopressin antagonism decreases urinary aquaporin-2 excretion in patients with chronic heart failure. J. Am. Soc. Nephrol. (1999) 10(10):2165-2170.
Morin et al. The D136A mutation of the V2 vasopressin receptor induces a constitutitve activity which permits discrimination between antagonists with partial agonsit and ivnerse agonist activites. FEBS Letters (1998) 441(3):470-475.
Murdin et al (2007) Hearing difficulties are common in patients with rheumatoid arthritis. Clin Rheumatol, 27(5):637-640.
Naha et al. Improved bioavailability of orally delivered insulin using Eudragit-L30D coated PLGA microparticles. Journal of Microencapsulation Feb. 4, 2008 25(4):248-256 (online publication).
Nakamura et al. Characterization of a novel nonpeptide vasopressin V(2)-agonist, OPC-51803, in cells transfected human vasopressin receptor subtypes. Br. J. Pharmacal. (2000) 129(8):1700-1706.
Nakamura et al. Antidiuretic effects of a nonpeptide vasopressin V(2)-receptor agonist, OPC-51803, administered orally to rats. J. Pharmacal. Exp. Ther. (2000) 295(3):1005-1011.
Norman et al. Conivaptan Hydrocholoride. Drugs of the Future. (2000), 25(11):1121-1130.
Palm et al. V2-vasopressin receptor antagonists-mechanism of effect and clinical implications in hyponatraemia. Nephrol Dial Transplant (1999) 14:2559-2562.
Park et al. Mechanisms of Mucoadhesion of Poly(acrylic Acid) Hydrogels. Pharm. Res. (1987) 4(6):457-464.
Parker et al. Triazolo-tetrahydrofluorenones as selective estrogen receptor beta agonists. Bioorg. & Med. Chem. Ltrs. 16:4652-4656 (2006).
Rahmen et al. Etanercept therapy for immune-mediated cochleovestibular disorders: preliminary results in a pilot study. Otol. Neurol. (2001) 22:619-624.
Richard et al. Effects of sterilizing-grade filters on the physico-chemical properties of onion-like vesicles. International Journal of Pharmaceutics (2006). 312(1-2):144-50.
Sanghi et al. Vasopressin antagonism: a future treatment option in heart failure. Eur. Heart J. (2005) 26:538-543.
Satoh et al. Proinflammatory cytokine expression in the endolymphatic sac during inner ear inflammation. Assoc. Res. Otolaryngol. (2003) 4:139-147.
Schuknecht. Ablation therapy for the relief of Ménière's disease. Laryngoscope (1956) 66:859-870.
Seidman et al. Biologic Activity of Mitochondrial Metabolites on Aging and Age-Relaed Hearing Loss. Am. J. Otol. (2000) 21:161-167.
Shore et al. Trigeminal ganglion Innervates the Auditory Brainstem. J. Comp. Neurology (2000) 10:271-285.
Sismanis et al. Methotrexate management of immune-mediated cochleovestibular disorders. Otolaryngol (1997) 116:146-152.

(56) References Cited

OTHER PUBLICATIONS

Sismanis et al. Methotrexate therapy for autoimmune hearing loss: a preliminary report. Laryngoscope (1994) 104:932-934.

Skotnicki et al. Chapter 16: TNF-α Converting Enzyme (TACE) as a Therapeutic Target. Annual Reports in Medicinal Chemistry (2003), 38:153-1621.

Takeda et al. Endolymphatic hydrops induced by chronic administration of vasopressin. Hear Res (2000). 140:1-6.

Takeda et al. A comparison of dehydration effects of V2-antagonist (OPC-31260) on the inner ear between systemic and round window applications. Hearing Res. (2006) 218:89-97.

The U. S. Food and Drug Administration has provided regulatory guidance in the publication Guidance for Industry: Sterile Drug Products Produced by Aseptic Processing available at: http://www.fda.gov/cder/guidance/5882fn1.htm.

Vass et al. Direct evidence of trigeminal innervation of the cochlear blood vessels. Neuroscience (1998) 84:559-567.

Viegas et. al. Osmotic behavior of poloxamer 407 and other non-ionic surfactants in aqueous solutions. Int. J. Pharm. 1998. 160:157-162.

Wang et al. Blockage of Immune-Mediated Inner Ear Damage by Etanercept. Otology and Neurotology. 24:52-57. 2003.

Wong et al. Sphincter of Oddi Manometry: Comparison of Post-Procedure Abdominal Pain and Post-Procedure Pancreatitis GSW. Gastroent Apr. 2000, 118(4):Suppl. 2, Part 1.

Yin et al. Pretreatment with soluble ST2 reduces warm hepatic ischemia/reperfusion injury. Biochem and Biophys Res Commun Dec. 29, 2006. 351(4):940-946.

Yingling et al. Development of TGF-beta signalling inhibitors for cancer therapy. Nature Reviews. 2004. 3:1011-1022.

Zou et al. Distibution of Lipid Nanocapsules in different cochlear Cell Populations After Round Window Membrane Permeation. J. Biomed. Materials Res., online pub. pp. 10-18(Apr. 24, 2008).

Chen et al. In vivo Distribution and Pharmacokinetics of Dexamethasone Acetate Nanoparticles Thermosensitive in situ Gel Following Intratympanic Injection. Chin. J. Otorhinolaryngol Head Neck Surg 42:533-534 (2007).

Chen et al. Preliminary study on brain-targeted drug delivery via inner ear. Acta Pharmaceutica Sinica 42:1102-1106 (2007) (English Abstract).

Pappas et al. Topical Antibiotic Ear Drops: Are They Safe? Int J Clin Pract. 60:1115-1119 (2006).

Ross et al. Aqueous Solubilities of some variously Substituted Quinole Antimicrobials. Int'l J of Pharm 63:237-250 (1990).

* cited by examiner

CONTROLLED-RELEASE OTIC STRUCTURE MODULATING AND INNATE IMMUNE SYSTEM MODULATING COMPOSITIONS AND METHODS FOR THE TREATMENT OF OTIC DISORDERS

CROSS-REFERENCE

This application claims the benefit of U.S. Provisional Application No. 61/082,450, filed 21 Jul. 2008; U.S. Provisional Application No. 61/091,205, filed 22 Aug. 2008; U.S. Provisional Application No. 61/094,384, filed 4 Sep. 2008; U.S. Provisional Application No. 61/101,112, filed 29 Sep. 2008; U.S. Provisional Application No. 61/108,845, filed 27 Oct. 2008; U.S. Provisional Application No. 61/140,033, filed 22 Dec. 2008; U.S. Provisional Application No. 61/156,771, filed 2 Mar. 2009; and U.S. Provisional Application No. 61/091,200, filed 22 Aug. 2008; all of which are incorporated by reference herein in their entirety.

BACKGROUND OF THE INVENTION

Vertebrates have a pair of ears, placed symmetrically on opposite sides of the head. The ear serves as both the sense organ that detects sound and the organ that maintains balance and body position. The ear is generally divided into three portions: the outer ear, auris media (or middle ear) and the auris interna (or inner ear).

SUMMARY OF THE INVENTION

Described herein, in certain embodiments, are compositions, compositions, manufacturing methods, therapeutic methods, uses, kits, and delivery devices for the controlled-release of an otic structure modulating agent or innate immune system modulating agent to at least one structure or region of the ear. Disclosed herein, in certain embodiments, are controlled-release compositions for delivering an otic structure modulating agent or innate immune system modulating agent to the ear. In some embodiments, the target portion of the ear is the middle ear (or auris media). In some embodiments, the target portion of the ear is the inner ear (or auris interna). In other embodiments, the target portion of the ear is both the auris media and the auris interna. In some embodiments, the controlled-release compositions further comprise a rapid or immediate release component for delivering an otic structure modulating agent or innate immune system modulating agent to the targeted auris structure. All compositions comprise excipients that are auris-acceptable.

Also disclosed herein, in certain embodiments, are compositions and devices for the treatment of otic disorders, said compositions and devices comprising an otic structure modulating agent or innate immune system modulating agent. Further disclosed herein, in certain embodiments, are methods for the treatment of otic disorders by administration of a controlled-release composition comprising an otic structure modulating agent or innate immune system modulating agent to an individual in need thereof. In some embodiments, the otic disorder is otitis externa, otitis media, mastoiditis, sensorineural hearing loss, ototoxicity, endolymphatic hydrops, labyrinthitis, Meniere's disease, Meniere's syndrome, microvascular compression syndrome, vestibular neuronitis, acoustic trauma, presbycusis, cholesteatoma, otosclerosis, Scheibe syndrome, Mondini-Michelle syndrome, Waardenburg's syndrome, Michel syndrome, Alexander's ear deformity, hypertelorism, Jervell-Lange Nielson syndrome, Refsum's syndrome, Usher's syndrome, or combinations thereof. In some embodiments, the otic disorder is otitis externa, otitis media, mastoiditis, AIED, Ramsay Hunt's, reperfusion injury, labyrinthitis ossificans or combinations thereof.

The auris compositions and therapeutic methods described herein have numerous advantages that overcome the previously-unrecognized limitations of compositions and therapeutic methods described in prior art.

Sterility

The environment of the inner ear is an isolated environment. The endolymph and the perilymph are static fluids and are not in contiguous contact with the circulatory system. The blood-labyrinth-barrier (BLB), which includes a blood-endolymph barrier and a blood-perilymph barrier, consists of tight junctions between specialized epithelial cells in the labyrinth spaces (i.e., the vestibular and cochlear spaces). The presence of the BLB limits delivery of active agents (e.g., otic structure modulating agent or innate immune system modulating agents) to the isolated microenvironment of the inner ear. Auris hair cells are bathed in endolymphatic or perilymphatic fluids and cochlear recycling of potassium ions is important for hair cell function. When the inner ear is infected, there is an influx of leukocytes and/or immunoglobulins (e.g. in response to a microbial infection) into the endolymph and/or the perilymph and the ionic composition of inner ear fluids is upset by the influx of leukocytes and/or immunoglobulins. In certain instances, a change in the ionic composition of inner ear fluids results in hearing loss, loss of balance and/or ossification of auditory structures. In certain instances, trace amounts of pyrogens and/or microbes trigger infections and related physiological changes in the isolated microenvironment of the inner ear.

Due to the susceptibility of the inner ear to infections, auris compositions require a level of sterility that has not been recognized hitherto in prior art. Provided herein are auris compositions that are sterilized with stringent sterility requirements and are suitable for administration to the middle and/or inner ear. In some embodiments, the auris compatible compositions described herein are substantially free of pyrogens and/or microbes.

Compatibility with Inner Ear Environment

Described herein are otic compositions with an ionic balance that is compatible with the perilymph and/or the endolymph and does not cause any change in cochlear potential. In specific embodiments, osmolarity/osmolality of the present compositions is adjusted, for example, by the use of appropriate salt concentrations (e.g., concentration of sodium salts) or the use of tonicity agents that render the compositions endolymph-compatible and/or perilymph-compatible (i.e. isotonic with the endolymph and/or perilymph). In some instances, the endolymph-compatible and/or perilymph-compatible compositions described herein cause minimal disturbance to the environment of the inner ear and cause minimum discomfort (e.g., vertigo) to a subject (e.g., a human) upon administration. Further, the compositions comprise polymers that are biodegradable and/or dispersible, and/or otherwise non-toxic to the inner ear environment. In some embodiments, the compositions described herein are free of preservatives and cause minimal disturbance (e.g., change in pH or osmolarity, irritation) in auditory structures. In some embodiments, the compositions described herein comprise antioxidants that are non-irritating and/or non-toxic to otic structures.

Dosing Frequency

The current standard of care for auris compositions requires multiple administrations of drops or injections (e.g. intratympanic injections) over several days (e.g., up to two weeks), including schedules of receiving multiple injections per day. In some embodiments, auris compositions described herein are controlled-release compositions and are administered at reduced dosing frequency compared to the current standard of care. In certain instances, when an auris composition is administered via intratympanic injection, a reduced frequency of administration alleviates discomfort caused by multiple intratympanic injections in individuals undergoing treatment for a middle and/or inner ear disease, disorder or condition. In certain instances, a reduced frequency of administration of intratympanic injections reduces the risk of permanent damage (e.g., perforation) to the tympanic membrane. The compositions described herein provide a constant, sustained, extended, delayed or pulsatile rate of release of an active agent into the inner ear environment and thus avoid any variability in drug exposure in treatment of otic disorders.

Therapeutic Index

Auris compositions described herein are administered into the ear canal, or in the vestibule of the ear. In some embodiments, access to the vestibular and cochlear apparatus occurs through the auris media (e.g., the round window membrane, the oval window/stapes footplate, the annular ligament and through the otic capsule/temporal bone). Otic administration of the compositions described herein avoids toxicity associated with systemic administration (e.g., hepatotoxicity, cardiotoxicity, gastrointestinal side effects, renal toxicity) of the active agents. In some instances, localized administration in the ear allows an active agent to reach a target (e.g., the inner ear) in the absence of systemic accumulation of the active agent. In some instances, local administration to the ear provides a higher therapeutic index for an active agent that would otherwise have dose-limiting systemic toxicity.

Prevention of Drainage into Eustachian Tube

In some instances, a disadvantage of liquid compositions is their propensity to drip into the eustachian tube and cause rapid clearance of the composition from the inner ear. Provided herein, in certain embodiments, are auris compositions comprising polymers that gel at body temperature and remain in contact with the target auditory surfaces (e.g., the round window) for extended periods of time. In some embodiments, the compositions further comprise a mucoadhesive that allows the compositions to adhere to otic mucosal surfaces. In some instances, the auris compositions described herein avoid attenuation of therapeutic benefit due to drainage or leakage of active agents via the eustachian tube.

DESCRIPTION OF CERTAIN EMBODIMENTS

Described herein, in certain embodiments, are controlled-release compositions and devices for treating otic disorders comprising a therapeutically-effective amount of an otic structure modulating agent or innate immune system modulating agent, a controlled-release auris-acceptable excipient and an auris-acceptable vehicle. In one aspect, the controlled-release auris-acceptable excipient is chosen from an auris-acceptable polymer, an auris-acceptable viscosity enhancing agent, an auris-acceptable gel, an auris-acceptable paint, an auris-acceptable foam, an auris-acceptable microsphere or microparticle, an auris-acceptable hydrogel, an auris-acceptable in situ forming spongy material, an auris-acceptable actinic radiation curable gel, an auris-acceptable liposome, an auris-acceptable nanocapsule or nanosphere, an auris-acceptable thermoreversible gel or combinations thereof. In further embodiments, the auris-acceptable viscosity enhancing agent is a cellulose, a cellulose ether, alginate, polyvinylpyrrolidone, a gum, a cellulosic polymer or combinations thereof. In yet another embodiment, the auris-acceptable viscosity enhancing agent is present in an amount sufficient to provide a viscosity of between about 1000 to about 1,000,000 centipoise. In still another aspect, the auris-acceptable viscosity enhancing agent is present in an amount sufficient to provide a viscosity of between about 50,000 to about 1,000,000 centipoise.

In some embodiments, the compositions disclosed herein are formulated for a pH that ensures that they are compatible with the targeted auris structure. In some embodiments, the compositions disclosed herein are formulated for a practical osmolality and/or osmolarity that ensures that homeostasis of the target auris structure is maintained. A perilymph-suitable osmolarity/osmolality is a practical osmolarity/osmolality that maintains the homeostasis of the target auris structure during administration of the pharmaceutical compositions described herein.

For example, the osmolarity of the perilymph is between about 270-300 mOsm/L and the compositions described herein are optionally formulated to provide a practical osmolarity of about 150 to about 1000 mOsm/L. In certain embodiments, the compositions described herein provide a practical osmolarity within about 150 to about 500 mOsm/L at the target site of action (e.g., the inner ear and/or the perilymph and/or the endolymph). In certain embodiments, the compositions described herein provide a practical osmolarity within about 200 to about 400 mOsm/L at the target site of action (e.g., the inner ear and/or the perilymph and/or the endolymph). In certain embodiments, the compositions described herein provide a practical osmolarity within about 250 to about 320 mOsm/L at the target site of action (e.g., the inner ear and/or the perilymph and/or the endolymph). In certain embodiments, the compositions described herein provide a perilymph-suitable osmolarity within about 150 to about 500 mOsm/L, about 200 to about 400 mOsm/L or about 250 to about 320 mOsm/L at the target site of action (e.g., the inner ear and/or the perilymph and/or the endolymph). In certain embodiments, the compositions described herein provide a perilymph-suitable osmolality within about 150 to about 500 mOsm/kg, about 200 to about 400 mOsm/kg or about 250 to about 320 mOsm/kg at the target site of action (e.g., the inner ear and/or the perilymph and/or the endolymph). Similarly, the pH of the perilymph is about 7.2-7.4, and the pH of the present compositions is formulated (e.g., with the use of buffers) to provide a perilymph-suitable pH of about 5.5 to about 9.0, about 6.0 to about 8.0 or about 7.0 to about 7.6. In certain embodiments, the pH of the compositions is within about 6.0 to about 7.6. In certain instances, the pH of the endolymph is about 7.2-7.9, and the pH of the present compositions is formulated (e.g., with the use of buffers) to be within about 5.5 to about 9.0, within about 6.5 to about 8.0 or within about 7.0 to about 7.6.

In some aspects, the controlled-release auris-acceptable excipient is biodegradable and/or bioeliminated (e.g., degraded and/or eliminated through urine, feces or other routes of elimination). In another aspect, the controlled-release composition further comprises an auris-acceptable mucoadhesive, an auris-acceptable penetration enhancer or an auris-acceptable bioadhesive.

In one aspect, the controlled-release composition is delivered using a drug delivery device, which is a needle and syringe, a pump, a microinjection device, and in situ forming spongy material or combinations thereof. In some embodiments, the otic structure modulating agent or innate immune system modulating agent of the controlled-release composition has limited or no systemic release, is toxic when administered systemically, has poor pK characteristics, or combinations thereof.

In some embodiments, the otic structure modulating agent is an otic structure enhancing agent (e.g., a molecular component of an otic structure). In some embodiments, the otic structure enhancing agent is actin, aggrecan, chondroitin, collagen, decorin, dermatan sulfate, elastin, fibrinogen, fibronectin, fimbrin, glial fibrillary acidic protein, heparan sulfate, hyaluronic acid, keratin, laminin, nestin, NF-L, NF-M, NF—H, NF66, peripherin, α-tubulin, β-tubulin, villin, vimentin, whirlin, or combinations thereof.

In some embodiments, the otic structure modulating agent is an otic structure degrading agent. In some embodiments, the otic structure degrading agent degrades bone. In some embodiments, the otic structure degrading agent degrades cartilage. In some embodiments, the otic structure degrading agent degrades a neuron. In some embodiments, the otic structure degrading agent degrades a membrane (e.g., a tympanic membrane). In some embodiments, the otic structure degrading agent degrades endolymph. In some embodiments, the otic structure degrading agent degrades perilymph. In some embodiments, the otic structure degrading agent degrades liquor puris (i.e., pus).

In some embodiments, the otic structure modulating agent is an otic structure degrading agent. In some embodiments, the otic structure degrading agent is an alcohol, an alkanol, an essential oil, a fatty acid, a glycol, laurocapram, a pyrrolidone, a sulfoxide, a surfactant, an enzyme, or a combination thereof. In some embodiments, the enzyme is a protease, a glycosidase, protease, a glycosidase, an actinase, a caseinase, a chondroitinase, a collagenase, a dermatanase, an elastase, a gelatinase, a heparanase, a hyaluronidase, a keratinase, a lipase, a metalloproteinase (e.g. matrix metalloproteinase), a staphylokinase, a streptokinase, chymotrypsin, endopeptidase V8, trypsin, thermolysin, pepsin, plasmin, or combinations thereof. In some embodiments, the otic structure modulating agent is a modulator of bone remodeling. In some embodiments, the modulator of bone remodeling is a modulator of osteoblasts or osteoclasts, including but not limited to, hormones; bisphosphonates; matrix metalloproteinase inhibitors; an adenylyl cyclase (AC) modulators; protease inhibitors; modulators of tartarate resistant acid phosphatase (TRACP); estrogen receptor modulators; PPAR γ modulators; HMG-CoA reductase inhibitors; statins; carbonic anhydrase inhibitors; modulators of the receptor activator of nuclear κB ligand (RANKL); COX-2 inhibitors; inhibitors of protein prenylation; 5-lipoxygenase inhibitors; inhibitors of TNF; inhibitors of leukotrienes; cytokine modulators; inhibitors of TSG-6, modulators of TGF β; nitiric oxide synthase inhibitors; acetylcysteine; modulators of aromatases; and strontium-based compounds as disclosed in WO/2008/027880, which is incorporated by reference herein.

In some embodiments, the otic structure modulating agent is an otic structure enhancing agent. In some embodiments, the otic structure enhancing agent rebuilds or supplements bone. In some embodiments, the otic structure enhancing agent rebuilds or supplements cartilage. In some embodiments, the otic structure enhancing agent rebuilds or supplements a membrane (e.g., a tympanic membrane). In some embodiments, the otic structure enhancing agent rebuilds or supplements endolymph. In some embodiments, the otic structure enhancing agent rebuilds or supplements perilymph.

In some embodiments, the otic structure modulating agent is an otic structure enhancing agent. In some embodiments, the otic structure enhancing agent is actin, aggrecan, chondroitin, collagen, decorin, dermatan sulfate, elastin, fibrinogen, fibronectin, fimbrin, glial fibrillary acidic protein, heparan sulfate, hyaluronic acid, keratin, laminin, nestin, NF-L, NF-M, NF—H, NF66, peripherin, α-tubulin, β-tubulin, villin, vimentin, whirlin, or combinations thereof.

In some embodiments, the innate immune system modulating agent is a complement cascade modulating agent and/or an anaphylatoxin modulator. In some embodiments, the innate immune system modulating agent is a complement cascade antagonist and/or an anaphylatoxin antagonist. In some embodiments, the innate immune system modulating agent is a complement cascade agonist and/or an anaphylatoxin agonist.

In some embodiments, the innate immune system modulating agent is CHIPS, PMX53, PMX205, PMX273, PMX201, PMX218, C089, L-156,602, C5aRAM, C5aRAD, PR226-MAP, PL37-MAP, SB-290157, GR-2II, AGIIa, AGIIb-1, AR-2IIa, AR-2IIb, AR-2IIc, AR-2IId, CVF, CVF, humanized CVF, rC3, HC3-1496, HC3-1496-2, HC3-1496-3, HC3-1496-4, HC3-1496/1617, HC3-1496-8, HC3-1496-9, HC3-1496-10, HC3-1496-11, HC3-1496-12, HC3-1496-13, HC3-1496-14, HC3-1496-15, HC3-1496-16, HC3-1496-17, complement component 1 inhibitor, dextran sulfate, complement component 1q receptor, C1q inhibitor, decorin, CSPG, CBP2, complement receptor 1, sCR1, APT070, TP10, TP20, sCR1[desLHR-A]), sCR1-SLe$^x$, Crry, Crry-Ig, a fucan, BS8, complestatin, Ecb, Efb, compstatin, rosmarinic acid, CRIT, CRIT-H17, glycyrrhetinic acid, an anti-complement component 5 (C5) murine monoclonal antibody, pexelizumab, an anti-C5 murine single-chain antibody, K76, TKIXc, K76 COOH, SCIN, SCIN-B, SCIN-C, CD55, sCD55, CD59, sCD59, a CD59/CD55 fusion protein, a CD55/MCP fusion protein, BCX-1470, FUT-175, Factor I, MCP, sMCP, heparin, LU 51198, clusterin, vitronectin, an anti-properdin antibody, SB 290157 (N2-((2,2-diphenylethoxy)acetyl)arginine), anti-MIF antibody, metformin, ISO-1,2-[(4-hydroxybenzylidene)amino]-3(1H-indol-3-yl)propionic acid methyl ester, NAPQI, AVP-28225, or combinations thereof.

Also disclosed herein, in certain embodiments, is a method for treating an otic disorder comprising administering a composition disclosed herein at least once every 3, 4, 5, 6, 7, 8, 9, 10, 11, 12, 13, 14, or 15 days; at least once a week, once every two weeks, once every three weeks, once every four weeks, once every five weeks, or once every six weeks; or at least once a month, once every two months, once every three months, once every four months, once every five months, once every six months, once every seven months, once every eight months, once every nine months, once every ten months, once every eleven months, or once every twelve months. In particular embodiments, the controlled-release compositions described herein provide a sustained dose of an otic structure modulating agent or innate immune system modulating agent to the inner ear between subsequent doses of the controlled-release composition. That is, taking one example only, if new doses of the otic structure modulating agent or innate immune system modulating agent controlled-release composition are administered via intratympanic injection to the round window membrane every 10 days, then the controlled-release composition provides an effective dose of an otic structure modulating agent or innate immune system modulating agent to the inner ear (e.g., across the round window membrane) during that 10-day period.

In one aspect, the composition is administered so that the composition is in contact with the crista fenestrae cochleae, the round window membrane or the tympanic cavity. In one aspect the composition is administered by intratympanic injection.

Provided herein are pharmaceutical compositions or devices for use in the treatment of an otic disease or condition formulated to provide a therapeutically effective amount of an otic structure modulating agent, the pharmaceutical compositions or devices comprising substantially low degradation products of the otic structure modulating agent, the pharmaceutical compositions or devices further comprising two or more characteristics selected from:
(i) between about 0.1% to about 10% by weight of the otic structure modulating agent, or pharmaceutically acceptable prodrug or salt thereof;
(ii) between about 14% to about 21% by weight of a polyoxyethylene-polyoxypropylene triblock copolymer of general formula E106 P70 E106;
(iii) sterile water, q.s., buffered to provide a pH between about 5.5 and about 8.0;
(iv) multiparticulate otic structure modulating agent;
(v) a gelation temperature between about 19° C. to about 42° C.;
(vi) less than about 50 colony forming units (cfu) of microbiological agents per gram of composition;
(vii) less than about 5 endotoxin units (EU) per kg of body weight of a subject;
(viii) a mean dissolution time of about 30 hours for the otic structure modulating agent; and
(ix) an apparent viscosity of about 100,000 cP to about 500,000 cP.

In some embodiments, the pharmaceutical composition comprises at least three of the aforementioned characteristics. In some embodiments, the pharmaceutical composition comprises at least four of the aforementioned characteristics. In some embodiments, the pharmaceutical composition comprises at least five of the aforementioned characteristics. In some embodiments, the pharmaceutical composition comprises at least six of the aforementioned characteristics. In some embodiments, the pharmaceutical composition comprises at least seven of the aforementioned characteristics. In some embodiments, the pharmaceutical composition comprises all of the aforementioned characteristics.

In some embodiments, a pharmaceutical composition or device described herein comprises:
(i) between about 0.1% to about 10% by weight of the otic structure modulating agent, or pharmaceutically acceptable prodrug or salt thereof;
(ii) between about 14% to about 21% by weight of a polyoxyethylene-polyoxypropylene triblock copolymer of general formula E106 P70 E106; and
(iii) multiparticulate otic structure modulating agent.

In some embodiments, a pharmaceutical composition or device described herein comprises:
(i) between about 0.1% to about 10% by weight of the otic structure modulating agent, or pharmaceutically acceptable prodrug or salt thereof;
(ii) between about 14% to about 21% by weight of a polyoxyethylene-polyoxypropylene triblock copolymer of general formula E106 P70 E106;
(iii) multiparticulate otic structure modulating agent; and
(iv) a gelation temperature between about 19° C. to about 42° C.

Provided herein are pharmaceutical compositions or devices for use in the treatment of an otic disease or condition formulated to provide a therapeutically effective amount of a molecular component of an otic structure, the pharmaceutical compositions or devices comprising substantially low degradation products of the otic structure enhancing agent, the pharmaceutical compositions or devices further comprising two or more characteristics selected from:
(i) between about 0.1% to about 10% by weight of the otic structure enhancing agent, or pharmaceutically acceptable prodrug or salt thereof;
(ii) between about 14% to about 21% by weight of a polyoxyethylene-polyoxypropylene triblock copolymer of general formula E106 P70 E106;
(iii) sterile water, q.s., buffered to provide a pH between about 5.5 and about 8.0;
(iv) multiparticulate molecular component of an otic structure;
(v) a gelation temperature between about 19° C. to about 42° C.;
(vi) less than about 50 colony forming units (cfu) of microbiological agents per gram of composition;
(vii) less than about 5 endotoxin units (EU) per kg of body weight of a subject;
(viii) a mean dissolution time of about 30 hours for the otic structure enhancing agent; and
(ix) an apparent viscosity of about 100,000 cP to about 500,000 cP.

In some embodiments, the pharmaceutical composition comprises at least three of the aforementioned characteristics. In some embodiments, the pharmaceutical composition comprises at least four of the aforementioned characteristics. In some embodiments, the pharmaceutical composition comprises at least five of the aforementioned characteristics. In some embodiments, the pharmaceutical composition comprises at least six of the aforementioned characteristics. In some embodiments, the pharmaceutical composition comprises at least seven of the aforementioned characteristics. In some embodiments, the pharmaceutical composition comprises all of the aforementioned characteristics.

In some embodiments, a pharmaceutical composition or device described herein comprises:
(i) between about 0.1% to about 10% by weight of the otic structure enhancing agent, or pharmaceutically acceptable prodrug or salt thereof;
(ii) between about 14% to about 21% by weight of a polyoxyethylene-polyoxypropylene triblock copolymer of general formula E106 P70 E106; and
(iii) multiparticulate molecular component of an otic structure.

In some embodiments, a pharmaceutical composition or device described herein comprises:
(i) between about 0.1% to about 10% by weight of the otic structure enhancing agent, or pharmaceutically acceptable prodrug or salt thereof;
(ii) between about 14% to about 21% by weight of a polyoxyethylene-polyoxypropylene triblock copolymer of general formula E106 P70 E106;
(iii) multiparticulate molecular component of an otic structure; and
(iv) a gelation temperature between about 19° C. to about 42° C.

Provided herein are pharmaceutical compositions or devices for use in the treatment of an otic disease or condition formulated to provide a therapeutically effective amount of an otic structure degrading agent, the pharmaceutical compositions or devices comprising substantially low degradation products of the otic structure degrading agent, the pharmaceutical compositions or devices further comprising two or more characteristics selected from:

(i) between about 0.1% to about 10% by weight of the otic structure degrading agent, or pharmaceutically acceptable prodrug or salt thereof;
(ii) between about 14% to about 21% by weight of a polyoxyethylene-polyoxypropylene triblock copolymer of general formula E106 P70 E106;
(iii) sterile water, q.s., buffered to provide a pH between about 5.5 and about 8.0;
(iv) multiparticulate otic structure degrading agent;
(v) a gelation temperature between about 19° C. to about 42° C.;
(vi) less than about 50 colony forming units (cfu) of microbiological agents per gram of composition;
(vii) less than about 5 endotoxin units (EU) per kg of body weight of a subject;
(viii) a mean dissolution time of about 30 hours for the otic structure degrading agent; and
(ix) an apparent viscosity of about 100,000 cP to about 500,000 cP.

In some embodiments, the pharmaceutical composition comprises at least three of the aforementioned characteristics. In some embodiments, the pharmaceutical composition comprises at least four of the aforementioned characteristics. In some embodiments, the pharmaceutical composition comprises at least five of the aforementioned characteristics. In some embodiments, the pharmaceutical composition comprises at least six of the aforementioned characteristics. In some embodiments, the pharmaceutical composition comprises at least seven of the aforementioned characteristics. In some embodiments, the pharmaceutical composition comprises all of the aforementioned characteristics.

In some embodiments, a pharmaceutical composition or device described herein comprises:
(i) between about 0.1% to about 10% by weight of the otic structure degrading agent, or pharmaceutically acceptable prodrug or salt thereof;
(ii) between about 14% to about 21% by weight of a polyoxyethylene-polyoxypropylene triblock copolymer of general formula E106 P70 E106; and
(iii) multiparticulate otic structure degrading agent.

In some embodiments, a pharmaceutical composition or device described herein comprises:
(i) between about 0.1% to about 10% by weight of the otic structure degrading agent, or pharmaceutically acceptable prodrug or salt thereof;
(ii) between about 14% to about 21% by weight of a polyoxyethylene-polyoxypropylene triblock copolymer of general formula E106 P70 E106;
(iii) multiparticulate otic structure degrading agent; and
(iv) a gelation temperature between about 19° C. to about 42° C.

Provided herein are pharmaceutical compositions or devices for use in the treatment of an otic disease or condition formulated to provide a therapeutically effective amount of an innate immune system modulating agent, the pharmaceutical compositions or devices comprising substantially low degradation products of the innate immune system modulating agent, the pharmaceutical compositions or devices further comprising two or more characteristics selected from:
(i) between about 0.1% to about 10% by weight of the innate immune system modulating agent, or pharmaceutically acceptable prodrug or salt thereof;
(ii) between about 14% to about 21% by weight of a polyoxyethylene-polyoxypropylene triblock copolymer of general formula E106 P70 E106;
(iii) sterile water, q.s., buffered to provide a pH between about 5.5 and about 8.0;
(iv) multiparticulate innate immune system modulating agent;
(v) a gelation temperature between about 19° C. to about 42° C.;
(vi) less than about 50 colony forming units (cfu) of microbiological agents per gram of composition;
(vii) less than about 5 endotoxin units (EU) per kg of body weight of a subject;
(viii) a mean dissolution time of about 30 hours for the innate immune system modulating agent; and
(ix) an apparent viscosity of about 100,000 cP to about 500,000 cP.

In some embodiments, the pharmaceutical composition comprises at least three of the aforementioned characteristics. In some embodiments, the pharmaceutical composition comprises at least four of the aforementioned characteristics. In some embodiments, the pharmaceutical composition comprises at least five of the aforementioned characteristics. In some embodiments, the pharmaceutical composition comprises at least six of the aforementioned characteristics. In some embodiments, the pharmaceutical composition comprises at least seven of the aforementioned characteristics. In some embodiments, the pharmaceutical composition comprises all of the aforementioned characteristics.

In some embodiments, a pharmaceutical composition or device described herein comprises:
(i) between about 0.1% to about 10% by weight of the innate immune system modulating agent, or pharmaceutically acceptable prodrug or salt thereof;
(ii) between about 14% to about 21% by weight of a polyoxyethylene-polyoxypropylene triblock copolymer of general formula E106 P70 E106; and
(iii) multiparticulate innate immune system modulating agent.

In some embodiments, a pharmaceutical composition or device described herein comprises:
(i) between about 0.1% to about 10% by weight of the innate immune system modulating agent, or pharmaceutically acceptable prodrug or salt thereof;
(ii) between about 14% to about 21% by weight of a polyoxyethylene-polyoxypropylene triblock copolymer of general formula E106 P70 E106;
(iii) multiparticulate innate immune system modulating agent; and
(iv) a gelation temperature between about 19° C. to about 42° C.

Provided herein are methods of treating an otic disease or condition characterized by excess otic structures comprising administering to an individual in need thereof an intratympanic composition or device comprising: a therapeutically effective amount of an otic structure degrading agent having substantially low degradation products; and wherein the composition or device comprises two or more characteristics selected from:
(i) between about 0.1% to about 10% by weight of the otic structure degrading agent, or pharmaceutically acceptable prodrug or salt thereof;
(ii) between about 14% to about 21% by weight of a polyoxyethylene-polyoxypropylene triblock copolymer of general formula E106 P70 E106;
(iii) sterile water, q.s., buffered to provide a pH between about 5.5 and about 8.0;
(iv) multiparticulate otic structure degrading agent;
(v) a gelation temperature between about 19° C. to about 42° C.;

(vi) less than about 50 colony forming units (cfu) of microbiological agents per gram of composition, and
(vii) less than about 5 endotoxin units (EU) per kg of body weight of a subject;
(viii) a mean dissolution time of about 30 hours for the otic structure degrading agent; and
(ix) an apparent viscosity of about 100,000 cP to about 500,000 cP.

In some embodiments, the pharmaceutical composition comprises at least three of the aforementioned characteristics. In some embodiments, the pharmaceutical composition comprises at least four of the aforementioned characteristics. In some embodiments, the pharmaceutical composition comprises at least five of the aforementioned characteristics. In some embodiments, the pharmaceutical composition comprises at least six of the aforementioned characteristics. In some embodiments, the pharmaceutical composition comprises at least seven of the aforementioned characteristics. In some embodiments, the pharmaceutical composition comprises all of the aforementioned characteristics.

In some embodiments, the otic structure degrading agent is released from the composition for a period of at least 3 days. In some embodiments, the otic structure degrading agent is essentially in the form of micronized particles. In some embodiments, the otic structure degrading agent degrades bone. In some embodiments, the otic structure degrading agent degrades a neuron. In some embodiments, the otic structure degrading agent degrades a membrane. In some embodiments, the otic structure degrading agent degrades liquor puris. In some embodiments, the otic structure degrading agent degrades endolymph or perilymph.

In some embodiments, a pharmaceutical composition or device described above provides a practical osmolarity between about 150 and 500 mOsm/L. In some embodiments, a pharmaceutical composition or device described above provides a practical osmolarity between about 200 and 400 mOsm/L. In some embodiments, a pharmaceutical composition or device described above provides a practical osmolarity between about 250 and 320 mOsm/L.

In some embodiments, the otic structure modulating agent or innate immune system modulating agent is released from the pharmaceutical composition or device described above for a period of at least 3 days. In some embodiments, the otic structure modulating agent or innate immune system modulating agent is released from the pharmaceutical composition or device described above for a period of at least 5 days. In some embodiments, the otic structure modulating agent or innate immune system modulating agent is released from the pharmaceutical composition or device described above for a period of at least 10 days. In some embodiments, the otic structure modulating agent or innate immune system modulating agent is released from the pharmaceutical composition or device described above for a period of at least 14 days. In some embodiments, the otic structure modulating agent or innate immune system modulating agent is released from the pharmaceutical composition or device described above for a period of at least one month.

In some embodiments, a pharmaceutical composition or device described above comprises an otic structure modulating agent or innate immune system modulating agent as a neutral molecule, a free acid, a free base, a salt or a prodrug. In some embodiments, a pharmaceutical composition or device described above comprises an otic structure modulating agent or innate immune system modulating agent as a neutral molecule, a free acid, a free base, a salt or a prodrug, or a combination thereof.

In some embodiments, a pharmaceutical composition or device described above comprises an otic structure modulating agent or innate immune system modulating agent as multiparticulates. In some embodiments, a pharmaceutical composition or device described above comprises an otic structure modulating agent or innate immune system modulating agent in the form of micronized particles. In some embodiments, a pharmaceutical composition or device described above comprises an otic structure modulating agent or innate immune system modulating agent as micronized powders.

In some embodiments, a pharmaceutical composition or device described above comprises about 10% of a polyoxyethylene-polyoxypropylene triblock copolymer of general formula E106 P70 E106 by weight of the composition. In some embodiments, a pharmaceutical composition or device described above comprises about 15% of a polyoxyethylene-polyoxypropylene triblock copolymer of general formula E106 P70 E106 by weight of the composition. In some embodiments, a pharmaceutical composition or device described above comprises about 20% of a polyoxyethylene-polyoxypropylene triblock copolymer of general formula E106 P70 E106 by weight of the composition. In some embodiments, a pharmaceutical composition or device described above comprises about 25% of a polyoxyethylene-polyoxypropylene triblock copolymer of general formula E106 P70 E106 by weight of the composition.

In some embodiments, a pharmaceutical composition or device described herein comprises about 1% of an otic structure modulating agent or innate immune system modulating agent, or pharmaceutically acceptable prodrug or salt thereof, by weight of the composition. In some embodiments, a pharmaceutical composition or device described above comprises about 2% of an otic structure modulating agent or innate immune system modulating agent, or pharmaceutically acceptable prodrug or salt thereof, by weight of the composition. In some embodiments, a pharmaceutical composition or device described herein comprises about 3% of an otic structure modulating agent or innate immune system modulating agent, or pharmaceutically acceptable prodrug or salt thereof, by weight of the composition. In some embodiments, a pharmaceutical composition or device described herein comprises about 4% of an otic structure modulating agent or innate immune system modulating agent, or pharmaceutically acceptable prodrug or salt thereof, by weight of the composition. In some embodiments, a pharmaceutical composition or device described above comprises about 5% of an otic structure modulating agent or innate immune system modulating agent, or pharmaceutically acceptable prodrug or salt thereof, by weight of the composition. In some embodiments, a pharmaceutical composition or device described above comprises about 10% of an otic structure modulating agent or innate immune system modulating agent, or pharmaceutically acceptable prodrug or salt thereof, by weight of the composition. In some embodiments, a pharmaceutical composition or device described above comprises about 15% of an otic structure modulating agent or innate immune system modulating agent, or pharmaceutically acceptable prodrug or salt thereof, by weight of the composition. In some embodiments, a pharmaceutical composition or device described above comprises about 20% of an otic structure modulating agent or innate immune system modulating agent, or pharmaceutically acceptable prodrug or salt thereof, by weight of the composition. In some embodiments, a pharmaceutical composition or device described above comprises about 25% of an otic structure modulating agent or innate immune system modulating agent, or pharmaceutically acceptable prodrug or salt thereof, by weight of the composition. In some embodiments, a pharmaceutical composition or device described above comprises about 30% of an otic structure modulating agent or innate immune system modulating agent, or pharmaceutically acceptable prodrug or salt thereof, by weight of the composition. In some embodiments, a pharmaceutical composition or device described above comprises about 40% of an otic structure modulating agent or innate immune system modulating agent, or pharmaceutically acceptable prodrug or salt thereof, by weight of the composition. In some embodiments, a pharmaceutical composition or device described above comprises about 50% of an otic structure modulating agent or innate immune system modulating agent, or pharmaceutically acceptable prodrug or salt thereof, by weight of the composition. In some embodiments, a pharmaceutical composition or device described above comprises about 60% of an otic structure modulating agent or innate immune system modulating agent, or pharmaceutically acceptable prodrug or salt thereof, by weight of the composition. In some embodiments, a pharmaceutical composition or device described above comprises about 70% of an otic structure modulating agent or innate immune system modulating agent, or pharmaceutically acceptable prodrug or salt thereof, by weight of the composition. In some embodiments, a pharmaceutical composition or device described above comprises about 80% of an otic structure modulating agent or innate immune system modulating agent, or pharmaceutically acceptable prodrug or salt thereof, by weight of the composition. In some embodiments, a pharmaceutical composition or device described above comprises about 90% of an otic structure modulating agent or innate immune system modulating agent, or pharmaceutically acceptable prodrug or salt thereof, by weight of the composition.

In some embodiments, a pharmaceutical composition or device described above has a pH between about 5.5 and about 8.0. In some embodiments, a pharmaceutical composition or device described above has a pH between about 6.0 and about 8.0. In some embodiments, a pharmaceutical composition or device described above has a pH between about 6.0 and about 7.6.

In some embodiments, a pharmaceutical composition or device described above contains less than 100 colony forming units (cfu) of microbiological agents per gram of composition. In some embodiments, a pharmaceutical composition or device described above contains less than 50 colony forming units (cfu) of microbiological agents per gram of composition. In some embodiments, a pharmaceutical composition or device described above contains less than 10 colony forming units (cfu) of microbiological agents per gram of composition.

In some embodiments, a pharmaceutical composition or device described above contains less than 5 endotoxin units (EU) per kg of body weight of a subject. In some embodiments, a pharmaceutical composition or device described above contains less than 4 endotoxin units (EU) per kg of body weight of a subject.

In some embodiments, a pharmaceutical composition or device described above provides a gelation temperature between about between about 19° C. to about 42° C. In some embodiments, a pharmaceutical composition or device described above provides a gelation temperature between about between about 19° C. to about 37° C. In some embodiments, a pharmaceutical composition or device described above provides a gelation temperature between about between about 19° C. to about 30° C.

In some embodiments, the pharmaceutical composition or device is an auris-acceptable thermoreversible gel. In some embodiments, the polyoxyethylene-polyoxypropylene triblock copolymer is biodegradable and/or bioeliminated (e.g., the copolymer is eliminated from the body by a biodegradation process, e.g., elimination in the urine, the feces or the like). In some embodiments, a pharmaceutical composition or device described herein further comprises a mucoadhesive. In some embodiments, a pharmaceutical composition or device described herein further comprises a penetration enhancer. In some embodiments, a pharmaceutical composition or device described herein further comprises a thickening agent. In some embodiments, a pharmaceutical composition or device described herein further comprises a dye.

In some embodiments, a pharmaceutical composition or device described herein further comprises a drug delivery device selected from a needle and syringe, a pump, a microinjection device, a wick, an in situ forming spongy material or combinations thereof.

In some embodiments, a pharmaceutical composition or device described herein is a pharmaceutical composition or device wherein the otic structure modulating agent or innate immune system modulating agent, or pharmaceutically acceptable salt thereof, has limited or no systemic release, systemic toxicity, poor PK characteristics, or combinations thereof. In some embodiments, of the pharmaceutical compositions or devices described herein, the otic structure modulating agent or innate immune system modulating agent is in the form of a neutral molecule, a free base, a free acid, a salt, a prodrug, or a combination thereof. In some embodiments, of the pharmaceutical compositions or devices described herein, the otic structure modulating agent or innate immune system modulating agent is administered in the form of a phosphate or ester prodrug. In some embodiments, pharmaceutical compositions or devices described herein comprise an otic structure modulating agent or innate immune system modulating agent, or pharmaceutically acceptable salt thereof, prodrug or combination thereof as an immediate release agent.

In some embodiments, pharmaceutical compositions or devices described herein further comprise an additional therapeutic agent. In some embodiments, the additional therapeutic agent is a an acidifying agent, an anesthetic, an analgesic, an antibiotic, antiemetic, an antifungal, an antimicrobial agent, an antipsychotic (especially those in the phenothiazine class), an antiseptic, an antiviral, an astringent, a chemotherapeutic agent, a collagen, a corticosteroid, a diuretic, a keratolytic agent, a nitric oxide synthase inhibitor, combinations thereof.

In some embodiments, pharmaceutical compositions or devices described herein are pharmaceutical compositions or devices wherein the pH of the pharmaceutical composition or device is between about 6.0 to about 7.6.

In some embodiments, of the pharmaceutical compositions or devices described herein, the ratio of a polyoxyethylene-polyoxypropylene triblock copolymer of general formula E106 P70 E106 to a thickening agent is from about 40:1 to about 5:1. In some embodiments, the thickening agent is carboxymethyl cellulose, hydroxypropyl cellulose or hydroxypropyl methylcellulose.

In some embodiments, the otic disease or condition is endolymphatic hydrops, kinetosis, labyrinthitis, mal de debarquement, Meniere's disease, Meniere's syndrome, Ramsay Hunt's syndrome (Herpes zoster infection), recurrent vestibulopathy, tinnitus, vertigo, microvascular compression syndrome, utricular dysfunction, vestibular neuronitis, benign paroxysmal positional vertigo, or combinations thereof.

Also provided herein is a method of treating an otic disease or condition comprising administering to an individual in need thereof an intratympanic composition or device comprising a therapeutically effective amount of an otic structure modulating agent, the composition or device comprising substantially low degradation products of an otic structure modulating agent, the composition or device further comprising two or more characteristics selected from:
(i) between about 0.1% to about 10% by weight of the otic structure modulating agent, or pharmaceutically acceptable prodrug or salt thereof;
(ii) between about 14% to about 21% by weight of a polyoxyethylene-polyoxypropylene triblock copolymer of general formula E106 P70 E106;
(iii) sterile water, q.s., buffered to provide a pH between about 5.5 and about 8.0;
(iv) multiparticulate otic structure modulating agent;
(v) a gelation temperature between about 19° C. to about 42° C.;
(vi) less than about 50 colony forming units (cfu) of microbiological agents per gram of composition, and
(vii) less than about 5 endotoxin units (EU) per kg of body weight of a subject.

Also provided herein is a method of treating an otic disease or condition comprising administering to an individual in need thereof an intratympanic composition or device comprising a therapeutically effective amount of an otic structure degrading agent, the composition or device comprising substantially low degradation products of an otic structure degrading agent, the composition or device further comprising two or more characteristics selected from:
(i) between about 0.1% to about 10% by weight of the otic structure degrading agent, or pharmaceutically acceptable prodrug or salt thereof;
(ii) between about 14% to about 21% by weight of a polyoxyethylene-polyoxypropylene triblock copolymer of general formula E106 P70 E106;
(iii) sterile water, q.s., buffered to provide a pH between about 5.5 and about 8.0;
(iv) multiparticulate otic structure degrading agent;
(v) a gelation temperature between about 19° C. to about 42° C.;
(vi) less than about 50 colony forming units (cfu) of microbiological agents per gram of composition, and
(vii) less than about 5 endotoxin units (EU) per kg of body weight of a subject.

Also provided herein is a method of treating an otic disease or condition comprising administering to an individual in need thereof an intratympanic composition or device comprising a therapeutically effective amount of otic structure enhancing agent, the composition or device comprising substantially low degradation products of otic structure enhancing agent, the composition or device further comprising two or more characteristics selected from:
(i) between about 0.1% to about 10% by weight of the otic structure enhancing agent, or pharmaceutically acceptable prodrug or salt thereof;
(ii) between about 14% to about 21% by weight of a polyoxyethylene-polyoxypropylene triblock copolymer of general formula E106 P70 E106;
(iii) sterile water, q.s., buffered to provide a pH between about 5.5 and about 8.0;
(iv) multiparticulate molecular component of an otic structure;
(v) a gelation temperature between about 19° C. to about 42° C.;
(vi) less than about 50 colony forming units (cfu) of microbiological agents per gram of composition, and
(vii) less than about 5 endotoxin units (EU) per kg of body weight of a subject.

Also provided herein is a method of treating an otic disease or condition comprising administering to an individual in need thereof an intratympanic composition or device comprising a therapeutically effective amount of an innate immune system modulating agent, the composition or device comprising substantially low degradation products of an innate immune system modulating agent, the composition or device further comprising two or more characteristics selected from:
(i) between about 0.1% to about 10% by weight of the innate immune system modulating agent, or pharmaceutically acceptable prodrug or salt thereof;
(ii) between about 14% to about 21% by weight of a polyoxyethylene-polyoxypropylene triblock copolymer of general formula E106 P70 E106;
(iii) sterile water, q.s., buffered to provide a pH between about 5.5 and about 8.0;
(iv) multiparticulate innate immune system modulating agent;
(v) a gelation temperature between about 19° C. to about 42° C.;
(vi) less than about 50 colony forming units (cfu) of microbiological agents per gram of composition, and
(vii) less than about 5 endotoxin units (EU) per kg of body weight of a subject.

In some embodiments of the methods described herein, the otic structure modulating agent or innate immune system modulating agent is released from the composition or devices for a period of at least 3 days. In some embodiments of the methods described herein, the otic structure modulating agent or innate immune system modulating agent is released from the composition or device for a period of at least 4 days. In some embodiments of the methods described herein, the otic structure modulating agent or innate immune system modulating agent is released from the composition or device for a period of at least 5 days. In some embodiments of the methods described herein, the otic structure modulating agent or innate immune system modulating agent is released from the composition or device for a period of at least 6 days. In some embodiments of the methods described herein, the otic structure modulating agent or innate immune system modulating agent is released from the composition or device for a period of at least 7 days. In some embodiments of the methods described herein, the otic structure modulating agent or innate immune system modulating agent is released from the composition or device for a period of at least 8 days. In some embodiments of the methods described herein, the otic structure modulating agent or innate immune system modulating agent is released from the composition or device for a period of at least 9 days. In some embodiments of the methods described herein, the otic structure modulating agent or innate immune system modulating agent is released from the composition or device for a period of at least 10 days. In some embodiments of the method described above, the otic structure modulating agent or innate immune system modulating agent is essentially in the form of micronized particles.

In some embodiments of the methods described herein, the composition is administered across the round window. In some embodiments of the methods described herein, the otic disease or condition is otitis externa, otitis media, mastoiditis, sensorineural hearing loss, ototoxicity, endolymphatic hydrops, labyrinthitis, Meniere's disease, Meniere's syndrome, microvascular compression syndrome, vestibular neuronitis, acoustic trauma, presbycusis, cholesteatoma, otosclerosis, Scheibe syndrome, Mondini-Michelle syndrome, Waardenburg's syndrome, Michel syndrome, Alexander's ear deformity, hypertelorism, Jervell-Lange Nielson syndrome, Refsum's syndrome, Usher's syndrome, or combinations thereof.

DETAILED DESCRIPTION OF THE INVENTION

Figure 1:
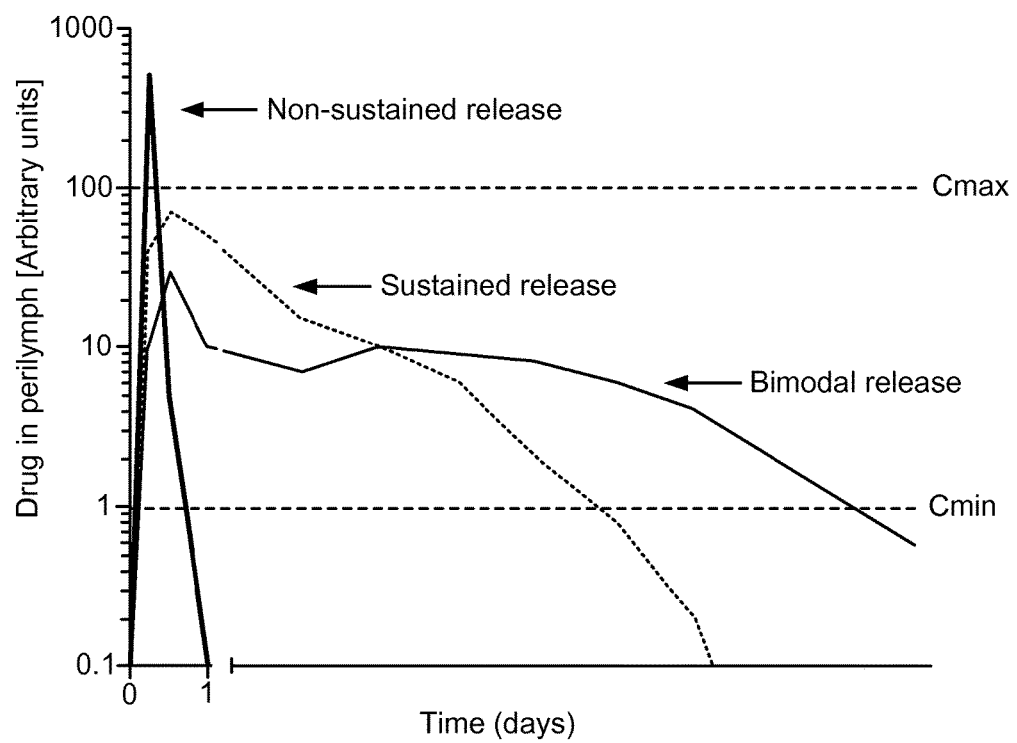
FIG. 1 illustrates a comparison of non-sustained release and sustained release compositions.
Figure 2:
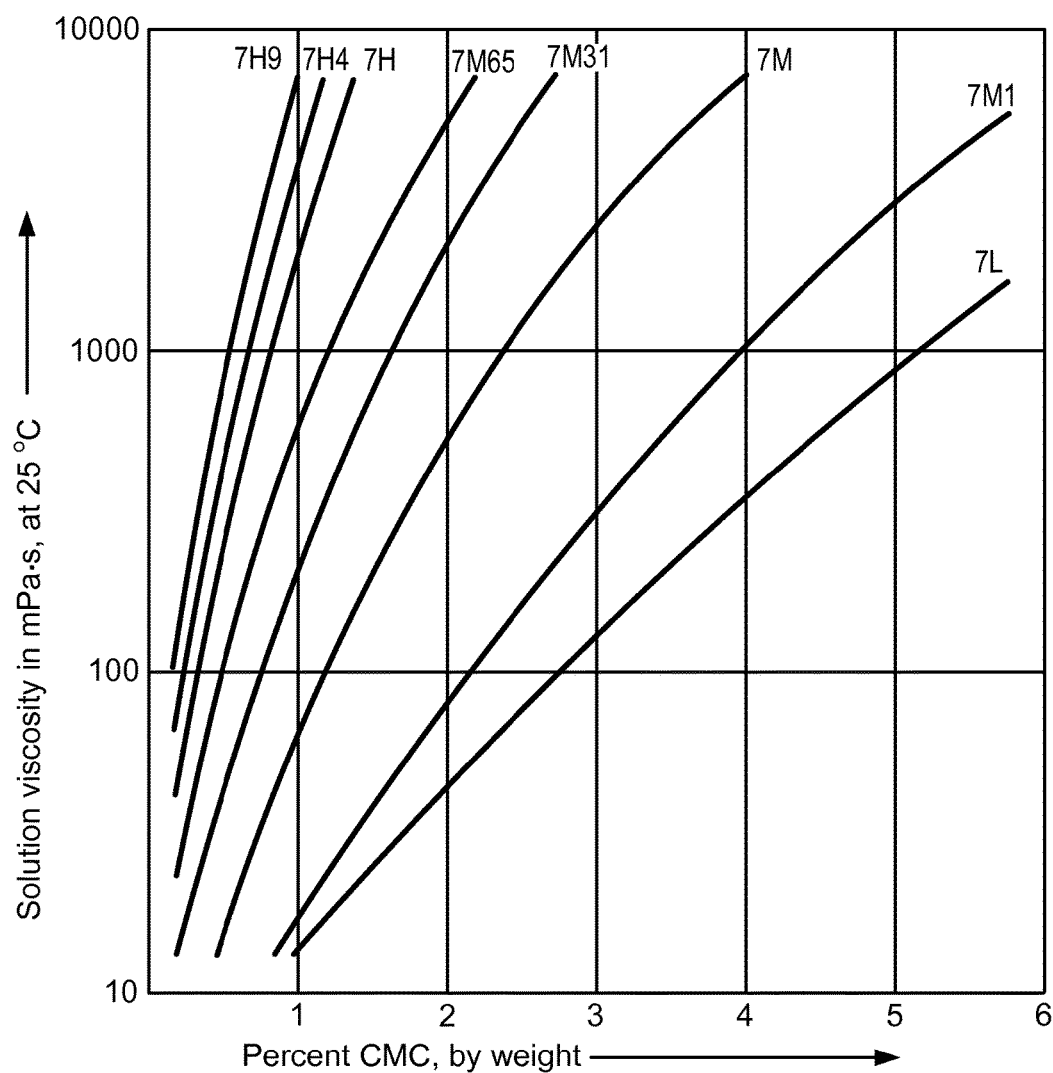
FIG. 2 illustrates the effect of concentration on the viscosity of aqueous solutions of Blanose refined CMC.
Figure 3:
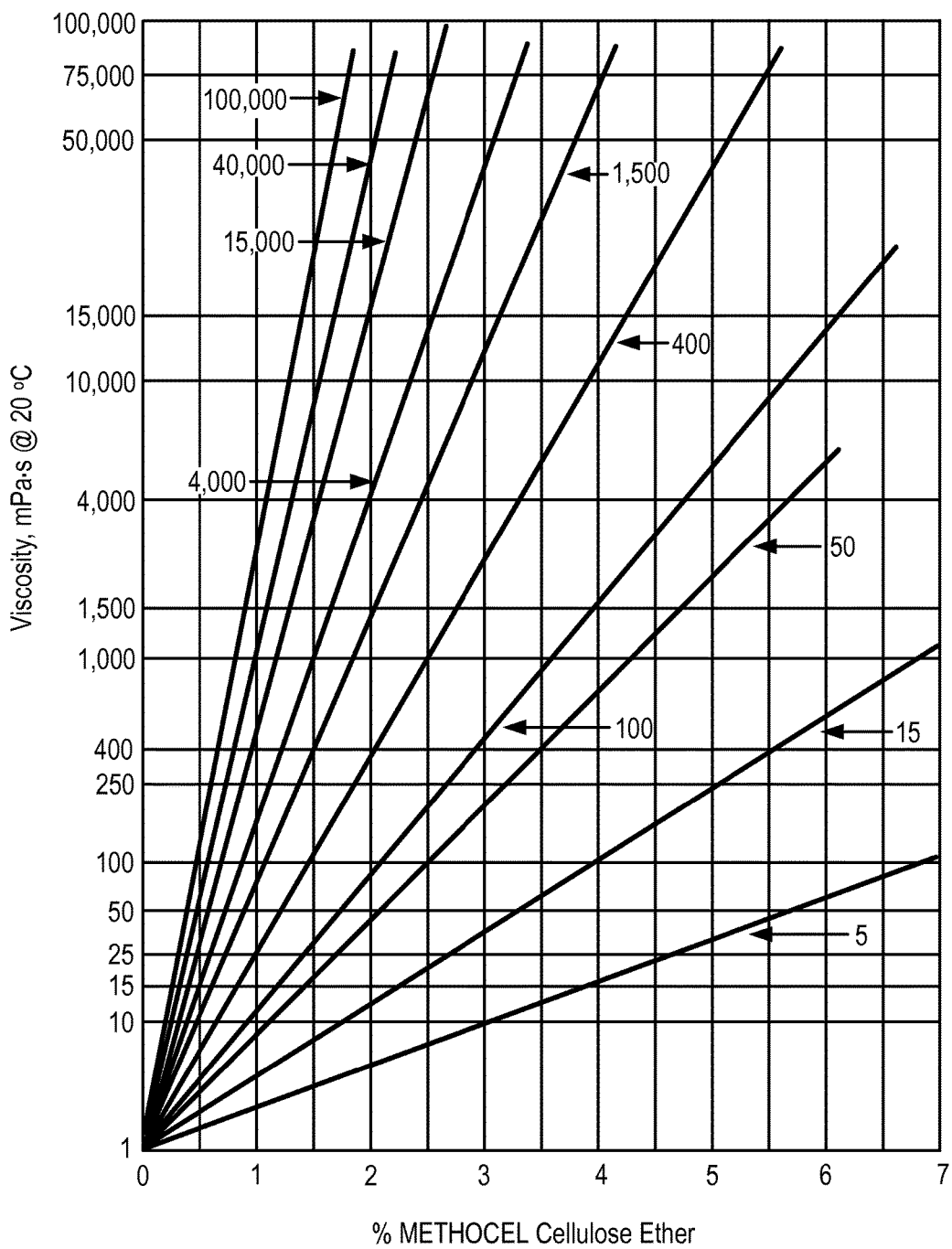
FIG. 3 illustrates the effect of concentration on the viscosity of aqueous solutions of Methocel.

Provided herein are controlled-release otic structure modulating compositions and compositions to treat (e.g., ameliorate or reduce the effects of) an otic disease, disorder, or condition characterized by an excess or deficiency in an otic structure. In some embodiments, the controlled-release otic structure modulating compositions and compositions treat (e.g., ameliorate or reduce the effects of) an otic disease, disorder, or condition characterized by an excess of otic structures. In some embodiments, the controlled-release otic structure modulating compositions and compositions treat (e.g., ameliorate or reduce the effects of) an otic disease, disorder, or condition characterized by a deficiency of otic structures. In some embodiments, the otic disease, disorder, or condition is otitis externa, otitis media, mastoiditis, sensorineural hearing loss, ototoxicity, endolymphatic hydrops, labyrinthitis, Meniere's disease, Meniere's syndrome, microvascular compression syndrome, vestibular neuronitis, acoustic trauma, presbycusis, cholesteatoma, otosclerosis, Scheibe syndrome, Mondini-Michelle syndrome, Waardenburg's syndrome, Michel syndrome, Alexander's ear deformity, hypertelorism, Jervell-Lange Nielson syndrome, Refsum's syndrome, Usher's syndrome, or combinations thereof.

Further provided herein are controlled-release complement modulating compositions and compositions to treat (e.g., ameliorate or reduce the effects of) an otic disease, disorder, or condition characterized by dysfunction of the innate immune system. In some embodiments, the controlled-release complement modulating compositions and devices treat (e.g., ameliorate or reduce the effects of) an otic disease, disorder, or condition characterized by the overactivity of the innate immune system. In some embodiments, the otic disease, disorder, or condition is otitis externa, otitis media, mastoiditis, AIED, Ramsay Hunt's, reperfusion injury, labyrinthitis ossificans or combinations thereof.

In some embodiments, the otic structure modulating agent is an otic structure degrading agent. In some embodiments, the otic structure modulating agent is otic structure enhancing agent.

In some embodiments, the innate immune system modulating agent is a complement cascade modulating agent and/or an anaphylatoxin modulator. In some embodiments, the innate immune system modulating agent is a complement cascade antagonist and/or an anaphylatoxin antagonist. In some embodiments, the innate immune system modulating agent is a complement cascade agonist and/or an anaphylatoxin agonist.

A few therapeutic products are available for the treatment of otic disorders; however, systemic routes via oral, intravenous or intramuscular routes are currently used to deliver these therapeutic agents. In some instances, systemic drug administration creates a potential inequality in drug concentration with higher circulating levels in the serum, and lower levels in the target auris media and auris interna organ structures. As a result, fairly large amounts of drug are required to overcome this inequality in order to deliver sufficient, therapeutically effective quantities to the inner ear. In addition, systemic drug administration may increase the likelihood of systemic toxicities and adverse side effects as a result of the high serum amounts required to effectuate sufficient local delivery to the target site. Systemic toxicities may also occur as a result of liver breakdown and processing of the therapeutic agents, forming toxic metabolites that effectively erase any benefit attained from the administered therapeutic.

To overcome the toxic and attendant side effects of systemic delivery, disclosed herein are methods and compositions and devices for local delivery of therapeutic agents to targeted auris structures. Access to, for example, the vestibular and cochlear apparatus will occur through the auris media including round window membrane, the oval window/stapes footplate, the annular ligament and through the otic capsule/temporal bone.

Intratympanic injection of therapeutic agents is the technique of injecting a therapeutic agent behind the tympanic membrane into the auris media and/or auris interna. This technique presents several challenges; for example, access to the round window membrane, the site of drug absorption into the auris interna, is challenging.

Further, intra-tympanic injections create several unrecognized problems not addressed by currently available treatment regimens, such as changing the osmolarity and pH of the perilymph and endolymph, and introducing pathogens and endotoxins that directly or indirectly damage inner ear structures. One of the reasons the art may not have recognized these problems is that there are no approved intratympanic compositions: the inner ear provides sui generis composition challenges. Thus, compositions developed for other parts of the body have little to no relevance for an intra-tympanic composition.

There is no guidance in the prior art regarding requirements (e.g., level of sterility, pH, osmolarity) for otic compositions that are suitable for administration to humans. There is wide anatomical disparity between the ears of animals across species. A consequence of the inter-species differences in auditory structures is that animal models of inner ear disease are often unreliable as a tool for testing therapeutics that are being developed for clinical approval.

Provided herein are otic compositions that meet stringent criteria for pH, osmolarity, ionic balance, sterility, endotoxin and/or pyrogen levels. The auris compositions described herein are compatible with the microenvironment of the inner ear (e.g., the perilymph) and are suitable for administration to humans. In some embodiments, the compositions described herein comprise dyes and aid visualization of the administered compositions obviating the need for invasive procedures (e.g., removal of perilymph) during preclinical and/or clinical development of intratympanic therapeutics.

Provided herein are controlled-release otic structure modulating compositions and compositions to locally treat targeted auris structures, thereby avoiding side effects as a result of systemic administration of the otic structure modulating compositions. The locally applied otic structure modulating compositions and devices are compatible with the targeted auris structures, and administered either directly to the desired targeted auris structure (e.g., the cochlear region, the tympanic cavity or the external ear), or administered to a structure in direct communication with areas of the auris interna (e.g., the round window membrane, the crista fenestrae cochleae or the oval window membrane). By specifically targeting an auris structure, adverse side effects as a result of systemic treatment are avoided. Moreover, clinical studies have shown the benefit of having long term exposure of drug to the perilymph of the cochlea, for example with improved clinical efficacy of sudden hearing loss when the therapeutic agent is given on multiple occasions. Thus, by providing a controlled-release otic structure modulating composition to treat otic disorders, a constant, variable and/or extended source of an otic structure modulating agent or innate immune system modulating agent is provided to the subject suffering from an otic disorder, reducing or eliminating uncertainty in treatment. Accordingly, one embodiment disclosed herein is to provide a composition that enables an otic structure modulating agent or innate immune system modulating agent to be released in therapeutically effective doses either at variable or constant rates such as to ensure a continuous release of an otic structure modulating agent or innate immune system modulating agent. In some embodiments, an otic structure modulating agent or innate immune system modulating agent disclosed herein is administered as an immediate release composition. In other embodiments, an otic structure modulating agent or innate immune system modulating agent is administered as a sustained release composition, released either continuously, variably or in a pulsatile manner, or variants thereof. In still other embodiments, an otic structure modulating agent or innate immune system modulating agent composition is administered as both an immediate release and sustained release composition, released either continuously, variably or in a pulsatile manner, or variants thereof. The release is optionally dependent on environmental or physiological conditions, for example, the external ionic environment (see, e.g. Oros® release system, Johnson & Johnson).

In addition, localized treatment of the targeted auris structure also affords the use of previously undesired therapeutic agents, including agents with poor pK profiles, poor uptake, low systemic release and/or toxicity issues. Because of the localized targeting of the otic structure modulating compositions and devices, as well as the biological blood barrier present in the auris interna, the risk of adverse effects will be reduced as a result of treatment with previously characterized toxic or ineffective otic structure modulating agent or innate immune system modulating agents. Accordingly, also contemplated within the scope of the embodiments herein is the use of an otic structure modulating agent or innate immune system modulating agents in the treatment of disorders that have been previously rejected by practitioners because of adverse effects or ineffectiveness of the otic structure modulating agent or innate immune system modulating agent.

Also included within the embodiments disclosed herein is the use of additional auris-compatible agents in combination with the otic structure modulating compositions and devices disclosed herein. When used, such agents assist in the treatment of hearing or equilibrium loss or dysfunction as a result of otitis externa, otitis media, mastoiditis, sensorineural hearing loss, ototoxicity, endolymphatic hydrops, labyrinthitis, Meniere's disease, Meniere's syndrome, microvascular compression syndrome, vestibular neuronitis, acoustic trauma, presbycusis, cholesteatoma, otosclerosis, Scheibe syndrome, Mondini-Michelle syndrome, Waardenburg's syndrome, Michel syndrome, Alexander's ear deformity, hypertelorism, Jervell-Lange Nielson syndrome, Refsum's syndrome, Usher's syndrome, or combinations thereof. Accordingly, additional agents that ameliorate or reduce the effects of otitis externa, otitis media, mastoiditis, sensorineural hearing loss, ototoxicity, endolymphatic hydrops, labyrinthitis, Meniere's disease, Meniere's syndrome, microvascular compression syndrome, vestibular neuronitis, acoustic trauma, presbycusis, cholesteatoma, otosclerosis, Scheibe syndrome, Mondini-Michelle syndrome, Waardenburg's syndrome, Michel syndrome, Alexander's ear deformity, hypertelorism, Jervell-Lange Nielson syndrome, Refsum's syndrome, Usher's syndrome, otitis externa, otitis media, mastoiditis, AIED, Ramsay Hunt's, reperfusion injury, labyrinthitis ossificans, or combinations thereof are also contemplated to be used in combination with an otic structure modulating agent or innate immune system modulating agent. In some embodiments, the additional agent is an acidifying agent, an anesthetic, an analgesic, an antibiotic, antiemetic, an antifungal, an anti-microbial agent, an antipsychotic (especially those in the phenothiazine class), an antiseptic, an antiviral, an astringent, a chemotherapeutic agent, a collagen, a corticosteroid, a diuretic, a keratolytic agent, a nitric oxide synthase inhibitor, or combinations thereof.

In some embodiments, an auris-acceptable controlled-release otic structure modulating composition described herein is administered to the target ear region and an oral dose of an otic structure modulating agent or innate immune system modulating agent is additionally administered. In some embodiments, an oral dose of an otic structure modulating agent or innate immune system modulating agent is administered before administration of the auris-acceptable controlled-release otic structure modulating composition, and then the oral dose is tapered off over the period of time that the controlled-release otic structure modulating composition is provided. Alternatively, an oral dose of an otic structure modulating agent or innate immune system modulating agent is administered during administration of the controlled-release otic structure modulating composition, and then the oral dose is tapered off over the period of time that the controlled-release otic structure modulating composition is provided. Alternatively, an oral dose of an otic structure modulating agent or innate immune system modulating agent is administered after administration of the controlled-release otic structure modulating composition, and then the oral dose is tapered off over the period of time that the controlled-release otic structure modulating composition is provided.

In addition, the otic structure modulating agent or innate immune system modulating agent pharmaceutical compositions or compositions or devices included herein also include carriers, adjuvants (e.g., preserving, stabilizing, wetting or emulsifying agents), solution promoters, salts for regulating the osmotic pressure, and/or buffers. Such carriers, adjuvants, and other excipients will be compatible with the environment in the targeted auris structure(s). Specifically contemplated are carriers, adjuvants and excipients that lack ototoxicity or are minimally ototoxic in order to allow effective treatment of the otic disorders contemplated herein with minimal side effects in the targeted regions or areas.

Intratympanic injection of delivery devices creates several additional problems that must also be addressed before the composition or device can be administered. For example, there are many excipients that are ototoxic. While these excipients can be used when formulating an active agent for delivery by another method (e.g., topical), their use should be limited, reduced or eliminated when formulating a composition or device to be administered to the ear due to their ototoxic effects.

By way of non-limiting example, the use of the following commonly used solvents should be limited, reduced or eliminated when formulating agents for administration to the ear: alcohols, propylene glycol, and cyclohexane. Thus, in some embodiments, a device disclosed herein is free or substantially free of alcohols, propylene glycol, and cyclohexane. In some embodiments, a device disclosed herein comprises less than about 50 ppm of each of alcohols, propylene glycol, and cyclohexane. In some embodiments, a device disclosed herein comprises less than about 25 ppm of each of alcohols, propylene glycol, and cyclohexane. In some embodiments, a device disclosed herein comprises less than about 20 ppm of each of alcohols, propylene glycol, and cyclohexane. In some embodiments, a device disclosed herein comprises less than about 10 ppm of each of alcohols, propylene glycol, and cyclohexane. In some embodiments, a device disclosed herein comprises less than about 5 ppm of each of alcohols, propylene glycol, and cyclohexane. In some embodiments, a device disclosed herein comprises less than about 1 ppm of each of alcohols, propylene glycol, and cyclohexane.

Further, by way of non-limiting example, the use of the following commonly utilized preservatives should be limited, reduced or eliminated when formulating agents for administration to the ear: Benzethonium chloride, Benzalkonium chloride, and Thiomersal. Thus, in some embodiments, a device disclosed herein is free or substantially free of benzethonium chloride, benzalkonium chloride, and thiomersal. In some embodiments, a device disclosed herein comprises less than about 50 ppm of each of benzethonium chloride, benzalkonium chloride, and thiomersal. In some embodiments, a device disclosed herein comprises less than about 25 ppm of each of benzethonium chloride, benzalkonium chloride, and thiomersal. In some embodiments, a device disclosed herein comprises less than about 20 ppm of each of benzethonium chloride, benzalkonium chloride, and thiomersal. In some embodiments, a device disclosed herein comprises less than about 10 ppm of each of benzethonium chloride, benzalkonium chloride, and thiomersal. In some embodiments, a device disclosed herein comprises less than about 5 ppm of each of benzethonium chloride, benzalkonium chloride, and thiomersal. In some embodiments, a device disclosed herein comprises less than about 1 ppm of each of benzethonium chloride, benzalkonium chloride, and thiomersal.

Certain antiseptics used to disinfect components of therapeutic preparations (or the devices utilized to administer the preparations) should be limited, reduced, or eliminated in otic preparations. For example, acetic acid, iodine, and merbromin are all known to be ototoxic. Additionally, chlorhexidene, a commonly used antiseptic, should be limited, reduced or eliminated to disinfect any component of an otic preparation (including devices used to administer the preparation) as it is highly ototoxic in minute concentrations (e.g., 0.05%). Thus, in some embodiments, a device disclosed herein is free or substantially free of acetic acid, iodine, merbromin, and chlorhexidene. In some embodiments, a device disclosed herein comprises less than about 50 ppm of each of acetic acid, iodine, merbromin, and chlorhexidene. In some embodiments, a device disclosed herein comprises less than about 25 ppm of each of acetic acid, iodine, merbromin, and chlorhexidene. In some embodiments, a device disclosed herein comprises less than about 20 ppm of each of acetic acid, iodine, merbromin, and chlorhexidene. In some embodiments, a device disclosed herein comprises less than about 10 ppm of each of acetic acid, iodine, merbromin, and chlorhexidene. In some embodiments, a device disclosed herein comprises less than about 5 ppm of each of acetic acid, iodine, merbromin, and chlorhexidene. In some embodiments, a device disclosed herein comprises less than about 1 ppm of each of acetic acid, iodine, merbromin, and chlorhexidene.

Further, otic preparations require particularly low concentrations of several potentially-common contaminants that are known to be ototoxic. Other dosage forms, while seeking to limit the contamination attributable to these compounds, do not require the stringent precautions that otic preparations require. For example, the following contaminants should be absent or nearly absent from otic preparations: arsenic, lead, mercury, and tin. Thus, in some embodiments, a device disclosed herein is free or substantially free of arsenic, lead, mercury, and tin. In some embodiments, a device disclosed herein comprises less than about 50 ppm of each of arsenic, lead, mercury, and tin. In some embodiments, a device disclosed herein comprises less than about 25 ppm of each of arsenic, lead, mercury, and tin. In some embodiments, a device disclosed herein comprises less than about 20 ppm of each of arsenic, lead, mercury, and tin. In some embodiments, a device disclosed herein comprises less than about 10 ppm of each of arsenic, lead, mercury, and tin. In some embodiments, a device disclosed herein comprises less than about 5 ppm of each of arsenic, lead, mercury, and tin. In some embodiments, a device disclosed herein comprises less than about 1 ppm of each of arsenic, lead, mercury, and tin.

To prevent ototoxicity, otic structure modulating agent or innate immune system modulating agent pharmaceutical compositions or compositions or devices disclosed herein are optionally targeted to distinct regions of the targeted auris structures, including but not limited to the tympanic cavity, vestibular bony and membranous labyrinths, cochlear bony and membranous labyrinths and other anatomical or physiological structures located within the auris interna.

Certain Definitions

The term "auris-acceptable" with respect to a composition, composition or ingredient, as used herein, includes having no persistent detrimental effect on the auris media (or middle ear) and the auris interna (or inner ear) of the subject being treated. By "auris-pharmaceutically acceptable," as used herein, refers to a material, such as a carrier or diluent, which does not abrogate the biological activity or properties of the compound in reference to the auris media (or middle ear) and the auris interna (or inner ear), and is relatively or is reduced in toxicity to the auris media (or middle ear) and the auris interna (or inner ear), i.e., the material is administered to an individual without causing undesirable biological effects or interacting in a deleterious manner with any of the components of the composition in that it is contained.

As used herein, amelioration or lessening of the symptoms of a particular otic disease, disorder or condition by administration of a particular compound or pharmaceutical composition refers to any decrease of severity, delay in onset, slowing of progression, or shortening of duration, whether permanent or temporary, lasting or transient that is attributed to or associated with administration of the compound or composition.

"Antioxidants" are auris-pharmaceutically acceptable antioxidants, and include, for example, butylated hydroxytoluene (BHT), sodium ascorbate, ascorbic acid, sodium metabisulfite and tocopherol. In certain embodiments, antioxidants enhance chemical stability where required. Antioxidants are also used to counteract the ototoxic effects of certain therapeutic agents, including agents that are used in combination with the otic structure modulating agent or innate immune system modulating agents disclosed herein.

"Auris interna" refers to the inner ear, including the cochlea and the vestibular labyrinth, and the round window that connects the cochlea with the middle ear.

"Auris-bioavailability" or "Auris-interna bioavailability" or "Auris-media bioavailability" or "Auris-externa bioavailability" refers to the percentage of the administered dose of compounds disclosed herein that becomes available in the targeted auris structure of the animal or human being studied.

"Auris media" refers to the middle ear, including the tympanic cavity, auditory ossicles and oval window, which connects the middle ear with the inner ear.

"Auris externa" refers to the outer ear, including the pinna, the auditory canal, and the tympanic membrane, which connects the outer ear with the middle ear.

"Blood plasma concentration" refers to the concentration of compounds provided herein in the plasma component of blood of a subject.

"Carrier materials" are excipients that are compatible with otic structure modulating agent or innate immune system modulating agent(s), the targeted auris structure(s) and the release profile properties of the auris-acceptable pharmaceutical compositions. Such carrier materials include, e.g., binders, suspending agents, disintegration agents, filling agents, surfactants, solubilizers, stabilizers, lubricants, wetting agents, diluents, and the like. "Auris-pharmaceutically compatible carrier materials" include, but are not limited to, acacia, gelatin, colloidal silicon dioxide, calcium glycerophosphate, calcium lactate, maltodextrin, glycerine, magnesium silicate, polyvinylpyrrolidone (PVP), cholesterol, cholesterol esters, sodium caseinate, soy lecithin, taurocholic acid, phosphatidylcholine, sodium chloride, tricalcium phosphate, dipotassium phosphate, cellulose and cellulose conjugates, sugars sodium stearoyl lactylate, carrageenan, monoglyceride, diglyceride, pregelatinized starch, and the like.

The term "complement modulating agent", as used herein, means an agent that increases or inhibits the activity of a component of the complement system. In some embodiments, the complement modulating agent increases the activity of a component of the complement system. In some embodiments, the complement modulating agent inhibits (partially or fully) the activity of a component of the complement system.

The term "diluent" refers to chemical compounds that are used to dilute the otic structure modulating agent or innate immune system modulating agent prior to delivery and that are compatible with the targeted auris structure(s).

"Dispersing agents," and/or "viscosity modulating agents" are materials that control the diffusion and homogeneity of the otic structure modulating agent or innate immune system modulating agent through liquid media. Examples of diffusion facilitators/dispersing agents include but are not limited to hydrophilic polymers, electrolytes, Tween® 60 or 80, PEG, polyvinylpyrrolidone (PVP; commercially known as Plasdone®, and the carbohydrate-based dispersing agents such as, for example, hydroxypropyl celluloses (e.g., HPC, HPC-SL, and HPC-L), hydroxypropyl methylcelluloses (e.g., HPMC K100, HPMC K4M, HPMC K15M, and HPMC K100M), carboxymethylcellulose sodium, methylcellulose, hydroxyethylcellulose, hydroxypropylcellulose, hydroxypropylmethylcellulose phthalate, hydroxypropylmethylcellulose acetate stearate (HPMCAS), noncrystalline cellulose, magnesium aluminum silicate, triethanolamine, polyvinyl alcohol (PVA), vinyl pyrrolidone/vinyl acetate copolymer (S630), 4-(1,1,3,3-tetramethylbutyl)-phenol polymer with ethylene oxide and formaldehyde (also known as tyloxapol), poloxamers (e.g., Pluronic F127, Pluronics F68®, F88®, and F108®, which are block copolymers of ethylene oxide and propylene oxide); and poloxamines (e.g., Tetronic 908®, also known as Poloxamine 908®, which is a tetrafunctional block copolymer derived from sequential addition of propylene oxide and ethylene oxide to ethylenediamine (BASF Corporation, Parsippany, N.J.)), polyvinylpyrrolidone K12, polyvinylpyrrolidone K17, polyvinylpyrrolidone K25, or polyvinylpyrrolidone K30, polyvinylpyrrolidone/vinyl acetate copolymer (S-630), polyethylene glycol, e.g., the polyethylene glycol has a molecular weight of about 300 to about 6000, or about 3350 to about 4000, or about 7000 to about 5400, sodium carboxymethylcellulose, methylcellulose, polysorbate-80, sodium alginate, gums, such as, e.g., gum tragacanth and gum acacia, guar gum, xanthans, including xanthan gum, sugars, cellulosics, such as, e.g., sodium carboxymethylcellulose, methylcellulose, sodium carboxymethylcellulose, polysorbate-80, sodium alginate, polyethoxylated sorbitan monolaurate, polyethoxylated sorbitan monolaurate, povidone, carbomers, polyvinyl alcohol (PVA), alginates, chitosans and combinations thereof. Plasticizers such as cellulose or triethyl cellulose are also be used as dispersing agents. Optional dispersing agents useful in liposomal dispersions and self-emulsifying dispersions of the otic structure modulating agent or innate immune system modulating agents disclosed herein are dimyristoyl phosphatidyl choline, phosphatidyl cholines (c8-c18), phosphatidylethanolamines (c8-c18), phosphatidyl glycerols (c8-c18), natural phosphatidyl choline from eggs or soy, natural phosphatidyl glycerol from eggs or soy, cholesterol and isopropyl myristate.

"Drug absorption" or "absorption" refers to the process of movement of the otic structure modulating agent or innate immune system modulating agent(s) from the localized site of administration, by way of example only, the round window membrane of the inner ear, and across a barrier (the round window membranes, as described below) into the auris interna or inner ear structures. The terms "co-administration" or the like, as used herein, are meant to encompass administration of the otic structure modulating agent or innate immune system modulating agents to a single patient, and are intended to include treatment regimens in that the otic structure modulating agent or innate immune system modulating agents are administered by the same or different route of administration or at the same or different time.

The terms "effective amount" or "therapeutically effective amount," as used herein, refer to a sufficient amount of the otic structure modulating agent or innate immune system modulating agents being administered that would be expected to relieve to some extent one or more of the symptoms of the disease or condition being treated. For example, the result of administration of the otic structure modulating agent or innate immune system modulating agents disclosed herein is reduction and/or alleviation of the signs, symptoms, or causes of Meniere's disease. For example, an "effective amount" for therapeutic uses is the amount of the otic structure modulating agent or innate immune system modulating agent, including a composition as disclosed herein required to provide a decrease or amelioration in disease symptoms without undue adverse side effects. The term "therapeutically effective amount" includes, for example, a prophylactically effective amount. An "effective amount" of an otic structure modulating agent or innate immune system modulating agent composition disclosed herein is an amount effective to achieve a desired pharmacologic effect or therapeutic improvement without undue adverse side effects. It is understood that "an effective amount" or "a therapeutically effective amount" varies, in some embodiments, from subject to subject, due to variation in metabolism of the compound administered, age, weight, general condition of the subject, the condition being treated, the severity of the condition being treated, and the judgment of the prescribing physician. It is also understood that "an effective amount" in an extended-release dosing format may differ from "an effective amount" in an immediate-release dosing format based upon pharmacokinetic and pharmacodynamic considerations.

The terms "enhance" or "enhancing" refers to an increase or prolongation of either the potency or duration of a desired effect of the otic structure modulating agent or innate immune system modulating agent, or a diminution of any adverse symptoms such as localized pain that is consequent upon administration of the therapeutic agent. Thus, in regard to enhancing the effect of the otic structure modulating agent or innate immune system modulating agents disclosed herein, the term "enhancing" refers to the ability to increase or prolong, either in potency or duration, the effect of other therapeutic agents that are used in combination with the otic structure modulating agent or innate immune system modulating agents disclosed herein. An "enhancing-effective amount," as used herein, refers to an amount of an otic structure modulating agent or innate immune system modulating agents, or other therapeutic agent, which is adequate to enhance the effect of another therapeutic agent or otic structure modulating agent or innate immune system modulating agents in a desired system. When used in a patient, amounts effective for this use will depend on the severity and course of the disease, disorder or condition, previous therapy, the patient's health status and response to the drugs, and the judgment of the treating physician.

The term "inhibiting" includes preventing, slowing, or reversing the development of a condition, for example, otitis externa, or advancement of a condition in a patient necessitating treatment.

The term "innate immune system modulating agent", as used herein, means an agent that increases or inhibits the activity of a component of the innate immune system. In some embodiments, the innate immune system modulating agent increases the activity of a component of the innate immune system. In some embodiments, the innate immune system modulating agent inhibits (partially or fully) the activity of a component of the innate immune system.

"Balance disorder" refers to a disorder, illness, or condition which causes a subject to feel unsteady, or to have a sensation of movement. Included in this definition are dizziness, vertigo, disequilibrium, and pre-syncope. Diseases which are classified as balance disorders include, but are not limited to, mal de debarquement, benign paroxysmal positional vertigo, and labyrinthitis.

The terms "kit" and "article of manufacture" are used as synonyms.

As used herein, the term "otic intervention" means an external insult or trauma to one or more auris structures and includes implants, otic surgery, injections, cannulations, or the like. Implants include auris-interna or auris-media medical devices, examples of which include cochlear implants, hearing sparing devices, hearing-improvement devices, short electrodes, micro-prostheses or piston-like prostheses; needles; stem cell transplants; drug delivery devices; any cell-based therapeutic; or the like. Otic surgery includes middle ear surgery, inner ear surgery, typanostomy, cochleostomy, labyrinthotomy, mastoidectomy, stapedectomy, stapedotomy, tympanostomy, endolymphatic sacculotomy or the like. Injections include intratympanic injections, intracochlear injections, injections across the round window membrane or the like. Cannulations include intratympanic, intracochlear, endolymphatic, perilymphatic or vestibular cannulations or the like.

"Otic structure modulating agent", as used herein, means otic structure enhancing agent, or an agent that degrades the molecular components of an otic structure.

"Pharmacokinetics" refers to the factors that determine the attainment and maintenance of the appropriate concentration of drug at the desired site within the targeted auris structure.

In prophylactic applications, compositions containing the agents described herein are administered to a patient susceptible to or otherwise at risk of a particular disease, disorder or condition, for otitis externa, otitis media, mastoiditis, sensorineural hearing loss, ototoxicity, endolymphatic hydrops, labyrinthitis, Meniere's disease, Meniere's syndrome, microvascular compression syndrome, vestibular neuronitis, acoustic trauma, presbycusis, cholesteatoma, otosclerosis, Scheibe syndrome, Mondini-Michelle syndrome, Waardenburg's syndrome, Michel syndrome, Alexander's ear deformity, hypertelorism, Jervell-Lange Nielson syndrome, Refsum's syndrome, and Usher's syndrome. Such an amount is defined to be a "prophylactically effective amount or dose." In this use, the precise amounts also depend on the patient's state of health, weight, and the like. As used herein, a "pharmaceutical device" includes any composition described herein that, upon administration to an ear, provides a reservoir for extended release of an active agent described herein.

The mean residence time (MRT) is the average time that molecules of an active agent reside in an otic structure after a dose.

A "prodrug" refers to the otic structure modulating agent or innate immune system modulating agent that is converted into the parent drug in vivo. In certain embodiments, a prodrug is enzymatically metabolized by one or more steps or processes to the biologically, pharmaceutically or therapeutically active form of the compound. To produce a prodrug, a pharmaceutically active compound is modified such that the active compound will be regenerated upon in vivo administration. In one embodiment, the prodrug is designed to alter the metabolic stability or the transport characteristics of a drug, to mask side effects or toxicity, or to alter other characteristics or properties of a drug. Compounds provided herein, in some embodiments, are derivatized into suitable prodrugs.

"Round window membrane" is the membrane in humans that covers the fenestrae cochlea (also known as the circular window, fenestrae rotunda, or round window). In humans, the thickness of round window membrane is about 70 micron.

"Solubilizers" refers to auris-acceptable compounds such as triacetin, triethylcitrate, ethyl oleate, ethyl caprylate, sodium lauryl sulfate, sodium caprate, sucrose esters, alkylglucosides, sodium doccusate, vitamin E TPGS, dimethylacetamide, N-methylpyrrolidone, N-hydroxyethylpyrrolidone, polyvinylpyrrolidone, hydroxypropylmethyl cellulose, hydroxypropyl cyclodextrins, ethanol, n-butanol, isopropyl alcohol, cholesterol, bile salts, polyethylene glycol 200-600, glycofurol, transcutol, propylene glycol, and dimethyl isosorbide and the like.

"Stabilizers" refers to compounds such as any antioxidation agents, buffers, acids, preservatives and the like that are compatible with the environment of the targeted auris structure. Stabilizers include but are not limited to agents that will do any of (1) improve the compatibility of excipients with a container, or a delivery system, including a syringe or a glass bottle, (2) improve the stability of a component of the composition, or (3) improve composition stability.

As used herein, the term "substantially low degradation products" means less than 5% by weight of the active agent are degradation products of the active agent. In further embodiments, the term means less than 3% by weight of the active agent are degradation products of the active agent. In yet further embodiments, the term means less than 2% by weight of the active agent are degradation products of the active agent. In further embodiments, the term means less than 1% by weight of the active agent are degradation products of the active agent.

As used herein, "excess otic structures" include, by way of example, excess bone growth (e.g. in the stapes), blockage of otic structures (e.g., due to excessive secretion of mucous, pus or effusion), excess effusion in the inner ear (e.g., due to inflammation) or any other abnormality in any otic structure that can cause an otic disease or condition described herein.

As used herein "essentially in the form of micronized powder" includes, by way of example only, greater than 70% by weight of the active agent is in the form of micronized particles of the active agent. In further embodiments, the term means greater than 80% by weight of the active agent is in the form of micronized particles of the active agent. In yet further embodiments, the term means greater than 90% by weight of the active agent is in the form of micronized particles of the active agent.

"Steady state," as used herein, is when the amount of drug administered to the targeted auris structure is equal to the amount of drug eliminated within one dosing interval resulting in a plateau or constant levels of drug exposure within the targeted structure.

As used herein, the term "subject" is used to mean any animal, preferably a mammal, including a human or non-human. The terms patient and subject may be used interchangeably. Neither term is to be interpreted as requiring the supervision of a medical professional (e.g., a doctor, nurse, physician's assistant, orderly, hospice worker).

"Surfactants" refers to compounds that are auris-acceptable, such as sodium lauryl sulfate, sodium docusate, Tween® 60 or 80, triacetin, vitamin E TPGS, sorbitan monooleate, polyoxyethylene sorbitan monooleate, polysorbates, polaxomers, bile salts, glyceryl monostearate, copolymers of ethylene oxide and propylene oxide, e.g., Pluronic® (BASF), and the like. Some other surfactants include polyoxyethylene fatty acid glycerides and vegetable oils, e.g., polyoxyethylene (60) hydrogenated castor oil; and polyoxyethylene alkylethers and alkylphenyl ethers, e.g., octoxynol 10, octoxynol 40. In some embodiments, surfactants are included to enhance physical stability or for other purposes.

The terms "treat," "treating" or "treatment," as used herein, include alleviating, abating or ameliorating a disease or condition symptoms, preventing additional symptoms, ameliorating or preventing the underlying metabolic causes of symptoms, inhibiting the disease or condition, e.g., arresting the development of the disease or condition, relieving the disease or condition, causing regression of the disease or condition, relieving a condition caused by the disease or condition, or stopping the symptoms of the disease or condition either prophylactically and/or therapeutically.

Other objects, features, and advantages of the methods and compositions described herein will become apparent from the following detailed description. It should be understood, however, which the detailed description and the specific examples, while indicating specific embodiments, are given by way of illustration only.

Anatomy of the Ear

Figure 4:
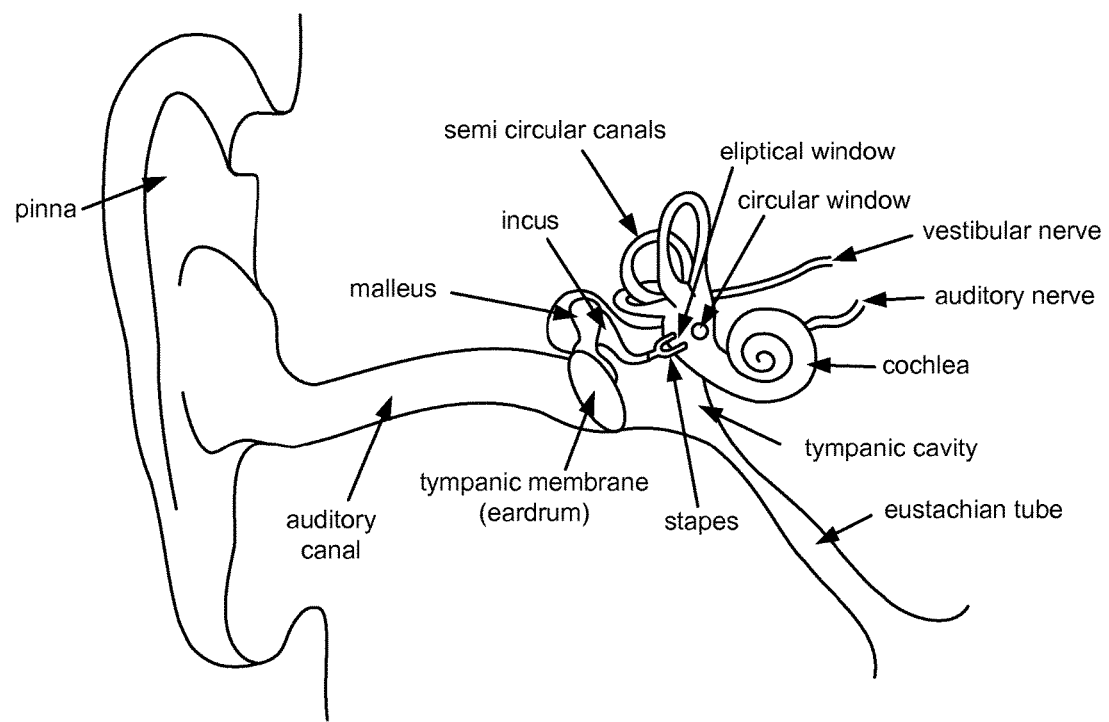
FIG. 4 provides an illustrative representation of the anatomy of the ear.
Figure 5:
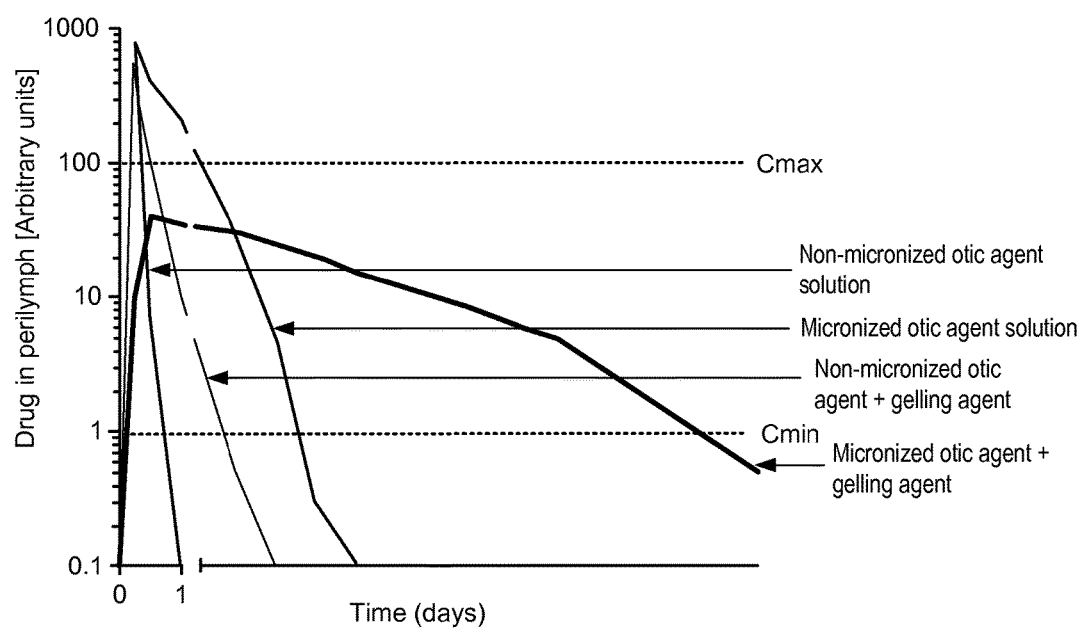
FIG. 5 illustrates tunable release of an active agent from four compositions.

As shown in FIG. 4, the outer ear is the external portion of the organ and is composed of the pinna (auricle), the auditory canal (external auditory meatus) and the outward facing portion of the tympanic membrane, also known as the ear drum. The pinna, which is the fleshy part of the external ear that is visible on the side of the head, collects sound waves and directs them toward the auditory canal. Thus, the function of the outer ear, in part, is to collect and direct sound waves towards the tympanic membrane and the middle ear.

The middle ear is an air-filled cavity, called the tympanic cavity, behind the tympanic membrane. The tympanic membrane, also known as the ear drum, is a thin membrane that separates the external ear from the middle ear. The middle ear lies within the temporal bone, and includes within this space the three ear bones (auditory ossicles): the malleus, the incus and the stapes. The auditory ossicles are linked together via tiny ligaments, which form a bridge across the space of the tympanic cavity. The malleus, which is attached to the tympanic membrane at one end, is linked to the incus at its anterior end, which in turn is linked to the stapes. The stapes is attached to the oval window, one of two windows located within the tympanic cavity. A fibrous tissue layer, known as the annular ligament connects the stapes to the oval window. Sound waves from the outer ear first cause the tympanic membrane to vibrate. The vibration is transmitted across to the cochlea through the auditory ossicles and oval window, which transfers the motion to the fluids in the auris interna. Thus, the auditory ossicles are arranged to provide a mechanical linkage between the tympanic membrane and the oval window of the fluid-filled auris interna, where sound is transformed and transduced to the auris interna for further processing. Stiffness, rigidity or loss of movement of the auditory ossicles, tympanic membrane or oval window leads to hearing loss, e.g. otosclerosis, or rigidity of the stapes bone.

The tympanic cavity also connects to the throat via the eustachian tube. The eustachian tube provides the ability to equalize the pressure between the outside air and the middle ear cavity. The round window, a component of the auris interna but that is also accessible within the tympanic cavity, opens into the cochlea of the auris interna. The round window is covered by round window membrane, which consists of three layers: an external or mucous layer, an intermediate or fibrous layer, and an internal membrane, which communicates directly with the cochlear fluid. The round window, therefore, has direct communication with the auris interna via the internal membrane.

Movements in the oval and round window are interconnected, i.e. as the stapes bone transmits movement from the tympanic membrane to the oval window to move inward against the auris interna fluid, the round window (round window membrane) is correspondingly pushed out and away from the cochlear fluid. This movement of the round window allows movement of fluid within the cochlea, which leads in turn to movement of the cochlear inner hair cells, allowing hearing signals to be transduced. Stiffness and rigidity in round window membrane leads to hearing loss because of the lack of ability of movement in the cochlear fluid. Recent studies have focused on implanting mechanical transducers onto the round window, which bypasses the normal conductive pathway through the oval window and provides amplified input into the cochlear chamber.

Auditory signal transduction takes place in the auris interna. The fluid-filled auris interna, or inner ear, consists of two major components: the cochlear and the vestibular apparatus. The auris interna is located in part within the osseous or bony labyrinth, an intricate series of passages in the temporal bone of the skull. The vestibular apparatus is the organ of balance and consists of the three semi-circular canals and the vestibule. The three semi-circular canals are arranged relative to each other such that movement of the head along the three orthogonal planes in space can be detected by the movement of the fluid and subsequent signal processing by the sensory organs of the semi-circular canals, called the crista ampullaris. The crista ampullaris contains hair cells and supporting cells, and is covered by a dome-shaped gelatinous mass called the cupula. The hairs of the hair cells are embedded in the cupula. The semi-circular canals detect dynamic equilibrium, the equilibrium of rotational or angular movements.

When the head turns rapidly, the semicircular canals move with the head, but endolymph fluid located in the membranous semi-circular canals tends to remain stationary. The endolymph fluid pushes against the cupula, which tilts to one side. As the cupula tilts, it bends some of the hairs on the hair cells of the crista ampullaris, which triggers a sensory impulse. Because each semicircular canal is located in a different plane, the corresponding crista ampullaris of each semi-circular canal responds differently to the same movement of the head. This creates a mosaic of impulses that are transmitted to the central nervous system on the vestibular branch of the vestibulocochlear nerve. The central nervous system interprets this information and initiates the appropriate responses to maintain balance. Of importance in the central nervous system is the cerebellum, which mediates the sense of balance and equilibrium.

The vestibule is the central portion of the auris interna and contains mechanoreceptors bearing hair cells that ascertain static equilibrium, or the position of the head relative to gravity. Static equilibrium plays a role when the head is motionless or moving in a straight line. The membranous labyrinth in the vestibule is divided into two sac-like structures, the utricle and the saccule. Each structure in turn contains a small structure called a macula, which is responsible for maintenance of static equilibrium. The macula consists of sensory hair cells, which are embedded in a gelatinous mass (similar to the cupula) that covers the macula. Grains of calcium carbonate, called otoliths, are embedded on the surface of the gelatinous layer.

When the head is in an upright position, the hairs are straight along the macula. When the head tilts, the gelatinous mass and otoliths tilts correspondingly, bending some of the hairs on the hair cells of the macula. This bending action initiates a signal impulse to the central nervous system, which travels via the vestibular branch of the vestibulocochlear nerve, which in turn relays motor impulses to the appropriate muscles to maintain balance.

The cochlea is the portion of the auris interna related to hearing. The cochlea is a tapered tube-like structure that is coiled into a shape resembling a snail. The inside of the cochlea is divided into three regions, which is further defined by the position of the vestibular membrane and the basilar membrane. The portion above the vestibular membrane is the scala vestibuli, which extends from the oval window to the apex of the cochlea and contains perilymph fluid, an aqueous liquid low in potassium and high in sodium content. The basilar membrane defines the scala tympani region, which extends from the apex of the cochlea to the round window and also contains perilymph. The basilar membrane contains thousands of stiff fibers, which gradually increase in length from the round window to the apex of the cochlea. The fibers of the basement membrane vibrate when activated by sound. In between the scala vestibuli and the scala tympani is the cochlear duct, which ends as a closed sac at the apex of the cochlea. The cochlear duct contains endolymph fluid, which is similar to cerebrospinal fluid and is high in potassium.

The organ of Corti, the sensory organ for hearing, is located on the basilar membrane and extends upward into the cochlear duct. The organ of Corti contains hair cells, which have hairlike projections that extend from their free surface, and contacts a gelatinous surface called the tectorial membrane. Although hair cells have no axons, they are surrounded by sensory nerve fibers that form the cochlear branch of the vestibulocochlear nerve (cranial nerve VIII).

As discussed, the oval window, also known as the elliptical window communicates with the stapes to relay sound waves that vibrate from the tympanic membrane. Vibrations transferred to the oval window increases pressure inside the fluid-filled cochlea via the perilymph and scala vestibuli/scala tympani, which in turn causes the round window membrane to expand in response. The concerted inward pressing of the oval window/outward expansion of the round window allows for the movement of fluid within the cochlea without a change of intra-cochlear pressure. However, as vibrations travel through the perilymph in the scala vestibuli, they create corresponding oscillations in the vestibular membrane. These corresponding oscillations travel through the endolymph of the cochlear duct, and transfer to the basilar membrane. When the basilar membrane oscillates, or moves up and down, the organ of Corti moves along with it. The hair cell receptors in the Organ of Corti then move against the tectorial membrane, causing a mechanical deformation in the tectorial membrane. This mechanical deformation initiates the nerve impulse that travels via the vestibulocochlear nerve to the central nervous system, mechanically transmitting the sound wave received into signals that are subsequently processed by the central nervous system.

Diseases

Autoimmune Inner Ear Disease

Autoimmune inner ear disease (AIED) is one of the few reversible causes of sensorineural hearing loss. It is a rare disorder appearing in both adults and children that often involves a bilateral disturbance of the audio and vestibular functions of the auris interna. In many cases, AIED occurs without systemic autoimmune symptoms, but up to one-third of patients also suffer from a systemic autoimmune illness, such as inflammatory bowel disease, rheumatoid arthritis (Murdin, L. et al (2007) Hearing difficulties are common in patients with rheumatoid arthritis, in *Clin Rheumatol*, 27(5):637-640), Ankylosing spondylitis, Systemic Lupus Erythematosus (SLE), Sjögren's Syndrome, Cogan's disease, ulcerative colitis, Wegener's granulomatosis and scleroderma. Behçet's disease, a multisystem disease, also commonly has audiovestibular problems. There is some evidence for food-related allergies as a cause for cochlear and vestibular autoimmunity, but there is presently no agreement as to its importance in the aetiology of the disease. A classification scheme for AIED has been developed (Harris and Keithley, (2002) Autoimmune inner ear disease, in *Otorhinolaryngology Head and Neck Surgery*. 91, 18-32).

The immune system normally performs a crucial role in protecting the inner ear from invasive pathogens such as bacteria and viruses. However, in AIED the immune system itself begins to damage the delicate inner ear tissues. The inner ear is fully capable of mounting a localized immune response to foreign antigens. When a foreign antigen enters the inner ear, it is first processed by immunocompetent cells which reside in and around the endolymphatic sac. Once the foreign antigen has been processed by these immunocompetent cells, these cells secrete various cytokines which modulate the immune response of the inner ear. One result of this cytokine release is to facilitate the influx of inflammatory cells which are recruited from the systemic circulation. These systemic inflammatory cells enter the cochlea via diapedesis through the spiral modiolar vein and its tributaries, and begin to participate in antigen uptake and deregulation just as it occurs in other parts of the body. Interleukin 1 (IL-1) plays an important role in modulating the innate (nonspecific) immune response and is a known activator of resting T helper cells and B-cells. T helper cells, once activated by IL-1, produce IL-2. IL-2 secretion results in differentiation of pluripotent T-cells into helper, cytotoxic and suppressor T-cell subtypes. IL-2 also assists T helper cells in the activation of B lymphocytes and probably plays a pivotal role in the immunoregulation of the immune response of the vestibular and cochlear regions. IL-2 is within the perilymph of the auris interna as early as 6 h after antigen challenge with peak levels at 18 h after antigen challenge. The perilymphatic levels of IL-2 then dissipate, and it is no longer present within the perilymph at 120 hours post antigen challenge.

Both IL-1β and tumor necrosis factor-α (TNF-α) may play a key role in the initiation and amplification of the immune response. IL-1β is expressed by the fibrocytes of the spiral ligament in the presence of trauma such as surgical trauma or acoustic trauma in a nonspecific response. TNF-α is expressed either by infiltrating systemic cells or by resident cells contained within the endolymphatic sac in the presence of antigen. TNF-α is released as part of the adaptive (specific) immune response in animal models. When antigen is injected into the auris interna of mice, IL-1β and TNF-α are both expressed and a vigorous immune response occurs. However, when antigen is introduced to the auris interna via the cerebral spinal fluid in the absence of trauma, only TNF-α is expressed and the immune response in minimal. Importantly, cochlear trauma in isolation also results in a minimal immune response. These results suggest that both the nonspecific and specific components of the immune response act in concert in the auris interna to achieve a maximal response.

Accordingly, if the cochlea is traumatized and an antigen is injected (or in the case of autoimmune disease, the patient has immune cells directed against inner ear antigens), both the nonspecific and the specific immune responses can be activated simultaneously. This results in the concurrent production of IL-1β as well as TNF-α which causes a greatly amplified level of inflammation leading to substantial damage to the auris interna. Subsequent experiments in animal models confirm that an important step in immune-mediated damage requires that the auris interna be conditioned by the non-specific innate immune response before the specific adaptive immune response can lead to enough inflammation to result in damage (Hashimoto, *Audiol. Neurootol.* (2005), 10, 35-43). As a result, agents which downregulate or block the specific immune response, and in particular the effect of TNF-α, prevent the excessive immune response seen when both the specific and nonspecific immune responses are simultaneously activated.

As such, some embodiments include the treatment of autoimmune ear disease by administering anti-TNF agents. Etanercept (ENBREL®), an anti-TNF drug, is emerging as a promising agent for treatment of autoimmune inner ear disease. Additionally, the anti-TNF agents infliximab (REMICADE®), adalimumab (HUMIRA®) and golimumab are also useful in treatment of autoimmune inner ear disorders. Clinical trial protocols of systemic treatment of individuals with AIED include injections of anti-TNF agents as an injection on a twice-weekly basis. Additional embodiments include the treatment of autoimmune ear disease by administering an immunomodulating agent selected from a TACE inhibitor, an IKK inhibitor, a calcineurin inhibitor, a flavone derivative, a toll-like inhibitor, an interleukin-inhibitor, or combinations thereof.

In other embodiments, included is the treatment of autoimmune otic disorders with a combination of an immunomodulating agent with another pharmaceutical agent including steroids, chemotherapeutic agents, collagen, gamma globulin infusion or other immune modulating drugs. Steroids include, e.g. prednisone or decadron. Chemotherapeutic agents, include, e.g. cytoxan, azathiaprine or methotrexate. Plasmapheresis procedures are optionally used. Treatment with oral collagen, gamma globulin infusions or other immune modulating drugs (e.g. beta-interferon, alpha interferon or copaxone) are also optionally used in combination with an anti-TNF drug.

Endolymphatic Hydrops

Endolymphatic hydrops refers to an increase in the hydraulic pressure within the endolymphatic system of the inner ear. The endolymph and perilymph are separated by thin membranes which contain multiple nerves. Fluctuation in the pressure stresses the membranes and the nerves they house. If the pressure is great enough, disruptions may form in the membranes. This results in a mixing of the fluids which can lead to a depolarization blockade and transient loss of function. Changes in the rate of vestibular nerve firing often lead to vertigo. Further, the organ of Corti may also be affected. Distortions of the basilar membrane and the inner and outer hair cells can lead to hearing loss and/or tinnitus.

Causes include metabolic disturbances, hormonal imbalances, autoimmune disease, and viral, bacterial, or fungal infections. Symptoms include hearing loss, vertigo, tinnitus, and aural fullness. Nystagmus may also be present. Treatment includes systemic administration of benzodiazepine, diuretics (to decrease the fluid pressure), corticosteroids, and/or anti-bacterial, anti-viral, or anti-fungal agents.

Recurrent Vestibulopathy

Recurrent vestibulopathy is a condition wherein the subject experiences multiple episodes of severe vertigo. The episodes of vertigo may last for minutes or hours. Unlike Meniere's Disease, it is not accompanied by hearing loss. In some cases it may develop into Meniere's Disease or Benign Paroxysmal Positional Vertigo. Treatment is similar to that of Meniere's Disease.

Tinnitus

Tinnitus is defined as the perception of sound in the absence of any external stimuli. It may occur in one or both ears, continuously or sporadically, and is most often described as a ringing sound. It is most often used as a diagnostic symptom for other diseases. There are two types of tinnitus: objective and subjective. The former is a sound created in the body which is audible to anyone. The latter is audible only to the affected individual. Studies estimate that over 50 million Americans experience some form of tinnitus. Of those 50 million, about 12 million experience severe tinnitus.

There are several treatments for tinnitus. Lidocaine, administered by IV, reduces or eliminates the noise associated with tinnitus in about 60-80% of sufferers. Selective neurotransmitter reuptake inhibitors, such as nortriptyline, sertraline, and paroxetine, have also demonstrated efficacy against tinnitus. Benzodiazepines are also prescribed to treat tinnitus.

Vertigo

Vertigo is described as a feeling of spinning or swaying while the body is stationary. There are two types of vertigo. Subjective vertigo is the false sensation of movement of the body. Objective vertigo is the perception that one's surrounding are in motion. It is often accompanied by nausea, vomiting, and difficulty maintaining balance.

While not wishing to be bound by any one theory, it is hypothesized that vertigo is caused by an over-accumulation of endolymph. This fluid imbalance results in increased pressure on the cells of the inner ear which leads to the sensation of movement. The most common cause of vertigo is benign paroxysmal positional vertigo, or BPPV. It can also be brought on by a head injury, or a sudden change of blood pressure. It is a diagnostic symptom of several diseases including superior canal dehiscence syndrome and Meniere's disease.

Benign Paroxysmal Positional Vertigo

Benign paroxysmal positional vertigo is caused by the movement of free floating calcium carbonate crystals (otoliths) from the utricle to one of the semicircular canals, most often the posterior semicircular canal. Movement of the head results in the movement of the otoliths causing abnormal endolymph displacement and a resultant sensation of vertigo. The episodes of vertigo usually last for about a minute and are rarely accompanied by other auditory symptoms.

Mal de Debarquement

Mal de debarquement is a condition which usually occurs subsequent to a sustained motion event, for example, a cruise, car trip, or airplane ride. It is characterized by a persistent sense of motion, difficulty maintaining balance, fatigue, and cognitive impairment. Symptoms may also include dizziness, headaches, hyperacusis, and/or tinnitus. Symptoms often last in excess of a month. Treatment includes benzodiazepines, diuretics, sodium channel blockers, and tricyclic antidepressants.

Otitis Externa

Otitis externa (OE), also referred to as swimmer's ear, is an inflammation and/or infection of the external ear. OE is often caused by bacteria in the outer ear, which establish infection following damage to the skin of the ear canal. Primary bacterial pathogens that cause OE are *Pseudomonas aeruginosa* and *Staphylococcus aureus*, but the condition is associated with the presence of many other strains of gram positive and negative bacteria. OE is also sometimes caused by fungal infection in the outer ear, including *Candida albicans* and *Aspergillus*. Symptoms of OE include otalgia, swelling, and otorrhea. If the condition progresses significantly, OE may cause temporary conductive hearing loss as a result of the swelling and discharge.

Treatment of OE involves eliminating the aggravating pathogen from the ear canal and reducing inflammation, which is usually accomplished by administering combinations of antimicrobial agents, e.g., antibacterial and antifungal agents, with anti-inflammatory agents, e.g., steroids. Typical antibacterial agents for the treatment of OE include aminoglycosides (e.g., neomycin, gentamycin, and tobramycin), polymyxins (e.g., polymyxin B), fluoroquinolone (e.g., ofloxacin and ciprofloxacin), cephalosporins (e.g., cefuroxime, ceflacor, cefprozil, loracarbef, cefindir, cefixime, cefpodoxime proxetil, cefibuten, and ceftriaxone), penicillins (e.g., amoxicillin, amoxicillin-clavulanate, and penicillinase-resistant penicillins), and combinations thereof. Typical antifungal agents for the treatment of OE include clotrimazole, thimerasol, M-cresyl acetate, tolnaftate, itraconazole, and combinations thereof. Acetic acid is also administered to the ear, alone and in combination with other agents, to treat bacterial and fungal infections. When the pain of OE is extremely severe such that it interferes with normal activity, e.g., sleeping, pain relievers such as topical analgesics or oral narcotics may be given until the underlying inflammation and infection are alleviated.

Otitis Media

Otitis media (OM), which includes acute otitis media (AOM), chronic otitis media, otitis media with effusion (OME), secretory otitis media, and chronic secretory otitis media as examples, is a condition that presents in the area between the ear drum and the inner ear. Bacterial infection accounts for a large percentage of OM cases, with more than 40% of cases attributed to *Streptococcus pneumoniae* infection. However, viruses, as well as other microbes, may also account for OM conditions.

AOM is a condition that is most often purely viral and self-limited. Viral AOM can lead to bacterial otitis media in a very short period of time, especially in children. Symptoms include, but are not limited to, congestion of the ears, discomfort, pus, and pressure imbalances. OME is a condition characterized by the accumulation of in the middle ear space. It often results from negative pressure produced by altered Eustachian tube function. The accumulation of fluid sometimes leads to conductive hearing impairment (e.g. when it interferes with the ability of the eardrum to vibrate). If the condition persists, the fluid can increase in viscosity increasing the likelihood of hearing loss.

Because OM can be caused by a virus, bacteria or both, it is often difficult to identify the exact cause and thus the most appropriate treatment. Treatment options for OM include antibiotics, such as penicillins (e.g., amoxicillin and amoxicillin-clavulanate), clavulanate acid, trimethoprim-sulfamethoxazole, cephalosporins (e.g., cefuroxime, ceflacor, cefprozil, loracarbef, cefindir, cefixime, cefpodoxime proxetil, cefibuten, and ceftriaxone), macrolides and azalides (e.g., erythromycin, clarithromycin, and azithromycin), sulfonamides, and combinations thereof. Surgical intervention is also available, including myringotomy, an operation to insert a tympanostomy tube through the tympanic membrane and into the patient's middle ear to drain the fluid and balance the pressure between the outer and middle ear. Antipyretics and analgesics, including benzocaine, ibuprofen and acetaminophen, may also be prescribed to treat accompanying fever or pain effects.

Mastoiditis

Mastoiditis is an infection of the mastoid process, which is the portion of the temporal bone behind the ear. It is typically caused by untreated acute otitis media. Madtoiditis may be acute or chronic. Symptoms include pain, swelling, and tenderness in the mastoid region, as well as otalgia, erythematosus, and otorrhea.

Mastoiditis typically occurs as bacteria spread from the middle ear to the mastoid air cells, where the inflammation causes damage to the bony structures. The most common bacterial pathogens are *Streptococcus pneumoniae, Streptococcus pyogenes, Staphylococcus aureus*, and gram-negative bacilli. Accordingly, antimicrobial agent formulations disclosed herein comprising antibacterial agents effective against the bacteria are useful for the treatment of mastoiditis, including acute mastoiditis and chronic mastoiditis.

Bullous myringitis is an infection of the tympanic membrane, caused by a variety of bacteria and viruses, including *Mycoplasma* bacteria. The infection leads to inflammation of the tympanic membrane and nearby canal, and causes the formation of blisters on the ear drum. The primary symptom of Bullous myringitis is pain, which may be relieved through the administration of analgesics. Antimicrobial formulations disclosed herein comprising antibacterial and antiviral agents are useful for the treatment of Bullous myringitis.

Sensorineural Hearing Loss

Sensorineural hearing loss is a type of hearing loss which results from defects (congenital and acquired) in the vestibulocochlear nerve (also known as cranial nerve VIII), or sensory cells of the inner ear. The majority of defects of the inner ear are defects of otic hair cells.

Aplasia of the cochlea, chromosomal defects, and congenital cholesteatoma are examples of congenital defects which can result in sensorineural hearing loss. By way of non-limiting example, inflammatory diseases (e.g. suppurative labyrinthitis, meningitis, mumps, measles, viral syphilis, and autoimmune disorders), Meniere's Disease, exposure to ototoxic drugs (e.g. aminoglycosides, loop diuretics, antimetabolites, salicylates, and cisplatin), physical trauma, presbyacusis, and acoustic trauma (prolonged exposure to sound in excess of 90 dB) can all result in acquired sensorineural hearing loss.

If the defect resulting in sensorineural hearing loss is a defect in the auditory pathways, the sensorineural hearing loss is called central hearing loss. If the defect resulting in sensorineural hearing loss is a defect in the auditory pathways, the sensorineural hearing loss is called cortical deafness.

Ototoxicity

Ototoxicity refers to hearing loss caused by a toxin. The hearing loss may be due to trauma to otic hair cells, the cochlea, and/or the cranial nerve VII. Multiple drugs are known to be ototoxic. Often ototoxicity is dose-dependent. It may be permanent or reversible upon withdrawal of the drug.

Known ototoxic drugs include, but are not limited to, the aminoglycoside class of antibiotics (e.g. gentamicin, and amikacin), some members of the macrolide class of antibiotics (e.g. erythromycin), some members of the glycopeptide class of antibiotics (e.g. vancomycin), salicylic acid, nicotine, some chemotherapeutic agents (e.g. actinomycin, bleomycin, cisplatin, carboplatin and vincristine), and some members of the loop diuretic family of drugs (e.g. furosemide).

Cisplatin and the aminoglycoside class of antibiotics induce the production of reactive oxygen species (ROS). ROS can damage cells directly by damaging DNA, polypeptides, and/or lipids. Antioxidants prevent damage of ROS by preventing their formation or scavenging free radicals before they can damage the cell. Both cisplatin and the aminoglycoside class of antibiotics are also thought to damage the ear by binding melanin in the stria vascularis of the inner ear.

Salicylic acid is classified as ototoxic as it inhibits the function of the polypeptide prestin. Prestin mediates outer otic hair cell motility by controlling the exchange of chloride and carbonate across the plasma membrane of outer otic hair cells. It is only found in the outer otic hair cells, not the inner otic hair cells. Accordingly, disclosed herein is the use of controlled release auris-compositions comprising antioxidants to prevent, ameliorate or lessen ototoxic effects of chemotherapy, including but not limited to cisplatin treatment, aminoglycoside or salicylic acid administration, or other ototoxic agents.

Excitotoxicity

Excitotoxicity refers to the death or damaging of neurons and/or otic hair cells by glutamate and/or similar substances.

Glutamate is the most abundant excitatory neurotransmitter in the central nervous system. Pre-synaptic neurons release glutamate upon stimulation. It flows across the synapse, binds to receptors located on post-synaptic neurons, and activates these neurons. The glutamate receptors include the NMDA, AMPA, and kainate receptors. Glutamate transporters are tasked with removing extracellular glutamate from the synapse. Certain events (e.g. ischemia or stroke) can damage the transporters. This results in excess glutamate accumulating in the synapse. Excess glutamate in synapses results in the over-activation of the glutamate receptors.

The AMPA receptor is activated by the binding of both glutamate and AMPA. Activation of certain isoforms of the AMPA receptor results in the opening of ion channels located in the plasma membrane of the neuron. When the channels open, $Na^+$ and $Ca^{2+}$ ions flow into the neuron and $K^+$ ions flow out of the neuron.

The NMDA receptor is activated by the binding of both glutamate and NMDA. Activation of the NMDA receptor, results in the opening of ion channels located in the plasma membrane of the neuron. However, these channels are blocked by $Mg^{2+}$ ions. Activation of the AMPA receptor results in the expulsion of $Mg^{2+}$ ions from the ion channels into the synapse. When the ion channels open, and the $Mg^{2+}$ ions evacuate the ion channels, $Na^+$ and $Ca^{2+}$ ions flow into the neuron, and $K^+$ ions flow out of the neuron.

Excitotoxicity occurs when the NMDA receptor and AMPA receptors are over-activated by the binding of excessive amounts of ligands, for example, abnormal amounts of glutamate. The over-activation of these receptors causes excessive opening of the ion channels under their control. This allows abnormally high levels of $Ca^{2+}$ and $Na^+$ to enter the neuron. The influx of these levels of $Ca^{2+}$ and $Na^+$ into the neuron causes the neuron to fire more often, resulting in a rapid buildup of free radicals and inflammatory compounds within the cell. The free radicals eventually damage the mitochondria, depleting the cell's energy stores. Furthermore, excess levels of $Ca^{2+}$ and $Na^+$ ions activate excess levels of enzymes including, but not limited to, phospholipases, endonucleases, and proteases. The over-activation of these enzymes results in damage to the cytoskeleton, plasma membrane, mitochondria, and DNA of the sensory neuron.

Ramsay Hunt's Syndrome (Herpes Zoster Infection)

Ramsay Hunt's Syndrome is caused by a herpes zoster infection of the auditory nerve. The infection may cause severe ear pain, hearing loss, vertigo, as well as blisters on the outer ear, in the ear canal, as well as on the skin of the face or neck supplied by the nerves. Facial muscles may also become paralyzed if the facial nerves are compressed by the swelling. Hearing loss may be temporary or permanent, with vertigo symptoms usually lasting from several days to weeks.

Treatment of Ramsay Hunt's syndrome includes administration of antiviral agents, including acyclovir. Other antiviral agents include famciclovir and valacyclovir. Combination of antiviral and corticosteroid therapy may also be employed to ameliorate herpes zoster infection. Analgesics or narcotics may also be administered to relieve the pain, and diazepam or other central nervous system agents to suppress vertigo. Capsaicin, lidocaine patches and nerve blocks are optionally used. Surgery may also be performed on compressed facial nerves to relieve facial paralysis.

Labyrinthitis

Labyrinthitis is an inflammation of the labyrinths of the ear which contain the vestibular system of the inner ear. Causes include bacterial, viral, and fungal infections. It may also be caused by a head injury or allergies. Symptoms of labyrinthitis include difficulty maintaining balance, dizziness, vertigo, tinnitus, and hearing loss. Recovery may take one to six weeks; however, chronic symptoms may be present for years.

There are several treatments for labyrinthitis. Prochlorperazine is often prescribed as an antiemetic. Serotonin-reuptake inhibitors have been shown to stimulate new neural growth within the inner ear. Additionally, treatment with antibiotics is prescribed if the cause is a bacterial infection, and treatment with corticosteroids and antivirals is recommended if the condition is caused by a viral infection.

Kinetosis

Kinetosis, also known as motion sickness, is a condition in which there is a disconnection between visually perceived movement and the vestibular system's sense of movement. Dizziness, fatigue, and nausea are the most common symptoms of kinetosis. Dimenhydrinate, cinnarizine, and meclizine are all systemic treatments for kinetosis. Additionally, benzodiazepines and antihistamines have demonstrated efficacy in treating kinetosis.

Meniere's Disease

Meniere's Disease is an idiopathic condition characterized by sudden attacks of vertigo, nausea and vomiting that may last for 3 to 24 hours, and may subside gradually. Progressive hearing loss, tinnitus and a sensation of pressure in the ears accompanies the disease through time. The cause of Meniere's disease is likely related to an imbalance of inner ear fluid homeostasis, including an increase in production or a decrease in reabsorption of inner ear fluid.

Studies of the vasopressin (VP)-mediated aquaporin 2 (AQP2) system in the inner ear suggest a role for VP in inducing endolymph production, thereby increasing pressure in the vestibular and cochlear structures. VP levels were found to be upregulated in endolymphatic hydrops (Meniere's Disease) cases, and chronic administration of VP in guinea pigs was found to induce endolymphatic hydrops. Treatment with VP antagonists, including infusion of OPC-31260 (a competitive antagonist of $V_2$-R) into the scala tympani resulted in a marked reduction of Meniere's disease symptoms. Other VP antagonists include WAY-140288, CL-385004, tolvaptan, conivaptan, SR 121463A and VPA 985. (Sanghi et al. *Eur. Heart J.* (2005) 26:538-543; Palm et al. *Nephrol. Dial Transplant* (1999) 14:2559-2562).

Other studies suggest a role for estrogen-related receptor β/NR3B2 (ERR/Nr3b2) in regulating endolymph production, and therefore pressure in the vestibular/cochlear apparatus. Knock-out studies in mice demonstrate the role of the polypeptide product of the Nr3b2 gene in regulating endolymph fluid production. Nr3b2 expression has been localized in the endolymph-secreting strial marginal cells and vestibular dark cells of the cochlea and vestibular apparatus, respectively. Moreover, conditional knockout of the Nr3b2 gene results in deafness and diminished endolymphatic fluid volume. Treatment with antagonists to ERR/Nr3b2 may assist in reducing endolymphatic volume, and thus alter pressure in the auris interna structures.

Other treatments may be aimed at dealing with the immediate symptoms and prevention of recurrence. Low-sodium diets, avoidance of caffeine, alcohol, and tobacco have been advocated. Medications that may temporarily relieve vertigo attacks include antihistamines (including meclizine and other antihistamines), and central nervous system agents, including barbiturates and/or benzodiazepines, including lorazepam or diazepam. Other examples of drugs that may be useful in relieving symptoms include muscarinic antagonists, including scopolamine. Nausea and vomiting may be relieved by suppositories containing antipsychotic agents, including the phenothiazine agent prochlorperazine.

Surgical procedures that have been used to relieve symptoms include the destruction of vestibular and/or cochlear function to relieve vertigo symptoms. These procedures aim to either reduce fluid pressure in the inner ear and/or to destroy inner ear balance function. An endolymphatic shunt procedure, which relieves fluid pressure, may be placed in the inner ear to relieve symptoms of vestibular dysfunction. Other treatments include gentamicin application, which when injected into the eardrum destroys sensory hair cell function, thereby eradicating inner ear balance function. Severing of the vestibular nerve may also be employed, which while preserving hearing, may control vertigo.

Meniere's Syndrome

Meniere's Syndrome, which displays similar symptoms as Meniere's disease, is attributed as a secondary affliction to another disease process, e.g. thyroid disease or inner ear inflammation due to syphilis infection. Meniere's syndrome, thus, are secondary effects to various process that interfere with normal production or resorption of endolymph, including endocrine abnormalities, electrolyte imbalance, autoimmune dysfunction, medications, infections (e.g. parasitic infections) or hyperlipidemia. Treatment of patients afflicted with Meniere's Syndrome is similar to Meniere's Disease.

Microvascular Compression Syndrome

Microvascular compression syndrome (MCS), also called "vascular compression" or "neurovascular compression", is a disorder characterized by vertigo and tinnitus. It is caused by the irritation of Cranial Nerve VII by a blood vessel. Other symptoms found in subjects with MCS include, but are not limited to, severe motion intolerance, and neuralgic like "quick spins." MCS is treated with carbamazepine, TRILEPTAL®, and baclofen. It can also be surgically treated.

Vestibular Neuronitis

Vestibular neuronitis, or vestibular neuropathy, is an acute, sustained dysfunction of the peripheral vestibular system. It is theorized that vestibular neuronitis is caused by a disruption of afferent neuronal input from one or both of the vestibular apparatuses. Sources of this disruption include viral infection and acute localized ischemia of the vestibular nerve and/or labyrinth.

The most significant finding when diagnosing vestibular neuronitis is spontaneous, unidirectional, horizontal nystagmus. It is often accompanied by nausea, vomiting, and vertigo. It is, however, generally not accompanied by hearing loss or other auditory symptoms.

There are several treatments for vestibular neuronitis. H1-receptor antagonists, such as dimenhydrinate, diphenhydramine, meclizine, and promethazine, diminish vestibular stimulation and depress labyrinthine function through anticholinergic effects. Benzodiazepines, such as diazepam and lorazepam, are also used to inhibit vestibular responses due to their effects on the $GABA_A$ receptor. Anticholinergics, for example scopolamine, are also prescribed. They function by suppressing conduction in the vestibular cerebellar pathways. Finally, corticosteroids (i.e. prednisone) are prescribed to ameliorate the inflammation of the vestibular nerve and associated apparatus.

Acoustic Trauma

Hearing loss may also occur from prolonged exposure to loud noises, such as loud music, heavy equipment or machinery, airplanes or gunfire. The hearing loss occurs as result of destruction of hair cell receptors in the inner ear. This hearing loss is often accompanied by tinnitus. Permanent damage to hearing loss is often diagnosed.

Although there is currently no treatment for noise-induced hearing loss, several treatment regimens have been experimentally developed, including treatment with insulin-like growth factor 1 (IGF-1). (Lee et al. *Otol. Neurotol.* (2007) 28:976-981).

Presbycusis

Presbycusis, or age-related hearing loss, occurs as a part of normal aging, and occurs as a result of degeneration of the receptor cells in the spiral organ of Corti in the inner ear. Other causes may also be attributed to a decrease in a number of nerve fibers in the vestibulocochlear nerve, as well as a loss of flexibility of the basilar membrane in the cochlea. There is currently no known cure for permanent hearing damage as a result of presbycusis or excessive noise.

Hereditary Disorders

Hereditary disorders, including Scheibe, Mondini-Michelle, Waardenburg's, Michel, Alexander's ear deformity, hypertelorism, Jervell-Lange Nielson, Refsum's and Usher's syndromes, are found in approximately 20% of patients with sensorineural hearing loss. Congenital ear malformations may result from defects in the development of the membranous labyrinthine, the osseous labyrinthine, or both. Along with profound hearing loss and vestibular function abnormalities, hereditary deformities may also be associated with other dysfunctions, including development of recurring meningitis, cerebral spinal fluid (CSF) leaks, as well as perilymphatic fistulas. Treatment of chronic infections may be necessitated in hereditary disorder patients.

Otosclerosis

Bone remodeling is a life long process where old bone is removed from the skeleton (bone resorption) and new bone is added (bone formation). These processes also control the reshaping or replacement of bone during growth and following injuries. An imbalance in the regulation of bone resorption and bone formation results in many bone diseases such as otosclerosis.

Bone remodeling involves erosion of bone by osteoclasts, which is followed by osteoblasts refilling the resorption sites. Osteoclasts adhere to bone and remove it by acidification and proteolytic digestion. Tunnels are then formed in the bone, and the tunnels function as pathways for osteoblasts and small blood vessels. Fresh layers of osteoid, a cement-like substance, are deposited in the tunnels by osteoblasts and this eventually becomes new bone matrix.

Osteoclasts secrete various enzymes that act in dissolution of bone material. For example, tartrate resistant acid phosphatase (TRACP) decalcifies the bone, while cathepsin K digests the bone matrix proteins. The modulation of bone homeostasis is controlled by several factors. These factors can be divided into three groups: 1) those influencing the activity of osteoblasts, e.g., parathyroid hormone (PTH) or 1, 25-dihydroxyvitamin $D_3$, 2) those affecting osteoclast precursors or osteoclasts, e.g., osteoblasts produce osteoprotegerin (OPG) and RANKL which play a role in osteoclast differentiation; and 3) those with bipotential effects (e.g., TGF-$\beta$ can either inhibit or promote osteoclast differentiation by acting on osteoblasts or osteoclasts, respectively).

"Otosclerosis" is localized bone remodeling within the otic capsule of the human temporal bone. Three ossicles, the malleus, incus and stapes conduct sound in the middle ear from the tympanic membrane to the oval window of the inner ear. The lesions in the bony structures of the ear begin by softening/resorption of stable otic capsule bone ("active phase"), followed by a reparative phase with bone deposition. There is an abundance of osteoclasts in the bone in the active phase of otosclerosis. Lamellar bone is removed by the osteoclasts and replaced by woven spongiotic bone of greater thickness and vascularity. This spongiotic phase ("otospongiosis") produces its most significant effect upon the inner ear. Otospongiosis can produce symptoms of progressive sensorineural hearing loss, tinnitus, dizziness, and Meniere's syndrome. The sclerotic phase may still have elements of active demineralization of the bone around the inner ear, but also with a harder or sclerotic element to it. A visual exam can not determine whether the bone is spongiotic or sclerotic. To the naked eye it appears to be hard bone and is therefore called otosclerosis, although it may be in its active phase and more aptly called otospongiosis. By common usage, both phases of this disorder are referred to as otosclerosis.

Conductive hearing loss in otosclerosis is caused by two main sites of involvement of the sclerotic (or scar-like) lesions. The abnormal bone growth fixates the stapes footplate to the oval window of the cochlea. This impairs movement of the stapes and therefore transmission of sound into the inner ear ("ossicular coupling"). Additionally the cochlear round window can also become sclerotic, and impair movement of sound pressure waves through the inner ear ("acoustic coupling"). Otosclerosis may also cause a sensorineural hearing loss, i.e. nerve fibers or hearing hair cells of the cochlea may be damaged in patients with otosclerosis. The release of hydrolytic enzymes into the inner ear structures by the spongiotic lesions may play a role in the loss of cochlear hearing cells.

Genetic factors play a role in the aetiology of the disease but measles virus infection and autoimmunity may also play contributing roles. Treatment of otosclerosis includes surgery to remove the fixated stapes bone, called a stapedectomy. Disclosed herein are non-surgical methods for treatment of otosclerosis.

Cholesteatoma

A cholesteatoma is a hyperproliferative cyst often found in the middle ear. Cholesteatoma are classified as congenital or acquired. Acquired cholesteatomas result from retraction of the ear drum (primary) and/or a tear in the ear drum (secondary).

The most common primary cholesteatoma results from the pars flaccida retracting into the epitympanum. As the pars flaccida continues to retract, the lateral wall of the epitympanum slowly erodes. This produces a defect in the lateral wall of the epitympanum that slowly expands. A less common type of primary acquired cholesteatoma results from the retraction of the posterior quadrant of the tympanic membrane retracts into the posterior middle ear. As the tympanic membrane retracts, squamous epithelium envelops the stapes and retracts into the sinus tympani. Secondary cholesteatomas result from injury to the tympanic membrane (e.g. a perforation resulting from otitis media; trauma; or a surgically-induced injury).

Complications associated with a growing cholesteatoma include injury to the osteoclasts and, in some cases, deterioration of the thin bone layer separating the top of the ear from the brain. Damage to the osteoclasts results from the persistent application of pressure to the bones resulting from the expansion of the cholesteatoma. Additionally, the presence of multiple cytokines (e.g. TNF-α, TGF-β1, TGF-β2, Il-1, and IL-6) in the epithelium of the cholesteatoma can result in further degradation of the surrounding bones.

Patients with a cholesteatoma often present with earache, hearing loss, mucopurulent discharge, and/or dizziness. Physical examination can confirm the presence of a cholesteatoma. Symptoms which can be identified upon physical examination include damage to the ossicles, and a canal filled with mucopus and granulation tissue.

There is currently no effective medical therapy for cholesteatomas. As a cholesteatoma has no blood supply, it cannot be treated with systemic antibiotics. Topical administration of antibiotics often fails to treat a cholesteatoma.

Reperfusion Injury

Ischemia is a condition characterized by a lack of, or an inadequate amount of, blood supply to an organ. Ischemia often results in irreversible damage to tissue (e.g. from necrosis) due to the resultant lack of, or insufficiency of, oxygen. Irreversible damage to an organ can arise from as little as 20 minutes of complete oxygen deprivation.

Ischemia is a sequelae of disorders such as, but not limited to, heart diseases, transient ischemic attacks, cerebrovascular accidents, ruptured arteriovenous malformations, peripheral artery occlusive disease, stroke, and head injury. Cochlear ischemia results from, among other causes, occlusion the vertebral arteries and/or cerebral arteries, stroke, cardiovascular disease, and acoustic trauma.

Reperfusion is the restoration of normal blood supply to an organ following ischemia. In certain instances, reperfusion results in additional damage to tissues already damaged due to an ischemic episode and surrounding tissues (reperfusion injury). In certain instances, reperfusion injury results from the white blood cells in the restored blood supply reacting to the tissue damaged by ischemia. Additionally, in certain instances, the complement system (which is carried in the restored blood supply) damages tissue injured by ischemia, and the surrounding tissues (e.g. by the MAC, facilitation of opsonization, and the presence of multiple anaphylatoxins). In certain instances, depletion or inactivation of the complement system ameliorates reperfusion injury.

Labyrinthitis Ossificans

Labyrinthitis ossificans (aka labyrinthine ossification, cochlear ossification, or vestibular ossification) is a condition characterized by the development or growth of bone (e.g. the deposition of osteoid followed by mineralization and reorganization) into the spaces within the lumen of the boney labyrinth. This ossification of the lumen of the labyrinth leads to the destruction of the endolymphatic and perilymphatic spaces, deafness, and dysfunction of the vestibular system. In the cochlear area of the labyrinth, the scala tympani is most often the site of ossification.

It is most often an inflammatory response resulting from AIED or the presence of a pathogen (e.g. *S. pneumoniae* and *H. influenzae*) that leads to the ossification of the labyrinth. With regards to pathogenic infections, complete ossification will occur within a few months of infection. In certain instances, depletion or inactivation of the complement system ameliorates the development of labyrinthitis ossificans. Additionally, disorders such as vascular obstruction of the labyrinthine artery, temporal bone trauma, leukemia, and tumors of the temporal bone can also result in the development of labyrinthitis ossificans.

Treatment of an underlying pathogenic infection (e.g. meningitis, otitis media, and labyrinthitis) fully or partially prevents the development of labyrinthitis ossificans. Further, deactivation of the complement system also fully or partially prevents the development of labyrinthitis ossificans. However, if the disease is allowed to progress surgical removal of the excess bone is a current remedy. Additionally, in severe cases of labyrinthitis ossificans, cochlear implants are required to restore hearing.

Pharmaceutical Agents

Provided herein are otic structure modulating agent compositions or formulations that modulate destroyed, stunted, malfunctioning, damaged, fragile or missing otic structures. In some embodiments, the otic structure modulating agent compositions or formulations participate in the degradation of destroyed, stunted, malfunctioning, damaged, fragile, or missing otic structures. In some embodiments, the otic structure modulating agent compositions or formulations participate in the construction of destroyed, stunted, malfunctioning, damaged, fragile, or missing otic structures. In some embodiments, the otic structure modulating agent is an agonist of an otic structure modulating target, a partial agonist of an otic structure modulating target, an antagonist of an otic structure modulating target, a partial antagonist of an otic structure modulating target, an inverse agonist of an otic structure modulating target, a competitive antagonist of an otic structure modulating target, a neutral antagonist of an otic structure modulating target, an orthosteric antagonist of an otic structure modulating target, an allosteric antagonist of an otic structure modulating target, a positive allosteric modulator of an otic structure modulating target or combinations thereof.

Provided herein are innate immune system modulating compositions or formulations that modulate a component of the innate immune system. In some embodiments, the innate immune system modulating agent increases the activity of a component of the innate immune system. In some embodiments, the innate immune system modulating agent inhibits (partially or fully) the activity of a component of the innate immune system. In some embodiments, the innate immune system is the complement system.

Otic and vestibular disorders have causes and symptoms that are responsive to the pharmaceutical agents disclosed herein, or other pharmaceutical agents. Otic structure modulating agent or innate immune system modulating agents which are not disclosed or exemplified herein but which ameliorate or eradicate otic disorders are expressly included and intended within the scope of the embodiments presented.

Moreover, pharmaceutical agents which have been previously shown to be toxic, harmful or non-effective during systemic or localized application in other organ systems, for example through toxic metabolites formed after hepatic processing, toxicity of the drug in particular organs, tissues or systems, through high levels needed to achieve efficacy, through the inability to be released through systemic pathways or through poor pK characteristics, are useful in some embodiments herein. Accordingly, pharmaceutical agents which have limited or no systemic release, systemic toxicity, poor pK characteristics or combinations thereof are contemplated within the scope of the embodiments disclosed herein.

The otic structure modulating agent or innate immune system modulating agent formulations disclosed herein are optionally targeted directly to otic structures where treatment is needed; for example, one embodiment contemplated is the direct application of the otic structure modulating agent or innate immune system modulating agent formulations disclosed herein onto the round window membrane or the crista fenestrae cochlea of the auris interna, allowing direct access and treatment of the auris interna, or inner ear components. In other embodiments, the otic structure modulating agent or innate immune system modulating agent formulation disclosed herein is applied directly to the oval window. In yet other embodiments, direct access is obtained through microinjection directly into the auris interna, for example, through cochlear microperfusion. Such embodiments also optionally comprise a drug delivery device, wherein the drug delivery device delivers the otic structure modulating agent or innate immune system modulating agent formulations through use of a needle and syringe, a pump, a microinjection device, an in situ forming spongy material or any combination thereof.

Some pharmaceutical agents, either alone or in combination, are ototoxic. For example, some chemotherapeutic agents, including actinomycin, bleomycin, cisplatin, carboplatin and vincristine; and antibiotics, including erythromycin, gentamicin, streptomycin, dihydrostreptomycin, tobramycin, netilmicin, amikacin, neomycin, kanamycin, etiomycin, vancomycin, metronidizole, capreomycin, are mildly to very toxic, and affect the vestibular and cochlear structures differentially. However, in some instances, the combination of an ototoxic drug, for example cisplatin, in combination with an otoprotectant is protective by lessening the ototoxic effects of the drug. Moreover, the localized application of the potentially ototoxic drug also lessens the toxic effects that would otherwise occur through systemic application through the use of lower amounts with maintained efficacy, or the use of targeted amounts for a shorter period of time.

Moreover, some pharmaceutical excipients, diluents or carriers are potentially ototoxic. For example, benzalkonium chloride, a common preservative, is ototoxic and therefore potentially harmful if introduced into the vestibular or cochlear structures. In formulating a controlled release otic structure modulating agent or innate immune system modulating agent formulation, it is advised to avoid or combine the appropriate excipients, diluents or carriers to lessen or eliminate potential ototoxic components from the formulation, or to decrease the amount of such excipients, diluents or carriers. Optionally, a controlled release otic structure modulating agent or innate immune system modulating agent formulation includes otoprotective agents, such as antioxidants, alpha lipoic acid, calcium, fosfomycin or iron chelators, to counteract potential ototoxic effects that may arise from the use of specific therapeutic agents or excipients, diluents or carriers.

Otic Structure Enhancing Agents

Contemplated for use with the formulations disclosed herein are agents for treating or ameliorating hearing loss or reduction resulting from destroyed, stunted, malfunctioning, damaged, fragile or missing otic structures (e.g. tissues, membranes, cells, cartilage, bone). Accordingly, some embodiments incorporate the use of molecular components of otic structures. In certain instances, the molecular components of otic structures are utilized by a body to replace or repair destroyed, stunted, malfunctioning, damaged, fragile or missing otic structures. In some embodiments, the components of otic structures are polypeptides or polyglycans. In some embodiments, the components of otic structures are actin, aggrecan, chondroitin, collagen, decorin, dermatan sulfate, elastin, fibrinogen, fibronectin, fimbrin, glial fibrillary acidic protein, heparan sulfate, hyaluronic acid, keratin, laminin, nestin, NF-L, NF-M, NF—H, NF66, peripherin, α-tubulin, β-tubulin, villin, vimentin, whirlin, or combinations thereof.

In certain instances, actin is a molecular component of a cytoskeleton, stereocilia, and/or an actoclampin motor. In certain instances, aggrecan is a molecular component of cartilage. In certain instances, chondroitin is a molecular component of cartilage. In certain instances, collagen is a molecular component of a major component of the extracellular matrix, cartilage, ligaments, tendons, bone, and/or blood vessels. In certain instances, decorin is a molecular component of the extracellular matrix, and/or connective tissue. In certain instances, dermatan sulfate is a molecular component of epithelial tissue. In certain instances, elastin is a molecular component of connective tissue. In certain instances, fibrinogen is a molecular component of blood. In certain instances, fibronectin is a molecular component of cytoskeleton and/or the extracellular matrix. In certain instances, fimbrin is a molecular component of a cytoskeleton, stereocilia, and/or an actoclampin motor. In certain instances, glial fibrillary acidic protein is a molecular component of glial cells. In certain instances, heparan sulfate is a molecular component of epithelial tissue and/or cytoskeleton. In certain instances, hyaluronic acid is a molecular component of connective, epithelial, and neural tissues, and/or the extracellular matrix. In certain instances, keratin is a molecular component of epithelium tissue. In certain instances, laminin is a molecular component of the extracellular matrix. In certain instances, α-tubulin is a molecular component of cytoskeletons. In certain instances, nestin is a molecular component of neurons. In certain instances, NF-L is a molecular component of neurons. In certain instances, NF-M is a molecular component of neurons. In certain instances, NF—H is a molecular component of neurons. In certain instances, NF66 is a molecular component of neurons. In certain instances, peripherin is a molecular component of neurons. In certain instances, vimentin is a molecular component of neurons. In certain instances, β-tubulin is a molecular component of cytoskeletons. In certain instances, villin is a molecular component of cytoskeleton, stereocilia, and/or an actoclampin motor. In certain instances, whirlin is a molecular component of stereocilia.

In certain instances, an otic structure enhancing agent is hyaluronic acid (e.g. Restylane®, Perlane®, (Q-Med AB, Sweden and Medicis Aesthetics)), Juvederm®. In some instances hyaluronic acid is obtained from pathogens (e.g., *streptococcus* bacteria). In some instances, hyaluronic acid is obtained from avian sources (e.g. Hyalofomm®, (Genzyme Corporation)). In some instances, an otic structure enhancing agent is collagen (e.g., Zyplast®, Zyderm®, Cosmoderm®, Cosmoplast® (Inamed Corporation)). In some instances collagen is obtained from humans. In some instances collagen is obtained from animal sources.

Otic Bone Remodeling Agents

Contemplated for use with the formulations disclosed herein are agents for treating or ameliorating hearing loss, and/or a balance disorder resulting from destroyed, stunted, malfunctioning, damaged, fragile or missing otic bone structures (e.g. otosclerosis). Further contemplated for use with the formulations disclosed herein are agents for modulating otic bone remodeling. In some embodiments, the modulator of bone remodeling is a modulator of osteoblasts or osteoclasts. In some instances, the modulator of bone remodeling is a hormone. In certain instances, the modular of bone remodeling is a bisphosphonate. In some embodiments, the modulator of bone remodeling is a matrix metalloproteinase inhibitor. In some instances, the modulator of bone remodeling is an adenylyl cyclase (AC) modulator. In certain instances, the modulator of bone remodeling is a protease inhibitor. In some embodiments, the modulator of bone remodeling is a modulator of tartarate resistant acid phosphatase (TRACP). In some instance, the modulator of bone remodeling is an estrogen receptor modulator. In some embodiments, the modulator of bone remodeling is a PPAR γ modulator. In certain instances, the modulator of bone remodeling is an HMG-CoA reductase inhibitor. In some embodiments, the modulator of bone remodeling is a statin. In some instances, the modulator of bone remodeling is a carbonic anhydrase inhibitor. In some embodiments, the modulator of bone remodeling is a modulator of the receptor activator of nuclear κB ligand (RANKL). In certain instances, the modulator of bone remodeling is a COX-2 inhibitor. In some embodiments, the modulator of bone remodeling is an inhibitor of protein prenylation. In certain instances, the modulator of bone remodeling is a 5-lipoxygenase inhibitor. In some instances, the modulator of bone remodeling is an inhibitor of TNF. In some embodiments, the modulator of bone remodeling is an inhibitor of leukotrienes. In some embodiments, the modulator of bone remodeling is a cytokine modulator. In some instances, the modulator of bone remodeling is an inhibitor of TSG-6. In some embodiments, the modulator of bone remodeling is a modulator of TGF β. In some instances, the modulator of bone remodeling is a nitiric oxide synthase inhibitors. In some embodiments, the modulator of bone remodeling is an acetylcysteine. In certain embodiments, the modulator of bone remodeling is a modulator of aromatases. In some instances, the modulator of bone remodeling is a strontium-based compound as disclosed in WO/2008/027880, which is incorporated by reference herein for the subject matter disclosed.

Otic Structure Degrading Agents

Contemplated for use with the formulations disclosed herein are agents for treating or ameliorating hearing loss, and/or a balance disorder resulting from destroyed, stunted, malfunctioning, damaged, fragile or missing otic structures (e.g. Meniere's disease, endolymphatic hydrops, vestibular neuronitis). Further contemplated for use with the formulations disclosed herein are agents which facilitate the penetration of an otic active agent into the middle and/or inner ear by degrading barriers (e.g. cells, lipid matrix, extracellular matrix, desmosome). Further contemplated for use with the formulations disclosed herein are agents that act as anti-microbial agents (e.g. agents that inhibit the adhesion of microbes to otic structures). Additionally, contemplated for use with the formulations disclosed herein are agents for treating or ameliorating hearing loss or reduction resulting from the accumulation of fluid (e.g. mucus and pus) and/or cerumen within the ear (e.g. the outer ear, middle ear, and inner ear). Accordingly, some embodiments incorporate the use of an agent that participates in the degradation an otic structure (e.g. a neuron, a membrane, cartilage, bone, endolymph, perilymph).

In some embodiments, the otic structure modulating agent is an otic structure degrading agent. In some embodiments, the otic structure degrading agent degrades bone. In some embodiments, the otic structure degrading agent degrades cartilage. In some embodiments, the otic structure degrading agent degrades a neuron. In some embodiments, the otic structure degrading agent degrades a membrane (e.g., a tympanic membrane). In some embodiments, the otic structure degrading agent degrades endolymph. In some embodiments, the otic structure degrading agent degrades perilymph. In some embodiments, the otic structure degrading agent degrades liquor puris (i.e., pus).

In some embodiments, the agent that participates in the degradation of an otic structure is an alcohol or alkanol (e.g. decanol, and ethanol), an essential oil (e.g. basil oil, palmarosa oil, petitgrain oil, and thyme oil), a fatty acid (capric acid, lauric acid, linoleic acid, myristic acid, and oleic acid), a glycol (e.g. polyethylene glycol, and propylene glycol), laurocapram, a pyrrolidone (e.g. 2-pyrrolidone, N-methylpyrrolidone, and N-(2-hydroxyethyl)-2-pyrrolidone), a sulfoxide (e.g. DMSO, n-Decylmethyl Sulfoxide), a surfactant (e.g. Span 80, sodium lauryl sulfate, Tween 20, and Tween 80), a bile salt (e.g. sodium glycocholate, sodium deoxycholate, sodium taurocholate, sodium taurodihydrofusidate, sodium glycodihydrofusidate and the like), a chelating agent (e.g. EDTA, citric acid, salicylates and the like), an enzyme, or combinations thereof. In some embodiments, the enzyme is a protease, a glycosidase, an actinase, a chondroitinase, a collagenase, a dermatanase, an elastase, a gelatinase, a heparanase, a hyaluronidase, a keratinase, a lipase, a metallproteinase (e.g. matrix metallproteinase), a staphylokinase, a streptokinase, chymotrypsin, endopeptidase V8, trypsin, thermolysin, pepsin, plasmin, or combinations thereof.

In some embodiments, the enzyme is an actinase (e.g. fragilysin). In certain instances, administration or application of an actinase degrades an actin.

In some embodiments, the enzyme degrades chondroitin, dermatan, and/or hyaluronic acid. In certain instances, administration or application of a chondroitinase (e.g. N-acetylgalactosamine-6-sulfatase; N-acetylgalactosamine-4-sulfatase; Chondroitin AC lyase; Chondroitin B lyase; Chondroitin-sulfate-ABC endolyase; and Chondroitin-sulfate-ABC exolyase) degrades a chondroitin, dermatan, and/or a hyaluronic acid. In certain instances, administration or application of a dermatanase degrades a dermatan sulfate. In certain instances, administration or application of a hyaluronidase (hyaluronoglucosaminidase; hyaluronoglucuronidase; hyaluronate lyase) degrades a hyaluronic acid, condroitin, and/or dermatan. In certain instances, hyaluronidase degrades fluids that accumulate in tympanostomy tubes and/or mucus that is present in the middle ear.

In certain instances, a glycosidase degrades mucus that is present in the middle ear.

In some embodiments, the enzyme is a heparanase (e.g. heparan-alpha-glucosaminide N-acetyltransferase; N-acetylglucosamine-6-sulfatase; and iduronate-2-sulfatase). In certain instances, administration or application of a heparanase degrades a heparan sulfate. In certain instances, a heparinase degrades heparin sulfate moieties from nasopharyngeal epithelia cells resulting in the detachment of pneumococci from nasopharyngeal epithelia cells.

In some embodiments, the enzyme is a keratinase (e.g. peptidase K; and candidapepsin). In certain instances, administration or application of a keratinase degrades a keratin.

In some embodiments, the enzyme is a lipase (e.g. triacylglycerol lipase; acylglycerol lipase; lipoprotein lipase; and hormone-sensitive lipase). In certain instances, administration or application of a lipase degrades a lipid. In certain instances, administration or application of a lipase degrades cerumen.

In some embodiments, the enzyme is a metallproteinase. In certain instances, administration or application of a metallproteinase degrades a polypeptide. In some embodiments, the metallproteinase is a matrix metalloproteinase or thermolysin. In some embodiments, the matrix metalloproteinase is a collagenase, a gelatinase, a stromelysin, an MT1-MMP, an MT2-MMP, an MT3-MMP, an MT4-MMP, an MT5-MMP, and an MT6-MMP. In certain instances, administration or application of a collagenase degrades a collagen. In certain instances, administration or application of a collagenase degrades cerumen. In certain instances, administration or application of a gelatinase degrades a gelatin and/or a type IV collagen. In certain instances, administration or application of a stromelysin degrades an extracellular matrix protein. In certain instances, administration or application of thermolysin degrades a polypeptide by cleaving the peptide chain at a hydrophobic amino acid.

In some embodiments, the enzyme is plasmin, a plasminogen activator, and/or combinations thereof. In certain instances, administration or application of a plasmin degrades a fibrin, a fibronectin, a thrombospondin, a laminin, and a von Willebrand factor. In some embodiments, the plasminogen activator is staphylokinase, streptokinase, and/or combinations thereof. In certain instances, administration or application of a staphylokinase activates a plasminogen to form a plasmin. In certain instances, administration or application of a streptokinase activates a plasminogen to form a plasmin. In certain instances, plasmin degrades basement membranes.

In some embodiments, the enzyme is a serine protease. In certain instances, administration or application of a serine protease degrades a polypeptide. In certain instances, administration or application of a serine protease degrades cerumen. In some embodiments, the serine protease is chymotrypsin, elastase, trypsin, and/or V8 protease. In certain instances, administration or application of chymotrypsin degrades a polypeptide by cleaving the peptide chain at the carboxyl side of a tyrosine, a tryptophan, and a phenylalanine. In certain instances, administration or application of an elastase degrades an elastin. In certain instances, administration or application of trypsin degrades a polypeptide by cleaving the peptide chain at the carboxyl side of a lysine or an arginine. In certain instances, administration or application of V8 protease degrades a polypeptide by cleaving the peptide chain at the carboxyl side of an aspartic acid and/or glutamic acid.

In some embodiments, the enzyme is an aspartic protease. In certain instances, administration or application of an aspartic protease degrades a polypeptide. In certain instances, administration or application of an aspartic protease degrades cerumen. In some embodiments, the aspartic protease is pepsin, plasmepsin, or combinations thereof. In certain instances, administration or application of a pepsin degrades a polypeptide by cleaving the peptide chain at carboxyl side of an aromatic amino acid such as phenylalanine and tyrosine. In certain instances, administration or application of a plasmepsin degrades a polypeptide (e.g. hemoglobin) by cleaving the peptide chain at two aspartic acid residues.

In certain instances, the otic structure degrading agent is a hyaluronidase. In certain instances, a hyaluronidase is a human or bovine hyaluronidase. In some instances, a hyaluronidase is a human hyaluronidase (e.g., hyaluronidase found in human sperm, PH20 (Halozyme), Hyelenex® (Baxter International, Inc.)). In some instances, a hyaluronidase is a bovine hyaluronidase (e.g., bovine testicular hyaluronidase, Amphadase® (Amphastar Pharmaceuticals), Hydase® (PrimaPharm, Inc). In some instances, a hyluronidase is an ovine hyaluronidase, Vitrase® (ISTA Pharmaceuticals). In certain instances, a hyaluronidase described herein is a recombinant hyaluronidase. In some instances, a hyaluronidase described herein is a humanized recombinant hyaluronidase. In some instances, a hyaluronidase described herein is a pegylated hyaluronidase (e.g., PEGPH20 (Halozyme)). In certain instances, the enzyme is obtained from a pathogen. In certain instances, the pathogen is *Streptococcus* and the enzyme is a hyaluronidase, and/or a streptokinase. In certain instances, the pathogen is *Staphylococcus* and the enzyme is a lipase, V8 protease, elastase, hyaluronidase, and/or a staphlokinase. In certain instances, the pathogen is *Bacillus anthracis*, or a *Clostridium* and the enzyme is a metalloproteinase. In certain instances, the pathogen is *Bacillus thermoproteolyticus* and the enzyme is thermolysin. In certain instances, the pathogen is *Candida albicans* and the enzyme is candidapepsin.

Anaphylatoxin Modulators

In some embodiments, an anaphylatoxin modulator is administered to a subject in need thereof. In some embodiments, the anaphylatoxin modulator is an antagonist of C5a. In some embodiments, the C5a antagonist is chemotaxis inhibitory protein of *S. aureus* (CHIPS), PMX53 (AcF[OP-DCha-WR]), PMX205 (HC—[OPdChaWR]), PMX273 (AcF[OP-DPhe-WR]), PMX201 (AcF[OP-DCha-WCit]), PMX218 (HC—[OPdPheWR]), C089 (NMePhe-Lys-Pro-dCha-X-dArg), L-156,602 (D-Alanine,(RS,2R,5R,6R)-tetrahydro-R,2-dihydroxy-R,6-dimethyl-5-[(2S)-2-methylbutyl]-2H-pyran-2-acetyl-(3S)-3-hydroxy-L-leucyl-(3R)-hexahydro-3-pyridazinecarbonyl-N-hydroxy-L-alanylglycyl-(3S)-hexahydro-3-pyridazinecarbonyl-N-hydroxy-(7f2)-lactone, CAS #: 125228-51-5), C5aRAM, C5aRAD, or combinations thereof. In certain instances, a C5a antagonist binds to a C5aR and thereby antagonizes the binding of C5a. In certain instances, CHIPS binds to the C5a receptor (C5aR) on a macrophage thereby inhibiting the C5a induced chemotaxis of a macrophage. In certain instances, C5aRAM and C5aRAD are derived from the modification of the C terminus of C5a.

In some embodiments, the antagonist of C5aR activation is an antisense peptide. In some embodiments, the antisense peptide of C5a is PR226-MAP (LRTWSRRATRSTK-TLKVV), PL37-MAP (RAARISLGPRCIKAFTE), or combinations thereof. In certain instances, a C5a antagonist binds to a C5aR and thereby antagonizes the binding of C5a.

In some embodiments, an anaphylatoxin modulator is administered to a subject in need thereof. In some embodiments, the anaphylatoxin modulator is an antagonist of C3a. In some embodiments, the C3a antagonist is SB-290157 (N(2)-[(2,2-diphenylethoxy)acetyl]-L-arginine). In certain instances, SB-290157 binds to the C3a receptor (C3aR) thereby blocking the binding of C3a.

Complement Activators

In some embodiments, a complement activator is administered to a subject in need thereof. In some embodiments, the complement activator is GR-2II, a pectic arabinogalactan (e.g. AGIIa, and AGIIb-1), a pectin (e.g. AR-2IIa, AR-2IIb, AR-2IIc, and AR-2IId), CVF, or combinations thereof. In certain instances, AR-2IIa, AR-2IIb, and AR-2IIc activate the complement system via the classical pathway and not the alternative pathway.

Cobra Venom Factor (CVF) is a three-chain (α-chain, β-chain, and γ-chain) glycoprotein extracted from the reptile *Naja* sp. CVF is a human complement system activating protein. It is structurally homologous to C3b. In certain instances, CVF binds to Factor B which is then cleaved by Factor D. The resulting complex, CVFBb, functions as a C3 convertase and a C5 convertase. At 7.5 hours CVFBb exhibits a longer half-life than C3bBb (1.5 minutes). Further, CVFBb is resistant to disassembly by Factor H and CVF is resistant to inactivation by Factor I. As a result, CVFBb will continuously hydrolyze C3 and C5. The continuous hydrolyzation of C3 and C5 results in the depletion (or exhaustion) of the complement system within several hours. However, resynthesis of the components of the complement system begins quickly and the entire system is reconstituted with 5-10 days.

In certain instances, CVF is highly antigenic in vivo. As a result, several humanized analogs and/or derivatives of CVF have been engineered. In certain instances, these derivatives exhibit similar activity to natural CVF (e.g. 50-97% of the activity of natural CVF); however, they do not or have a reduced capability of activating an immune response in vivo. In certain analogs and/or derivatives, several amino acids from the β-chain of the CVF polypeptide are removed. In further analogs and/or derivatives, the CVF polypeptide is conjugated to a human antibody (e.g. monoclonal antibodies against antigen on human leukemia cells, human neuroblastoma cells, and human melanoma cells). In some analogs and/or derivatives, a human C3 derivative and/or analog (e.g. recombinant C3, rC3, humanized CVF) is engineered such that the human C3 derivative and/or analog comprises a portion of a CVF polypeptide sequence. In other analogs and/or derivatives, portions of a human C3 polypeptide (e.g. the α-chain; or portions of the carboxy terminal) are replaced with the corresponding portion of the CVF polypeptide. In certain derivatives and/or analogs, the α-chain of the human C3 is replaced by the corresponding carboxy terminal amino acids of the CVF polypeptide. In some embodiments, the CVF analog and/or derivative is HC3-1496, HC3-1496-2, HC3-1496-3, HC3-1496-4, HC3-1496/1617, HC3-1496-8, HC3-1496-9, HC3-1496-10, HC3-1496-11, HC3-1496-12, HC3-1496-13, HC3-1496-14, HC3-1496-15, HC3-1496-16, HC3-1496-17, or combinations thereof. For disclosures regarding the aforementioned CVF analogs and/or derivatives see PCT Pub. No. WO 2005/003159; and PCT Pub. No. WO 2008/060634, which are herein incorporated by reference for such disclosures. For additional disclosures regarding CVF derivatives and/or analogs see U.S. Pat. No. 5,714,344, which is hereby incorporated by reference for such disclosures.

In some embodiments, CVF is administered to a subject in need thereof (e.g. a subject who will benefit from complement depletion). In some embodiments, a CVF derivative is administered to a subject in need thereof.

Complement Component 1 Modulators

In some embodiments, a complement component 1 (C1) modulator is administered to a subject in need thereof. In some embodiments, the complement C1 modulator is a C1 inhibitor. In certain instances, the C1 inhibitor prevents fluid-phase C1 activation. In certain instances, administration of C1 inhibitor prevents reperfusion injury. In some embodiments, dextran sulfate is administered to a subject in need thereof. In some embodiments, C1 inhibitor is administered before, after, or simultaneous with dextran sulfate. In certain instances, dextran sulfate potentiates C1 inhibitor.

In some embodiments, a complement component 1q receptor (C1qR) is administered to a subject in need thereof. In certain instances, C1q regulates the presentation of adhesion molecules on endothelial cells. In certain instances, a C1q receptor (e.g. cC1qR, C1qRp, and gC1qR) prevents complement-mediated lysis of C1q sensitized erythrocytes. In certain instances, administration of C1 inhibitor prevents reperfusion injury.

In some embodiments, an antagonist of C1q binding is administered to a subject in need thereof. In some embodiments, the antagonist of C1q binding is C1q inhibitor, decorin, CSPG (chondroitin sulfate proteoglycan), CBP2 (complement binding peptide 2), or combinations thereof. In certain instances, CSPG partially or fully inhibits the binding of C1q to C1s and C1r, thereby interfering with the formation of the enzyme $C_1$. In certain instances, CBP2 interferes with the binding of C1q to an antigen or antigen-bound antibody.

Complement Receptor 1

In some embodiments, a complement receptor 1 (CR1) is administered to a subject in need thereof. By binding to C3b and C4b CR1 promotes phagocytosis and clearance of antigen-antibody complexes. Further, it inhibits both the classic and alternative pathways. In certain instances, CR1 acts as a decay-accelerator for both C3 and C5. Additionally, in certain instances, CR1 acts as a Factor I cofactor.

In some embodiments, a soluble CR1 (sCR1) is administered to a subject in need thereof. Soluble CR1 lacks the transmembrane and cytoplasmic domains of CR1. In certain instances, sCR1 decrease the amount of MAC produced by the complement system. In certain instances, sCR1 ameliorates ischemic/reperfusion injuries. In certain instances, sCR1 reduces cellular and tissue injuries in animal models with acute or chronic inflammatory disorders. In some embodiments, the sCR1 is APT070 (Mirococept), TP10 (Avant Immunotherapeutics), TP20 (Avant Immunotherapeutics), or combinations thereof.

In some embodiments, a soluble CR1 (sCR1) lacking the long homologous repeat A (LHR-A) domain (sCR1 [desLHR-A]) is administered to a subject in need thereof. sCR1[desLHR-A] lacks the transmembrane and cytoplasmic domains of CR1 and the C4b binding domain. In certain instances, sCR1[desLHR-A] inhibits the alternative pathway but exhibits a diminished ability to inhibit the classical pathway as compared to sCR1.

In some embodiments, a soluble CR1 (sCR1) bound by $SLe^x$ moieties is administered to a subject in need thereof. $SLe^x$ is a carbohydrate ligand for selectins that, in certain instances, inhibits E-selectin and P-selectin mediated neutrophil adhesion. In certain instances, $sCR1\text{-}SLe^x$ inhibits complement activation and inhibits the recruitment of neutrophils to the site of inflammation.

Complement Receptor 1-Related Gene/Protein

In some embodiments, a complement receptor 1-related gene/protein y (Crry) is administered to a subject in need thereof. In some embodiments, a recombinant Crry (Crry-Ig) is administered to a subject in need thereof. Crry inhibits both the classic and alternative pathways. In certain instances, Crry acts as a decay-accelerator for both C3 and C5. Additionally, in certain instances, Crry acts as a Factor I cofactor.

Complement Component 3 Convertase Modulators

In some embodiments, a modulator of C3 convertase is administered to a subject in need thereof. In some embodiments, the C3 convertase modulator is a fucan. In some embodiments, a fucan is extracted from brown seaweed (e.g. *Phaeophyceae, Ascophyllum nodosum,* and *Ecklonia kurome*). In certain instances, a fucan partially or fully suppresses the classical pathway. In certain instances, a fucan partially or fully suppresses the alternative pathway. In some embodiments, the fucan is BS8. In certain instances, BS8 partially or fully inhibited formation of C4bC2a by interfering with C1 activation. In certain instances, BS8 partially or fully inhibited formation of C4bC2a by interfering C4 cleavage. In certain instances, BS8, partially or fully inhibits C3Bb by interfering with the binding of Factor B to C3b and by interfering with the binding of properdin.

In some embodiments, a modulator of C3 convertase is administered to a subject in need thereof. In some embodiments, the C3 convertase modulator is complestatin. In certain instances, complestatin interferes with the binding of C4b and C2b, and thus antagonizes the formation of the classical C3 convertase (C4bC2b).

In some embodiments, a modulator of C3 convertase is administered to a subject in need thereof. In some embodiments, the C3 convertase modulator is extracellular complement-binding protein (Ecb). In certain instances, Ecb is isolated from *S. aureus*. In certain instances, it modulates C3b containing molecules (e.g. the alternative C3 convertase C3bB3, and the C5 convertases C4bC2aC3b and C3bBbC3b) by blocking the ability of C3b containing molecules to cleave their substrates (e.g. C3 and C5).

In some embodiments, a modulator of C3 convertase is administered to a subject in need thereof. In some embodiments, the C3 convertase modulator is extracellular fibrinogen-binding protein (Efb). In certain instances, Efb is isolated from *S. aureus*. In certain instances, Efb modulates C3b containing molecules (e.g. the alternative C3 convertase C3bB3) by blocking the ability of C3bBb to cleave C3.

In some embodiments, a modulator of C3 convertase is administered to a subject in need thereof. In some embodiments, the C3 convertase modulator is compstatin. In certain instances, compstatin antagonizes C3 convertases by binding to C3 and partially or fully inhibiting the ability for a C3 convertase to bind to and cleave C3.

In some embodiments, a modulator of C3 convertase is administered to a subject in need thereof. In some embodiments, the C3 convertase modulator is rosmarinic acid. In certain instances, rosmarinic acid reacts with the activated thioester of metastable C3b. In certain instances, the reaction of rosmarinic acid and the activated thioester of metastable C3b results in covalent attachment of rosmarinic acid to a C3 convertase. In certain instances, the covalent attachment of rosmarinic acid to a C3 convertase prevents the binding of a C3 convertase to a host cell or pathogen.

In some embodiments, a modulator of C3 convertase is administered to a subject in need thereof. In some embodiments, the C3 convertase modulator is CRIT. In some embodiments, the C3 convertase modulator is a peptide sequence comprising the C-terminal 11-amino-acid of the first CRIT-extracellular domain (CRIT-H17). In certain instances, CRIT inhibits the formation of C3 convertase. In certain instances, CRIT binds to C2, thus inhibiting C4b from binding to C2 and forming C3 convertase.

In some embodiments, a modulator of C3 convertase is administered to a subject in need thereof. In some embodiments, the C3 convertase modulator is glycyrrhetinic acid. In certain instances, glycyrrhetinic acid modulates C2 and thus modulates the formation of the classical pathway C3 convertase.

Complement Component 5 Convertase Modulators

In some embodiments, a modulator of C5 convertase is administered to a subject in need thereof. In some embodiments, the C5 convertase modulator is an anti-complement component 5 (C5) murine monoclonal. In certain instances, an anti-C5 mAb partially or fully inhibits the cleavage of C5 by C5 convertase. In certain instances, an anti-C5 mAB inhibits the formation of C5a. In certain instances, an anti-C5 mAb partially or fully inhibits the formation of C5b and thus the formation of a MAC. In certain instances, an anti-C5 mAB does not inhibit the cleavage of a C3. In some embodiments, an anti-C5 mAB is derived from the variable region of the N19/8 mAb. In certain instances, administration of an anti-C5 mAB ameliorates an autoimmune disease. In certain instances, an anti-C5 mAB partially or fully inhibits CD11b up-regulation. In certain instances, decreases the number of P-selectin presenting platelets. In certain instances, an anti-C5 mAB reduces the formation of leukocyte-platelet aggregates. In some embodiments, the C5 antibody is pexelizumab.

In some embodiments, an anti-C5 murine single-chain antibody is administered to a subject in need thereof. In some embodiments, an anti-C5 murine single-chain antibody is derived from the variable region of the N19/8 mAb. In certain instances, an anti-C5 murine single-chain antibody is inhibits the cleavage of C5 and the production of C5a. In certain instances, an anti-C5 murine single-chain antibody is partially or fully inhibits C5b-9-mediated hemolysis of erythrocytes. In some embodiments, an anti-C5 humanized single-chain antibody (e.g. 5G1.1-SC) is administered to a subject in need thereof.

In some embodiments, a modulator of C5 convertase is administered to a subject in need thereof. In some embodiments, the C5 convertase modulator is K76 (6,7-diformyl-3',4',4a',5',6',7',8',8a'-octahydro-4,6',7'-trihydroxy-2',5',5', 8a'-tetramethyl spiro[1'(2'H)-naphthalene-2(3M)-benzofuran]), or a derivative thereof (e.g. TKIXc, and K76 COOH). In certain instances, K76 antagonizes C5 convertase by interfering with the ability of C5 convertase to bind to and/or cleave C5.

In some embodiments, a modulator of C5 convertase is administered to a subject in need thereof. In some embodiments, the C5 convertase modulator is a staphylococcal complement inhibitor (e.g. SCIN, SCIN-B, and SCIN-C). In certain instances, a staphylococcal complement inhibitor is isolated from *S. aureus*. In certain instances, an SCIN binds to and stabilizes a C3 convertase (e.g. C4bC2a and C3bBb). In certain instances, the binding of an SCIN prevents the binding of a C3b subunit to the complex; thus, preventing the formation of a C5 convertase from a C3 convertase.

CD55

In some embodiments, a CD55 is administered to a subject in need thereof. CD55, also known as Decay Accelerating Factor (DAF), binds both C4b and C3b. In certain instances, the binding of CD55 to C4b disassociates the C3 convertase of the classical pathway and thus also inhibits the formation of the classical C5 convertase. In certain instances, the binding of CD55 to C3b disassociates the C3 and C5 convertases of the alternative pathway. In some embodiments, a CD55 protein is a soluble protein (sCD55). In some embodiments, sCD55 is administered to a subject in need thereof.

CD59

In some embodiments, a CD59 protein is administered to a subject in need thereof. In certain instances, CD59 inhibits the formation of a MAC by binding to C8 and C9 and thereby preventing their binding to the C5bC6C7 complex. In some embodiments, a soluble CD59 (sCD59) protein is administered to a subject in need thereof.

CD55/CD59 Fusion Proteins

In some embodiments, a CD59/CD55 fusion protein is administered to a subject in need thereof. In certain instances, the CD59 subunit inhibits the formation of a MAC by binding to C8 and C9 and thereby preventing their binding to the C5bC6C7 complex. In certain instances, a CD59/CD55 fusion protein prevents the formation of a MAC, and prevents the formation of or inhibits the activity of a C5 convertase. In certain instances, the CD55 subunit binds to C4b thereby disassociating the C3 convertase of the classical pathway and inhibiting the formation of the classical C5 convertase. In certain instances, the CD55 subunit binds to C3b thereby disassociating the C5 convertase of the alternative pathway.

CD55/MCP Fusion Proteins

In some embodiments, a CD55/MCP fusion protein is administered to a subject in need thereof. In certain instances, the CD55 subunit binds to C4b thereby disassociating the C3 convertase of the classical pathway and inhibiting the formation of the classical C5 convertase. In certain instances, the CD55 subunit binds to C3b thereby disassociating the C5 convertase of the alternative pathway. In certain instances, the MCP (Membrane Cofactor Protein, or CD46) subunit is a co-factor of Factor I. In certain instances, the MCP subunit activates Factor I leading to the inactivation of a C3 convertase of the classical pathway and/or a C3 convertase of the alternative pathway. In some embodiments, the CD55/MCP fusion protein is a soluble protein sCD55/MCP (Complement Activation Blocker-2, CAB-2). In certain instances, CAB-2 exhibits greater antagonism of convertases (e.g. C3 and C5) as compared to either CD55 administered alone, MCP administer alone, or CD55 and MCP administered in combination. In certain instances, CAB-2 inhibits complement activation in vivo.

Factor D Modulators

In some embodiments, a Factor D modulator is administered to a subject in need thereof. In some embodiments, the Factor D modulator is a Factor D antagonist. In some embodiments, the Factor D antagonist is BCX-1470 (2-amidino-6-(2-thiophene carboxy)benzothiophene methanesulfonate); FUT-175 (6-amidino-2-naphthyl p-guanidinobenzoate dimethane-sulphonate); or combinations thereof. In certain instances, Factor D antagonists inhibit the formation of the alternative pathway fluid phase C3 convertase by antagonizing Factor D's ability to bind to and cleave Factor B.

Factor I and Factor I Co-Factors

In some embodiments, a Factor I protease and a co-factor thereof are administered to a subject in need thereof. In certain instances, Factor I when bound to a co-factor, cleaves C3b and/or C4b; thus, inactivating them. The inactivation of C4b (iC4b) inhibits the activity of a C3 convertase of the classical pathway and thus also inhibits the formation of the classical C5 convertase. Further, the inactivation of C3b (iC3b) inhibits the activity of a C3 and C5 convertases of the alternative pathway.

In some embodiments, a Membrane Cofactor Protein (MCP OR CD46) is administered to a subject in need thereof. MCP is a co-factor of Factor I. In some embodiments, MCP is administered to a subject in need thereof in soluble form (sMCP). In some embodiments, sMCP and/or MCP is administered before, after, or simultaneously with Factor I. In some embodiments, sMCP and/or MCP is administered with CD55. In certain instances, administration of sMCP inhibits complement-mediated inflammation. In certain instances, administration of MCP activates Factor I leading to the inactivation of a C3 convertase of the classical pathway and/or a C3 convertase of the alternative pathway. In certain instances, administration of MCP activates Factor I leading to a decrease in the production of C5 convertase the classical pathway and/or inactivation of a C5 convertase of the alternative pathway.

Heparin

In some embodiments, heparin or a derivative thereof (e.g. LU 51198) is administered to a subject in need thereof. In certain instances, heparin interacts with $C_1$, C2, C3, C4, C5, C6, C7, C8, C9, C11NH, factor I, factor H, factor B and factor P. In certain instances, heparin partially or fully inhibits the formation of the alternative pathway C3 convertase (C3Bb) and the classical pathway C3 convertase (C4bC2a).

MAC Modulators

In some embodiments, an MAC modulator is administered to a subject in need thereof. In some embodiments, the MAC modulator is clusterin, vitronectin. In certain instances, clusterin partially or fully inhibits the formation of fluid-phase MAC. In certain instances, vitronectin partially or fully inhibits the formation of fluid-phase MAC.

MIF Modulators

In some embodiments, an MIF modulator is administered to a subject in need thereof. In some embodiments, the MIF modulator is an inhibitor and/or an antagonist of MIF. In some embodiments, an MIF modulator decreases inflammation. In some embodiments, an MIF modulator downregulates the production of a cytokine (e.g. TNF-α and IL-8). In some embodiments, an MIF modulator ameliorates the symptoms of OME. In some embodiments, the inhibitor and/or antagonist of MIF is an anti-MIF antibody. In certain instances, the administration of an anti-MIF antibody decreases the production of TNF-α and IL-8. In some embodiments, the inhibitor and/or antagonist of MIF is metformin. In certain instances, the administration of metformin decreases plasma MIF concentrations. In some embodiments, the inhibitor and/or antagonist of MIF is ISO-1 ((S,R)-3(4-hydroxyphenyl)-4,5-dihydro-5-isoxazole acetic acid methyl ester). In certain instances, the administration of an ISO-1 decreases the production of TNF-α and IL-8. In some embodiments, the inhibitor and/or antagonist of MIF is 2-[(4-hydroxybenzylidene)amino]-3(1H-indol-3-yl)propionic acid methyl ester. In some embodiments, the inhibitor and/or antagonist of MIF is NAPQI (N-acetyl-p-benzoquinone imine). In some embodiments, the inhibitor and/or antagonist of MIF is AVP-28225 (Avanir Pharmaceuticals).

Properdin Antibodies

In some embodiments, an anti-properdin antibody is administered to a subject in need thereof. In some embodiments, the anti-properdin antibody is a monoclonal antibody. In certain instances, an anti-properdin inhibits the stabilization of the alternative pathway unstable C3 convertase (C3Bb). In certain instances, an anti-properdin antibody inhibits the formation of the alternative pathway C5 convertase (C3BbC3). In certain instances, an anti-properdin antibody inhibits the formation of MAC.

Miscellaneous Complement Modulators

In some embodiments, the complement modulator is glycyrrhizin, glycyrrhetinic acid, or combinations thereof. In certain instances, glycyrrhetinic acid modulates C2 and thus modulates the formation of the classical pathway C3 convertase.

Concentration of Active Agent

In some embodiments, the concentration of an otic structure modulating agent or innate immune system modulating agent in a pharmaceutical composition or device described herein is about 1% by weight of the composition. In some embodiments, the concentration of an otic structure modulating agent or innate immune system modulating agent in a pharmaceutical composition or device described herein is about 2% by weight of the composition. In some embodiments, the concentration of an otic structure modulating agent or innate immune system modulating agent in a pharmaceutical composition or device described herein is about 3% by weight of the composition. In some embodiments, the concentration of an otic structure modulating agent or innate immune system modulating agent in a pharmaceutical composition or device described herein is about 4% by weight of the composition. In some embodiments, the concentration of an otic structure modulating agent or innate immune system modulating agent in a pharmaceutical composition or device described herein is about 5% by weight of the composition. In some embodiments, the concentration of an otic structure modulating agent or innate immune system modulating agent in a pharmaceutical composition or device described herein is about 10% by weight of the composition. In some embodiments, the concentration of an otic structure modulating agent or innate immune system modulating agent in a pharmaceutical composition or device described herein is about 15% by weight of the composition. In some embodiments, the concentration of an otic structure modulating agent or innate immune system modulating agent in a pharmaceutical composition or device described herein is about 20% by weight of the composition. In some embodiments, the concentration of an otic structure modulating agent or innate immune system modulating agent in a pharmaceutical composition or device described herein is about 25% by weight of the composition. In some embodiments, the concentration of an otic structure modulating agent or innate immune system modulating agent in a pharmaceutical composition or device described herein is about 30% by weight of the composition. In some embodiments, the concentration of an otic structure modulating agent or innate immune system modulating agent in a pharmaceutical composition or device described herein is about 40% by weight of the composition. In some embodiments, the concentration of an otic structure modulating agent or innate immune system modulating agent in a pharmaceutical composition or device described herein is about 50% by weight of the composition. In some embodiments, the concentration of an otic structure modulating agent or innate immune system modulating agent in a pharmaceutical composition or device described herein is about 60% by weight of the composition. In some embodiments, the concentration of an otic structure modulating agent or innate immune system modulating agent in a pharmaceutical composition or device described herein is about 70% by weight of the composition. In some embodiments, the concentration of an otic structure modulating agent or innate immune system modulating agent in a pharmaceutical composition or device described herein is about 80% by weight of the composition. In some embodiments, the concentration of an otic structure modulating agent or innate immune system modulating agent in a pharmaceutical composition or device described herein is about 90% by weight of the composition.

In some embodiments, the compositions described herein have a concentration of active pharmaceutical ingredient, or pharmaceutically acceptable prodrug or salt thereof, between about 0.1 to about 70 mg/mL, between about 0.5 mg/mL to about 70 mg/mL, between about 0.5 mg/mL to about 50 mg/mL, between about 0.5 mg/mL to about 20 mg/mL, between about 1 mg to about 70 mg/mL, between about 1 mg to about 50 mg/mL, between about 1 mg/mL and about 20 mg/mL, between about 1 mg/mL to about 10 mg/mL, or between about 1 mg/mL to about 5 mg/mL, of the active agent, or pharmaceutically acceptable prodrug or salt thereof, by volume of the composition.

Combination Therapy

In some embodiments, the formulations disclosed herein are administered in combination with an additional otic active agent. In some embodiments, the formulations disclosed herein are administered before, during, or after administration of an additional active agent. In some embodiments, the additional otic active agent is an antihistamine, GABA receptor modulator, a neurotransmitter reuptake inhibitor, an anticholinergic, a local anesthetic, an inhibitor of the MAPK/JNK cascade, a calcium channel blocker, a sodium channel blocker, an agonist of HO, an antagonist of a caspase, an antagonist of a calpain, a sirtuin agonist, an Src antagonist, a carbamate, a gamma-secretase inhibitor, a glutamate receptor modulator, a growth factor, an ototoxic agent, a thyroid hormone receptor modulator, a TRPV modulator, an antiemetic agent, an antimicrobial agent, an antiseptic agent, an antioxidant, a TNF antagonist, a TNF-α converting enzyme inhibitor, an IKK inhibitor, a calcineurin inhibitor, a toll-like receptor inhibitor, an interleukin inhibitor, a NOS inhibitor, a platelet activating factor antagonist, or combinations thereof.

In certain instances, the otic structure degrading agents and compositions disclosed herein facilitate the penetration of an otic active agent into the middle and/or inner ear by degrading otic structures (e.g. cells, lipid matrix, extracellular matrix, desmosome). In certain instances, a smaller dose of the additional active agent is administered to a subject in need thereof when the otic active agent is administered with the otic structure degrading agents and compositions disclosed herein. In certain instances, an improved pharmacokinetic profile for the otic active agent is obtained when the otic active agent is administered with the otic structure degrading agents and compositions disclosed herein.

Anticholinergics

Anticholinergics are optionally used with the formulations disclosed herein. Anticholinergics include glycopyrrolate, homatropine, scopolamine or atropine.

Anti-Emetic Agents

Anti-Emetic agents are optionally used in the formulations disclosed herein. Exemplary anti-emetic agents include promethazine, prochlorperazine, trimethobenzamide, and triethylperazine. Other anti-emetic agents include 5HT3 antagonists such as dolasetron, granisetron, ondansetron, tropisetron, and palonosetron; and neuroleptics such as droperidol. Further anti-emetic agents include antihistamines, such as meclizine; phenothiazines such as perphenazine, and thiethyl perazine; dopamine antagonists, including domperidone, properidol, haloperidol, chlorpromazine, promethazine, prochlorperazine, metoclopramide and combinations thereof, cannabinoids, including dronabinol, nabilone, sativex, and combinations thereof, anticholinergics, including scopolamine; and steroids, including dexamethasone; trimethobenzamine, emetrol, propofol, muscimol, and combinations thereof.

Antihistamines

Antihistamines are optionally used in the formulations disclosed herein. Antihistamines include, and are not limited to, meclizine, diphenhydramine, dimenhydrinate, loratadine, quetiapine, mepyramine, piperoxan, antazoline, carbinoxamine, doxylamine, clemastine, pheniramine, chlorphenamine, chlorpheniramine, dexchlorpheniramine, brompheniramine, triprolidine, cyclizine, chlorcyclizine, hydroxyzine, promethazine, alimemazine, trimeprazine, cyproheptadine, azatadine, ketotifen, oxatomide, betahistine dihydrochloride.

Antimicrobial Agents

Antimicrobial agents are also contemplated as useful with the formulations disclosed herein. Some examples of antimicrobial agents include agents that act to inhibit or eradicate microbes, including bacteria, fungi or parasites. Specific antimicrobial agents may be used to combat specific microbes. Accordingly, a skilled practitioner would know which antimicrobial agent would be relevant or useful depending on the microbe identified, or the symptoms displayed. Antimicrobial agents include antibiotics, antiviral agents, antifungal agents, and antiparasitic agents.

Antibiotics may also include amikacin, gentamicin, kanamycin, neomycin, netilmicin, streptomycin, tobramycin, paromomycin, geldanmycin, herbimycin, loracarbef, ertapenem, doripenem, imipenem, cilastatin, meropenem, cefadroxil, cefazolin, cefalotin, cefalexin, cefaclor, cefamandole, cefoxitin, defprozil, cefuroxime, cefixime, cefdinir, cefditoren, cefoperazone, cefotaxime, cefpodoxime, ceftazidime, ceftibuten, ceftizoxime, ceftriaxone, cefepime, ceftobiprole, teicoplanin, vancomycin, azithromycin, clarithromycin, dirithromycin, erythromycin, roxithromycin, troleandomycin, telithromycin, spectinomycin, aztreonam, amoxicillin, ampicillin, azlocillin, carbenicillin, cloxacillin, dicloxacillin, flucloxacillin, mezlocillin, meticillin, nafcillin, oxacillin, penicillin, piperacillin, ticarcillan, bacitracin, colistin, polymyxin B, ciprofloxacin, enoxacin, gatifloxacin, levofloxacin, lomefloxacin, moxifloxacin, norfloxacin, ofloxacin, trovfloxacin, mafenide, prontosil, sulfacetamide, sulfamethizole, sulfanimilimde, sulfsalazine, sulfsioxazole, trimethoprim, demeclocycline, doxycycline, minocycline, oxetetracycline, tetracycline, arsphenamine, chloramphenicol, clindamycin, lincomycin, ethambutol, fosfomycin, fusidic acid, furazolidone, isoniazid, linezolid, metronidazole, mupirocin, nitrofurantoin, platensimycin, pyrazinamide, quinuspristin/dalfopristin, rifampin, tinidazole, and combinations thereof.

Antiviral agents may include acyclovir, famciclovir and valacyclovir. Other antiviral agents include abacavir, aciclovir, adfovir, amantadine, amprenavir, arbidol, atazanavir, artipla, brivudine, cidofovir, combivir, edoxudine, efavirenz, emtricitabine, enfuvirtide, entecavir, fomvirsen, fosamprenavir, foscarnet, fosfonet, ganciclovir, gardasil, ibacitabine, immunovir, idoxuridine, imiquimod, indinavir, inosine, integrase inhibitors, interferons, including interferon type III, interferon type II, interferon type I, lamivudine, lopinavir, loviride, MK-0518, maraviroc, moroxydine, nelfinavir, nevirapine, nexavir, nucleoside analogues, oseltamivir, penciclovir, peramivir, pleconaril, podophyllotoxin, protease inhibitors, reverse transcriptase inhibitors, ribavirin, rimantadine, ritonavir, saquinavir, stavudine, tenofovir, tenofovir disoproxil, tipranavir, trifluridine, trizivir, tromantadine, truvada, valganciclovir, vicriviroc, vidarabine, viramidine, zalcitabine, zanamivir, zidovudine, and combinations thereof.

Antifungal agents may include ammolfine, utenafine, naftifine, terbinafine, flucytosine, fluconazole, itraconazole, ketoconazole, posaconazole, ravuconazole, voriconazole, clotrimazole, econazole, miconazole, oxiconazole, sulconazole, terconazole, tioconazole, nikkomycin Z, caspofungin, micafungin, anidulafungin, amphotericin B, liposomal nystastin, pimaricin, griseofulvin, ciclopirox olamine, haloprogin, tolnaftate, undecylenate, and combinations thereof.

Antiparasitic agents may include amitraz, amoscanate, avermectin, carbadox, diethylcarbamizine, dimetridazole, diminazene, ivermectin, macrofilaricide, malathion, mitaban, oxamniquine, permethrin, praziquantel, prantel pamoate, selamectin, sodium stibogluconate, thiabendazole, and combinations thereof.

Antioxidants

Antioxidants are also contemplated as being useful with the formulations disclosed herein are agents that modulate the degeneration of neurons and/or hair cells of the auris. Accordingly, some embodiments incorporate the use of antioxidants. In some embodiments, the antioxidant is vitamin C, N-acetylcysteine, vitamin E, Ebselen (2-phenyl-1,2-benzisoselenazol-3(2H)-one (also called PZ 51 or DR3305), L-methionine, Idebenone (2-(10-hydroxydecyl)-5,6-dimethoxy-3-methyl-cyclohexa-2,5-diene-1,4-dione).

Anti-Septic Agents

Anti-septic agents are also contemplated as useful with the formulations disclosed herein. Anti-septic agents include, but are not limited to, acetic acid, boric acid, gentian violet, hydrogen peroxide, carbamide peroxide, chlorhexidine, saline, mercurochrome, povidone iodine, polyhyroxine iodine, cresylate and aluminum acetate, and mixtures thereof.

Calcium Channel Blockers

Calcium channel blockers are optionally used with the formulations disclosed herein. Exemplary calcium channel blockers include verapamil, nimodipine, diltiazem, omega-conotoxin, GVIA, amlodipine, felodipine, lacidipine, mibefradil, NPPB (5-Nitro-2-(3-phenylpropylamino)benzoic Acid), flunarizine, or combinations thereof.

Caspase Antagonists

Caspase antagonists are optionally used in the formulations disclosed herein. Caspase antagonists include, but are not limited to, z-VAD-FMK (Benzyloxycarbonyl-Val-Ala-Asp(OMe)-fluoromethylketone); z-LEHD-FMK (benzyloxycarbonyl-Leu-Glu(OMe)-His-Asp(OMe)-fluoromethylketone); B-D-FMK (boc-aspartyl(Ome)-fluoromethylketone); Ac-LEHD-CHO(N-acetyl-Leu-Glu-His-Asp-CHO); Ac-IETD-CHO(N-acetyl-Ile-Glu-Thr-Asp-CHO); z-IETD-FMK (benzyloxycarbonyl-Ile-Glu(OMe)-Thr-Asp(OMe)-fluoromethylketone); FAM-LEHD-FMK (benzyloxycarbonyl Leu-Glu-His-Asp-fluoromethyl ketone); FAM-LETD-FMK (benzyloxycarbonyl Leu-Glu-Thr-Asp-fluoromethyl ketone); Q-VD-OPH (Quinoline-Val-Asp-$CH_2$—O-Ph); or combinations thereof.

Calcineurin Inhibitors

Calcineurin inhibitors are optionally used in the formulations disclosed herein. Some examples of calcineurin inhibitors include cyclosporine, tacrolimus and pimecrolimus.

Calpain Antagonists

Calpain antagonists are optionally used with the formulations disclosed herein. Calpain antagonists include, but are not limited to, leupeptine; PD-150606 (3-(4-Iodophenyl)-2-mercapto-(Z)-2-propenoic acid); MDL-28170 (Z-Val-Phe-CHO); calpeptin; acetyl-calpastatin; MG 132 (N-[(phenylmethoxy)carbonyl]-L-leucyl-N-[(1S)-1-formyl-3- methylbutyl]-L-leucinamide); MYODUR; BN 82270 (Ipsen); BN 2204 (Ipsen); or combinations thereof.

Carbamates

Carbamates are optionally used in the formulations disclosed herein. Examples of carbamates include 2-phenyl-1, 2-ethanediol monocarbomates and dicarbamates, derivatives thereof, and/or combinations thereof.

GABA Receptor Modulators

GABA Receptor Modulators are optionally used with the formulations disclosed herein. By way of example, GABA Receptor Modulators include alprazolam, bromazepam, brotizolam, chlordiazepoxide, clonazepam, clorazepate, diazepam, estazolam, flunitrazepam, flurazepam, loprazolam, lorazepam, lormetazepam, idazolam, nimetazepam, nitrazepam, oxazepam, prazepam, temazepam, triazolam, furosemide, bumetanide, ethacrynic acid, gabapentin, pregabalin, muscimol, or baclofen.

Gamma-Secretase Inhibitors

Gamma-Secretase Inhibitors are optionally used in the formulations disclosed herein. Gamma-Secretase Inhibitors include, but are not limited to, LY450139 (hydroxylvaleryl monobenzocaprolactam), L685458 (1S-benzyl-4R[1-[1-S-carbamoyl-2-phenethylcarbamoyl)-1S-3-methylbutylcarbamoyl]-2R-hydroxy-5-phenylpentyl}carbamic acid tert-butyl ester); LY411575 ($N^2$-[(2S)-2-(3,5-difluorophenyl)-2-hydroxyethanoyl]-$N^1$[(7S)-5-methyl-6-oxo-6,7-dihydro-5H-dibenzo[bid]azepin-7yl]-L-alaninamide), MK-0752 (Merck), tarenflurbil, and/or BMS-299897 (2-[(1R)-1-[[(4-chlorophenyl)sulfony](2,5-difluorophenyl)amino]ethyl]-5-fluorobenzenepropanoic acid).

Glutamate-Receptor Modulators

Glutamate receptor modulating agents are optionally used with the formulations disclosed herein. In some embodiments, glutamate receptor modulating agents include CNQX (6-cyano-7-nitroquinoxaline-2,3-dione); NBQX (2,3-dihydroxy-6-nitro-7-sulfamoyl-benzo[f]quinoxaline-2,3-dione); DNQX (6,7-dinitroquinoxaline-2,3-dione); kynurenic acid; 2,3-dihydroxy-6-nitro-7-sulfamoylbenzo-[f]quinoxaline; 1-aminoadamantane, dextromethorphan, dextrorphan, ibogaine, ketamine, nitrous oxide, phencyclidine, riluzole, tiletamine, memantine, dizocilpine, aptiganel, remacimide, 7-chlorokynurenate, DCKA (5,7-dichlorokynurenic acid), kynurenic acid, 1-aminocyclopropanecarboxylic acid (ACPC), AP7 (2-amino-7-phosphonoheptanoic acid); APV (R-2-amino-5-phosphonopentanoate), CPPene (3-[(R)-2-carboxypiperazin-4-yl]-prop-2-enyl-1-phosphonic acid); (+)-(1S,2S)-1-(4-hydroxy-phenyl)-2-(4-hydroxy-4-phenylpiperidino)-1-pro-panol; (1S,2S)-1-(4-hydroxy-3-methoxyphenyl)-2-(4-hydroxy-4-phenylpiperi-dino)-1-pro-panol; (3R,4S)-3-(4-(4-fluorophenyl)-4-hydroxypiperidin-1-yl-)-chroman-4,7-diol; (1R*,2R*)-1-(4-hydroxy-3-methylphenyl)-2-(4-(4-fluoro-phenyl)-4-hydroxypiperidin-1-yl)-propan-1-ol-mesylate; LY389795 ((−)-2-thia-4-aminobicyclo-hexane-4,6-dicarboxylate); LY379268 ((−)-2-oxa-4-aminobicyclo-hexane-4,6-dicarboxylate); LY354740 ((+)-2-aminobicyclo-hexane-2,6dicarboxylate); DCG-IV ((2S,2'R,3'R)-2-(2',3'-dicarboxycyclopropyl)glycine); 2R,4R-APDC (2R,4R-4-aminopyrrolidine-2,4-dicarboxylate), (S)-3C4HPG ((S)-3-carboxy-4-hydroxyphenylglycine); (S)-4C3HPG ((S)-4-carboxy-3-hydroxyphenylglycine); L-CCG-1 ((2S,1'S,2'S)-2-(carboxycyclopropyl)glycine); ACPT-1 ((1S,3R,4S)-1-aminocyclopentane-1,3,4-tricarboxylic acid); L-AP4 (L-(+)-2-Amino-4-phosphonobutyric acid); (S)-3,4-DCPG ((S)-3,4-dicarboxyphenylglycine); (RS)-3,4-DCPG ((RS)-3,4-dicarboxyphenylglycine); (RS)-4-phosphonophenylglycine ((RS)PPG); AMN082 (N'-bis(diphenylmethyl)-1,2-ethane-diamine dihydrochloride); DCG-IV ((2S,2'R,3'R)-2-(2',3'-dicarboxycyclopropyl)glycine); 3,5-Dimethylpyrrole-2,4-dicarboxylic acid 2-propyl ester 4-(1,2,2-trimethyl-propyl) ester (3,5-dimethyl PPP); 3,3'-difluorobenzaldazine (DFB), 3,3'-dimlethoxybenzaldazine (DMeOB), 3,3'-dichlorobenzaldazine (DCB) and other allosteric modulators of mGluR$_5$ disclosed in Mol. Pharmacol. 2003, 64, 731-740; (E)-6-methyl-2-(phenyldiazenyl)pyridin-3-ol (SIB 1757); (E)-2-methyl-6-styrylpyridine (SIB 1893); 2-methyl-6-(phenylethynyl)pyridine (MPEP), 2-methyl-4-((6-methylpyridin-2-yl)ethynyl)thiazole (MTEP); 7-(Hydroxyimino)cyclopropa[b]chromen-1-carboxylate ethyl ester (CPCCOEt), N-cyclohexyl-3-methylbenzo[d]thiazolo[3,2-a]imidazole-2-carboxamide (YM-298198), tricyclo[3.3.3.1]nonanyl quinoxaline-2-carboxamide (NPS 2390); 6-methoxy-N-(4-methoxyphenyl)quinazolin-4-amine (LY 456239); mGluR1 antagonists disclosed in WO2004/058754 and WO2005/009987; 2-(4-(2,3-dihydro-1H-inden-2-ylamino)-5,6,7,8-tetrahydroquinazolin-2-ylthio)ethanol; 3-(5-(pyridin-2-yl)-2H-tetrazol-2-yl)benzonitrile, 2-(2-methoxy-4-(4-(pyridin-2-yl)oxazol-2-yl)phenyl)acetonitrile; 2-(4-(benzo[d]oxazol-2-yl)-2-methoxyphenyl)acetonitrile; 6-(3-methoxy-4-(pyridin-2-yl)phenyl)imidazo[2,1-b]thiazole; (S)-(4-fluorophenyl)(3-(3-(4-fluorophenyl)-1,2,4-oxadiazol-5-yl) piperidin-1-yl)methanone (ADX47273) and/or combinations thereof.

Growth Factors

Growth factors are optionally used in the formulations disclosed herein. Exemplary growth factors include brain-derived neurotrophic factor (BDNF), ciliary neurotrophic factor (CNTF), glial cell-line derived neurotrophic factor (GDNF), neurotrophin-3, neurotrophin-4, and/or combinations thereof. In some embodiments, the growth factor is a fibroblast growth factor (FGF), an insulin-like growth factor (IGF), an epidermal growth factor (EGF), a platlet-derived growth factor (PGF) and/or agonists thereof.

HO-1 Agonists

Agoniosts of HO-1 are optionally used with the formulations disclosed herein. Agonists of HO-1 include, but are not limited to, piperine, hemin, and/or brazilin.

IKK Inhibitors

IKK inhibitors are optionally used in the formulations disclosed herein. Examples of IKK inhibitors include SPC-839, PS-1145, BMS-345541, and SC-514.

Interleukin Inhibitors

Interleukins inhibitors are optionally used with the formulations disclosed herein. In some embodiments, interleukin inhibitors include WS-4 (an antibody against IL-8); [Ser IL-8]$_{72}$; or [Ala IL-8]$_{77}$ (See U.S. Pat. No. 5,451,399 which is hereby incorporated by reference for disclosures relating to these peptides); IL-IRA; SB 265610 (N-(2-Bromophenyl)-N'-(7-cyano-1H-benzotriazol-4-yl)urea); SB 225002 (N-(2-Bromophenyl)-N'-(2-hydroxy-4-nitrophenyl)urea); SB203580 (4-(4-Fluorophenyl)-2-(4-methylsulfinyl phenyl)-5-(4-pyridyl) 1H-imidazole); SB272844 (GlaxoSmithKline); SB517785 (GlaxoSmithKline); SB656933 (GlaxoSmithKline); Sch527123 (2-hydroxy-N,N-dimethyl-3-{2-[[(R)-1-(5-methyl-furan-2-yl)-propyl]amino]-3,4-dioxo-cyclobut-1-enylamino}-benzamide); PD98059(2-(2-amino-3-methoxyphenyl)-4H-1-Benzopyran-4-one); reparixin; N-[4-chloro-2-hydroxy-3-(piperazine-1-sulfonyl)phenyl]-N'-(2-chloro-3-fluorophenyl)urea p-toluenesulfonate (See WO/2007/150016 which is hereby incorporated by reference for disclosures relating to this compound); sivelestat; bG31P (CXCL8((3-74))K11R/G31P); basiliximab; cyclosporin A; SDZ RAD (40-O-(2-hydroxyethyl)-rapamycin); FR235222 (Astellas Pharma); daclizumab; anakinra;

AF12198 (Ac-Phe-Glu-Trp-Thr-Pro-Gly-Trp-Tyr-Gln-L-azetidine-2-carbonyl-Tyr-Ala-Leu-Pro-Leu-NH2); or combinations thereof.

Local Anesthetics

Local anesthetics are optionally used with the formulations disclosed herein. Local anesthetics include, and are not limited to, benzocaine, carticaine, cinchocaine, cyclomethycaine, lidocaine, prilocalne, propxycaine, proparacaine, tetracaine, tocamide, and trimecaine.

MAPK/JNK Signaling Cascade Inhibitors

Inhibitors of the MAPK/JNK signaling cascade are optionally used with the formulations disclosed herein. Exemplary inhibitors of the MAPK/JNK signaling cascade include minocycline; SB-203580 (4-(4-Fluorophenyl)-2-(4-methylsulfinyl phenyl)-5-(4-pyridyl) 1H-imidazole); PD 169316 (4-(4-Fluorophenyl)-2-(4-nitrophenyl)-5-(4-pyridyl)-1H-imidazole); SB 202190 (4-(4-Fluorophenyl)-2-(4-hydroxyphenyl)-5-(4-pyridyl) 1H-imidazole); RWJ 67657 (4-[4-(4-fluorophenyl)-1-(3-phenylpropyl)-5-(4-pyridinyl)-1H-imidazol-2-yl]-3-butyn-1-ol); SB 220025 (5-(2-Amino-4-pyrimidinyl)-4-(4-fluorophenyl)-1-(4-piperidinyl)imidazole); or combinations thereof. Minocycline prevents the apoptosis of otic hair cells following treatment with the ototoxic antibiotic gentamicin by inhibiting the induction of p38 MAPK phosphorylation. In some embodiments, the agent which antagonizes the MAPK/JNK signaling cascade is D-JNKI-1 ((D)-hJIP$_{175-157}$-DPro-DPro-(D)-HIV-TAT$_{57-48}$), SP600125 (anthra[1,9-cd]pyrazol-6(2H)-one), JNK Inhibitor I ((L)-HIV-TAT$_{48-57}$-PP-JBD$_{20}$), JNK Inhibitor III ((L)-HIV-TAT$_{47-57}$-gaba-c-Junδ$_{33-57}$), AS601245 (1,3-benzothiazol-2-yl (2-[[2-(3-pyridinyl)ethyl]amino]-4 pyrimidinyl)acetonitrile), JNK Inhibitor VI (H$_2$N—RPKRPTTLNLF-NH$_2$), JNK Inhibitor VIII (N-(4-Amino-5-cyano-6-ethoxypyridin-2-yl)-2-(2,5-dimethoxyphenyl)acetamide), JNK Inhibitor IX (N-(3-Cyano-4,5,6,7-tetrahydro-1-benzothien-2-yl)-1-naphthamide), dicumarol (3,3'-Methylenebis(4-hydroxycoumarin)), SC-236 (4-[5-(4-chlorophenyl)-3-(trifluoromethyl)-1H-pyrazol-1-yl]benzene-sulfonamide), CEP-1347 (Cephalon), CEP-11004 (Cephalon); or combinations thereof.

Neurotransmitter Reuptake Inhibitors

Neurotransmitter Reuptake Inhibitors are optionally used in the formulations disclosed herein. By way of example only, Neurotransmitter Reuptake Inhibitors include amitriptyline, nortriptyline, trimipramine, fluoxetine, paroxetine, sertraline.

Nitric Oxide Synthase Inhibitors

Nitric oxide synthase (NOS) inhibitors are contemplated for use in the immunomodulating formulations disclosed herein. NOS inhibitors are also contemplated as inhibitors of bone modeling in the otic capsule. NOS inhibitors include, by way of example only, aminoguanidine, 1-Amino-2-hydroxyguanidine p-Toluensulfate, guanidinoethyldisulfide (GED), Bromocriptine Mesylate, Dexamethasone, N$^G$,N$^G$-Dimethyl-L-arginine, Dihydrochloride, Diphenyleneiodonium Chloride, 2-Ethyl-2-thiopseudourea, haloperidol, L-N$^5$-(1-Iminoethyl)ornithine, MEG, S-Methylisothiourea Sulfate (SMT), S-Methyl-L-thiocitrulline, N$^G$-Monoethyl-L-arginine, N-Monomethyl-D-arginine, N$^G$-Nitro-L-arginine Methyl Ester, L-NIL, N$^G$-Nitro-L-arginine (L-NNA), 7-Nitroindazole, nNOS Inhibitor I, 1,3-PBITU, L-Thiocitrulline, N$^G$-Propyl-L-arginine, SKF-525A, TRIM, N$^G$-nitro-L-arginine methyl ester (L-NAME), MTR-105, L-NMMA, BBS-2, ONO-1714 and combinations thereof.

Ototoxic Agents

Ototoxic agents are optionally used with the formulations disclosed herein. Exemplary ototoxic agents include aminoglycoside antibiotics (e.g. gentamicin, and amikacin), the macrolide antibiotics (e.g erythromycin), the glycopeptide antibiotics (e.g. vancomycin), the loop diuretics (e.g. furosemide) salicylic acid, and nicotine.

Platelet Activating Factor Antagonists

Platelet activating factor antagonists are also contemplated for use with the immunomodulating formulations disclosed herein. Platelet activating factor antagonists include, by way of example only, kadsurenone, phomactin G, ginsenosides, apafant (4-(2-chlorophenyl)-9-methyl-2[3 (4-morpholinyl)-3-propanol-1-yl[6H-thieno[3,2-[[[1.2.4]triazolo]4,3-1]]1.4]diazepine), A-85783, BN-52063, BN-52021, BN-50730 (tetrahedra-4,7,8,10 methyl-1 (chloro-1 phenyl)-6 (methoxy-4 phenyl-carbamoyl)-9 pyrido[4',3'-4,5]thieno[3,2-f]triazolo-1,2,4[4,3-a]diazepine-1,4), BN 50739, SM-12502, RP-55778, Ro 24-4736, SR27417A, CV-6209, WEB 2086, WEB 2170, 14-deoxyandrographolide, CL 184005, CV-3988, TCV-309, PMS-601, TCV-309 and combinations thereof.

Sirtuin Agonists

Sirtuin agonists are optionally used in the formulations disclosed herein. Examples of Sirtuin agonists include trans-stilbene, cis-stilbene, resveratrol, piceatannol, rhapontin, deoxyrhapontin, butein, chalcon; isoliquirtigen; butein; 4,2',4'-trihydroxychalcone; 3,4,2',4',6'-pentahydroxychalcone; flavone, morin, fisetin; luteolin; quercetin; kaempferol; apigenin; gossypetin; myricetin; 6-hydroxyapigenin; 5-hydroxyflavone; 5,7,3',4',5'-pentahydroxyflavone; 3,7,3',4',5'-pentahydroxyflavone; 3,6,3',4'-tetrahydroxyflavone; 7,3',4',5'-tetrahydroxyflavone; 3,6,2',4'-tetrahydroxyflavone; 7,4'-dihydroxyflavone; 7,8,3',4'-tetrahydroxyflavone; 3,6,2',3'-tetrahydroxyflavone; 4'-hydroxyflavone; 5-hydroxyflavone; 5,4'-dihydroxyflavone; 5,7-dihydroxyflavone; daidzein, genistein, naringenin; flavanone; 3,5,7,3',4'-pentahydroxyflavanone; pelargonidin chloride, cyanidin chloride, delphinidin chloride, (−)-epicatechin (Hydroxy Sites: 3,5,7,3',4'); (−)-catechin (Hydroxy Sites: 3,5,7,3',4'); (−)-gallocatechin (Hydroxy Sites: 3,5,7,3',4',5') (+)-catechin (Hydroxy Sites: 3,5,7,3',4'); (+)-epicatechin (Hydroxy Sites: 3,5,7,3',4'); Hinokitiol (b-Thujaplicin; 2-hydroxy-4-isopropyl-2,4,6-cycloheptatrien-1-one); L-(+)-Ergothioneine ((S)-a-Carboxy-2,3-dihydro-N,N,N-trimethyl-2-thioxo-1H-imidazole4-ethanaminium inner salt); Caffeic Acid Phenyl Ester; MCI-186 (3-Methyl-1-phenyl-2-pyrazolin-5-one); HBED (N,N'-Di-(2-hydroxybenzyl)ethylenediamine-N,N'-diacetic acid.H2O); Ambroxol (trans-4-(2-Amino-3,5-dibromobenzylamino)cyclohexane-HCl; and U-83836E ((−)-2-((4-(2,6-di-1-Pyrrolidinyl-4-pyrimidinyl)-1-piperzainyl) methyl)-3,4-dihydro-2,5,7,8-tetramethyl-2H-1-benzopyran-6-ol.2HCl); β-1'-5-methyl-nicotinamide-2'-deoxyribose; β-D-1'-5-methyl-nico-tinamide-2'-deoxyribofuranoside; β-1'-4,5-dimethyl-nicotinamide-2'-de-oxyribose; or β-D-1'-4,5-dimethyl-nicotinamide-2'-deoxyribofuranoside; dipyridamole, ZM 336372 (3-(dimethylamino)-N-[3-[(4-hydroxybenzoyl)-amino]-4-met hylphenyl]benzamide), camptothecin, coumestrol, nordihydroguaiaretic acid, esculetin, SRT-1720 (Sirtris), SRT-1460 (Sirtris), SRT-2183 (Sirtris), analogs thereof, or combinations thereof.

Sodium Channel Blockers

Sodium channel blocking agents are optionally used in the formulations disclosed herein. Sodium channel blocking agents include, but are not limited to, vinpocetine ((3a,16a)-Eburnamenine-14-carboxylic acid ethyl ester); sipatrigine (2-(4-Methylpiperazin-1-yl)-5-(2,3,5-trichlorophenyl)-pyrimidin-4-amine); amiloride (3,5-diamino-N-(aminoiminomethyl)-6-chloropyrazinecarbox amide hydrochloride); carbamazepine (5H-dibenzo[b,f]azepine-5-carboxamide);

TTX (octahydro-12-(hydroxymethyl)-2-imino-5,9:7,10a-dimethano-10aH-[1,3]dioxocino[6,5-d]pyrimidine-4,7,10,11,12-pen tol); RS100642 (1-(2,6-dimethyl-phenoxy)-2-ethylaminopropane hydrochloride); mexiletine ((1-(2,6-dimethylphenoxy)-2-aminopropane hydrochloride)); QX-314 (N-(2,6-Dimethylphenylcarbamoylmethyl)triethylammonium bromide); phenyloin (5,5-diphenylimidazolidine-2,4-dione); lamotrigine (6-(2,3-dichlorophenyl)-1,2,4-triazine-3,5-diamine); 4030W92 (2,4-diamino-5-(2,3-dichlorophenyl)-6-fluoromethylpyrimidine); BW1003C87 (5-(2,3,5-trichlorophenyl) pyrimidine-2,4-1.1 ethanesulphonate); QX-222 (2-[(2,6-dimethylphenyl)amino]-N,N,N-trimethyl-2-oxoetha niminium chloride); ambroxol (trans-4-[[(2-Amino-3,5-dibromophenyl)methyl]amino]cyclo hexanol hydrochloride); R56865 (N-[1-(4-(4-fluorophenoxy)butyl]-4-piperidinyl-N-methyl-2-benzo-thiazolamine); lubeluzole; ajmaline ((17R,21 alpha)-ajmalan-17,21-diol); procainamide (4-amno-N-(2-diethylaminoethyl) benzamide hydrochloride); flecainide; riluzoleor; or combinations thereof.

Src Antagonists

SRC antagonists are optionally used with the formulations disclosed herein. Src antagonists are also contemplated as modulators of bone remodeling in the otic capsule. SRC antagonists include, and are not limited to, 1-Naphthyl PP1 (1-(1,1-Dimethylethyl)-3-(1-naphthalenyl)-1H-pyrazolo[3,4-d]pyrimidin-4-amine); Lavendustin A (5-[[(2,5-Dihydroxyphenyl)methyl][(2-hydroxyphenyl)methyl]amino]-2-hydroxybenzoic acid); MNS (3,4-Methylenedioxy-b-nitrostyrene); PP1(1-(1,1-Dimethylethyl)-1-(4-methylphenyl)-1H-pyrazolo[3,4-d]pyrimidin-4-amine); PP2 (3-(4-chlorophenyl) 1-(1,1-dimethylethyl)-1H-pyrazolo[3,4-d]pyrimidin-4-amine); KX1-004 (Kinex); KX1-005 (Kinex); KX1-136 (Kinex); KX1-174 (Kinex); KX1-141 (Kinex); KX2-328 (Kinex); KX1-306 (Kinex); KX1-329 (Kinex); KX2-391 (Kinex); KX2-377 (Kinex); ZD4190 (Astra Zeneca; N-(4-bromo-2-fluorophenyl)-6-methoxy-7-(2-(1H-1,2,3-triazol-1-yl)ethoxy)quinazolin-4-amine); AP22408 (Ariad Pharmaceuticals); AP23236 (Ariad Pharmaceuticals); AP23451 (Ariad Pharmaceuticals); AP23464 (Ariad Pharmaceuticals); AZD0530 (Astra Zeneca); AZM475271 (M475271; Astra Zeneca); Dasatinib (N-(2-chloro-6-methylphenyl)-2-(6-(4-(2-hydroxyethyl)-piperazin-1-yl)-2-methylpyrimidin-4-ylamino) thiazole-5-carboxamide); GN963 (trans-4-(6,7-dimethoxyquinoxalin-2-ylamino)cyclohexanol sulfate); Bosutinib (4-((2,4-dichloro-5-methoxyphenyl)amino)-6-methoxy-7-(3-(4-methyl-1-piperazinyl)propoxy)-3-quinolinecarbonitrile); CPG-77675; or combinations thereof. For disclosure of additional antagonists of the Src family of kinases, see U.S. Pub. No. 2006/0172971, which is hereby incorporated by reference for those disclosures.

TACE Inhibitors

TACE inhibitors are optionally used in the formulations disclosed herein. Examples of TACE inhibitors include Nitroarginine analog A, GW3333, TMI-1, BMS-561392, DPC-3333, TMI-2, BMS-566394, TMI-005, apratastat, GW4459, W-3646, IK-682, GI-5402, GI-245402, BB-2983, DPC-A38088, DPH-067517, R-618, and CH-138.

Thyroid Hormone Receptor Modulation

Thyroid Hormone Receptor modulating agents are optionally used with the formulations disclosed herein. In some instances, Thyroid Hormone Receptor modulating agents include $T_3$ (3,5,3'-triiodo-L-thyronine); KB-141 (3,5-dichloro-4-(4'-hydroxy-3-isopropylphenoxy)phenylacetic acid); GC-1 (3,5-dimethyl-4-(4'-hydroxy-3'-isopropylbenzyl)-phenoxy acetic acid); GC-24 (3,5-dimethyl-4-(4'-hydroxy-3'-benzyl)benzylphenoxyacetic acid); sobetirome (QRX-431); 4-OH—PCB106 (4-OH-2',3,3',4',5'-pentachlorobiphenyl); MB07811 ((2R,4S)-4-(3-chlorophenyl)-2-[(3,5-dimethyl-4-(4-hydroxy-3-isopropylbenzyl)phenoxy) methyl]-2-oxido-[1,3,2]-dioxaphosphonane); MB07344 (3,5-dimethyl-4-(4-hydroxy-3-isopropylbenzyl)phenoxy) methylphosphonic acid); and combinations thereof. In certain instances, KB-141; GC-1; sobetirome; and GC-24 are selective for TRβ.

Toll-Like Receptor Inhibitors

Toll-like receptor (TLR) inhibitors are optionally used in the formulations disclosed herein. By way of example, TLR inhibitors include ST2 antibody; sST2-Fc (functional murine soluble ST2-human IgG1 Fc fusion protein; see Biochemical and Biophysical Research Communications, 29 Dec. 2006, vol. 351, no. 4, 940-946 which is herein incorporated by reference for disclosures related to sST2-Fc); CRX-526 (Corixa); lipid $IV_A$; RSLA (*Rhodobacter sphaeroides* lipid A); E5531 ((6-O-{2-deoxy-6-O-methyl-4-O-phosphono-3-O—[(R)-3-Z-dodec-5-endoyloxydecl]-2-[3-oxo-tetradecanoylamino]-β-O-phosphono-α-D-glucopyranose tetrasodium salt); E5564 (α-D-Glucopyranose,3-O-decyl-2-deoxy-6-O-[2-deoxy-3-O-[(3R)-3-methoxydecyl]-6-O-methyl-2-[[(11Z)-1-oxo-11-octadecenyl]amino]-4-O-phosphono-β-D-glucopyranosyl]-2-[(1,3-dioxotetradecyl) amino]-1-(dihydrogen phosphate), tetrasodium salt); compound 4a (hydrocinnamoyl-L-valyl pyrrolidine; see PNAS, Jun. 24, 2003, vol. 100, no. 13, 7971-7976 which is herein incorporated by reference for disclosures related to compound 4a); CPG 52364 (Coley Pharmaceutical Group); LY294002 (2-(4-Morpholinyl)-8-phenyl-4H-1-benzopyran-4-one); PD98059 (2-(2-amino-3-methoxyphenyl)-4H-1-Benzopyran-4-one); chloroquine; and an immune regulatory oligonucleotide (for disclosures relating to IROs see U.S. Patent Application Publication No. 2008/0089883).

TNF Antagonists

Anti-TNF agents are also contemplated as useful with the formulations disclosed herein. Anti-TNF agents are also contemplated as useful in modulation of bone remodeling in the otic capsule. Anti-TNF agents include, by way of example, etanercept (ENBREL®), infliximab (REMICADE®), adalimumab (HUMIRA®), and golimumab (CNTO 148), TNF receptors (pegylated soluble TNF receptor type 1; Amgen); TNF binding factors (Onercept; Serono); TNF antibodies (US Patent App. No. 2005/0123541; US Patent App. No. 2004/0185047); single domain antibodies against the p55 TNF receptor (US Patent App. No. 2008/00088713); soluble TNF receptors (US Patent App. No. 2007/0249538); fusion polypeptides binding to TNF (US Patent App. No. 2007/0128177); TNF-converting enzyme inhibitors (Skotnicki et al., Annual Reports in Medicinal Chemistry (2003), 38, 153-162); IKK inhibitors (Karin et al., Nature Reviews Drug Discovery (2004), 3, 17-26) and flavone derivatives (US Patent App. No. 2006/0105967), all of which are incorporated by reference for such disclosure.

Estrogen Receptor Modulators

Estrogen Receptor Modulators are optionally used in the formulations disclosed herein and are also contemplated as modulators of bone remodeling in the otic capsule. Estrogen receptor modulators include, and are not limited to, afimoxifene (4-hydroxytamoxifen); arzoxifene; bazedoxifene; clomifene; femarelle (DT56a); lasofoxifene; ormeloxifene; ospemifine; raloxifene; tamoxifen; GW5638; LY353381; ICI 182,780 (fulvestrant, FASLODEX®); isoflavones, and SR16234.

Bisphosphonates

Bisphosphonates are optionally used in the formulations disclosed herein. Bisphosphonates are contemplated as modulators of bone remodeling in the otic capsule. Examples of Bisphosphonates include Etidronate (DIDRONEL®); Clodronate (BONEFOS®); Tiludronate (SKELID®); Pamidronate (APD, AREDIA®); Neridronate; Olpadronate; Alendronate (FOSFAMAX®); Ibandronate (BONIVA®); Risedronate (ACTONEL®); Zoledronate (ZOMETA®).

Carbonic Anhydrase Inhibitors

Carbonic anhydrase inhibitors are optionally used in the formulations disclosed herein. Carbonic anhydrase inhibitors are also contemplated as modulators of bone remodeling in the otic capsule. Exemplary carbonic anhydrase inhibitors include Acetazolamide, Brinzolamide, Methazolamide, Dorzolamide, Sezolamide, Topiramate, MK-927, MK-417, and MK-507.

Matrix MetalloProteinase Modulators

Matrix metalloproteinase inhibitors are optionally used in the formulations disclosed herein. Matrix metalloproteinase inhibitors are also contemplated as modulators of bone remodeling in the otic capsule. Matrix metalloproteinase inhibitors include, and are not limited to, Ro 28-2653; MMI-166; MMI270 (CGS27023A), COL-3 (NSC-683551), PG-530742, S-3304, and ACZ885.

Cathepsin K Inhibitors and Protease Inhibitors

Cathepsin K inhibitors are optionally used in the formulations disclosed herein. Cathepsin K inhibitors and other protease inhibitors are also contemplated as modulators of bone remodeling in the otic capsule. Examples of Cathepsin K inhibitors include balicatib, odanacatib (MK-0822), CRA-013783/L-006235, AAE581, and MK886. Other protease inhibitors include, by way of example, Saquinavir (FORTOVASE®, INVIRASE®); Ritonavir (NORVIR®); Indinavir (CRIXIVAN®); Nelfinavir (VIRACEPT®); Amprenavir (AGENERASE®); Lopinavir (KALETRA®); Atazanavir (REYATAZ®); Fosamprenavir (LEXIVA®); Tipranavir (APTIVUS®); Darunavir (PREZISTA®) and cystatin B.

Leukotriene Inhibitors

Leukotriene inhibitors are optionally used in the formulations disclosed herein. Leukotriene inhibitors are also contemplated as modulators of bone remodeling in the otic capsule and include, by way of example, BAYX 1005, montelukast, zafirlukast, LY-171,883 (tomelukast), and zileuton.

Lipoxygenase Inhibitors and Protein Prenylation Inhibitors

Lipoxygenase inhibitors are optionally used in the formulations disclosed herein and are also contemplated as modulators of bone remodeling in the otic capsule. Lipoxygenase inhibitors include, and are not limited to, azelastine; diethylcarbamazine; nordihydroguaiaretic acid; zileuton; A63162; and A-64077. Other protein prenylation inhibitors are also contemplated as modulators of bone remodeling in the otic capsule including farnesyl transferase inhibitors R115777 (tipifarnib), BMS-214662, CP-609,754, and SCH66336 (lonafarnib).

RANKL Modulators

RANKL inhibitors are optionally used in the formulations disclosed herein and are contemplated as modulators of bone remodeling in the otic capsule. Exemplary RANKL modulators include denosumab (AMG-162), and SCIO-469.

Aromatase Inhibitors

Aromatase inhibitors are optionally used in the formulations disclosed herein and are contemplated as modulators of bone remodeling in the otic capsule. Aromatase inhibitors include, by way of example, 4OH androstenedione; AROMASIN® (exemestane); FEMARA® (letrozole); and ARIMIDEX® (anastrozole).

COX-2 Inhibitors

COX-2 inhibitors are optionally used in the formulations disclosed herein and are contemplated as modulators of bone remodeling in the otic capsule. Examples of COX-2 inhibitors include, and are not limited to, celecoxib (CELEBREX®), rofecoxib (VIOXX®), valdecoxib (BEXTRA®); aspirin; ibuprofen, meloxicam and naproxen.

Adenylyl Cyclase (AC) Modulators

AC inhibitors are optionally used in the formulations disclosed herein and are contemplated as modulators of bone remodeling in the otic capsule. AC modulators include hormones such as parathyroid hormone and analogues thereof including the analogues disclosed in U.S. Pat. No. 6,541,450, which is herein incorporated by reference.

Hormones

Hormones are optionally used in the formulations disclosed herein and are contemplated as modulators of bone remodeling in the otic capsule. Exemplary hormones include parathyroid hormone (PTH) and analogues thereof, vitamin D and analogues thereof; calcitonin; growth factors including IL-6, CSF; and estrogen.

PPAR γ Modulators

PPAR γ modulators are optionally used in the formulations disclosed herein and are contemplated as modulators of bone remodeling in the otic capsule. Non-limiting examples of PPAR γ modulators include rosiglitazone, pioglitazone, GW9662, SR-202, ciglitazone, troglitazone, GW1929, GW7647

RNAi

In some embodiments, where inhibition or down-regulation of a target is desired (e.g. genes in the MAPK/JNK cascade, caspase genes, Src genes, calpain genes, $Ca^{2+}$ channel genes), RNA interference may be utilized. In some embodiments, the agent that inhibits or down-regulates the target is an siRNA molecule. In certain instances, the siRNA molecule inhibits the transcription of a target by RNA interference (RNAi). In some embodiments, a double stranded RNA (dsRNA) molecule with sequences complementary to a target is generated (e.g by PCR). In some embodiments, a 20-25 bp siRNA molecule with sequences complementary to a target is generated. In some embodiments, the 20-25 bp siRNA molecule has 2-5 bp overhangs on the 3' end of each strand, and a 5' phosphate terminus and a 3' hydroxyl terminus. In some embodiments, the 20-25 bp siRNA molecule has blunt ends. For techniques for generating RNA sequences see Molecular Cloning: A Laboratory Manual, second edition (Sambrook et al., 1989) and Molecular Cloning: A Laboratory Manual, third edition (Sambrook and Russel, 2001), jointly referred to herein as "Sambrook"); Current Protocols in Molecular Biology (F. M. Ausubel et al., eds., 1987, including supplements through 2001); Current Protocols in Nucleic Acid Chemistry John Wiley & Sons, Inc., New York, 2000) which are hereby incorporated by reference for such disclosure.

In some embodiments, the dsRNA or siRNA molecule is incorporated into a controlled-release auris-acceptable microsphere or microparticle, hydrogel, liposome, or thermoreversible gel. In some embodiments, the auris-acceptable microsphere, hydrogel, liposome, paint, foam, in situ forming spongy material, nanocapsule or nanosphere or thermoreversible gel is injected into the inner ear. In some embodiments, the auris-acceptable microsphere or microparticle, hydrogel, liposome, or thermoreversible gel. In some embodiments, the auris-acceptable microsphere, hydrogel, liposome, paint, foam, in situ forming spongy material, nanocapsule or nanosphere or thermoreversible gel is injected into the cochlea, the organ of Corti, the vestibular labyrinth, or a combination thereof.

In certain instances, after administration of the dsRNA or siRNA molecule, cells at the site of administration (e.g. the cells of cochlea, organ of Corti, and/or the vestibular labyrinth) are transformed with the dsRNA or siRNA molecule. In certain instances following transformation, the dsRNA molecule is cleaved into multiple fragments of about 20-25 bp to yield siRNA molecules. In certain instances, the fragments have about 2 bp overhangs on the 3' end of each strand.

In certain instances, an siRNA molecule is divided into two strands (the guide strand and the anti-guide strand) by an RNA-induced Silencing Complex (RISC). In certain instances, the guide strand is incorporated into the catalytic component of the RISC (i.e. argonaute). In certain instances, the guide strand binds to a complementary target mRNA sequence. In certain instances, the RISC cleaves the target mRNA. In certain instances, the expression of the target gene is down-regulated.

In some embodiments, a sequence complementary to a target is ligated into a vector. In some embodiments, the sequence is placed between two promoters. In some embodiments, the promoters are orientated in opposite directions. In some embodiments, the vector is contacted with a cell. In certain instances, a cell is transformed with the vector. In certain instances following transformation, sense and anti-sense strands of the sequence are generated. In certain instances, the sense and anti-sense strands hybridize to form a dsRNA molecule which is cleaved into siRNA molecules. In certain instances, the strands hybridize to form an siRNA molecule. In some embodiments, the vector is a plasmid (e.g., pSUPER; pSUPER.neo; pSUPER.neo+gfp).

In some embodiments, the vector is incorporated into a controlled-release auris-acceptable microsphere or microparticle, hydrogel, liposome, or thermoreversible gel. In some embodiments, the auris-acceptable microsphere, hydrogel, liposome, paint, foam, in situ forming spongy material, nanocapsule or nanosphere or thermoreversible gel is injected into the inner ear. In some embodiments, the auris-acceptable microsphere or microparticle, hydrogel, liposome, or thermoreversible gel. In some embodiments, the auris-acceptable microsphere, hydrogel, liposome, paint, foam, in situ forming spongy material, nanocapsule or nanosphere or thermoreversible gel is injected into the cochlea, the organ of Corti, the vestibular labyrinth, or a combination thereof.

Statins

Statins (or HMG-CoA reductase inhibitors) are optionally used in the formulations disclosed herein and are contemplated as modulators of bone remodeling in the otic capsule. Statins include, by way of example, Atorvastatin (LIPITOR®, TORVAST®); Cerivastatin (LIPOBAY®, BAYCOL®); Fluvastatin (LESCOL®); Lovastatin (MEVACOR®, ALTOCOR®, ALTOPREV®); Mevastatin; Pitavastatin (LIVALO®, PITAVA®); Pravastatin (PRAVACHOL®, SELEKTINE®, LIPOSTAT®); Rosuvastatin (CRESTOR®); Simvastatin (ZOCOR®); Simvastatin+Ezetimibe (VYTORIN®); Lovastatin+Niacin (ADVICOR® Combination therapy); Atorvastatin+Amlodipine Besylate (CADUET® Combination therapy); Simvastatin+Niacin (SIMCOR® Combination therapy).

TRACP Modulators

TRACP modulators are optionally used in the formulations disclosed herein and are contemplated as modulators of bone remodeling in the otic capsule. TRACP modulators include, by way of example only, cystatin B.

TGF β Modulators

TGF β inhibitors are optionally used in the formulations disclosed herein and are contemplated as modulators of bone remodeling in the otic capsule. TGF β inhibitors include, and are not limited to, CAT-192 (Human Anti-TGF-Beta1 Monoclonal Antibody); GC1008 (human anti-transforming growth factor-beta (TGFβ) monoclonal antibody); and other small molecule modulators of TGF β disclosed in Yingling et al., Nature Reviews, 2004, 3, 1011-1022, which is incorporated by reference herein.

TRPV Modulation

TRPV modulating agents are optionally used with the formulations disclosed herein. Examples of TRPV modulating agents include capsaicin, resiniferatoxin, the TRPV modulators disclosed in US application publications 2005/0277643, 2005/0215572, 2006/0194801, 2006/0205773, 2006/0194801, 2008/0175794, 2008/0153857, 2008/0085901, 20080015183, 2006/0030618, 2005/0277646, 2005/0277631, 2005/0272931, 2005/0227986, 2005/0153984, 2006/0270682, 2006/0211741, 2006/0205980, and 2006/0100490, and/or combinations thereof.

Presented below (Table 1) are examples of active agents contemplated for use with the compositions and devices disclosed herein. In some embodiments, one or more active agents disclosed in Table 1 are used in a composition or device described herein.

TABLE 1

| Auris Condition | Therapeutic Agent |
| --- | --- |
| Benign Paroxysmal Positional Vertigo | Diphenhydramine |
| Benign Paroxysmal Positional Vertigo | Lorazepam |
| Benign Paroxysmal Positional Vertigo | Meclizine |
| Benign Paroxysmal Positional Vertigo | Oldansetron |
| Hearing Loss | Estrogen |
| AIED | Etanercept (Enbrel) |
| AIED | GW3333 |
| AIED | Copaxone |
| Hearing Loss | Estrogen and progesterone (E + P) |
| Hearing Loss | Folic acid |
| Hearing Loss | Lactated Ringer's with 0.03% Ofloxacin |
| Hearing Loss | Methotrexate |
| Hearing Loss | N-acetyl cysteine |
| Meniere's Disease | Betahistine |
| Meniere's Disease | Sildenafil |
| Meniere's Disease | Tacrolimus |
| Middle Ear Effusion | Pneumonococcal vaccine |
| Otitis Externa | Diclofenac sodium; dexotc |
| Otitis Externa, Acute | AL-15469A/AL-38905 |
| Otitis Media | Amoxicillin/clavulanate |
| Otitis Media | Dornase alfa |
| Otitis Media | *Echinacea purpurea* |
| Otitis Media | Faropenem medoxomil |
| Otitis Media | Levofloxacin |
| Otitis Media | PNCRM9 |
| Otitis Media | Pneumococcal vaccine |
| Otitis Media | Telithromycin |
| Otitis Media | Zmax |
| Otitis Media with Effusion | Lansoprazole |
| Otitis Media, Acute | AL-15469A; AL-38905 |
| Otitis Media, Acute | Amoxicillin |
| Otitis Media, Acute | Amoxicillin-clavulanate |
| Otitis Media, Acute | Azithromycin |

TABLE 1-continued

| Auris Condition | Therapeutic Agent |
|---|---|
| Otitis Media, Acute | Azithromycin SR |
| Otitis Media, Acute | Cefdinir |
| Otitis Media, Acute | Hyland's earache drops |
| Otitis Media, Acute | Montelukast |
| Otitis Media, Acute | Pneumonococcal vaccine |
| Otitis Media, Acute with Typanostomy Tubes | AL-15469A/AL38905 |
| Otitis Media, Chronic | Sulfamethoxazole-trimethoprim |
| Otitis Media, Suppurative | Azithromycin |
| Otitis Media, Suppurative | Telithromycin |
| Otosclerosis | Acetylcysteine |
| Ototoxicity | Aspirin |
| Tinnitus | Acamprosate |
| Tinnitus | Gabapentin |
| Tinnitus | Modafinil |
| Tinnitus | Neramexane |
| Tinnitus | Neramexane mesylate |
| Tinnitus | Piribedil |
| Tinnitus | Vardenafil |
| Tinnitus | Vestipitant + Paroxetine |
| Tinnitus | Vestiplitant |
| Tinnitus | Zinc sulfate |

In some embodiments, the additional therapeutic agent is an immediate release agent. In some embodiments, the additional therapeutic agent is a controlled-release agent.

General Methods of Sterilization

Provided herein are otic compositions that ameliorate or lessen otic disorders described herein. Further provided herein, in some embodiments, are methods comprising the administration of said otic compositions. In some embodiments, the compositions or devices are sterilized. Included within the embodiments disclosed herein are means and processes for sterilization of a pharmaceutical composition or device disclosed herein for use in humans. The goal is to provide a safe pharmaceutical product, relatively free of infection causing micro-organisms. The U. S. Food and Drug Administration has provided regulatory guidance in the publication "Guidance for Industry: Sterile Drug Products Produced by Aseptic Processing" which is incorporated herein by reference in its entirety.

As used herein, "sterilization" means a process used to destroy or remove microorganisms that are present in a product or packaging. Any suitable method available for sterilization of objects and compositions is contemplated for use with the compositions and devices disclosed herein. Available methods for the inactivation of microorganisms include, but are not limited to, the application of extreme heat, lethal chemicals, or gamma radiation. Disclosed herein, in some embodiments, are processes for the preparation of an otic therapeutic composition comprising subjecting the composition to a sterilization method selected from heat sterilization, chemical sterilization, radiation sterilization or filtration sterilization. The method used depends largely upon the nature of the device or composition to be sterilized. Detailed descriptions of many methods of sterilization are given in Chapter 40 of Remington: The Science and Practice of Pharmacy published by Lippincott, Williams & Wilkins, and is incorporated by reference with respect to this subject matter.

Sterilization by Heat

Many methods are available for sterilization by the application of extreme heat. One method is through the use of a saturated steam autoclave. In this method, saturated steam at a temperature of at least 121° C. is allowed to contact the object to be sterilized. The transfer of heat is either directly to the microorganism, in the case of an object to be sterilized, or indirectly to the microorganism by heating the bulk of an aqueous solution to be sterilized. This method is widely practiced as it allows flexibility, safety and economy in the sterilization process.

Dry heat sterilization is a method that is used to kill microorganisms and perform depyrogenation at elevated temperatures. This process takes place in an apparatus suitable for heating HEPA-filtered microorganism-free air to temperatures of at least 130-180° C. for the sterilization process and to temperatures of at least 230-250° C. for the depyrogenation process. Water to reconstitute concentrated or powdered compositions is also sterilized by autoclave. In some embodiments, the compositions described herein comprise micronized pharmaceutical that are sterilized by dry heating, e.g., heating for about 7-11 hours at internal powder temperatures of 130-140° C., or for 1-2 hours at internal temperatures of 150-180° C.

Chemical Sterilization

Chemical sterilization methods are an alternative for products that do not withstand the extremes of heat sterilization. In this method, a variety of gases and vapors with germicidal properties, such as ethylene oxide, chlorine dioxide, formaldehyde or ozone are used as the anti-apoptotic agents. The germicidal activity of ethylene oxide, for example, arises from its ability to serve as a reactive alkylating agent. Thus, the sterilization process requires the ethylene oxide vapors to make direct contact with the product to be sterilized.

Radiation Sterilization

One advantage of radiation sterilization is the ability to sterilize many types of products without heat degradation or other damage. The radiation commonly employed is beta radiation or alternatively, gamma radiation from a $^{60}$Co source. The penetrating ability of gamma radiation allows its use in the sterilization of many product types, including solutions, compositions and heterogeneous mixtures. The germicidal effects of irradiation arise from the interaction of gamma radiation with biological macromolecules. This interaction generates charged species and free radicals. Subsequent chemical reactions, such as rearrangements and cross-linking processes, result in the loss of normal function for these biological macromolecules. The compositions described herein are also optionally sterilized using beta irradiation.

Filtration

Filtration sterilization is a method used to remove but not destroy microorganisms from solutions. Membrane filters are used to filter heat-sensitive solutions. Such filters are thin, strong, homogenous polymers of mixed cellulosic esters (MCE), polyvinylidene fluoride (PVF; also known as PVDF), or polytetrafluoroethylene (PTFE) and have pore sizes ranging from 0.1 to 0.22 µm. Solutions of various characteristics are optionally filtered using different filter membranes. For example, PVF and PTFE membranes are well suited to filtering organic solvents while aqueous solutions are filtered through PVF or MCE membranes. Filter apparatus are available for use on many scales ranging from the single point-of-use disposable filter attached to a syringe up to commercial scale filters for use in manufacturing plants. The membrane filters are sterilized by autoclave or chemical sterilization. Validation of membrane filtration systems is performed following standardized protocols (Microbiological Evaluation of Filters for Sterilizing Liquids, Vol 4, No. 3. Washington, D.C.: Health Industry Manufacturers Association, 1981) and involve challenging the membrane filter with a known quantity (ca. $10^7$ cm$^2$) of unusually small microorganisms, such as Brevundimonas diminuta (ATCC 19146).

Pharmaceutical compositions are optionally sterilized by passing through membrane filters. Compositions comprising nanoparticles (U.S. Pat. No. 6,139,870) or multilamellar vesicles (Richard et al., International Journal of Pharmaceutics (2006), 312(1-2): 144-50) are amenable to sterilization by filtration through 0.22 m filters without destroying their organized structure.

In some embodiments, the methods disclosed herein comprise sterilizing the composition (or components thereof) by means of filtration sterilization. In another embodiment the auris-acceptable otic therapeutic agent composition comprises a particle wherein the particle composition is suitable for filtration sterilization. In a further embodiment said particle composition comprises particles of less than 300 nm in size, of less than 200 nm in size, of less than 100 nm in size. In another embodiment the auris-acceptable composition comprises a particle composition wherein the sterility of the particle is ensured by sterile filtration of the precursor component solutions. In another embodiment the auris-acceptable composition comprises a particle composition wherein the sterility of the particle composition is ensured by low temperature sterile filtration. In a further embodiment, low temperature sterile filtration is carried out at a temperature between 0 and 30° C., between 0 and 20° C., between 0 and 10° C., between 10 and 20° C., or between 20 and 30° C.

In another embodiment is a process for the preparation of an auris-acceptable particle composition comprising: filtering the aqueous solution containing the particle composition at low temperature through a sterilization filter; lyophilizing the sterile solution; and reconstituting the particle composition with sterile water prior to administration. In some embodiments, a composition described herein is manufactured as a suspension in a single vial composition containing the micronized active pharmaceutical ingredient. A single vial composition is prepared by aseptically mixing a sterile poloxamer solution with sterile micronized active ingredient (e.g., PD98059) and transferring the composition to sterile pharmaceutical containers. In some embodiments, a single vial containing a composition described herein as a suspension is resuspended before dispensing and/or administration.

In specific embodiments, filtration and/or filling procedures are carried out at about 5° C. below the gel temperature ($T_{gel}$) of a composition described herein and with viscosity below a theoretical value of 100 cP to allow for filtration in a reasonable time using a peristaltic pump.

In another embodiment the auris-acceptable otic therapeutic agent composition comprises a nanoparticle composition wherein the nanoparticle composition is suitable for filtration sterilization. In a further embodiment the nanoparticle composition comprises nanoparticles of less than 300 nm in size, of less than 200 nm in size, or of less than 100 nm in size. In another embodiment the auris-acceptable composition comprises a microsphere composition wherein the sterility of the microsphere is ensured by sterile filtration of the precursor organic solution and aqueous solutions. In another embodiment the auris-acceptable composition comprises a thermoreversible gel composition wherein the sterility of the gel composition is ensured by low temperature sterile filtration. In a further embodiment, the low temperature sterile filtration occurs at a temperature between 0 and 30° C., or between 0 and 20° C., or between 0 and 10° C., or between 10 and 20° C., or between 20 and 30° C. In another embodiment is a process for the preparation of an auris-acceptable thermoreversible gel composition comprising: filtering the aqueous solution containing the thermoreversible gel components at low temperature through a sterilization filter; lyophilizing the sterile solution; and reconstituting the thermoreversible gel composition with sterile water prior to administration.

In certain embodiments, the active ingredients are dissolved in a suitable vehicle (e.g. a buffer) and sterilized separately (e.g. by heat treatment, filtration, gamma radiation). In some instances, the active ingredients are sterilized separately in a dry state. In some instances, the active ingredients are sterilized as a suspension or as a colloidal suspension. The remaining excipients (e.g., fluid gel components present in auris compositions) are sterilized in a separate step by a suitable method (e.g. filtration and/or irradiation of a cooled mixture of excipients); the two solutions that are separately sterilized are then mixed aseptically to provide a final auris composition. In some instances, the final aseptic mixing is performed just prior to administration of a composition described herein.

In some instances, conventionally used methods of sterilization (e.g., heat treatment (e.g., in an autoclave), gamma irradiation, filtration) lead to irreversible degradation of polymeric components (e.g., thermosetting, gelling or mucoadhesive polymer components) and/or the active agent in the composition. In some instances, sterilization of an auris composition by filtration through membranes (e.g., 0.2 μM membranes) is not possible if the composition comprises thixotropic polymers that gel during the process of filtration.

Accordingly, provided herein are methods for sterilization of auris compositions that prevent degradation of polymeric components (e.g., thermosetting and/or gelling and/or mucoadhesive polymer components) and/or the active agent during the process of sterilization. In some embodiments, degradation of the active agent (e.g., any therapeutic otic agent described herein) is reduced or eliminated through the use of specific pH ranges for buffer components and specific proportions of gelling agents in the compositions. In some embodiments, the choice of an appropriate gelling agent and/or thermosetting polymer allows for sterilization of compositions described herein by filtration. In some embodiments, the use of an appropriate thermosetting polymer and an appropriate copolymer (e.g., a gelling agent) in combination with a specific pH range for the composition allows for high temperature sterilization of compositions described with substantially no degradation of the therapeutic agent or the polymeric excipients. An advantage of the methods of sterilization provided herein is that, in certain instances, the compositions are subjected to terminal sterilization via autoclaving without any loss of the active agent and/or excipients and/or polymeric components during the sterilization step and are rendered substantially free of microbes and/or pyrogens.

Microorganisms

Provided herein are auris-acceptable compositions or devices that ameliorate or lessen otic disorders described herein. Further provided herein are methods comprising the administration of said otic compositions. In some embodiments, the compositions or devices are substantially free of microorganisms. Acceptable sterility levels are based on applicable standards that define therapeutically acceptable otic compositions, including but not limited to United States Pharmacopeia Chapters <1111> et seq. For example, acceptable sterility levels include about 10 colony forming units (cfu) per gram of composition, about 50 cfu per gram of composition, about 100 cfu per gram of composition, about 500 cfu per gram of composition or about 1000 cfu per gram of composition. In some embodiments, acceptable sterility levels for compositions include less than 10 cfu/mL, less that 50 cfu/mL, less than 500 cfu/mL or less than 1000 cfu/mL microbial agents. In addition, acceptable sterility levels include the exclusion of specified objectionable microbiological agents. By way of example, specified objectionable microbiological agents include but are not limited to *Escherichia coli* (*E. coli*), *Salmonella* sp., *Pseudomonas aeruginosa* (*P. aeruginosa*) and/or other specific microbial agents.

Sterility of the auris-acceptable otic therapeutic agent composition is confirmed through a sterility assurance program in accordance with United States Pharmacopeia Chapters <61>, <62> and <71>. A key component of the sterility assurance quality control, quality assurance and validation process is the method of sterility testing. Sterility testing, by way of example only, is performed by two methods. The first is direct inoculation wherein a sample of the composition to be tested is added to growth medium and incubated for a period of time up to 21 days. Turbidity of the growth medium indicates contamination. Drawbacks to this method include the small sampling size of bulk materials that reduces sensitivity, and detection of microorganism growth based on a visual observation. An alternative method is membrane filtration sterility testing. In this method, a volume of product is passed through a small membrane filter paper. The filter paper is then placed into media to promote the growth of microorganisms. This method has the advantage of greater sensitivity as the entire bulk product is sampled. The commercially available Millipore Steritest sterility testing system is optionally used for determinations by membrane filtration sterility testing. For the filtration testing of creams or ointments Steritest filter system No. TLHVSL210 are used. For the filtration testing of emulsions or viscous products Steritest filter system No. TLAREM210 or TDAREM210 are used. For the filtration testing of pre-filled syringes Steritest filter system No. TTHASY210 are used. For the filtration testing of material dispensed as an aerosol or foam Steritest filter system No. TTHVA210 are used. For the filtration testing of soluble powders in ampoules or vials Steritest filter system No. TTHADA210 or TTHADV210 are used.

Testing for *E. coli* and *Salmonella* includes the use of lactose broths incubated at 30-35° C. for 24-72 hours, incubation in MacConkey and/or EMB agars for 18-24 hours, and/or the use of Rappaport medium. Testing for the detection of *P. aeruginosa* includes the use of NAC agar. United States Pharmacopeia Chapter <62> further enumerates testing procedures for specified objectionable microorganisms.

In certain embodiments, any controlled-release composition described herein has less than about 60 colony forming units (CFU), less than about 50 colony forming units, less than about 40 colony forming units, or less than about 30 colony forming units of microbial agents per gram of composition. In certain embodiments, the otic compositions described herein are formulated to be isotonic with the endolymph and/or the perilymph.

Endotoxins

Provided herein are otic compositions that ameliorate or lessen otic disorders described herein. Further provided herein are methods comprising the administration of said otic compositions. In some embodiments, the compositions or devices are substantially free of endotoxins. An additional aspect of the sterilization process is the removal of by-products from the killing of microorganisms (hereinafter, "Product"). The process of depyrogenation removes pyrogens from the sample. Pyrogens are endotoxins or exotoxins that induce an immune response. An example of an endotoxin is the lipopolysaccharide (LPS) molecule found in the cell wall of gram-negative bacteria. While sterilization procedures such as autoclaving or treatment with ethylene oxide kill the bacteria, the LPS residue induces a proinflammatory immune response, such as septic shock. Because the molecular size of endotoxins can vary widely, the presence of endotoxins is expressed in "endotoxin units" (EU). One EU is equivalent to 100 picograms of *E. coli* LPS. Humans can develop a response to as little as 5 EU/kg of body weight. The sterility is expressed in any units as recognized in the art. In certain embodiments, otic compositions described herein contain lower endotoxin levels (e.g. <4 EU/kg of body weight of a subject) when compared to conventionally acceptable endotoxin levels (e.g., 5 EU/kg of body weight of a subject). In some embodiments, the auris-acceptable otic therapeutic agent composition has less than about 5 EU/kg of body weight of a subject. In other embodiments, the auris-acceptable otic therapeutic agent composition has less than about 4 EU/kg of body weight of a subject. In additional embodiments, the auris-acceptable otic therapeutic agent composition has less than about 3 EU/kg of body weight of a subject. In additional embodiments, the auris-acceptable otic therapeutic agent composition has less than about 2 EU/kg of body weight of a subject.

In some embodiments, the auris-acceptable otic therapeutic agent composition or device has less than about 5 EU/kg of composition. In other embodiments, the auris-acceptable otic therapeutic agent composition has less than about 4 EU/kg of composition. In additional embodiments, the auris-acceptable otic therapeutic agent composition has less than about 3 EU/kg of composition. In some embodiments, the auris-acceptable otic therapeutic agent composition has less than about 5 EU/kg Product. In other embodiments, the auris-acceptable otic therapeutic agent composition has less than about 1 EU/kg Product. In additional embodiments, the auris-acceptable otic therapeutic agent composition has less than about 0.2 EU/kg Product. In some embodiments, the auris-acceptable otic therapeutic agent composition has less than about 5 EU/g of unit or Product. In other embodiments, the auris-acceptable otic therapeutic agent composition has less than about 4 EU/g of unit or Product. In additional embodiments, the auris-acceptable otic therapeutic agent composition has less than about 3 EU/g of unit or Product. In some embodiments, the auris-acceptable otic therapeutic agent composition has less than about 5 EU/mg of unit or Product. In other embodiments, the auris-acceptable otic therapeutic agent composition has less than about 4 EU/mg of unit or Product. In additional embodiments, the auris-acceptable otic therapeutic agent composition has less than about 3 EU/mg of unit or Product. In certain embodiments, otic compositions described herein contain from about 1 to about 5 EU/mL of composition. In certain embodiments, otic compositions described herein contain from about 2 to about 5 EU/mL of composition, from about 3 to about 5 EU/mL of composition, or from about 4 to about 5 EU/mL of composition.

In certain embodiments, otic compositions or devices described herein contain lower endotoxin levels (e.g. <0.5 EU/mL of composition) when compared to conventionally acceptable endotoxin levels (e.g., 0.5 EU/mL of composition). In some embodiments, the auris-acceptable otic therapeutic agent composition or device has less than about 0.5 EU/mL of composition. In other embodiments, the auris-acceptable otic therapeutic agent composition has less than about 0.4 EU/mL of composition. In additional embodiments, the auris-acceptable otic therapeutic agent composition has less than about 0.2 EU/mL of composition.

Pyrogen detection, by way of example only, is performed by several methods. Suitable tests for sterility include tests described in United States Pharmacopoeia (USP) <71> Sterility Tests (23rd edition, 1995). The rabbit pyrogen test and the *Limulus amebocyte* lysate test are both specified in the United States Pharmacopeia Chapters <85> and <151> (USP23/NF 18, Biological Tests, The United States Pharmacopeial Convention, Rockville, Md., 1995). Alternative pyrogen assays have been developed based upon the monocyte activation-cytokine assay. Uniform cell lines suitable for quality control applications have been developed and have demonstrated the ability to detect pyrogenicity in samples that have passed the rabbit pyrogen test and the *Limulus amebocyte* lysate test (Taktak et al, J. Pharm. Pharmacol. (1990), 43:578-82). In an additional embodiment, the auris-acceptable otic therapeutic agent composition is subject to depyrogenation. In a further embodiment, the process for the manufacture of the auris-acceptable otic therapeutic agent composition comprises testing the composition for pyrogenicity. In certain embodiments, the compositions described herein are substantially free of pyrogens.

pH and Practical Osmolarity

In some embodiments, an otic composition or device disclosed herein is formulated to provide an ionic balance that is compatible with inner ear fluids (e.g., endolymph and/or perilymph).

In certain instances, the ionic composition of the endolymph and perilymph regulate the electrochemical impulses of hair cells and thus hearing. In certain instances, changes in the conduction of electrochemical impulses along otic hair cells results in hearing loss. In certain instances, changes in the ionic balance of the endolymph or perilymph results in complete hearing loss. In certain instances, changes in the ionic balance of the endolymph or perilymph results in partial hearing loss. In certain instances, changes in the ionic balance of the endolymph or perilymph results in permanent hearing loss. In certain instances, changes in the ionic balance of the endolymph or perilymph results in temporary hearing loss.

In some embodiments, a composition or device disclosed herein is formulated in order to not disrupt the ionic balance of the endolymph. In some embodiments, a composition or device disclosed herein has an ionic balance that is the same as or substantially the same as the endolymph. In some embodiments, a composition or device disclosed herein does not does not disrupt the ionic balance of the endolymph so as to result in partial or complete hearing loss. In some embodiments, a composition or device disclosed herein does not does not disrupt the ionic balance of the endolymph so as to result in temporary or permanent hearing loss.

In some embodiments, a composition or device disclosed herein does not substantially disrupt the ionic balance of the perilymph. In some embodiments, a composition or device disclosed herein has an ionic balance that is the same as or substantially the same as the perilymph. In some embodiments, a composition or device disclosed herein does not result in partial or complete hearing loss as the composition or device does not disrupt the ionic balance of the perilymph. In some embodiments, a composition or device disclosed herein does not result in temporary or permanent hearing loss as the composition or device does not disrupt the ionic balance of the perilymph.

As used herein, "practical osmolarity/osmolality" or "deliverable osmolarity/osmolality" means the osmolarity/osmolality of a composition or device as determined by measuring the osmolarity/osmolality of the active agent and all excipients except the gelling and/or the thickening agent (e.g., polyoxyethylene-polyooxypropylene copolymers, carboxymethylcellulose or the like). The practical osmolarity of a composition or device disclosed herein is measured by a suitable method, e.g., a freezing point depression method as described in Viegas et. al., Int. J. Pharm., 1998, 160, 157-162. In some instances, the practical osmolarity of a composition or device disclosed herein is measured by vapor pressure osmometry (e.g., vapor pressure depression method) that allows for determination of the osmolarity of a composition or device at higher temperatures. In some instances, vapor pressure depression method allows for determination of the osmolarity of a composition or device comprising a gelling agent (e.g., a thermoreversible polymer) at a higher temperature wherein the gelling agent is in the form of a gel.

In some embodiments, the osmolarity at a target site of action (e.g., the perilymph) is about the same as the delivered osmolarity (i.e., osmolarity of materials that cross or penetrate the round window membrane) of a composition or device described herein. In some embodiments, a composition or device described herein has a deliverable osmolarity of about 150 mOsm/L to about 500 mOsm/L, about 250 mOsm/L to about 500 mOsm/L, about 250 mOsm/L to about 350 mOsm/L, about 280 mOsm/L to about 370 mOsm/L or about 250 mOsm/L to about 320 mOsm/L.

The practical osmolality of an otic composition or device disclosed herein is from about 100 mOsm/kg to about 1000 mOsm/kg, from about 200 mOsm/kg to about 800 mOsm/kg, from about 250 mOsm/kg to about 500 mOsm/kg, or from about 250 mOsm/kg to about 320 mOsm/kg, or from about 250 mOsm/kg to about 350 mOsm/kg or from about 280 mOsm/kg to about 320 mOsm/kg. In some embodiments, a composition or device described herein has a practical osmolarity of about 100 mOsm/L to about 1000 mOsm/L, about 200 mOsm/L to about 800 mOsm/L, about 250 mOsm/L to about 500 mOsm/L, about 250 mOsm/L to about 350 mOsm/L, about 250 mOsm/L to about 320 mOsm/L, or about 280 mOsm/L to about 320 mOsm/L.

The main cation present in the endolymph is potassium. In addition the endolymph has a high concentration of positively charged amino acids. The main cation present in the perilymph is sodium. In certain instances, the ionic composition of the endolymph and perilymph regulate the electrochemical impulses of hair cells. In certain instances, any change in the ionic balance of the endolymph or perilymph results in a loss of hearing due to changes in the conduction of electrochemical impulses along otic hair cells. In some embodiments, a composition disclosed herein does not disrupt the ionic balance of the perilymph. In some embodiments, a composition disclosed herein has an ionic balance that is the same as or substantially the same as the perilymph. In some embodiments, a composition disclosed herein does not disrupt the ionic balance of the endolymph. In some embodiments, a composition disclosed herein has an ionic balance that is the same as or substantially the same as the endolymph. In some embodiments, an otic composition described herein is formulated to provide an ionic balance that is compatible with inner ear fluids (e.g., endolymph and/or perilymph).

The endolymph and the perilymph have a pH that is close to the physiological pH of blood. The endolymph has a pH range of about 7.2-7.9; the perilymph has a pH range of about 7.2-7.4. The in situ pH of the proximal endolymph is about 7.4 while the pH of distal endolymph is about 7.9.

In some embodiments, the pH of a composition described herein is adjusted (e.g., by use of a buffer) to an endolymph-compatible pH range of about 5.5 to 9.0. In specific embodiments, the pH of a composition described herein is adjusted to a perilymph-suitable pH range of about 5.5 to about 9.0.

In some embodiments, the pH of a composition described herein is adjusted to a perilymph-suitable range of about 5.5 to about 8.0, about 6 to about 8.0 or about 6.6 to about 8.0. In some embodiments, the pH of a composition described herein is adjusted to a perilymph-suitable pH range of about 7.0-7.6.

In some embodiments, useful compositions also include one or more pH adjusting agents or buffering agents. Suitable pH adjusting agents or buffers include, but are not limited to acetate, bicarbonate, ammonium chloride, citrate, phosphate, pharmaceutically acceptable salts thereof and combinations or mixtures thereof.

In one embodiment, when one or more buffers are utilized in the compositions of the present disclosure, they are combined (e.g., with a pharmaceutically acceptable vehicle) and are present in the final composition (e.g., in an amount ranging from about 0.1% to about 20%, from about 0.5% to about 10%). In certain embodiments of the present disclosure, the amount of buffer included in the gel compositions are an amount such that the pH of the gel composition does not interfere with the body's natural buffering system.

In one embodiment, diluents are also used to stabilize compounds because they can provide a more stable environment. Salts dissolved in buffered solutions (that also can provide pH control or maintenance) are utilized as diluents in the art, including, but not limited to a phosphate buffered saline solution.

In some embodiments, any gel composition described herein has a pH that allows for sterilization (e.g., by filtration or aseptic mixing or heat treatment and/or autoclaving (e.g., terminal sterilization)) of a gel composition without degradation of the pharmaceutical agent or the polymers comprising the gel. In order to reduce hydrolysis and/or degradation of the otic agent and/or the gel polymer during sterilization, the buffer pH is designed to maintain pH of the composition in the 7-8 range during the process of sterilization (e.g., high temperature autoclaving).

In specific embodiments, any gel composition described herein has a pH that allows for terminal sterilization (e.g., by heat treatment and/or autoclaving) of a gel composition without degradation of the pharmaceutical agent or the polymers comprising the gel. For example, in order to reduce hydrolysis and/or degradation of the otic agent and/or the gel polymer during autoclaving, the buffer pH is designed to maintain pH of the composition in the 7-8 range at elevated temperatures. Any appropriate buffer is used depending on the otic agent used in the composition. In some instances, since $pK_a$ of TRIS decreases as temperature increases at approximately $-0.03/°$ C. and $pK_a$ of PBS increases as temperature increases at approximately $0.003/°$ C., autoclaving at 250° F. (121° C.) results in a significant downward pH shift (i.e. more acidic) in the TRIS buffer whereas a relatively much less upward pH shift in the PBS buffer and therefore much increased hydrolysis and/or degradation of an otic agent in TRIS than in PBS. Degradation of an otic agent is reduced by the use of an appropriate combination of a buffer and polymeric additives (e.g. P407, CMC) as described herein.

In some embodiments, a composition pH of between about 5.0 and about 9.0, between about 5.5 and about 8.5, between about 6.0 and about 7.6, between about 7 and about 7.8, between about 7.0 and about 7.6, between about 7.2 and 7.6, or between about 7.2 and about 7.4 is suitable for sterilization (e.g., by filtration or aseptic mixing or heat treatment and/or autoclaving (e.g., terminal sterilization)) of auris compositions described herein. In specific embodiments a composition pH of about 6.0, about 6.5, about 7.0, about 7.1, about 7.2, about 7.3, about 7.4, about 7.5, or about 7.6 is suitable for sterilization (e.g., by filtration or aseptic mixing or heat treatment and/or autoclaving (e.g., terminal sterilization)) of any composition described herein.

In some embodiments, the compositions have a pH as described herein, and include a thickening agent (e.g., a viscosity enhancing agent) such as, by way of non-limiting example, a cellulose based thickening agent described herein. In some instances, the addition of a secondary polymer (e.g., a thickening agent) and a pH of composition as described herein, allows for sterilization of a composition described herein without any substantial degradation of the otic agent and/or the polymer components in the otic composition. In some embodiments, the ratio of a thermoreversible poloxamer to a thickening agent in a composition that has a pH as described herein, is about 40:1, about 35:1, about 30:1, about 25:1, about 20:1, about 15:1 about 10:1, or about 5:1. For example, in certain embodiments, a sustained and/or extended release composition described herein comprises a combination of poloxamer 407 (pluronic F127) and carboxymethylcellulose (CMC) in a ratio of about 40:1, about 35:1, about 30:1, about 25:1, about 20:1, about 15:1, about 10:1 or about 5:1.

In some embodiments, the amount of thermoreversible polymer in any composition described herein is about 10%, about 15%, about 20%, about 25%, about 30%, about 35% or about 40% of the total weight of the composition. In some embodiments, the amount of thermoreversible polymer in any composition described herein is about 10%, about 11%, about 12%, about 13%, about 14%, about 15%, about 16%, about 17%, about 18%, about 19%, about 20%, about 21%, about 22%, about 23%, about 24% or about 25% of the total weight of the composition. In some embodiments, the amount of thermoreversible polymer (e.g., pluronic F127) in any composition described herein is about 7.5% of the total weight of the composition. In some embodiments, the amount of thermoreversible polymer (e.g., pluronic F127) in any composition described herein is about 10% of the total weight of the composition.

In some embodiments, the amount of thermoreversible polymer (e.g., pluronic F127) in any composition described herein is about 11% of the total weight of the composition. In some embodiments, the amount of thermoreversible polymer (e.g., pluronic F127) in any composition described herein is about 12% of the total weight of the composition. In some embodiments, the amount of thermoreversible polymer (e.g., pluronic F127) in any composition described herein is about 13% of the total weight of the composition. In some embodiments, the amount of thermoreversible polymer (e.g., pluronic F127) in any composition described herein is about 14% of the total weight of the composition. In some embodiments, the amount of thermoreversible polymer (e.g., pluronic F127) in any composition described herein is about 15% of the total weight of the composition. In some embodiments, the amount of thermoreversible polymer (e.g., pluronic F127) in any composition described herein is about 16% of the total weight of the composition. In some embodiments, the amount of thermoreversible polymer (e.g., pluronic F127) in any composition described herein is about 17% of the total weight of the composition. In some embodiments, the amount of thermoreversible polymer (e.g., pluronic F127) in any composition described herein is about 18% of the total weight of the composition. In some embodiments, the amount of thermoreversible polymer (e.g., pluronic F127) in any composition described herein is about 19% of the total weight of the composition. In some embodiments, the amount of thermoreversible polymer (e.g., pluronic F127) in any composition described herein is about 20% of the total weight of the composition. In some embodiments, the amount of thermoreversible polymer (e.g., pluronic F127) in any composition described herein is about 21% of the total weight of the composition. In some embodiments, the amount of thermoreversible polymer (e.g., pluronic F127) in any composition described herein is about 23% of the total weight of the composition. In some embodiments, the amount of thermoreversible polymer (e.g., pluronic F127) in any composition described herein is about 25% of the total weight of the composition.

In some embodiments, the amount of thickening agent (e.g., a gelling agent) in any composition described herein is about 1%, about 5%, about 10%, or about 15% of the total weight of the composition. In some embodiments, the amount of thickening agent (e.g., a gelling agent) in any composition described herein is about 0.5%, about 1%, about 1.5%, about 2%, about 2.5%, about 3%, about 3.5%, about 4%, about 4.5%, or about 5% of the total weight of the composition.

In some embodiments, the pharmaceutical compositions described herein are stable with respect to pH over a period of any of at least about 1 day, at least about 2 days, at least about 3 days, at least about 4 days, at least about 5 days, at least about 6 days, at least about 1 week, at least about 2 weeks, at least about 3 weeks, at least about 4 weeks, at least about 5 weeks, at least about 6 weeks, at least about 7 weeks, at least about 8 weeks, at least about 1 month, at least about 2 months, at least about 3 months, at least about 4 months, at least about 5 months, or at least about 6 months. In other embodiments, the compositions described herein are stable with respect to pH over a period of at least about 1 week. Also described herein are compositions that are stable with respect to pH over a period of at least about 1 month.

Tonicity Agents

In general, the endolymph has a higher osmolality than the perilymph. For example, the endolymph has an osmolality of about 304 mOsm/kg $H_2O$ while the perilymph has an osmolality of about 294 mOsm/kg $H_2O$. In certain embodiments, tonicity agents are added to the compositions described herein in an amount as to provide a practical osmolality of an otic composition of about 100 mOsm/kg to about 1000 mOsm/kg, from about 200 mOsm/kg to about 800 mOsm/kg, from about 250 mOsm/kg to about 500 mOsm/kg, or from about 250 mOsm/kg to about 350 mOsm/kg or from about 280 mOsm/kg to about 320 mOsm/kg. In some embodiments, the compositions described herein have a practical osmolarity of about 100 mOsm/L to about 1000 mOsm/L, about 200 mOsm/L to about 800 mOsm/L, about 250 mOsm/L to about 500 mOsm/L, about 250 mOsm/L to about 350 mOsm/L, about 280 mOsm/L to about 320 mOsm/L or about 250 mOsm/L to about 320 mOsm/L.

In some embodiments, the deliverable osmolarity of any composition described herein is designed to be isotonic with the targeted otic structure (e.g., endolymph, perilymph or the like). In specific embodiments, auris compositions described herein are formulated to provide a delivered perilymph-suitable osmolarity at the target site of action of about 250 to about 320 mOsm/L (osmolality of about 250 to about 320 mOsm/kg $H_2O$); and preferably about 270 to about 320 mOsm/L (osmolality of about 270 to about 320 mOsm/kg $H_2O$). In specific embodiments, the deliverable osmolarity/osmolality of the compositions (i.e., the osmolarity/osmolality of the composition in the absence of gelling or thickening agents (e.g., thermoreversible gel polymers)) is adjusted, for example, by the use of appropriate salt concentrations (e.g., concentration of potassium or sodium salts) or the use of tonicity agents that renders the compositions endolymph-compatible and/or perilymph-compatible (i.e. isotonic with the endolymph and/or perilymph) upon delivery at the target site. The osmolarity of a composition comprising a thermoreversible gel polymer is an unreliable measure due to the association of varying amounts of water with the monomeric units of the polymer. The practical osmolarity of a composition is a reliable measure and is measured by any suitable method (e.g., freezing point depression method, vapor depression method). In some instances, the compositions described herein provide a deliverable osmolarity (e.g., at a target site (e.g., perilymph)) that causes minimal disturbance to the environment of the inner ear and causes minimum discomfort (e.g., vertigo and/or nausea) to a mammal upon administration.

In some embodiments, any composition described herein is isotonic with the perilymph and/or endolymph. Isotonic compositions are provided by the addition of a tonicity agent. Suitable tonicity agents include, but are not limited to any pharmaceutically acceptable sugar, salt or any combinations or mixtures thereof, such as, but not limited to dextrose, glycerin, mannitol, sorbitol, sodium chloride, and other electrolytes.

Useful auris compositions include one or more salts in an amount required to bring osmolality of the composition into an acceptable range. Such salts include those having sodium, potassium or ammonium cations and chloride, citrate, ascorbate, borate, phosphate, bicarbonate, sulfate, thiosulfate or bisulfite anions; suitable salts include sodium chloride, potassium chloride, sodium thiosulfate, sodium bisulfite and ammonium sulfate.

In some embodiments, the compositions described herein have a pH and/or practical osmolarity as described herein, and have a concentration of active pharmaceutical ingredient between about 1 μM and about 10 μM, between about 1 mM and about 100 mM, between about 0.1 mM and about 100 mM, between about 0.1 mM and about 100 nM. In some embodiments, the compositions described herein have a pH and/or practical osmolarity as described herein, and have a concentration of active pharmaceutical ingredient between about 0.01%-about 20%, between about 0.01%-about 10%, between about 0.01%-about 7.5%, between about 0.01%-6%, between about 0.01-5%, between about 0.1-about 10%, or between about 0.1-about 6% of the active ingredient by weight of the composition. In some embodiments, the compositions described herein have a pH and/or practical osmolarity as described herein, and have a concentration of active pharmaceutical ingredient between about 0.1 and about 70 mg, between about 1 mg and about 70 mg/mL, between about 1 mg and about 50 mg/mL, between about 1 mg/mL and about 20 mg/mL, between about 1 mg/mL to about 10 mg/mL, between about 1 mg/mL to about 5 mg/mL, or between about 0.5 mg/mL to about 5 mg/mL of the active agent by volume of the composition. In some embodiments, the compositions described herein have a pH and/or practical osmolarity as described herein, and have a concentration of active pharmaceutical ingredient between about 1 μg/mL and about 500 μg/mL, between about 1 μg/mL and about 250 μg/mL, between about 1 μg and about 100 μg/mL, between about 1 μg/mL and about 50 μg/mL, or between about 1 μg/mL and about 20 μg/mL of the active agent by volume of the composition.

Particle Size

Size reduction is used to increase surface area and/or modulate composition dissolution properties. It is also used to maintain a consistent average particle size distribution (PSD) (e.g., micrometer-sized particles, nanometer-sized particles or the like) for any composition described herein. In some embodiments, any composition described herein is multiparticulate (i.e., comprises a plurality of particle sizes (e.g., micronized particles, nano-sized particles, non-sized particles, colloidal particles)).

In some embodiments, any composition described herein comprises one or more multiparticulate (e.g., micronized) therapeutic agents. Micronization is a process of reducing the average diameter of particles of a solid material. Micronized particles are from about micrometer-sized in diameter to about nanometer-sized in diameter. In some embodiments, the average diameter of particles in a micronized solid is from about 0.5 µm to about 500 µm. In some embodiments, the average diameter of particles in a micronized solid is from about 1 µm to about 200 µm. In some embodiments, the average diameter of particles in a micronized solid is from about 2 µm to about 100 µm. In some embodiments, the average diameter of particles in a micronized solid is from about 3 µm to about 50 µm. In some embodiments, a particulate micronized solid comprises particle sizes of less than about 5 microns, less than about 20 microns and/or less than about 100 microns. In some embodiments, the use of particulates (e.g., micronized particles) of an otic structure modulating agent or innate immune system modulating agent allows for extended and/or sustained release of the otic structure modulating agent or innate immune system modulating agent from any composition described herein compared to a composition comprising non-multiparticulate (e.g., non-micronized) otic structure modulating agent or innate immune system modulating agent. In some instances, compositions containing multiparticulate (e.g. micronized) otic structure modulating agent or innate immune system modulating agent are ejected from a 1 mL syringe adapted with a 27G needle without any plugging or clogging.

In some instances, any particle in any composition described herein is a coated particle (e.g., a coated micronized particle, nano-particle) and/or a microsphere and/or a liposomal particle. Particle size reduction techniques include, by way of example, grinding, milling (e.g., air-attrition milling (jet milling), ball milling), coacervation, complex coacervation, high pressure homogenization, spray drying and/or supercritical fluid crystallization. In some instances, particles are sized by mechanical impact (e.g., by hammer mills, ball mill and/or pin mills). In some instances, particles are sized via fluid energy (e.g., by spiral jet mills, loop jet mills, and/or fluidized bed jet mills). In some embodiments, compositions described herein comprise crystalline particles and/or isotropic particles. In some embodiments, compositions described herein comprise amorphous particles and/or anisotropic particles. In some embodiments, compositions described herein comprise therapeutic agent particles wherein the therapeutic agent is a neutral molecule, a free acid, a free base, or a salt, or a prodrug of a therapeutic agent, or any combination thereof.

In some embodiments, a composition described herein comprises an otic structure modulating agent or innate immune system modulating agents wherein the otic structure modulating agent or innate immune system modulating agent comprises nanoparticulates. In some embodiments, a composition described herein comprises otic structure modulating agent or innate immune system modulating agent beads (e.g., tacrolimus beads) that are optionally coated with controlled-release excipients. In some embodiments, a composition described herein comprises an otic structure modulating agent or innate immune system modulating agent that is granulated and/or reduced in size and coated with controlled-release excipients; the granulated coated otic structure modulating agent or innate immune system modulating agent particulates are then optionally micronized and/or formulated in any of the compositions described herein.

In some instances, a combination of an otic structure modulating agent or innate immune system modulating agent as a neutral molecule, a free acid, a free base and a salt of the otic structure modulating agent or innate immune system modulating agent is used to prepare pulsed release otic agent compositions using the procedures described herein. In some compositions, a combination of a micronized otic structure modulating agent or innate immune system modulating agent (and/or salt or prodrug thereof) and coated particles (e.g., nanoparticles, liposomes, microspheres) is used to prepare pulsed release otic agent compositions using any procedure described herein. Alternatively, a pulsed release profile is achieved by solubilizing up to 20% of the delivered dose of the otic structure modulating agent or innate immune system modulating agent (e.g., micronized otic structure modulating agent or innate immune system modulating agent, a neutral molecule, free base, free acid or salt or prodrug thereof, multiparticulate otic structure modulating agent or innate immune system modulating agent, a neutral molecule, a free base, free acid or salt or prodrug thereof) with the aid of cyclodextrins, surfactants (e.g., poloxamers (407, 338, 188), tween (80, 60, 20, 81), PEG-hydrogenated castor oil, cosolvents like N-methyl-2-Pyrrolidone or the like and preparing pulsed release compositions using any procedure described herein.

In specific embodiments, any auris-compatible composition described herein comprises one or more micronized pharmaceutical agents (e.g., otic structure modulating agent or innate immune system modulating agents). In some of such embodiments, a micronized pharmaceutical agent comprises micronized particles, coated (e.g., with an extended release coat) micronized particles, or a combination thereof. In some of such embodiments, a micronized pharmaceutical agent comprising micronized particles, coated micronized particles, or a combination thereof, comprises an otic structure modulating agent or innate immune system modulating agent as a neutral molecule, a free acid, a free base, a salt, a prodrug or any combination thereof. In certain embodiments, a pharmaceutical composition described herein comprises an otic structure modulating agent or innate immune system modulating agent as a micronized powder.

The multiparticulates and/or micronized otic structure modulating agent or innate immune system modulating agents described herein are delivered to an auris structure (e.g., inner ear) by means of any type of matrix including solid, liquid or gel matrices. In some embodiments, the multiparticulates and/or micronized otic structure modulating agent or innate immune system modulating agents described herein are delivered to an auris structure (e.g., inner ear) by means of any type of matrix including solid, liquid or gel matrices via intratympanic injection.

Pharmaceutical Compositions

Provided herein are pharmaceutical compositions or devices that include an otic structure modulating agent or innate immune system modulating agent and a pharmaceutically acceptable diluent(s), excipient(s), or carrier(s). In some embodiments, the pharmaceutical compositions include other medicinal or pharmaceutical agents, carriers, adjuvants, such as preserving, stabilizing, wetting or emulsifying agents, solution promoters, salts for regulating the osmotic pressure, and/or buffers. In other embodiments, the pharmaceutical compositions also contain other therapeutic substances.

Some pharmaceutical excipients, diluents or carriers are potentially ototoxic. For example, benzalkonium chloride, a common preservative, is ototoxic and therefore potentially harmful if introduced into the vestibular or cochlear structures. In formulating a controlled-release otic structure modulating composition, it is advised to avoid or combine the appropriate excipients, diluents or carriers to lessen or eliminate potential ototoxic components from the composition, or to decrease the amount of such excipients, diluents or carriers. Optionally, a controlled-release otic structure modulating composition includes otoprotective agents, such as antioxidants, alpha lipoic acid, calcium, fosfomycin or iron chelators, to counteract potential ototoxic effects that may arise from the use of specific therapeutic agents or excipients, diluents or carriers.

In some embodiments, the compositions or devices described herein include a dye to help enhance the visualization of the gel when applied. In some embodiments, dyes that are compatible with the auris-acceptable compositions or devices described herein include Evans blue (e.g., 0.5% of the total weight of an otic composition), Methylene blue (e.g., 1% of the total weight of an otic composition), Isosulfan blue (e.g., 1% of the total weight of an otic composition), Trypan blue (e.g., 0.15% of the total weight of an otic composition), and/or indocyanine green (e.g., 25 mg/vial). Other common dyes, e.g., FD&C red 40, FD&C red 3, FD&C yellow 5, FD&C yellow 6, FD&C blue 1, FD&C blue2, FD&C green 3, fluorescence dyes (e.g., Fluorescein isothiocyanate, rhodamine, Alexa Fluors, DyLight Fluors) and/or dyes that are visualizable in conjunction with non-invasive imaging techniques such as MRI, CAT scans, PET scans or the like. Gadolinium-based MRI dyes, iodine-base dyes, barium-based dyes or the like are also contemplated for use with any otic composition described herein. Other dyes that are compatible with any composition described herein are listed in the Sigma-Aldrich catalog under dyes (that is included herein by reference for such disclosure).

Any pharmaceutical composition or device described herein is administered by locating the composition or device in contact with the crista fenestrae cochlea, the round window, the tympanic cavity, the tympanic membrane, the auris media or the auris externa.

In one specific embodiment of the auris-acceptable controlled-release otic structure modulating agent or innate immune system modulating agent pharmaceutical compositions described herein, the otic structure modulating agent or innate immune system modulating agent is provided in a gel matrix, also referred to herein as "auris acceptable gel compositions," "auris interna-acceptable gel compositions," "auris media-acceptable gel compositions," "auris externa-acceptable gel compositions", "auris gel compositions" or variations thereof. All of the components of the gel composition must be compatible with the targeted auris structure. Further, the gel compositions provide controlled-release of the otic structure modulating agent or innate immune system modulating agent to the desired site within the targeted auris structure; in some embodiments, the gel composition also has an immediate or rapid release component for delivery of the otic structure modulating agent or innate immune system modulating agent to the desired target site. In other embodiments, the gel composition has a sustained release component for delivery of the otic structure modulating agent or innate immune system modulating agent. In some embodiments, the gel composition comprises a multiparticulate (e.g., micronized) otic structure modulating agent or innate immune system modulating agent. In some embodiments, the auris gel compositions are biodegradable. In other embodiments, the auris gel compositions include a mucoadhesive excipient to allow adhesion to the external mucous layer of the round window membrane. In yet other embodiments, the auris gel compositions include a penetration enhancer excipient; in further embodiments, the auris gel composition contains a viscosity enhancing agent sufficient to provide a viscosity of between about 500 and 1,000,000 centipoise, between about 750 and 1,000,000 centipoise; between about 1000 and 1,000,000 centipoise; between about 1000 and 400,000 centipoise; between about 2000 and 100,000 centipoise; between about 3000 and 50,000 centipoise; between about 4000 and 25,000 centipoise; between about 5000 and 20,000 centipoise; or between about 6000 and 15,000 centipoise. In some embodiments, the auris gel composition contains a viscosity enhancing agent sufficient to provide a viscosity of between about 50,0000 and 1,000,000 centipoise.

In other embodiments, the auris interna pharmaceutical compositions described herein further provide an auris-acceptable hydrogel; in yet other embodiments, the auris pharmaceutical compositions provide an auris-acceptable microsphere or microparticle; in still other embodiments, the auris pharmaceutical compositions provide an auris-acceptable liposome. In some embodiments, the auris pharmaceutical compositions provide an auris-acceptable foam; in yet other embodiments, the auris pharmaceutical compositions provide an auris-acceptable paint; in still further embodiments, the auris pharmaceutical compositions provide an auris-acceptable in situ forming spongy material. In some embodiments, the auris pharmaceutical compositions provide an auris-acceptable solvent release gel. In some embodiments, the auris pharmaceutical compositions provide an actinic radiation curable gel. Further embodiments include a thermoreversible gel in the auris pharmaceutical composition, such that upon preparation of the gel at room temperature or below, the composition is a fluid, but upon application of the gel into or near the auris interna and/or auris media target site, including the tympanic cavity, round window membrane or the crista fenestrae cochleae, the auris-pharmaceutical composition stiffens or hardens into a gel-like substance.

In further or alternative embodiments, the auris gel compositions are capable of being administered on or near the round window membrane via intratympanic injection. In other embodiments, the auris gel compositions are administered on or near the round window or the crista fenestrae cochleae through entry via a post-auricular incision and surgical manipulation into or near the round window or the crista fenestrae cochleae area. Alternatively, the auris gel composition is applied via syringe and needle, wherein the needle is inserted through the tympanic membrane and guided to the area of the round window or crista fenestrae cochleae. The auris gel compositions are then deposited on or near the round window or crista fenestrae cochleae for localized treatment. In other embodiments, the auris gel compositions are applied via microcatheters implanted into the patient, and in yet further embodiments the compositions are administered via a pump device onto or near the round window membrane. In still further embodiments, the auris gel compositions are applied at or near the round window membrane via a microinjection device. In yet other embodiments, the auris gel compositions are applied in the tympanic cavity. In some embodiments, the auris gel compositions are applied on the tympanic membrane. In still other embodiments, the auris gel compositions are applied onto or in the auditory canal.

In further specific embodiments, any pharmaceutical composition or device described herein comprises a multiparticulate otic structure modulating agent or innate immune system modulating agent in a liquid matrix (e.g., a liquid composition for intratympanic injection, or otic drops). In certain embodiments, any pharmaceutical composition described herein comprises a multiparticulate otic structure modulating agent or innate immune system modulating agent in a solid matrix.

Controlled-Release Compositions

In general, controlled-release drug compositions impart control over the release of drug with respect to site of release and time of release within the body. As discussed herein, controlled-release refers to immediate release, delayed release, sustained release, extended release, variable release, pulsatile release and bi-modal release. Many advantages are offered by controlled-release. First, controlled-release of a pharmaceutical agent allows less frequent dosing and thus minimizes repeated treatment. Second, controlled-release treatment results in more efficient drug utilization and less of the compound remains as a residue. Third, controlled-release offers the possibility of localized drug delivery by placement of a delivery device or composition at the site of disease. Still further, controlled-release offers the opportunity to administer and release two or more different drugs, each having a unique release profile, or to release the same drug at different rates or for different durations, by means of a single dosage unit.

Accordingly, one aspect of the embodiments disclosed herein is to provide a controlled-release otic structure modulating auris-acceptable composition or. The controlled-release aspect of the compositions and/or compositions and/or devices disclosed herein is imparted through a variety of agents, including but not limited to excipients, agents or materials that are acceptable for use in the auris interna or other otic structure. By way of example only, such excipients, agents or materials include an auris-acceptable polymer, an auris-acceptable viscosity enhancing agent, an auris-acceptable gel, an auris-acceptable paint, an auris-acceptable foam, an auris-acceptable xerogel, an auris-acceptable microsphere or microparticle, an auris-acceptable hydrogel, an auris-acceptable in situ forming spongy material, an auris-acceptable actinic radiation curable gel, an auris-acceptable solvent release gel, an auris-acceptable liposome, an auris-acceptable nanocapsule or nanosphere, an auris-acceptable thermoreversible gel, or combinations thereof.

Auris-Acceptable Gels

Gels, sometimes referred to as jellies, have been defined in various ways. For example, the United States Pharmacopoeia defines gels as semisolid systems consisting of either suspensions made up of small inorganic particles or large organic molecules interpenetrated by a liquid. Gels include a single-phase or a two-phase system. A single-phase gel consists of organic macromolecules distributed uniformly throughout a liquid in such a manner that no apparent boundaries exist between the dispersed macromolecules and the liquid. Some single-phase gels are prepared from synthetic macromolecules (e.g., carbomer) or from natural gums, (e.g., tragacanth). In some embodiments, single-phase gels are generally aqueous, but will also be made using alcohols and oils. Two-phase gels consist of a network of small discrete particles.

Gels can also be classified as being hydrophobic or hydrophilic. In certain embodiments, the base of a hydrophobic gel consists of a liquid paraffin with polyethylene or fatty oils gelled with colloidal silica, or aluminum or zinc soaps. In contrast, the base of hydrophobic gels usually consists of water, glycerol, or propylene glycol gelled with a suitable gelling agent (e.g., tragacanth, starch, cellulose derivatives, carboxyvinylpolymers, and magnesium-aluminum silicates). In certain embodiments, the rheology of the compositions or devices disclosed herein is pseudo plastic, plastic, thixotropic, or dilatant.

In one embodiment the enhanced viscosity auris-acceptable composition described herein is not a liquid at room temperature. In certain embodiments, the enhanced viscosity composition is characterized by a phase transition between room temperature and body temperature (including an individual with a serious fever, e.g., up to about 42° C.). In some embodiments, the phase transition occurs at 1° C. below body temperature, at 2° C. below body temperature, at 3° C. below body temperature, at 4° C. below body temperature, at 6° C. below body temperature, at 8° C. below body temperature, or at 10° C. below body temperature. In some embodiments, the phase transition occurs at about 15° C. below body temperature, at about 20° C. below body temperature or at about 25° C. below body temperature. In specific embodiments, the gelation temperature (Tgel) of a composition described herein is about 20° C., about 25° C., or about 30° C. In certain embodiments, the gelation temperature (Tgel) of a composition described herein is about 35° C., or about 40° C. In one embodiment, administration of any composition described herein at about body temperature reduces or inhibits vertigo associated with intratympanic administration of otic compositions. Included within the definition of body temperature is the body temperature of a healthy individual, or an unhealthy individual, including an individual with a fever (up to ~42° C.). In some embodiments, the pharmaceutical compositions or devices described herein are liquids at about room temperature and are administered at or about room temperature, reducing or ameliorating side effects such as, for example, vertigo.

Polymers composed of polyoxypropylene and polyoxyethylene form thermoreversible gels when incorporated into aqueous solutions. These polymers have the ability to change from the liquid state to the gel state at temperatures close to body temperature, therefore allowing useful compositions that are applied to the targeted auris structure(s). The liquid state-to-gel state phase transition is dependent on the polymer concentration and the ingredients in the solution.

Poloxamer 407 (PF-127) is a nonionic surfactant composed of polyoxyethylene-polyoxypropylene copolymers. Other poloxamers include 188 (F-68 grade), 237 (F-87 grade), 338 (F-108 grade). Aqueous solutions of poloxamers are stable in the presence of acids, alkalis, and metal ions. PF-127 is a commercially available polyoxyethylene-polyoxypropylene triblock copolymer of general formula E106 P70 E106, with an average molar mass of 13,000. The polymer can be further purified by suitable methods that will enhance gelation properties of the polymer. It contains approximately 70% ethylene oxide, which accounts for its hydrophilicity. It is one of the series of poloxamer ABA block copolymers, whose members share the chemical formula shown below.

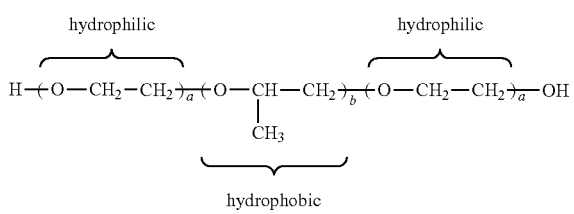

PF-127 is of particular interest since concentrated solutions (>20% w/w) of the copolymer are transformed from low viscosity transparent solutions to solid gels on heating to body temperature. This phenomenon, therefore, suggests that when placed in contact with the body, the gel preparation will form a semi-solid structure and a sustained release depot. Furthermore, PF-127 has good solubilizing capacity, low toxicity and is, therefore, considered a good medium for drug delivery systems.

In an alternative embodiment, the thermogel is a PEG-PLGA-PEG triblock copolymer (Jeong et al, Nature (1997), 388:860-2; Jeong et al, J. Control. Release (2000), 63:155-63; Jeong et al, Adv. Drug Delivery Rev. (2002), 54:37-51). The polymer exhibits sol-gel behavior over a concentration of about 5% w/w to about 40% w/w. Depending on the properties desired, the lactide/glycolide molar ratio in the PLGA copolymer ranges from about 1:1 to about 20:1. The resulting copolymers are soluble in water and form a free-flowing liquid at room temperature, but form a hydrogel at body temperature. A commercially available PEG-PLGA-PEG triblock copolymer is RESOMER RGP t50106 manufactured by Boehringer Ingelheim. This material is composed of a PGLA copolymer of 50:50 poly(DL-lactide-co-glycolide) and is 10% w/w of PEG and has a molecular weight of about 6000.

ReGel® is a tradename of MacroMed Incorporated for a class of low molecular weight, biodegradable block copolymers having reverse thermal gelation properties as described in U.S. Pat. Nos. 6,004,573, 6,117,949, 6,201,072, and 6,287,588. It also includes biodegradable polymeric drug carriers disclosed in pending U.S. patent application Ser. Nos. 09/906,041, 09/559,799 and 10/919,603. The biodegradable drug carrier comprises ABA-type or BAB-type triblock copolymers or mixtures thereof, wherein the A-blocks are relatively hydrophobic and comprise biodegradable polyesters or poly(orthoester)s, and the B-blocks are relatively hydrophilic and comprise polyethylene glycol (PEG), said copolymers having a hydrophobic content of between 50.1 to 83% by weight and a hydrophilic content of between 17 to 49.9% by weight, and an overall block copolymer molecular weight of between 2000 and 8000 Daltons. The drug carriers exhibit water solubility at temperatures below normal mammalian body temperatures and undergo reversible thermal gelation to then exist as a gel at temperatures equal to physiological mammalian body temperatures. The biodegradable, hydrophobic A polymer block comprises a polyester or poly(ortho ester), in that the polyester is synthesized from monomers selected from the group consisting of D,L-lactide, D-lactide, L-lactide, D,L-lactic acid, D-lactic acid, L-lactic acid, glycolide, glycolic acid, ε-caprolactone, ε-hydroxyhexanoic acid, γ-butyrolactone, γ-hydroxybutyric acid, β-valerolactone, β-hydroxyvaleric acid, hydroxybutyric acids, malic acid, and copolymers thereof and having an average molecular weight of between about 600 and 3000 Daltons. The hydrophilic B-block segment is preferably polyethylene glycol (PEG) having an average molecular weight of between about 500 and 2200 Daltons.

Additional biodegradable thermoplastic polyesters include AtriGel® (provided by Atrix Laboratories, Inc.) and/or those disclosed, e.g., in U.S. Pat. Nos. 5,324,519; 4,938,763; 5,702,716; 5,744,153; and 5,990,194; wherein the suitable biodegradable thermoplastic polyester is disclosed as a thermoplastic polymer. Examples of suitable biodegradable thermoplastic polyesters include polylactides, polyglycolides, polycaprolactones, copolymers thereof, terpolymers thereof, and any combinations thereof. In some such embodiments, the suitable biodegradable thermoplastic polyester is a polylactide, a polyglycolide, a copolymer thereof, a terpolymer thereof, or a combination thereof. In one embodiment, the biodegradable thermoplastic polyester is 50/50 poly(DL-lactide-co-glycolide) having a carboxy terminal group; is present in about 30 wt. % to about 40 wt. % of the composition; and has an average molecular weight of about 23,000 to about 45,000. Alternatively, in another embodiment, the biodegradable thermoplastic polyester is 75/25 poly (DL-lactide-co-glycolide) without a carboxy terminal group; is present in about 40 wt. % to about 50 wt. % of the composition; and has an average molecular weight of about 15,000 to about 24,000. In further or alternative embodiments, the terminal groups of the poly(DL-lactide-co-glycolide) are either hydroxyl, carboxyl, or ester depending upon the method of polymerization. Polycondensation of lactic or glycolic acid provides a polymer with terminal hydroxyl and carboxyl groups. Ring-opening polymerization of the cyclic lactide or glycolide monomers with water, lactic acid, or glycolic acid provides polymers with the same terminal groups. However, ring-opening of the cyclic monomers with a monofunctional alcohol such as methanol, ethanol, or 1-dodecanol provides a polymer with one hydroxyl group and one ester terminal groups. Ring-opening polymerization of the cyclic monomers with a diol such as 1,6-hexanediol or polyethylene glycol provides a polymer with only hydroxyl terminal groups.

Since the polymer systems of thermoreversible gels dissolve more completely at reduced temperatures, methods of solubilization include adding the required amount of polymer to the amount of water to be used at reduced temperatures. Generally after wetting the polymer by shaking, the mixture is capped and placed in a cold chamber or in a thermostatic container at about 0-10° C. in order to dissolve the polymer. The mixture is stirred or shaken to bring about a more rapid dissolution of the thermoreversible gel polymer. The otic structure modulating agent or innate immune system modulating agent and various additives such as buffers, salts, and preservatives are subsequently added and dissolved. In some instances the otic structure modulating agent or innate immune system modulating agent and/or other pharmaceutically active agent is suspended if it is insoluble in water. The pH is modulated by the addition of appropriate buffering agents. round window membrane mucoadhesive characteristics are optionally imparted to a thermoreversible gel by incorporation of round window membrane mucoadhesive carbomers, such as Carbopol® 934P, to the composition (Majithiya et al, AAPS PharmSciTech (2006), 7(3), p. E1; EP0551626, both of that is incorporated herein by reference for such disclosure).

In one embodiment are auris-acceptable pharmaceutical gel compositions that do not require the use of an added viscosity enhancing agent. Such gel compositions incorporate at least one pharmaceutically acceptable buffer. In one aspect is a gel composition comprising an otic structure modulating agent or innate immune system modulating agent and a pharmaceutically acceptable buffer. In another embodiment, the pharmaceutically acceptable excipient or carrier is a gelling agent.

In other embodiments, useful otic structure modulating agent or innate immune system modulating agent auris-acceptable pharmaceutical compositions also include one or more pH adjusting agents or buffering agents to provide an endolymph or perilymph suitable pH. Suitable pH adjusting agents or buffers include, but are not limited to acetate, bicarbonate, ammonium chloride, citrate, phosphate, pharmaceutically acceptable salts thereof and combinations or mixtures thereof. Such pH adjusting agents and buffers are included in an amount required to maintain pH of the composition between a pH of about 5 and about 9, in one embodiment a pH between about 6.5 to about 7.5, and in yet another embodiment at a pH of about 6.5, 6.6, 6.7, 6.8, 6.9, 7.0, 7.1, 7.2, 7.3, 7.4, 7.5. In one embodiment, when one or more buffers are utilized in the compositions of the present disclosure, they are combined, e.g., with a pharmaceutically acceptable vehicle and are present in the final composition, e.g., in an amount ranging from about 0.1% to about 20%, from about 0.5% to about 10%. In certain embodiments of the present disclosure, the amount of buffer included in the gel compositions is an amount such that the pH of the gel composition does not interfere with the natural buffering system of the auris media or auris interna, or does not interfere with the natural pH of the endolymph or perilymph: depending on where in the cochlea the otic structure modulating agent or innate immune system modulating agent composition is targeted. In some embodiments, from about 10 µM to about 200 mM concentration of a buffer is present in the gel composition. In certain embodiments, from about a 5 mM to about a 200 mM concentration of a buffer is present. In certain embodiments, from about a 20 mM to about a 100 mM concentration of a buffer is present. In one embodiment is a buffer such as acetate or citrate at slightly acidic pH. In one embodiment the buffer is a sodium acetate buffer having a pH of about 4.5 to about 6.5. In one embodiment the buffer is a sodium citrate buffer having a pH of about 5.0 to about 8.0, or about 5.5 to about 7.0.

In an alternative embodiment, the buffer used is tris (hydroxymethyl)aminomethane, bicarbonate, carbonate or phosphate at slightly basic pH. In one embodiment, the buffer is a sodium bicarbonate buffer having a pH of about 6.5 to about 8.5, or about 7.0 to about 8.0. In another embodiment the buffer is a sodium phosphate dibasic buffer having a pH of about 6.0 to about 9.0.

Also described herein are controlled-release compositions or devices comprising an otic structure modulating agent or innate immune system modulating agent and a viscosity enhancing agent. Suitable viscosity-enhancing agents include by way of example only, gelling agents and suspending agents. In one embodiment, the enhanced viscosity composition does not include a buffer. In other embodiments, the enhanced viscosity composition includes a pharmaceutically acceptable buffer. Sodium chloride or other tonicity agents are optionally used to adjust tonicity, if necessary.

By way of example only, the auris-acceptable viscosity agent include hydroxypropyl methylcellulose, hydroxyethyl cellulose, polyvinylpyrrolidone, carboxymethyl cellulose, polyvinyl alcohol, sodium chondroitin sulfate, sodium hyaluronate. Other viscosity enhancing agents compatible with the targeted auris structure include, but are not limited to, acacia (gum arabic), agar, aluminum magnesium silicate, sodium alginate, sodium stearate, bladderwrack, bentonite, carbomer, carrageenan, Carbopol, xanthan, cellulose, microcrystalline cellulose (MCC), ceratonia, chitin, carboxymethylated chitosan, chondrus, dextrose, furcellaran, gelatin, Ghatti gum, guar gum, hectorite, lactose, sucrose, maltodextrin, mannitol, sorbitol, honey, maize starch, wheat starch, rice starch, potato starch, gelatin, sterculia gum, xanthum gum, gum tragacanth, ethyl cellulose, ethylhydroxyethyl cellulose, ethylmethyl cellulose, methyl cellulose, hydroxyethyl cellulose, hydroxyethylmethyl cellulose, hydroxypropyl cellulose, poly(hydroxyethyl methacrylate), oxypolygelatin, pectin, polygeline, povidone, propylene carbonate, methyl vinyl ether/maleic anhydride copolymer (PVM/MA), poly(methoxyethyl methacrylate), poly (methoxyethoxyethyl methacrylate), hydroxypropyl cellulose, hydroxypropylmethyl-cellulose (HPMC), sodium carboxymethyl-cellulose (CMC), silicon dioxide, polyvinylpyrrolidone (PVP: povidone), Splenda® (dextrose, maltodextrin and sucralose) or combinations thereof. In specific embodiments, the viscosity-enhancing excipient is a combination of MCC and CMC. In another embodiment, the viscosity-enhancing agent is a combination of carboxymethylated chitosan, or chitin, and alginate. The combination of chitin and alginate with the otic structure modulating agent or innate immune system modulating agents disclosed herein acts as a controlled-release composition, restricting the diffusion of the otic structure modulating agent or innate immune system modulating agents from the composition. Moreover, the combination of carboxymethylated chitosan and alginate is optionally used to assist in increasing the permeability of the otic structure modulating agent or innate immune system modulating agents through the round window membrane.

In some embodiments, is an enhanced viscosity composition, comprising from about 0.1 mM and about 100 mM of an otic structure modulating agent or innate immune system modulating agent, a pharmaceutically acceptable viscosity agent, and water for injection, the concentration of the viscosity agent in the water being sufficient to provide a enhanced viscosity composition with a final viscosity from about 100 to about 100,000 cP. In certain embodiments, the viscosity of the gel is in the range from about 100 to about 50,000 cP, about 100 cP to about 1,000 cP, about 500 cP to about 1500 cP, about 1000 cP to about 3000 cP, about 2000 cP to about 8,000 cP, about 4,000 cP to about 50,000 cP, about 10,000 cP to about 500,000 cP, about 15,000 cP to about 1,000,000 cP. In other embodiments, when an even more viscous medium is desired, the biocompatible gel comprises at least about 35%, at least about 45%, at least about 55%, at least about 65%, at least about 70%, at least about 75%, or even at least about 80% or so by weight of the otic structure modulating agent or innate immune system modulating agent. In highly concentrated samples, the biocompatible enhanced viscosity composition comprises at least about 25%, at least about 35%, at least about 45%, at least about 55%, at least about 65%, at least about 75%, at least about 85%, at least about 90% or at least about 95% or more by weight of the otic structure modulating agent or innate immune system modulating agent.

In some embodiments, the viscosity of the gel compositions presented herein are measured by any means described. For example, in some embodiments, an LVDV-II+CP Cone Plate Viscometer and a Cone Spindle CPE-40 is used to calculate the viscosity of the gel composition described herein. In other embodiments, a Brookfield (spindle and cup) viscometer is used to calculate the viscosity of the gel composition described herein. In some embodiments, the viscosity ranges referred to herein are measured at room temperature. In other embodiments, the viscosity ranges referred to herein are measured at body temperature (e.g., at the average body temperature of a healthy human).

In one embodiment, the pharmaceutically acceptable enhanced viscosity auris-acceptable composition comprises an otic structure modulating agent or innate immune system modulating agent and at least one gelling agent. Suitable gelling agents for use in preparation of the gel composition include, but are not limited to, celluloses, cellulose derivatives, cellulose ethers (e.g., carboxymethylcellulose, ethylcellulose, hydroxyethylcellulose, hydroxymethylcellulose, hydroxypropylmethylcellulose, hydroxypropylcellulose, methylcellulose), guar gum, xanthan gum, locust bean gum, alginates (e.g., alginic acid), silicates, starch, tragacanth, carboxyvinyl polymers, carrageenan, paraffin, petrolatum and any combinations or mixtures thereof. In some other embodiments, hydroxypropylmethylcellulose (Methocel®) is utilized as the gelling agent. In certain embodiments, the viscosity enhancing agents described herein are also utilized as the gelling agent for the gel compositions presented herein.

In some embodiments, the otic therapeutic agents disclosed herein are dispensed as an auris-acceptable paint. As used herein, paints (also known as film formers) are solutions comprised of a solvent, a monomer or polymer, an active agent, and optionally one or more pharmaceutically-acceptable excipients. After application to a tissue, the solvent evaporates leaving behind a thin coating comprised of the monomers or polymers, and the active agent. The coating protects active agents and maintains them in an immobilized state at the site of application. This decreases the amount of active agent that may be lost and correspondingly increases the amount delivered to the subject. By way of non-limiting example, paints include collodions (e.g. Flexible Collodion, USP), and solutions comprising saccharide siloxane copolymers and a cross-linking agent. Collodions are ethyl ether/ethanol solutions containing pyroxylin (a nitrocellulose). After application, the ethyl ether/ethanol solution evaporates leaving behind a thin film of pyroxylin. In solutions comprising saccharide siloxane copolymers, the saccharide siloxane copolymers form the coating after evaporation of the solvent initiates the cross-linking of the saccharide siloxane copolymers. For additional disclosures regarding paints, see *Remington: The Science and Practice of Pharmacy* that is hereby incorporated with respect to this subject matter. The paints contemplated for use herein, are flexible such that they do not interfere with the propagation of pressure waves through the ear. Further, the paints may be applied as a liquid (i.e. solution, suspension, or emulsion), a semisolid (i.e., a gel, foam, paste, or jelly) or an aerosol.

In some embodiments, the otic therapeutic agents disclosed herein are dispensed as a controlled-release foam. Examples of suitable foamable carriers for use in the compositions disclosed herein include, but are not limited to, alginate and derivatives thereof, carboxymethylcellulose and derivatives thereof, collagen, polysaccharides, including, for example, dextran, dextran derivatives, pectin, starch, modified starches such as starches having additional carboxyl and/or carboxamide groups and/or having hydrophilic side-chains, cellulose and derivatives thereof, agar and derivatives thereof, such as agar stabilized with polyacrylamide, polyethylene oxides, glycol methacrylates, gelatin, gums such as xanthum, guar, karaya, gellan, arabic, tragacanth and locust bean gum, or combinations thereof. Also suitable are the salts of the aforementioned carriers, for example, sodium alginate. The composition optionally further comprises a foaming agent, which promotes the formation of the foam, including a surfactant or external propellant. Examples of suitable foaming agents include cetrimide, lecithin, soaps, silicones and the like. Commercially available surfactants such as Tween® are also suitable.

In some embodiments, other gel compositions are useful depending upon the particular otic structure modulating agent or innate immune system modulating agent, other pharmaceutical agent or excipients/additives used, and as such are considered to fall within the scope of the present disclosure. For example, other commercially-available glycerin-based gels, glycerin-derived compounds, conjugated, or crosslinked gels, matrices, hydrogels, and polymers, as well as gelatins and their derivatives, alginates, and alginate-based gels, and even various native and synthetic hydrogel and hydrogel-derived compounds are all expected to be useful in the otic structure modulating compositions described herein. In some embodiments, auris-acceptable gels include, but are not limited to, alginate hydrogels SAF®-Gel (ConvaTec, Princeton, N.J.), Duoderm® Hydroactive Gel (ConvaTec), Nu-Gel® (Johnson & Johnson Medical, Arlington, Tex.); Carrasyn® (V) Acemannan Hydrogel (Carrington Laboratories, Inc., Irving, Tex.); glycerin gels Elta® Hydrogel (Swiss-American Products, Inc., Dallas, Tex.) and K-Y® Sterile (Johnson & Johnson). In further embodiments, biodegradable biocompatible gels also represent compounds present in auris-acceptable compositions disclosed and described herein.

In some compositions developed for administration to a mammal, and for compositions formulated for human administration, the auris-acceptable gel comprises substantially all of the weight of the composition. In other embodiments, the auris-acceptable gel comprises as much as about 98% or about 99% of the composition by weight. This is desirous when a substantially non-fluid, or substantially viscous composition is needed. In a further embodiment, when slightly less viscous, or slightly more fluid auris-acceptable pharmaceutical gel compositions are desired, the biocompatible gel portion of the composition comprises at least about 50% by weight, at least about 60% by weight, at least about 70% by weight, or even at least about 80% or 90% by weight of the compound. All intermediate integers within these ranges are contemplated to fall within the scope of this disclosure, and in some alternative embodiments, even more fluid (and consequently less viscous) auris-acceptable gel compositions are formulated, such as for example, those in that the gel or matrix component of the mixture comprises not more than about 50% by weight, not more than about 40% by weight, not more than about 30% by weight, or even those than comprise not more than about 15% or about 20% by weight of the composition.

Auris-Acceptable Suspending Agents

In one embodiment, an otic structure modulating agent or innate immune system modulating agent is included in a pharmaceutically acceptable enhanced viscosity composition wherein the composition further comprises at least one suspending agent, wherein the suspending agent assists in imparting controlled-release characteristics to the composition. In some embodiments, suspending agents also serve to increase the viscosity of the auris-acceptable otic structure modulating compositions and compositions.

Suspending agents include, by way of example only, compounds such as polyvinylpyrrolidone, e.g., polyvinylpyrrolidone K12, polyvinylpyrrolidone K17, polyvinylpyrrolidone K25, or polyvinylpyrrolidone K30, vinyl pyrrolidone/vinyl acetate copolymer (S630), sodium carboxymethylcellulose, methylcellulose, hydroxypropylmethylcellulose (hypromellose), hydroxymethylcellulose acetate stearate, polysorbate-80, hydroxyethylcellulose, sodium alginate, gums, such as, e.g., gum tragacanth and gum acacia, guar gum, xanthans, including xanthan gum, sugars, cellulosics, such as, e.g., sodium carboxymethylcellulose, methylcellulose, sodium carboxymethylcellulose, hydroxypropylmethylcellulose, hydroxyethylcellulose, polysorbate-80, sodium alginate, polyethoxylated sorbitan monolaurate, polyethoxylated sorbitan monolaurate, povidone and the like. In some embodiments, useful aqueous suspensions also contain one or more polymers as suspending agents. Useful polymers include water-soluble polymers such as cellulosic polymers, e.g., hydroxypropyl methylcellulose, and water-insoluble polymers such as cross-linked carboxyl-containing polymers.

In one embodiment, the present disclosure provides auris-acceptable gel compositions comprising a therapeutically effective amount of an otic structure modulating agent or innate immune system modulating agent in a hydroxyethyl cellulose gel. Hydroxyethyl cellulose (HEC) is obtained as a dry powder that is reconstituted in water or an aqueous buffer solution to give the desired viscosity (generally about 200 cps to about 30,000 cps, corresponding to about 0.2 to about 10% HEC). In one embodiment the concentration of HEC is between about 1% and about 15%, about 1% and about 2%, or about 1.5% to about 2%.

In other embodiments, the auris-acceptable compositions, including gel compositions and viscosity-enhanced compositions, further include excipients, other medicinal or pharmaceutical agents, carriers, adjuvants, such as preserving, stabilizing, wetting or emulsifying agents, solution promoters, salts, solubilizers, an antifoaming agent, an antioxidant, a dispersing agent, a wetting agent, a surfactant, and combinations thereof.

Auris-Acceptable Actinic Radiation Curable Gel

In other embodiments, the gel is an actinic radiation curable gel, such that following administration to or near the targeted auris structure, use of actinic radiation (or light, including UV light, visible light, or infrared light) the desired gel properties are formed. By way of example only, fiber optics are used to provide the actinic radiation so as to form the desired gel properties. In some embodiments, the fiber optics and the gel administration device form a single unit. In other embodiments, the fiber optics and the gel administration device are provided separately.

Auris-Acceptable Solvent Release Gel

In some embodiments, the gel is a solvent release gel such that the desired gel properties are formed after administration to or near the targeted auris structure, which is, as the solvent in the injected gel composition diffuses out the gel, a gel having the desired gel properties is formed. For example, a composition that comprises sucrose acetate isobutyrate, a pharmaceutically acceptable solvent, one or more additives, and the otic structure modulating agent or innate immune system modulating agent is administered at or near the round window membrane: diffusion of the solvent out of the injected composition provides a depot having the desired gel properties. For example, use of a water soluble solvent provides a high viscosity depot when the solvent diffuses rapidly out of the injected composition. On the other hand, use of a hydrophobic solvent (e.g., benzyl benzoate) provides a less viscous depot. One example of an auris-acceptable solvent release gel composition is the SABER™ Delivery System marketed by DURECT Corporation.

Auris-Acceptable In Situ Forming Spongy Material

Also contemplated within the scope of the embodiments is the use of a spongy material, formed in situ in the auris interna or auris media. In some embodiments, the spongy material is formed from hyaluronic acid or its derivatives. The spongy material is impregnated with a desired otic structure modulating agent or innate immune system modulating agent and placed within the auris media so as to provide controlled-release of the otic structure modulating agent or innate immune system modulating agent within the auris media, or in contact with the round window membrane so as to provide controlled-release of the otic structure modulating agent or innate immune system modulating agent into the auris interna. In some embodiments, the spongy material is biodegradable.

Round Window Membrane Mucoadhesives

Also contemplated within the scope of the embodiments is the addition of a round window membrane mucoadhesive with the otic structure modulating compositions and devices disclosed herein. The term 'mucoadhesion' is used for materials that bind to the mucin layer of a biological membrane, such as the external membrane of the 3-layered round window membrane. To serve as round window membrane mucoadhesive polymers, the polymers possess some general physiochemical features such as predominantly anionic hydrophilicity with numerous hydrogen bond forming groups, suitable surface property for wetting mucus/mucosal tissue surfaces or sufficient flexibility to penetrate the mucus network.

Round window membrane mucoadhesive agents that are used with the auris-acceptable compositions include, but are not limited to, at least one soluble polyvinylpyrrolidone polymer (PVP); a water-swellable, but water-insoluble, fibrous, cross-linked carboxy-functional polymer; a cross-linked poly(acrylic acid) (e.g. Carbopol® 947P); a carbomer homopolymer; a carbomer copolymer; a hydrophilic polysaccharide gum, maltodextrin, a cross-linked alignate gum gel, a water-dispersible polycarboxylated vinyl polymer, at least two particulate components selected from the group consisting of titanium dioxide, silicon dioxide, and clay, or a mixture thereof. The round window membrane mucoadhesive agent is optionally used in combination with an auris-acceptable viscosity increasing excipient, or used alone to increase the interaction of the composition with the mucosal layer target otic component. In one non-limiting example, the mucoadhesive agent is maltodextrin and/or an alginate gum. When used, the round window membrane mucoadhesive character imparted to the composition is at a level that is sufficient to deliver an effective amount of the otic structure modulating agent or innate immune system modulating agent composition to, for example, the mucosal layer of round window membrane or the crista fenestrae cochleae in an amount that coats the mucosal membrane, and thereafter deliver the composition to the affected areas, including by way of example only, the vestibular and/or cochlear structures of the auris interna. When used, the mucoadhesive characteristics of the compositions provided herein are determined, and using this information (along with the other teachings provided herein), the appropriate amounts are determined. One method for determining sufficient mucoadhesiveness includes monitoring changes in the interaction of the composition with a mucosal layer, including but not limited to measuring changes in residence or retention time of the composition in the absence and presence of the mucoadhesive excipient.

Mucoadhesive agents have been described, for example, in U.S. Pat. Nos. 6,638,521, 6,562,363, 6,509,028, 6,348,502, 6,319,513, 6,306,789, 5,814,330, and 4,900,552, each of that is hereby incorporated by reference for such disclosure.

In another non-limiting example, a mucoadhesive agent is, for example, at least two particulate components selected from titanium dioxide, silicon dioxide, and clay, wherein the composition is not further diluted with any liquid prior to administration and the level of silicon dioxide, if present, is from about 3% to about 15%, by weight of the composition. Silicon dioxide, if present, includes fumed silicon dioxide, precipitated silicon dioxide, coacervated silicon dioxide, gel silicon dioxide, and mixtures thereof. Clay, if present, includes kaolin minerals, serpentine minerals, smectites, illite or a mixture thereof. For example, clay includes laponite, bentonite, hectorite, saponite, montmorillonites or a mixture thereof.

In one non-limiting example, the round window membrane mucoadhesive agent is maltodextrin. Maltodextrin is a carbohydrate produced by the hydrolysis of starch that is optionally derived from corn, potato, wheat or other plant products. Maltodextrin is optionally used either alone or in combination with other round window membrane mucoadhesive agents to impart mucoadhesive characteristics on the compositions disclosed herein. In one embodiment, a combination of maltodextrin and a carbopol polymer are used to increase the round window membrane mucoadhesive characteristics of the compositions or devices disclosed herein.

In another embodiment, the round window membrane mucoadhesive agent is an alkyl-glycoside and/or a saccharide alkyl ester. As used herein, an "alkyl-glycoside" means a compound comprising any hydrophilic saccharide (e.g. sucrose, maltose, or glucose) linked to a hydrophobic alkyl. In some embodiments, the round window membrane mucoadhesive agent is an alkyl-glycoside wherein the alkylglycoside comprises a sugar linked to a hydrophobic alkyl (e.g., an alkyl comprising about 6 to about 25 carbon atoms) by an amide linkage, an amine linkage, a carbamate linkage, an ether linkage, a thioether linkage, an ester linkage, a thioester linkage, a glycosidic linkage, a thioglycosidic linkage, and/or a ureide linkage. In some embodiments, the round window membrane mucoadhesive agent is a hexyl-, heptyl-, octyl-, nonyl-, decyl-, undecyl-, dodecyl-, tridecyl-, tetradecyl, pentadecyl-, hexadecyl-, heptadecyl-, and octadecyl α- or β-D-maltoside; hexyl-, heptyl-, octyl-, nonyl-, decyl-, undecyl-, dodecyl-, tridecyl-, tetradecyl, pentadecyl-, hexadecyl-, heptadecyl-, and octadecyl α- or β-D-glucoside; hexyl-, heptyl-, octyl-, nonyl-, decyl-, undecyl-, dodecyl-, tridecyl-, tetradecyl, pentadecyl-, hexadecyl-, heptadecyl-, and octadecyl α- or β-D-sucroside; hexyl-, heptyl-, octyl-, dodecyl-, tridecyl-, and tetradecyl-β-D-thiomaltoside; heptyl- or octyl-1-thio-α- or β-D-glucopyranoside; alkyl thiosucroses; alkyl maltotriosides; long chain aliphatic carbonic acid amides of sucrose β-amino-alkyl ethers; derivatives of palatinose or isomaltamine linked by an amide linkage to an alkyl chain and derivatives of isomaltamine linked by urea to an alkyl chain; long chain aliphatic carbonic acid ureides of sucrose β-amino-alkyl ethers and long chain aliphatic carbonic acid amides of sucrose β-amino-alkyl ethers. In some embodiments, the round window membrane mucoadhesive agent is an alkyl-glycoside wherein the alkyl glycoside is maltose, sucrose, glucose, or a combination thereof linked by a glycosidic linkage to an alkyl chain of 9-16 carbon atoms (e.g., nonyl-, decyl-, dodecyl- and tetradecyl sucroside; nonyl-, decyl-, dodecyl- and tetradecyl glucoside; and nonyl-, decyl-, dodecyl- and tetradecyl maltoside). In some embodiments, the round window membrane mucoadhesive agent is an alkyl-glycoside wherein the alkyl glycoside is dodecylmaltoside, tridecylmaltoside, and tetradecylmaltoside.

In some embodiments, the round window membrane mucoadhesive agent is an alkyl-glycoside wherein the alkyl-glycoside is a disaccharide with at least one glucose. In some embodiments, the auris acceptable penetration enhancer is a surfactant comprising α-D-glucopyranosyl-β-glycopyranoside, n-Dodecyl-4-O-α-D-glucopyranosyl-β-glycopyranoside, and/or n-tetradecyl-4-O-α-D-glucopyranosyl-β-glycopyranoside. In some embodiments, the round window membrane mucoadhesive agent is an alkyl-glycoside wherein the alkyl-glycoside has a critical miscelle concentration (CMC) of less than about 1 mM in pure water or in aqueous solutions. In some embodiments, the round window membrane mucoadhesive agent is an alkyl-glycoside wherein an oxygen atom within the alkyl-glycoside is substituted with a sulfur atom. In some embodiments, the round window membrane mucoadhesive agent is an alkyl-glycoside wherein the alkylglycoside is the β anomer. In some embodiments, the round window membrane mucoadhesive agent is an alkyl-glycoside wherein the alkylglycoside comprises 90%, 91%, 92%, 93%, 94%, 95%, 96%, 97%, 98%, 99%, 99.1%, 99.5%, or 99.9% of the β anomer.

Auris-Acceptable Controlled-Release Particles

Otic structure modulating agent or innate immune system modulating agents and/or other pharmaceutical agents disclosed herein are optionally incorporated within controlled-release particles, lipid complexes, liposomes, nanoparticles, microparticles, microspheres, coacervates, nanocapsules or other agents that enhance or facilitate the localized delivery of the otic structure modulating agent or innate immune system modulating agent. In some embodiments, a single enhanced viscosity composition is used, in that an otic structure modulating agent or innate immune system modulating agent is present, while in other embodiments, a pharmaceutical composition that comprises a mixture of two or more distinct enhanced viscosity compositions is used, in that an otic structure modulating agent or innate immune system modulating agent is present. In some embodiments, combinations of sols, gels and/or biocompatible matrices is also employed to provide desirable characteristics of the controlled-release otic structure modulating compositions or compositions. In certain embodiments, the controlled-release otic structure modulating compositions or compositions are cross-linked by one or more agents to alter or improve the properties of the composition.

Examples of microspheres relevant to the pharmaceutical compositions disclosed herein include: Luzzi, L. A., J. Pharm. Psy. 59:1367 (1970); U.S. Pat. No. 4,530,840; Lewis, D. H., "Controlled-release of Bioactive Agents from Lactides/Glycolide Polymers" in Biodegradable Polymers as Drug Delivery Systems, Chasin, M. and Langer, R., eds., Marcel Decker (1990); U.S. Pat. No. 4,675,189; Beck et al., "Poly(lactic acid) and Poly(lactic acid-co-glycolic acid) Contraceptive Delivery Systems," in Long Acting Steroid Contraception, Mishell, D. R., ed., Raven Press (1983); U.S. Pat. No. 4,758,435; U.S. Pat. No. 3,773,919; U.S. Pat. No. 4,474,572. Examples of protein therapeutics formulated as microspheres include: U.S. Pat. No. 6,458,387; U.S. Pat. No. 6,268,053; U.S. Pat. No. 6,090,925; U.S. Pat. No. 5,981,719; and U.S. Pat. No. 5,578,709, and are herein incorporated by reference for such disclosure.

Microspheres usually have a spherical shape, although irregularly-shaped microparticles are possible. Microspheres may vary in size, ranging from submicron to 1000 micron diameters. Microspheres suitable for use with the auris-acceptable compositions disclosed herein are submicron to 250 micron diameter microspheres, allowing administration by injection with a standard gauge needle. The auris-acceptable microspheres are prepared by any method that produces microspheres in a size range acceptable for use in an injectable composition. Injection is optionally accomplished with standard gauge needles used for administering liquid compositions.

Suitable examples of polymeric matrix materials for use in the auris-acceptable controlled-release particles herein include poly(glycolic acid), poly-d,1-lactic acid, poly-1-lactic acid, copolymers of the foregoing, poly(aliphatic carboxylic acids), copolyoxalates, polycaprolactone, polydioxonene, poly(orthocarbonates), poly(acetals), poly(lactic acid-caprolactone), polyorthoesters, poly(glycolic acid-caprolactone), polydioxonene, polyanhydrides, polyphosphazines, and natural polymers including albumin, casein, and some waxes, such as, glycerol mono- and distearate, and the like. Various commercially available poly (lactide-co-glycolide) materials (PLGA) are optionally used in the method disclosed herein. For example, poly (d,1-lactic-co-glycolic acid) is commercially available from Boehringer-Ingelheim as RESOMER RG 503H. This product has a mole percent composition of 50% lactide and 50% glycolide. These copolymers are available in a wide range of molecular weights and ratios of lactic acid to glycolic acid. One embodiment includes the use of the polymer poly(d,1-lactide-co-glycolide). The molar ratio of lactide to glycolide in such a copolymer includes the range of from about 95:5 to about 50:50.

The molecular weight of the polymeric matrix material is of some importance. The molecular weight should be high enough so that it forms satisfactory polymer coatings, i.e., the polymer should be a good film former. Usually, a satisfactory molecular weight is in the range of 5,000 to 500,000 Daltons. The molecular weight of a polymer is also important from the point of view that molecular weight influences the biodegradation rate of the polymer. For a diffusional mechanism of drug release, the polymer should remain intact until all of the drug is released from the microparticles and then degrade. The drug is also released from the microparticles as the polymeric excipient bioerodes. By an appropriate selection of polymeric materials a microsphere composition is made such that the resulting microspheres exhibit both diffusional release and biodegradation release properties. This is useful in affording multiphasic release patterns.

A variety of methods are known by that compounds are encapsulated in microspheres. In these methods, the otic structure modulating agent or innate immune system modulating agent is generally dispersed or emulsified, using stirrers, agitators, or other dynamic mixing techniques, in a solvent containing a wall-forming material. Solvent is then removed from the microspheres, and thereafter the microsphere product is obtained.

In one embodiment, controlled-release otic structure modulating compositions are made through the incorporation of the otic structure modulating agent or innate immune system modulating agents and/or other pharmaceutical agents into ethylene-vinyl acetate copolymer matrices. (See U.S. Pat. No. 6,083,534, incorporated herein for such disclosure). In another embodiment, otic structure modulating agent or innate immune system modulating agents are incorporated into poly (lactic-glycolic acid) or poly-L-lactic acid microspheres. Id. In yet another embodiment, the otic structure modulating agent or innate immune system modulating agents are encapsulated into alginate microspheres. (See U.S. Pat. No. 6,036,978, incorporated herein for such disclosure). Biocompatible methacrylate-based polymers to encapsulate the otic structure modulating compounds or compositions are optionally used in the compositions and methods disclosed herein. A wide range of methacrylate-based polymer systems are commercially available, such as the EUDRAGIT polymers marketed by Evonik. One useful aspect of methacrylate polymers is that the properties of the composition are varied by incorporating various co-polymers. For example, poly(acrylic acid-co-methylmethacrylate) microparticles exhibit enhanced mucoadhesion properties as the carboxylic acid groups in the poly(acrylic acid) form hydrogen bonds with mucin (Park et al, Pharm. Res. (1987) 4(6):457-464). Variation of the ratio between acrylic acid and methylmethacrylate monomers serves to modulate the properties of the co-polymer. Methacrylate-based microparticles have also been used in protein therapeutic compositions (Naha et al, Journal of Microencapsulation 4 Feb. 2008 (online publication)). In one embodiment, the enhanced viscosity auris-acceptable compositions described herein comprises otic structure modulating microspheres wherein the microspheres are formed from a methacrylate polymer or copolymer. In an additional embodiment, the enhanced viscosity composition described herein comprises otic structure modulating microspheres wherein the microspheres are mucoadhesive. Other controlled-release systems, including incorporation or deposit of polymeric materials or matrices onto solid or hollow spheres containing otic structure modulating agent or innate immune system modulating agents, are also explicitly contemplated within the embodiments disclosed herein. The types of controlled-release systems available without significantly losing activity of the otic structure modulating agent or innate immune system modulating agent are determined using the teachings, examples, and principles disclosed herein An example of a conventional microencapsulation process for pharmaceutical preparations is shown in U.S. Pat. No. 3,737,337, incorporated herein by reference for such disclosure. The otic structure modulating substances to be encapsulated or embedded are dissolved or dispersed in the organic solution of the polymer (phase A), using conventional mixers, including (in the preparation of dispersion) vibrators and high-speed stirrers, etc. The dispersion of phase (A), containing the core material in solution or in suspension, is carried out in the aqueous phase (B), again using conventional mixers, such as high-speed mixers, vibration mixers, or even spray nozzles, in that case the particle size of the microspheres will be determined not only by the concentration of phase (A), but also by the emulsate or microsphere size. With conventional techniques for the microencapsulation of an otic structure modulating agent or innate immune system modulating agents, the microspheres form when the solvent containing an active agent and a polymer is emulsified or dispersed in an immiscible solution by stirring, agitating, vibrating, or some other dynamic mixing technique, often for a relatively long period of time.

Methods for the construction of microspheres are also described in U.S. Pat. No. 4,389,330, and U.S. Pat. No. 4,530,840, incorporated herein by reference for such disclosure. The desired otic structure modulating agent or innate immune system modulating agent is dissolved or dispersed in an appropriate solvent. To the agent-containing medium is added the polymeric matrix material in an amount relative to the active ingredient that gives a product of the desired loading of active agent. Optionally, all of the ingredients of the otic structure modulating microsphere product can be blended in the solvent medium together. Suitable solvents for the agent and the polymeric matrix material include organic solvents such as acetone, halogenated hydrocarbons such as chloroform, methylene chloride and the like, aromatic hydrocarbon compounds, halogenated aromatic hydrocarbon compounds, cyclic ethers, alcohols, ethyl acetate and the like.

The mixture of ingredients in the solvent is emulsified in a continuous-phase processing medium; the continuous-phase medium being such that a dispersion of microdroplets containing the indicated ingredients is formed in the continuous-phase medium. Naturally, the continuous-phase processing medium and the organic solvent must be immiscible, and includes water although nonaqueous media such as xylene and toluene and synthetic oils and natural oils are optionally used. Optionally, a surfactant is added to the continuous-phase processing medium to prevent the microparticles from agglomerating and to control the size of the solvent microdroplets in the emulsion. A preferred surfactant-dispersing medium combination is a 1 to 10 wt. % poly (vinyl alcohol) in water mixture. The dispersion is formed by mechanical agitation of the mixed materials. An emulsion is optionally formed by adding small drops of the active agent-wall forming material solution to the continuous phase processing medium. The temperature during the formation of the emulsion is not especially critical but influences the size and quality of the microspheres and the solubility of the drug in the continuous phase. It is desirable to have as little of the agent in the continuous phase as possible. Moreover, depending on the solvent and continuous-phase processing medium employed, the temperature must not be too low or the solvent and processing medium will solidify or the processing medium will become too viscous for practical purposes, or too high that the processing medium will evaporate, or that the liquid processing medium will not be maintained. Moreover, the temperature of the medium cannot be so high that the stability of the particular agent being incorporated in the microspheres is adversely affected. Accordingly, the dispersion process is conducted at any temperature that maintains stable operating conditions, which preferred temperature being about 15° C. to 60° C., depending upon the drug and excipient selected.

The dispersion that is formed is a stable emulsion and from this dispersion the organic solvent immiscible fluid is optionally partially removed in the first step of the solvent removal process. The solvent is removed by techniques such as heating, the application of a reduced pressure or a combination of both. The temperature employed to evaporate solvent from the microdroplets is not critical, but should not be that high that it degrades the otic structure modulating agent or innate immune system modulating agent employed in the preparation of a given microparticle, nor should it be so high as to evaporate solvent at such a rapid rate to cause defects in the wall forming material. Generally, from 5 to 75%, of the solvent is removed in the first solvent removal step.

After the first stage, the dispersed microparticles in the solvent immiscible fluid medium are isolated from the fluid medium by any convenient means of separation. Thus, for example, the fluid is decanted from the microsphere or the microsphere suspension is filtered. Still other, various combinations of separation techniques are used if desired.

Following the isolation of the microspheres from the continuous-phase processing medium, the remainder of the solvent in the microspheres is removed by extraction. In this step, the microspheres are suspended in the same continuous-phase processing medium used in step one, with or without surfactant, or in another liquid. The extraction medium removes the solvent from the microspheres and yet does not dissolve the microspheres. During the extraction, the extraction medium with dissolved solvent is optionally removed and replaced with fresh extraction medium. This is best done on a continual basis. The rate of extraction medium replenishment of a given process is a variable that is determined at the time the process is performed and, therefore, no precise limits for the rate must be predetermined. After the majority of the solvent has been removed from the microspheres, the microspheres are dried by exposure to air or by other conventional drying techniques such as vacuum drying, drying over a desiccant, or the like. This process is very efficient in encapsulating the otic structure modulating agent or innate immune system modulating agent since core loadings of up to 80 wt. %, preferably up to 60 wt. % are obtained.

Alternatively, controlled-release microspheres containing an otic structure modulating agent or innate immune system modulating agent is prepared through the use of static mixers. Static or motionless mixers consist of a conduit or tube in that is received a number of static mixing agents. Static mixers provide homogeneous mixing in a relatively short length of conduit, and in a relatively short period of time. With static mixers, the fluid moves through the mixer, rather than some part of the mixer, such as a blade, moving through the fluid.

A static mixer is optionally used to create an emulsion. When using a static mixer to form an emulsion, several factors determine emulsion particle size, including the density and viscosity of the various solutions or phases to be mixed, volume ratio of the phases, interfacial tension between the phases, static mixer parameters (conduit diameter; length of mixing element; number of mixing elements), and linear velocity through the static mixer. Temperature is a variable because it affects density, viscosity, and interfacial tension. The controlling variables are linear velocity, sheer rate, and pressure drop per unit length of static mixer.

In order to create microspheres containing an otic structure modulating agent or innate immune system modulating agent using a static mixer process, an organic phase and an aqueous phase are combined. The organic and aqueous phases are largely or substantially immiscible, with the aqueous phase constituting the continuous phase of the emulsion. The organic phase includes an otic structure modulating agent or innate immune system modulating agent as well as a wall-forming polymer or polymeric matrix material. The organic phase is prepared by dissolving an otic structure modulating agent or innate immune system modulating agent in an organic or other suitable solvent, or by forming a dispersion or an emulsion containing the otic structure modulating agent or innate immune system modulating agent. The organic phase and the aqueous phase are pumped so that the two phases flow simultaneously through a static mixer, thereby forming an emulsion that comprises microspheres containing the otic structure modulating agent or innate immune system modulating agent encapsulated in the polymeric matrix material. The organic and aqueous phases are pumped through the static mixer into a large volume of quench liquid to extract or remove the organic solvent. Organic solvent is optionally removed from the microspheres while they are washing or being stirred in the quench liquid. After the microspheres are washed in a quench liquid, they are isolated, as through a sieve, and dried.

In one embodiment, microspheres are prepared using a static mixer. The process is not limited to the solvent extraction technique discussed above, but is used with other encapsulation techniques. For example, the process is optionally used with a phase separation encapsulation technique. To do so, an organic phase is prepared that comprises an otic structure modulating agent or innate immune system modulating agent suspended or dispersed in a polymer solution. The non-solvent second phase is free from solvents for the polymer and active agent. A preferred non-solvent second phase is silicone oil. The organic phase and the non-solvent phase are pumped through a static mixer into a non-solvent quench liquid, such as heptane. The semi-solid particles are quenched for complete hardening and washing. The process of microencapsulation includes spray drying, solvent evaporation, a combination of evaporation and extraction, and melt extrusion.

In another embodiment, the microencapsulation process involves the use of a static mixer with a single solvent. This process is described in detail in U.S. application Ser. No. 08/338,805, herein incorporated by reference for such disclosure. An alternative process involves the use of a static mixer with co-solvents. In this process, biodegradable microspheres comprising a biodegradable polymeric binder and an otic structure modulating agent or innate immune system modulating agent are prepared, which comprises a blend of at least two substantially non-toxic solvents, free of halogenated hydrocarbons to dissolve both the agent and the polymer. The solvent blend containing the dissolved agent and polymer is dispersed in an aqueous solution to form droplets. The resulting emulsion is then added to an aqueous extraction medium preferably containing at least one of the solvents of the blend, whereby the rate of extraction of each solvent is controlled, whereupon the biodegradable microspheres containing the pharmaceutically active agent are formed. This process has the advantage that less extraction medium is required because the solubility of one solvent in water is substantially independent of the other and solvent selection is increased, especially with solvents that are particularly difficult to extract.

Nanoparticles are also contemplated for use with the otic structure modulating agent or innate immune system modulating agents disclosed herein. Nanoparticles are material structures of about 100 nm or less in size. One use of nanoparticles in pharmaceutical compositions is the formation of suspensions as the interaction of the particle surface with solvent is strong enough to overcome differences in density. Nanoparticle suspensions are sterilized as the nanoparticles are small enough to be subjected to sterilizing filtration (see, e.g., U.S. Pat. No. 6,139,870, herein incorporated by reference for such disclosure). Nanoparticles comprise at least one hydrophobic, water-insoluble and water-indispersible polymer or copolymer emulsified in a solution or aqueous dispersion of surfactants, phospholipids or fatty acids. The otic structure modulating agent or innate immune system modulating agent is optionally introduced with the polymer or the copolymer into the nanoparticles.

Lipid nanocapsules as controlled-release structures, as well for penetrating the round window membrane and reaching auris interna and/or auris media targets, is also contemplated herein. Lipid nanocapsules are optionally formed by emulsifying capric and caprylic acid triglycerides (Labrafac WL 1349; avg. mw 512), soybean lecithin (LIPOID® S75-3; 69% phosphatidylcholine and other phospholipids), surfactant (for example, Solutol HS15), a mixture of polyethylene glycol 660 hydroxystearate and free polyethylene glycol 660; NaCl and water. The mixture is stirred at room temperature to obtain an oil emulsion in water. After progressive heating at a rate of 4° C./min under magnetic stirring, a short interval of transparency should occur close to 70° C., and the inverted phase (water droplets in oil) obtained at 85° C. Three cycles of cooling and heating is then applied between 85° C. and 60° C. at the rate of 4° C./min, and a fast dilution in cold water at a temperature close to 0° C. to produce a suspension of nanocapsules. To encapsulate the otic structure modulating agent or innate immune system modulating agents, the agent is optionally added just prior to the dilution with cold water.

Otic structure modulating agent or innate immune system modulating agents are also inserted into the lipid nanocapsules by incubation for 90 minutes with an aqueous micellar solution of the auris active agent. The suspension is then vortexed every 15 minutes, and then quenched in an ice bath for 1 minute.

Suitable auris-acceptable surfactants are, by way of example, cholic acid or taurocholic acid salts. Taurocholic acid, the conjugate formed from cholic acid and taurine, is a fully metabolizable sulfonic acid surfactant. An analog of taurocholic acid, tauroursodeoxycholic acid (TUDCA), is a naturally occurring bile acid and is a conjugate of taurine and ursodeoxycholic acid (UDCA). Other naturally occurring anionic (e.g., galactocerebroside sulfate), neutral (e.g., lactosylceramide) or zwitterionic surfactants (e.g., sphingomyelin, phosphatidyl choline, palmitoyl carnitine) are optionally used to prepare nanoparticles.

The auris-acceptable phospholipids are chosen, by way of example, from natural, synthetic or semi-synthetic phospholipids; lecithins (phosphatidylcholine) such as, for example, purified egg or soya lecithins (lecithin E100, lecithin E80 and phospholipons, for example phospholipon 90), phosphatidylethanolamine, phosphatidylserine, phosphatidylinositol, phosphatidylglycerol, dipalmitoylphosphatidylcholine, dipalmitoylglycerophosphatidylcholine, dimyristoylphosphatidylcholine, distearoylphosphatidylcholine and phosphatidic acid or mixtures thereof are used more particularly.

Fatty acids for use with the auris-acceptable compositions are chosen from, by way of example, lauric acid, mysristic acid, palmitic acid, stearic acid, isostearic acid, arachidic acid, behenic acid, oleic acid, myristoleic acid, palmitoleic acid, linoleic acid, alpha-linoleic acid, arachidonic acid, eicosapentaenoic acid, erucic acid, docosahexaenoic acid, and the like.

Suitable auris-acceptable surfactants are selected from known organic and inorganic pharmaceutical excipients. Such excipients include various polymers, low molecular weight oligomers, natural products, and surfactants. Preferred surface modifiers include nonionic and ionic surfactants. Two or more surface modifiers are used in combination.

Representative examples of auris-acceptable surfactants include cetyl pyridinium chloride, gelatin, casein, lecithin (phosphatides), dextran, glycerol, gum acacia, cholesterol, tragacanth, stearic acid, calcium stearate, glycerol monostearate, cetostearyl alcohol, cetomacrogol emulsifying wax, sorbitan esters, polyoxyethylene alkyl ethers, polyoxyethylene castor oil derivatives, polyoxyethylene sorbitan fatty acid esters; dodecyl trimethyl ammonium bromide, polyoxyethylenestearates, colloidal silicon dioxide, phosphates, sodium dodecylsulfate, carboxymethylcellulose calcium, hydroxypropyl cellulose (HPC, HPC-SL, and HPC-L), hydroxypropyl methylcellulose (HPMC), carboxymethylcellulose sodium, methylcellulose, hydroxyethylcellulose, hydroxypropylcellulose, hydroxypropylmethyl-cellulose phthalate, noncrystalline cellulose, magnesium aluminum silicate, triethanolamine, polyvinyl alcohol (PVA), polyvinylpyrrolidone (PVP), 4-(1,1,3,3-tetaamethylbutyl)-phenol polymer with ethylene oxide and formaldehyde (also known as tyloxapol, superione, and triton), poloxamers, poloxamines, a charged phospholipid such as dimyristoyl phophatidyl glycerol, dioctylsulfosuccinate (DOSS); Tetronic® 1508, dialkylesters of sodium sulfosuccinic acid, Duponol P, Tritons X-200, Crodestas F-110, p-isononylphenoxypoly-(glycidol), Crodestas SL-40 (Croda, Inc.); and SA9OHCO, which is $C_{18}H_{37}CH_2$ $(CON(CH_3)$—$CH_2$ $(CHOH)_4$ $(CH_2OH)_2$ (Eastman Kodak Co.); decanoyl-N-methylglucamide; n-decyl β-D-glucopyranoside; n-decyl β-D-maltopyranoside; n-dodecyl β-D-glucopyranoside; n-dodecyl β-D-maltoside; heptanoyl-N-methylglucamide; n-heptyl-β-D-glucopyranoside; n-heptyl β-D-thioglucoside; n-hexyl β-D-glucopyranoside; nonanoyl-N-methylglucamide; n-noyl β-D-glucopyranoside; octanoyl-N-methylglucamide; n-octyl-β-D-glucopyranoside; octyl β-D-thioglucopyranoside; and the like. Most of these surfactants are known pharmaceutical excipients and are described in detail in the Handbook of Pharmaceutical Excipients, published jointly by the American Pharmaceutical Association and The Pharmaceutical Society of Great Britain (The Pharmaceutical Press, 1986), specifically incorporated by reference for such disclosure.

The hydrophobic, water-insoluble and water-indispersible polymer or copolymer may be chosen from biocompatible and biodegradable polymers, for example lactic or glycolic acid polymers and copolymers thereof, or polylactic/polyethylene (or polypropylene) oxide copolymers, preferably with molecular weights of between 1000 and 200,000, polyhydroxybutyric acid polymers, polylactones of fatty acids containing at least 12 carbon atoms, or polyanhydrides.

The nanoparticles may be obtained by coacervation, or the technique of evaporation of solvent, from an aqueous dispersion or solution of phospholipids and of an oleic acid salt into that is added an immiscible organic phase comprising the active principle and the hydrophobic, water-insoluble and water-indispersible polymer or copolymer. The mixture is pre-emulsified and then subjected to homogenization and evaporation of the organic solvent to obtain an aqueous suspension of very small-sized nanoparticles.

A variety of methods are optionally employed to fabricate the otic structure modulating nanoparticles that are within the scope of the embodiments. These methods include vaporization methods, such as free jet expansion, laser vaporization, spark erosion, electro explosion and chemical vapor deposition; physical methods involving mechanical attrition (e.g., "pearlmilling" technology, Elan Nanosystems), super critical CO2 and interfacial deposition following solvent displacement. In one embodiment, the solvent displacement method is used. The size of nanoparticles produced by this method is sensitive to the concentration of polymer in the organic solvent; the rate of mixing; and to the surfactant employed in the process. Continuous flow mixers provide the necessary turbulence to ensure small particle size. One type of continuous flow mixing device that is optionally used to prepare nanoparticles has been described (Hansen et al J Phys Chem 92, 2189-96, 1988). In other embodiments, ultrasonic devices, flow through homogenizers or supercritical CO2 devices may be used to prepare nanoparticles.

If suitable nanoparticle homogeneity is not obtained on direct synthesis, then size-exclusion chromatography is used to produce highly uniform drug-containing particles that are freed of other components involved in their fabrication. Size-exclusion chromatography (SEC) techniques, such as gel-filtration chromatography, is used to separate particle-bound otic structure modulating agent or innate immune system modulating agent or other pharmaceutical compound from free otic structure modulating agent or innate immune system modulating agent or other pharmaceutical compound, or to select a suitable size range of otic structure modulating-containing nanoparticles. Various SEC media, such as Superdex 200, Superose 6, Sephacryl 1000 are commercially available and are employed for the size-based fractionation of such mixtures. Additionally, nanoparticles are optionally purified by centrifugation, membrane filtration and by use of other molecular sieving devices, cross-linked gels/materials and membranes.

Auris-Acceptable Cyclodextrin and Other Stabilizing Compositions

In a specific embodiment, the auris-acceptable formulations alternatively comprise a cyclodextrin. Cyclodextrins are cyclic oligosaccharides containing 6, 7, or 8 glucopyranose units, referred to as α-cyclodextrin, β-cyclodextrin, or γ-cyclodextrin respectively. Cyclodextrins have a hydrophilic exterior, which enhances water-solublility, and a hydrophobic interior, which forms a cavity. In an aqueous environment, hydrophobic portions of other molecules often enter the hydrophobic cavity of cyclodextrin to form inclusion compounds. Additionally, cyclodextrins are capable of other types of nonbonding interactions with molecules that are not inside the hydrophobic cavity. Cyclodextrins have three free hydroxyl groups for each glucopyranose unit, or 18 hydroxyl groups on α-cyclodextrin, 21 hydroxyl groups on β-cyclodextrin, and 24 hydroxyl groups on γ-cyclodextrin. One or more of these hydroxyl groups can be reacted with any of a number of reagents to form a large variety of cyclodextrin derivatives, including hydroxypropyl ethers, sulfonates, and sulfoalkylethers. Shown below is the structure of β-cyclodextrin and the hydroxypropyl-β-cyclodextrin (HPβCD).

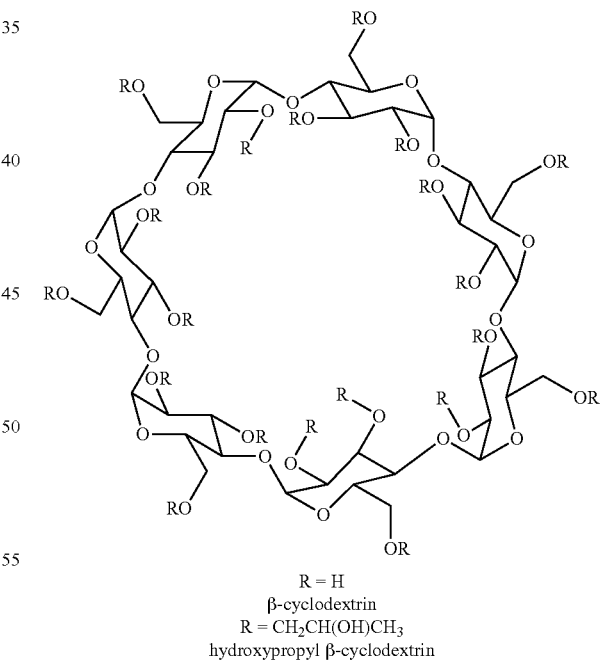

R = H
β-cyclodextrin
R = $CH_2CH(OH)CH_3$
hydroxypropyl β-cyclodextrin

In some embodiments, the use of cyclodextrins in the pharmaceutical compositions described herein improves the solubility of the drug. Inclusion compounds are involved in many cases of enhanced solubility; however other interactions between cyclodextrins and insoluble compounds also improves solubility. Hydroxypropyl-β-cyclodextrin (HPβCD) is commercially available as a pyrogen free product. It is a nonhygroscopic white powder that readily dissolves in water. HPβCD is thermally stable and does not degrade at neutral pH. Thus, cyclodextrins improve the solubility of a therapeutic agent in a composition. Accordingly, in some embodiments, cyclodextrins are included to increase the solubility of the auris-acceptable otic structure modulating agent or innate immune system modulating agents within the compositions described herein. In other embodiments, cyclodextrins in addition serve as controlled-release excipients within the compositions described herein.

By way of example only, cyclodextrin derivatives for use include α-cyclodextrin, β-cyclodextrin, γ-cyclodextrin, hydroxyethyl β-cyclodextrin, hydroxypropyl γ-cyclodextrin, sulfated β-cyclodextrin, sulfated α-cyclodextrin, sulfobutyl ether β-cyclodextrin.

The concentration of the cyclodextrin used in the compositions and methods disclosed herein varies according to the physiochemical properties, pharmacokinetic properties, side effect or adverse events, composition considerations, or other factors associated with the therapeutically active agent, or a salt or prodrug thereof, or with the properties of other excipients in the composition. Thus, in certain circumstances, the concentration or amount of cyclodextrin used in accordance with the compositions and methods described herein will vary, depending on the need. When used, the amount of cyclodextrins needed to increase solubility of the otic structure modulating agent or innate immune system modulating agent and/or function as a controlled-release excipient in any of the compositions described herein is selected using the principles, examples, and teachings described herein.

Other stabilizers that are useful in the auris-acceptable compositions disclosed herein include, for example, fatty acids, fatty alcohols, alcohols, long chain fatty acid esters, long chain ethers, hydrophilic derivatives of fatty acids, polyvinyl pyrrolidones, polyvinyl ethers, polyvinyl alcohols, hydrocarbons, hydrophobic polymers, moisture-absorbing polymers, and combinations thereof. In some embodiments, amide analogues of stabilizers are also used. In further embodiments, the chosen stabilizer changes the hydrophobicity of the composition (e.g., oleic acid, waxes), or improves the mixing of various components in the composition (e.g., ethanol), controls the moisture level in the formula (e.g., PVP or polyvinyl pyrrolidone), controls the mobility of the phase (substances with melting points higher than room temperature such as long chain fatty acids, alcohols, esters, ethers, amides etc. or mixtures thereof, waxes), and/or improves the compatibility of the formula with encapsulating materials (e.g., oleic acid or wax). In another embodiment some of these stabilizers are used as solvents/co-solvents (e.g., ethanol). In other embodiments, stabilizers are present in sufficient amounts to inhibit the degradation of the otic structure modulating agent or innate immune system modulating agent. Examples of such stabilizing agents, include, but are not limited to: (a) about 0.5% to about 2% w/v glycerol, (b) about 0.1% to about 1% w/v methionine, (c) about 0.1% to about 2% w/v monothioglycerol, (d) about 1 mM to about 10 mM EDTA, (e) about 0.01% to about 2% w/v ascorbic acid, (f) 0.003% to about 0.02% w/v polysorbate 80, (g) 0.001% to about 0.05% w/v. polysorbate 20, (h) arginine, (i) heparin, (j) dextran sulfate, (k) cyclodextrins, (l) pentosan polysulfate and other heparinoids, (m) divalent cations such as magnesium and zinc; or (n) combinations thereof.

Additional useful otic structure modulating agent or innate immune system modulating agent auris-acceptable compositions include one or more anti-aggregation additives to enhance stability of a otic structure modulating compositions by reducing the rate of protein aggregation. The anti-aggregation additive selected depends upon the nature of the conditions to that the otic structure modulating agent or innate immune system modulating agents, for example otic structure modulating agent or innate immune system modulating agent antibodies are exposed. For example, certain compositions undergoing agitation and thermal stress require a different anti-aggregation additive than a composition undergoing lyophilization and reconstitution. Useful anti-aggregation additives include, by way of example only, urea, guanidinium chloride, simple amino acids such as glycine or arginine, sugars, polyalcohols, polysorbates, polymers such as polyethylene glycol and dextrans, alkyl saccharides, such as alkyl glycoside, and surfactants.

Other useful compositions optionally include one or more auris-acceptable antioxidants to enhance chemical stability where required. Suitable antioxidants include, by way of example only, ascorbic acid, methionine, sodium thiosulfate and sodium metabisulfite. In one embodiment, antioxidants are selected from metal chelating agents, thiol containing compounds and other general stabilizing agents.

Still other useful compositions include one or more auris-acceptable surfactants to enhance physical stability or for other purposes. Suitable nonionic surfactants include, but are not limited to, polyoxyethylene fatty acid glycerides and vegetable oils, e.g., polyoxyethylene (60) hydrogenated castor oil; and polyoxyethylene alkylethers and alkylphenyl ethers, e.g., octoxynol 10, octoxynol 40.

In some embodiments, the auris-acceptable pharmaceutical compositions described herein are stable with respect to compound degradation over a period of any of at least about 1 day, at least about 2 days, at least about 3 days, at least about 4 days, at least about 5 days, at least about 6 days, at least about 1 week, at least about 2 weeks, at least about 3 weeks, at least about 4 weeks, at least about 5 weeks, at least about 6 weeks, at least about 7 weeks, at least about 8 weeks, at least about 3 months, at least about 4 months, at least about 5 months, or at least about 6 months. In other embodiments, the compositions described herein are stable with respect to compound degradation over a period of at least about 1 week. Also described herein are compositions that are stable with respect to compound degradation over a period of at least about 1 month.

In other embodiments, an additional surfactant (co-surfactant) and/or buffering agent is combined with one or more of the pharmaceutically acceptable vehicles previously described herein so that the surfactant and/or buffering agent maintains the product at an optimal pH for stability. Suitable co-surfactants include, but are not limited to: a) natural and synthetic lipophilic agents, e.g., phospholipids, cholesterol, and cholesterol fatty acid esters and derivatives thereof, b) nonionic surfactants, which include for example, polyoxyethylene fatty alcohol esters, sorbitan fatty acid esters (Spans), polyoxyethylene sorbitan fatty acid esters (e.g., polyoxyethylene (20) sorbitan monooleate (Tween 80), polyoxyethylene (20) sorbitan monostearate (Tween 60), polyoxyethylene (20) sorbitan monolaurate (Tween 20) and other Tweens, sorbitan esters, glycerol esters, e.g., Myrj and glycerol triacetate (triacetin), polyethylene glycols, cetyl alcohol, cetostearyl alcohol, stearyl alcohol, polysorbate 80, poloxamers, poloxamines, polyoxyethylene castor oil derivatives (e.g., Cremophor® RH40, Cremphor A25, Cremphor A20, Cremophor® EL) and other Cremophors, sulfosuccinates, alkyl sulphates (SLS); PEG glyceryl fatty acid esters such as PEG-8 glyceryl caprylate/caprate (Labrasol), PEG-4 glyceryl caprylate/caprate (Labrafac Hydro WL 1219), PEG-32 glyceryl laurate (Gelucire 444/14), PEG-6 glyceryl mono oleate (Labrafil M 1944 CS), PEG-6 glyceryl linoleate (Labrafil M 2125 CS); propylene glycol mono- and di-fatty acid esters, such as propylene glycol laurate, propylene glycol caprylate/caprate; Brij® 700, ascorbyl-6-palmitate, stearylamine, sodium lauryl sulfate, polyoxethyleneglycerol triiricinoleate, and any combinations or mixtures thereof; c) anionic surfactants include, but are not limited to, calcium carboxymethylcellulose, sodium carboxymethylcellulose, sodium sulfosuccinate, dioctyl, sodium alginate, alkyl polyoxyethylene sulfates, sodium lauryl sulfate, triethanolamine stearate, potassium laurate, bile salts, and any combinations or mixtures thereof, and d) cationic surfactants such as cetyltrimethylammonium bromide, and lauryldimethylbenzyl-ammonium chloride.

In a further embodiment, when one or more co-surfactants are utilized in the auris-acceptable compositions of the present disclosure, they are combined, e.g., with a pharmaceutically acceptable vehicle and is present in the final composition, e.g., in an amount ranging from about 0.1% to about 20%, from about 0.5% to about 10%.

In one embodiment, the surfactant has an HLB value of 0 to 20. In additional embodiments, the surfactant has an HLB value of 0 to 3, of 4 to 6, of 7 to 9, of 8 to 18, of 13 to 15, of 10 to 18.

In one embodiment, diluents are also used to stabilize the otic structure modulating agent or innate immune system modulating agent or other pharmaceutical compounds because they provide a more stable environment. Salts dissolved in buffered solutions (that also can provide pH control or maintenance) are utilized as diluents, including, but not limited to a phosphate buffered saline solution. In other embodiments, the gel composition is isotonic with the endolymph or the perilymph: depending on the portion of the cochlea that the otic structure modulating agent or innate immune system modulating agent composition is targeted. Isotonic compositions are provided by the addition of a tonicity agent. Suitable tonicity agents include, but are not limited to any pharmaceutically acceptable sugar, salt or any combinations or mixtures thereof, such as, but not limited to dextrose and sodium chloride. In further embodiments, the tonicity agents are present in an amount from about 100 mOsm/kg to about 500 mOsm/kg. In some embodiments, the tonicity agent is present in an amount from about 200 mOsm/kg to about 400 mOsm/kg, from about 280 mOsm/kg to about 320 mOsm/kg. The amount of tonicity agents will depend on the target structure of the pharmaceutical composition, as described herein.

Useful tonicity compositions also include one or more salts in an amount required to bring osmolality of the composition into an acceptable range for the perilymph or the endolymph. Such salts include those having sodium, potassium or ammonium cations and chloride, citrate, ascorbate, borate, phosphate, bicarbonate, sulfate, thiosulfate or bisulfite anions; suitable salts include sodium chloride, potassium chloride, sodium thiosulfate, sodium bisulfite and ammonium sulfate.

In some embodiments, the auris-acceptable gel compositions disclosed herein alternatively or additionally contains preservatives to prevent microbial growth. Suitable auris-acceptable preservatives for use in the enhanced viscosity compositions described herein include, but are not limited to benzoic acid, boric acid, p-hydroxybenzoates, alcohols, quarternary compounds, stabilized chlorine dioxide, mercurials, such as merfen and thiomersal, mixtures of the foregoing and the like.

In a further embodiment, the preservative is, by way of example only, an antimicrobial agent, within the auris-acceptable compositions presented herein. In one embodiment, the composition includes a preservative such as by way of example only, methyl paraben, sodium bisulfite, sodium thiosulfate, ascorbate, chorobutanol, thimerosal, parabens, benzyl alcohol, phenylethanol and others. In another embodiment, the methyl paraben is at a concentration of about 0.05% to about 1.0%, about 0.1% to about 0.2%. In a further embodiment, the gel is prepared by mixing water, methylparaben, hydroxyethylcellulose and sodium citrate. In a further embodiment, the gel is prepared by mixing water, methylparaben, hydroxyethylcellulose and sodium acetate. In a further embodiment, the mixture is sterilized by autoclaving at 120° C. for about 20 minutes, and tested for pH, methylparaben concentration and viscosity before mixing with the appropriate amount of the otic structure modulating agent or innate immune system modulating agent disclosed herein.

Suitable auris-acceptable water soluble preservatives that are employed in the drug delivery vehicle include sodium bisulfite, sodium thiosulfate, ascorbate, chorobutanol, thimerosal, parabens, benzyl alcohol, Butylated hydroxytoluene (BHT), phenylethanol and others. These agents are present, generally, in amounts of about 0.001% to about 5% by weight or, in the amount of about 0.01 to about 2% by weight. In some embodiments, auris-compatible compositions described herein are free of preservatives.

Round Window Membrane Penetration Enhancers

In another embodiment, the composition further comprises one or more round window membrane penetration enhancers. Penetration across the round window membrane is enhanced by the presence of round window membrane penetration enhancers. Round window membrane penetration enhancers are chemical entities that facilitate transport of coadministered substances across the round window membrane. Round window membrane penetration enhancers are grouped according to chemical structure. Surfactants, both ionic and non-ionic, such as sodium lauryl sulfate, sodium laurate, polyoxyethylene-20-cetyl ether, laureth-9, sodium dodecylsulfate, dioctyl sodium sulfosuccinate, polyoxyethylene-9-lauryl ether (PLE), Tween® 80, nonylphenoxypolyethylene (NP—POE), polysorbates and the like, function as round window membrane penetration enhancers. Bile salts (such as sodium glycocholate, sodium deoxycholate, sodium taurocholate, sodium taurodihydrofusidate, sodium glycodihydrofusidate and the like), fatty acids and derivatives (such as oleic acid, caprylic acid, mono- and di-glycerides, lauric acids, acylcholines, caprylic acids, acylcarnitines, sodium caprates and the like), chelating agents (such as EDTA, citric acid, salicylates and the like), sulfoxides (such as dimethyl sulfoxide (DMSO), decylmethyl sulfoxide and the like), and alcohols (such as ethanol, isopropanol, glycerol, propanediol and the like) also function as round window membrane penetration enhancers.

In some embodiments, the auris acceptable penetration enhancer is a surfactant comprising an alkyl-glycoside wherein the alkyl glycoside is tetradecyl-β-D-maltoside. In some embodiments, the auris acceptable penetration enhancer is a surfactant comprising an alkyl-glycoside wherein the alkyl glycoside is dodecyl-maltoside. In certain instances, the penetration enhancing agent is a hyaluronidase. In certain instances, a hyaluronidase is a human or bovine hyaluronidase. In some instances, a hyaluronidase is a human hyaluronidase (e.g., hyaluronidase found in human sperm, PH20 (Halozyme), Hyelenex® (Baxter International, Inc.)). In some instances, a hyaluronidase is a bovine hyaluronidase (e.g., bovine testicular hyaluronidase, Amphadase® (Amphastar Pharmaceuticals), Hydase® (PrimaPharm, Inc). In some instances, a hyaluronidase is an ovine hyaluronidase, Vitrase® (ISTA Pharmaceuticals). In certain instances, a hyaluronidase described herein is a recombinant hyaluronidase. In some instances, a hyaluronidase described herein is a humanized recombinant hyaluronidase. In some instances, a hyaluronidase described herein is a pegylated hyaluronidase (e.g., PEGPH20 (Halozyme)). In addition, the peptide-like penetration enhancers described in U.S. Pat. Nos. 7,151,191, 6,221,367 and 5,714,167, herein incorporated by references for such disclosure, are contemplated as an additional embodiment. These penetration enhancers are amino-acid and peptide derivatives and enable drug absorption by passive transcellular diffusion without affecting the integrity of membranes or intercellular tight junctions.

Round Window Membrane Permeable Liposomes

Liposomes or lipid particles may also be employed to encapsulate the otic structure modulating compositions or compositions. Phospholipids that are gently dispersed in an aqueous medium form multilayer vesicles with areas of entrapped aqueous media separating the lipid layers. Sonication, or turbulent agitation, of these multilayer vesicles results in the formation of single layer vesicles, commonly referred to as liposomes, with sizes of about 10-1000 nm. These liposomes have many advantages as otic structure modulating agent or innate immune system modulating agents or other pharmaceutical agent carriers. They are biologically inert, biodegradable, non-toxic and non-antigenic. Liposomes are formed in various sizes and with varying compositions and surface properties. Additionally, they are able to entrap a wide variety of agents and release the agent at the site of liposome collapse.

Suitable phospholipids for use in auris-acceptable liposomes here are, for example, phosphatidyl cholines, ethanolamines and serines, sphingomyelins, cardiolipins, plasmalogens, phosphatidic acids and cerebrosides, in particular those that are soluble together with the otic structure modulating agent or innate immune system modulating agents herein in non-toxic, pharmaceutically acceptable organic solvents. Preferred phospholipids are, for example, phosphatidyl choline, phosphatidyl ethanolmine, phosphatidyl serine, phosphatidyl inositol, lysophosphatidyl choline, phosphatidyl glycerol and the like, and mixtures thereof especially lecithin, e.g. soya lecithin. The amount of phospholipid used in the present composition range from about 10 to about 30%, preferably from about 15 to about 25% and in particular is about 20%.

Lipophilic additives may be employed advantageously to modify selectively the characteristics of the liposomes. Examples of such additives include by way of example only, stearylamine, phosphatidic acid, tocopherol, cholesterol, cholesterol hemisuccinate and lanolin extracts. The amount of lipophilic additive used range from 0.5 to 8%, preferably from 1.5 to 4% and in particular is about 2%. Generally, the ratio of the amount of lipophilic additive to the amount of phospholipid ranges from about 1:8 to about 1:12 and in particular is about 1:10. Said phospholipid, lipophilic additive and the otic structure modulating agent or innate immune system modulating agent and other pharmaceutical compounds are employed in conjunction with a non-toxic, pharmaceutically acceptable organic solvent system that dissolve said ingredients. Said solvent system not only must dissolve the otic structure modulating agent or innate immune system modulating agent completely, but it also has to allow the composition of stable single bilayered liposomes. The solvent system comprises dimethylisosorbide and tetraglycol (glycofurol, tetrahydrofurfuryl alcohol polyethylene glycol ether) in an amount of about 8 to about 30%. In said solvent system, the ratio of the amount of dimethylisosorbide to the amount of tetraglycol range from about 2:1 to about 1:3, in particular from about 1:1 to about 1:2.5 and preferably is about 1:2. The amount of tetraglycol in the final composition thus vary from 5 to 20%, in particular from 5 to 15% and preferably is approximately 10%. The amount of dimethylisosorbide in the final composition thus range from 3 to 10%, in particular from 3 to 7% and preferably is approximately 5%.

The term "organic component" as used hereinafter refers to mixtures comprising said phospholipid, lipophilic additives and organic solvents. The otic structure modulating agent or innate immune system modulating agent may be dissolved in the organic component, or other means to maintain full activity of the agent. The amount of an otic structure modulating agent or innate immune system modulating agent in the final composition may range from 0.1 to 5.0%. In addition, other ingredients such as anti-oxidants may be added to the organic component. Examples include tocopherol, butylated hydroxyanisole, butylated hydroxytoluene, ascorbyl palmitate, ascorbyl oleate and the like.

Liposomal compositions are alternatively prepared, for otic structure modulating agent or innate immune system modulating agents or other pharmaceutical agents that are moderately heat-resistant, by (a) heating the phospholipid and the organic solvent system to about 60-80° C. in a vessel, dissolving the active ingredient, then adding any additional formulating agents, and stirring the mixture until complete dissolution is obtained; (b) heating the aqueous solution to 90-95° C. in a second vessel and dissolving the preservatives therein, allowing the mixture to cool and then adding the remainder of the auxiliary formulating agents and the remainder of the water, and stirring the mixture until complete dissolution is obtained; thus preparing the aqueous component; (c) transferring the organic phase directly into the aqueous component, while homogenizing the combination with a high performance mixing apparatus, for example, a high-shear mixer; and (d) adding a viscosity enhancing agent to the resulting mixture while further homogenizing. The aqueous component is optionally placed in a suitable vessel that is equipped with a homogenizer and homogenization is effected by creating turbulence during the injection of the organic component. Any mixing means or homogenizer that exerts high shear forces on the mixture may be employed. Generally, a mixer capable of speeds from about 1,500 to 20,000 rpm, in particular from about 3,000 to about 6,000 rpm may be employed. Suitable viscosity enhancing agents for use in process step (d) are for example, xanthan gum, hydroxypropyl cellulose, hydroxypropyl methylcellulose or mixtures thereof. The amount of viscosity enhancing agent depends on the nature and the concentration of the other ingredients and in general ranges from about 0.5 to 2.0%, or approximately 1.5%. In order to prevent degradation of the materials used during the preparation of the liposomal composition, it is advantageous to purge all solutions with an inert gas such as nitrogen or argon, and to conduct all steps under an inert atmosphere. Liposomes prepared by the above described method usually contain most of the active ingredient bound in the lipid bilayer and separation of the liposomes from unencapsulated material is not required.

In other embodiments, the auris-acceptable compositions, including gel compositions and viscosity-enhanced compositions, further include excipients, other medicinal or pharmaceutical agents, carriers, adjuvants, such as preserving, stabilizing, wetting or emulsifying agents, solution promoters, salts, solubilizers, an antifoaming agent, an antioxidant, a dispersing agent, a wetting agent, a surfactant, and combinations thereof.

Suitable carriers for use in an auris-acceptable composition described herein include, but are not limited to, any pharmaceutically acceptable solvent compatible with the targeted auris structure's physiological environment. In other embodiments, the base is a combination of a pharmaceutically acceptable surfactant and solvent.

In some embodiments, other excipients include, sodium stearyl fumarate, diethanolamine cetyl sulfate, isostearate, polyethoxylated castor oil, nonoxyl 10, octoxynol 9, sodium lauryl sulfate, sorbitan esters (sorbitan monolaurate, sorbitan monooleate, sorbitan monopalmitate, sorbitan monostearate, sorbitan sesquioleate, sorbitan trioleate, sorbitan tristearate, sorbitan laurate, sorbitan oleate, sorbitan palmitate, sorbitan stearate, sorbitan dioleate, sorbitan sesqui-isostearate, sorbitan sesquistearate, sorbitan tri-isostearate), lecithin pharmaceutical acceptable salts thereof and combinations or mixtures thereof.

In other embodiments, the carrier is a polysorbate. Polysorbates are nonionic surfactants of sorbitan esters. Polysorbates useful in the present disclosure include, but are not limited to polysorbate 20, polysorbate 40, polysorbate 60, polysorbate 80 (Tween 80) and any combinations or mixtures thereof. In further embodiments, polysorbate 80 is utilized as the pharmaceutically acceptable carrier.

In one embodiment, water-soluble glycerin-based auris-acceptable enhanced viscosity compositions utilized in the preparation of pharmaceutical delivery vehicles comprise an otic structure modulating agent or innate immune system modulating agent containing at least about 0.1% of the water-soluble glycerin compound or more. In some embodiments, the percentage of an otic structure modulating agent or innate immune system modulating agent is varied between about 1% and about 95%, between about 5% and about 80%, between about 10% and about 60% or more of the weight or volume of the total pharmaceutical composition. In some embodiments, the amount of the compound(s) in each therapeutically useful otic structure modulating agent or innate immune system modulating agent composition is prepared in such a way that a suitable dosage will be obtained in any given unit dose of the compound. Factors such as solubility, bioavailability, biological half-life, route of administration, product shelf life, as well as other pharmacological considerations are contemplated herein.

If desired, the auris-acceptable pharmaceutical gels also contain co-solvents, preservatives, cosolvents, ionic strength and osmolality adjustors and other excipients in addition to buffering agents. Suitable auris-acceptable water soluble buffering agents are alkali or alkaline earth metal carbonates, phosphates, bicarbonates, citrates, borates, acetates, succinates and the like, such as sodium phosphate, citrate, borate, acetate, bicarbonate, carbonate and tromethamine (TRIS). These agents are present in amounts sufficient to maintain the pH of the system at 7.4±0.2 and preferably, 7.4. As such, the buffering agent is as much as 5% on a weight basis of the total composition.

Cosolvents are used to enhance otic structure modulating agent or innate immune system modulating agent solubility, however, some otic structure modulating agent or innate immune system modulating agents or other pharmaceutical compounds are insoluble. These are often suspended in the polymer vehicle with the aid of suitable suspending or viscosity enhancing agents.

Moreover, some pharmaceutical excipients, diluents or carriers are potentially ototoxic. For example, benzalkonium chloride, a common preservative, is ototoxic and therefore potentially harmful if introduced into the vestibular or cochlear structures. In formulating a controlled-release otic structure modulating agent or innate immune system modulating agent composition, it is advised to avoid or combine the appropriate excipients, diluents or carriers to lessen or eliminate potential ototoxic components from the composition, or to decrease the amount of such excipients, diluents or carriers. Optionally, a controlled-release otic structure modulating agent or innate immune system modulating agent composition includes otoprotective agents, such as antioxidants, alpha lipoic acid, calcium, fosfomycin or iron chelators, to counteract potential ototoxic effects that may arise from the use of specific therapeutic agents or excipients, diluents or carriers.

The following are examples of therapeutically acceptable otic compositions:

| Example Composition | Example Characteristics |
| --- | --- |
| Chitosan glycerophosphate (CGP) | tunable degradation of matrix in vitro<br>tunable TACE inhibitor release in vitro: e.g., ~50% of drug released after 24 hrs<br>biodegradable<br>compatible with drug delivery to the inner ear<br>suitable for macromolecules and hydrophobic drugs |
| PEG-PLGA-PEG triblock polymers | tunable high stability: e.g., maintains mechanical integrity >1 month in vitro<br>tunable fast release of hydrophilic drugs: e.g., ~50% of drug released after 24 hrs, and remainder released over ~5 days<br>tunable slow release of hydrophobic drugs: e.g., ~80% released after 8 weeks<br>biodegradable<br>subcutaneous injection of solution: e.g., gel forms within seconds and is intact after 1 month |
| PEO-PPO-PEO triblock copolymers (e.g., Pluronic or Poloxameres) (e.g., F127) | Tunable sol-gel transition temperature: e.g., decreases with increasing F127 concentration |
| Chitosan glycerophosphate with drug-loaded liposomes | CGP composition tolerates liposomes: e.g., up to 15 uM/ml liposomes.<br>liposomes tunably reduce drug release time (e.g., up to 2 weeks in vitro).<br>increase in liposome diameter optionally reduces drug release kinetics (e.g., liposome size between 100 and 300 nm)<br>release parameters are controlled by changing composition of liposomes |

The compositions disclosed herein alternatively encompass an otoprotectant agent in addition to the at least one active agent and/or excipients, including but not limited to such agents as antioxidants, alpha lipoic acid, calcium, fosfomycin or iron chelators, to counteract potential ototoxic effects that may arise from the use of specific therapeutic agents or excipients, diluents or carriers.

Modes of Treatment

Dosing Methods and Schedules

Drugs delivered to the inner ear have been administered systemically via oral, intravenous or intramuscular routes. However, systemic administration for pathologies local to the inner ear increases the likelihood of systemic toxicities and adverse side effects and creates a non-productive distribution of drug in that high levels of drug are found in the serum and correspondingly lower levels are found at the inner ear.

Intratympanic injection of therapeutic agents is the technique of injecting a therapeutic agent behind the tympanic membrane into the middle and/or inner ear. In one embodiment, the compositions described herein are administered directly onto the round window membrane via transtympanic injection. In another embodiment, the otic structure modulating agent or innate immune system modulating agent auris-acceptable compositions described herein are administered onto the round window membrane via a non-transtympanic approach to the inner ear. In additional embodiments, the composition described herein is administered onto the round window membrane via a surgical approach to the round window membrane comprising modification of the crista fenestrae cochleae.

In one embodiment the delivery system is a syringe and needle apparatus that is capable of piercing the tympanic membrane and directly accessing the round window membrane or crista fenestrae cochleae of the auris interna. In some embodiments, the needle on the syringe is wider than a 18 gauge needle. In another embodiment, the needle gauge is from 18 gauge to 31 gauge. In a further embodiment, the needle gauge is from 25 gauge to 30 gauge. Depending upon the thickness or viscosity of the otic structure modulating compositions or compositions, the gauge level of the syringe or hypodermic needle may be varied accordingly. In another embodiment, the internal diameter of the needle can be increased by reducing the wall thickness of the needle (commonly referred as thin wall or extra thin wall needles) to reduce the possibility of needle clogging while maintaining an adequate needle gauge.

In another embodiment, the needle is a hypodermic needle used for instant delivery of the gel composition. The hypodermic needle may be a single use needle or a disposable needle. In some embodiments, a syringe may be used for delivery of the pharmaceutically acceptable gel-based otic structure modulating agent or innate immune system modulating agent-containing compositions as disclosed herein wherein the syringe has a press-fit (Luer) or twist-on (Luer-lock) fitting. In one embodiment, the syringe is a hypodermic syringe. In another embodiment, the syringe is made of plastic or glass. In yet another embodiment, the hypodermic syringe is a single use syringe. In a further embodiment, the glass syringe is capable of being sterilized. In yet a further embodiment, the sterilization occurs through an autoclave. In another embodiment, the syringe comprises a cylindrical syringe body wherein the gel composition is stored before use. In other embodiments, the syringe comprises a cylindrical syringe body wherein the otic structure modulating agent or innate immune system modulating agent pharmaceutically acceptable gel-based compositions as disclosed herein is stored before use that conveniently allows for mixing with a suitable pharmaceutically acceptable buffer. In other embodiments, the syringe may contain other excipients, stabilizers, suspending agents, diluents or a combination thereof to stabilize or otherwise stably store the otic structure modulating agent or innate immune system modulating agent or other pharmaceutical compounds contained therein.

In some embodiments, the syringe comprises a cylindrical syringe body wherein the body is compartmentalized in that each compartment is able to store at least one component of the auris-acceptable otic structure modulating agent or innate immune system modulating agent gel composition. In a further embodiment, the syringe having a compartmentalized body allows for mixing of the components prior to injection into the auris media or auris interna. In other embodiments, the delivery system comprises multiple syringes, each syringe of the multiple syringes contains at least one component of the gel composition such that each component is pre-mixed prior to injection or is mixed subsequent to injection. In a further embodiment, the syringes disclosed herein comprise at least one reservoir wherein the at least one reservoir comprises an otic structure modulating agent or innate immune system modulating agent, or a pharmaceutically acceptable buffer, or a viscosity enhancing agent, such as a gelling agent or a combination thereof. Commercially available injection devices are optionally employed in their simplest form as ready-to-use plastic syringes with a syringe barrel, needle assembly with a needle, plunger with a plunger rod, and holding flange, to perform an intratympanic inj ection.

In some embodiments, the delivery device is an apparatus designed for administration of therapeutic agents to the middle and/or inner ear. By way of example only: GYRUS Medical Gmbh offers micro-otoscopes for visualization of and drug delivery to the round window niche; Arenberg has described a medical treatment device to deliver fluids to inner ear structures in U.S. Pat. Nos. 5,421,818; 5,474,529; and 5,476,446, each of that is incorporated by reference herein for such disclosure. U.S. patent application Ser. No. 08/874,208, which is incorporated herein by reference for such disclosure, describes a surgical method for implanting a fluid transfer conduit to deliver therapeutic agents to the inner ear. U.S. Patent Application Publication 2007/0167918, which is incorporated herein by reference for such disclosure, further describes a combined otic aspirator and medication dispenser for intratympanic fluid sampling and medicament application.

The compositions described herein, and modes of administration thereof, are also applicable to methods of direct instillation or perfusion of the inner ear compartments. Thus, the compositions described herein are useful in surgical procedures including, by way of non-limiting examples, cochleostomy, labyrinthotomy, mastoidectomy, stapedectomy, endolymphatic sacculotomy or the like.

The auris-acceptable compositions or compositions containing the otic structure modulating agent or innate immune system modulating agent compound(s) described herein are administered for prophylactic and/or therapeutic treatments. In therapeutic applications, the otic structure modulating compositions are administered to a patient already suffering from a disorder disclosed herein, in an amount sufficient to cure or at least partially arrest the symptoms of the disease, disorder or condition. Amounts effective for this use will depend on the severity and course of the disease, disorder or condition, previous therapy, the patient's health status and response to the drugs, and the judgment of the treating physician.

In the case wherein the patient's condition does not improve, upon the doctor's discretion the administration of the otic structure modulating agent or innate immune system modulating agent compounds may be administered chronically, which is, for an extended period of time, including throughout the duration of the patient's life in order to ameliorate or otherwise control or limit the symptoms of the patient's disease or condition.

In the case wherein the patient's status does improve, upon the doctor's discretion the administration of the otic structure modulating agent or innate immune system modulating agent compounds may be given continuously; alternatively, the dose of drug being administered may be temporarily reduced or temporarily suspended for a certain length of time (i.e., a "drug holiday"). The length of the drug holiday varies between 2 days and 1 year, including by way of example only, 2 days, 3 days, 4 days, 5 days, 6 days, 7 days, 10 days, 12 days, 15 days, 20 days, 28 days, 35 days, 50 days, 70 days, 100 days, 120 days, 150 days, 180 days, 200 days, 250 days, 280 days, 300 days, 320 days, 350 days, and 365 days. The dose reduction during a drug holiday may be from 10%-100%, including by way of example only 10%, 15%, 20%, 25%, 30%, 35%, 40%, 45%, 50%, 55%, 60%, 65%, 70%, 75%, 80%, 85%, 90%, 95%, and 100%.

Once improvement of the patient's otic conditions has occurred, a maintenance otic structure modulating agent or innate immune system modulating agent dose is administered if necessary. Subsequently, the dosage or the frequency of administration, or both, is optionally reduced, as a function of the symptoms, to a level at that the improved disease, disorder or condition is retained. In certain embodiments, patients require intermittent treatment on a long-term basis upon any recurrence of symptoms.

The amount of an otic structure modulating agent or innate immune system modulating agent that will correspond to such an amount will vary depending upon factors such as the particular compound, disease condition and its severity, according to the particular circumstances surrounding the case, including, e.g., the specific otic structure modulating agent or innate immune system modulating agent being administered, the route of administration, the condition being treated, the target area being treated, and the subject or host being treated. In general, however, doses employed for adult human treatment will typically be in the range of 0.02-50 mg per administration, preferably 1-15 mg per administration. The desired dose is presented in a single dose or as divided doses administered simultaneously (or over a short period of time) or at appropriate intervals.

In some embodiments, the initial administration is a particular otic structure modulating agent or innate immune system modulating agent and the subsequent administration a different composition or otic structure modulating agent or innate immune system modulating agent.

Implants of Exogenous Materials

In some embodiments, the pharmaceutical formulations, compositions and devices described herein are used in combination with (e.g., implantation, short-term use, long-term use, or removal of) the implantation of an exogenous material (e.g., a medical device or a plurality of cells (e.g., stem cells)). As used herein, the term "exogenous material" includes auris-interna or auris-media medical devices (e.g., hearing sparing devices, hearing improving devices, short electrodes, micro-prostheses or piston-like prostheses); needles; drug delivery devices, and cells (e.g., stem cells). In some instances, the implants of exogenous materials are used in conjunction with a patient experiencing hearing loss. In some instances, the hearing loss is present at birth. In some instances, the hearing loss is associated with conditions that develop or progress after birth (e.g., Merniere's disease) resulting in osteoneogenesis, nerve damage, obliteration of cochlear structures, or combinations thereof.

In some instances, the exogenous material is a plurality of cells. In some instances, the exogenous material is a plurality of stem cells.

In some instances, the exogenous material is an electronic device. In some embodiments, the electronic device has an external portion placed behind the ear, and a second portion that is surgically placed under the skin that helps provide a sense of sound to a person who is profoundly deaf or severely hard-of-hearing. By way of example only, such medical device implants bypass damaged portions of the ear and directly stimulate the auditory nerve. In some instances cochlear implants are used in single sided deafness. In some instances cochlear implants are used for deafness in both ears.

In some embodiments, administration of an active agent described herein in combination with the implantation of an exogenous material (e.g., a medical device implant or a stem cell transplant) delays or prevents damage of auris structures, e.g., irritation, cell death osteoneogeneis and/or further neuronal degeneration, caused by installation of an external device and/or a plurality cells (e.g., stem cells) in the ear. In some embodiments, administration of a composition or device described herein in combination with an implant allows for a more effective restoration of hearing loss compared to an implant alone.

In some embodiments, administration of an active agent described herein reduces damage to auris structures caused by underlying conditions allowing for successful implantation. In some embodiments, administration of an active agent described herein, in conjunction surgery and/or with the implantation of an exogenous material reduces or prevents negative side-effects (e.g., cell death).

In some embodiments, administration of an active agent described herein in conjunction with the implantation of an exogenous material has a trophic effect (i.e., promotes healthy growth of cells and healing of tissue in the area of an implant or transplant). In some embodiments, a trophic effect is desirable during otic surgery or during intratympanic injection procedures. In some embodiments, a trophic effect is desirable after installation of a medical device or after a cell (e.g., stem cell) transplant. In some of such embodiments, the compositions or devices described herein are administered via direct cochlear injection, through a chochleostomy or via deposition on the round window In some embodiments, administration of an active agent described herein reduces inflammation and/or infections associated with otic surgery, or implantation of an exogenous material (e.g., a medical device or a plurality of cells (e.g., stem cells)). In some instances, perfusion of a surgical area with a formulation described herein reduces or eliminates post-surgical and/or post-implantation complications (e.g., inflammation, hair cell damage, neuronal degeneration, osteoneogenesis or the like). In some instances, perfusion of a surgical area with a formulation described herein reduces post-surgery or post-implantation recuperation time.

In one aspect, the formulations described herein, and modes of administration thereof, are applicable to methods of direct perfusion of the inner ear compartments. Thus, the formulations described herein are useful in combination with surgical procedures including, by way of non-limiting examples, cochleostomy, labyrinthotomy, mastoidectomy, stapedectomy, stapedotomy, endolymphatic sacculotomy or the like. In some embodiments, the inner ear compartments are perfused with a formulation described herein prior to otic surgery, during otic surgery, after otic surgery, or a combination thereof. In some of such embodiments, the formulations described herein are substantially free of extended release components (e.g., gelling components such as polyoxyethylene-polyoxypropylene copolymers). In some of such embodiments, the formulations described herein contain less than 5% of the extended release components (e.g., gelling components such as polyoxyethylene-polyoxypropylene triblock copolymers) by weight of the formulation. In some of such embodiments, the formulations described herein contain less than 2% of the extended release components (e.g., gelling components such as polyoxyethylene-polyoxypropylene triblock copolymers) by weight of the formulation. In some of such embodiments, the formulations described herein contain less than 1% of the extended release components (e.g., gelling components such as polyoxyethylene-polyoxypropylene triblock copolymers) by weight of the formulation. In some of such embodiments, a composition described herein that is used for perfusion of a surgical area contains substantially no gelling component.

Viscosity

In further embodiments, the auris gel formulation contains a viscosity enhancing agent sufficient to provide a viscosity of between about 500 and 1,000,000 centipoise, between about 750 and 1,000,000 centipoise; between about 1000 and 1,000,000 centipoise; between about 1000 and 400,000 centipoise; between about 2000 and 100,000 centipoise; between about 3000 and 50,000 centipoise; between about 4000 and 25,000 centipoise; between about 5000 and 20,000 centipoise; or between about 6000 and 15,000 centipoise. In some embodiments, the auris gel formulation contains a viscosity enhancing agent sufficient to provide a viscosity of between about 50,0000 and 1,000,000 centipoise.

In some embodiments, the compositions or devices described herein are low viscosity compositions or devices at body temperature. In some embodiments, low viscosity compositions or devices contain from about 1% to about 10% of a viscosity enhancing agent (e.g., gelling components such as polyoxyethylene-polyoxypropylene copolymers). In some embodiments, low viscosity compositions or devices contain from about 2% to about 10% of a viscosity enhancing agent (e.g., gelling components such as polyoxyethylene-polyoxypropylene copolymers). In some embodiments, low viscosity compositions or devices contain from about 5% to about 10% of a viscosity enhancing agent (e.g., gelling components such as polyoxyethylene-polyoxypropylene copolymers). In some embodiments, low viscosity compositions or devices are substantially free of a viscosity enhancing agent (e.g., gelling components such as polyoxyethylene-polyoxypropylene copolymers). In some embodiments, a low viscosity otic structure modulating or complement modulating composition or device described herein provides an apparent viscosity of from about 100 cP to about 10,000 cP. In some embodiments, a low viscosity otic structure modulating or complement modulating composition or device described herein provides an apparent viscosity of from about 500 cP to about 10,000 cP. In some embodiments, a low viscosity otic structure modulating or complement modulating composition or device described herein provides an apparent viscosity of from about 1000 cP to about 10,000 cP. In some of such embodiments, a low viscosity otic structure modulating or complement modulating composition or device is administered in combination with an external otic intervention, e.g., a surgical procedure including but not limited to middle ear surgery, inner ear surgery, typanostomy, cochleostomy, labyrinthotomy, mastoidectomy, stapedectomy, stapedotomy, endolymphatic sacculotomy or the like. In some of such embodiments, a low viscosity otic structure modulating or complement modulating composition or device is administered during an otic intervention. In other such embodiments, a low viscosity otic structure modulating or complement modulating composition or device is administered before the otic intervention.

In some embodiments, the compositions or devices described herein are high viscosity compositions or devices at body temperature. In some embodiments, high viscosity compositions or devices contain from about 10% to about 25% of a viscosity enhancing agent (e.g., gelling components such as polyoxyethylene-polyoxypropylene copolymers). In some embodiments, high viscosity compositions or devices contain from about 14% to about 22% of a viscosity enhancing agent (e.g., gelling components such as polyoxyethylene-polyoxypropylene copolymers). In some embodiments, high viscosity compositions or devices contain from about 15% to about 21% of a viscosity enhancing agent (e.g., gelling components such as polyoxyethylene-polyoxypropylene copolymers). In some embodiments, a high viscosity otic structure modulating or complement modulating composition or device described herein provides an apparent viscosity of from about 100,000 cP to about 1,000,000 cP.

In some embodiments, a high viscosity otic structure modulating or complement modulating composition or device described herein provides an apparent viscosity of from about 150,000 cP to about 500,000 cP. In some embodiments, a high viscosity otic structure modulating or complement modulating composition or device described herein provides an apparent viscosity of from about 250,000 cP to about 500,000 cP. In some of such embodiments, a high viscosity composition or device is a liquid at room temperature and gels at about between room temperature and body temperature (including an individual with a serious fever, e.g., up to about 42° C.). In some embodiments, an otic structure modulating or complement modulating high viscosity composition or device is administered as monotherapy for treatment of an otic disease or condition described herein. In some embodiments, an otic structure modulating or complement modulating high viscosity composition or device is administered in combination with an external otic intervention, e.g., a surgical procedure including but not limited to middle ear surgery, inner ear surgery, typanostomy, cochleostomy, labyrinthotomy, mastoidectomy, stapedectomy, stapedotomy, endolymphatic sacculotomy or the like. In some of such embodiments, a high viscosity otic structure modulating or complement modulating composition or device is administered after the otic intervention. In other such embodiments, a high viscosity otic structure modulating or complement modulating composition or device is administered before the otic intervention.

Pharmacokinetics of Controlled-Release Compositions

In one embodiment, the compositions disclosed herein additionally provides an immediate release of an otic structure modulating agent or innate immune system modulating agent from the composition, or within 1 minute, or within 5 minutes, or within 10 minutes, or within 15 minutes, or within 30 minutes, or within 60 minutes or within 90 minutes. In other embodiments, a therapeutically effective amount of an otic structure modulating agent or innate immune system modulating agent is released from the composition immediately, or within 1 minute, or within 5 minutes, or within 10 minutes, or within 15 minutes, or within 30 minutes, or within 60 minutes or within 90 minutes. In certain embodiments the composition comprises an auris-pharmaceutically acceptable gel composition providing immediate release of an otic structure modulating agent or innate immune system modulating agent. Additional embodiments of the composition may also include an agent that enhances the viscosity of the compositions included herein.

In other or further embodiments, the composition provides an extended release composition of an otic structure modulating agent or innate immune system modulating agent. In certain embodiments, diffusion of an otic structure modulating agent or innate immune system modulating agent from the composition occurs for a time period exceeding 5 minutes, or 15 minutes, or 30 minutes, or 1 hour, or 4 hours, or 6 hours, or 12 hours, or 18 hours, or 1 day, or 2 days, or 3 days, or 4 days, or 5 days, or 6 days, or 7 days, or 10 days, or 12 days, or 14 days, or 18 days, or 21 days, or 25 days, or 30 days, or 45 days, or 2 months or 3 months or 4 months or 5 months or 6 months or 9 months or 1 year. In other embodiments, a therapeutically effective amount of an otic structure modulating agent or innate immune system modulating agent is released from the composition for a time period exceeding 5 minutes, or 15 minutes, or 30 minutes, or 1 hour, or 4 hours, or 6 hours, or 12 hours, or 18 hours, or 1 day, or 2 days, or 3 days, or 4 days, or 5 days, or 6 days, or 7 days, or 10 days, or 12 days, or 14 days, or 18 days, or 21 days, or 25 days, or 30 days, or 45 days, or 2 months or 3 months or 4 months or 5 months or 6 months or 9 months or 1 year.

In other embodiments, the composition provides both an immediate release and an extended release composition of an otic structure modulating agent or innate immune system modulating agent. In yet other embodiments, the composition contains a 0.25:1 ratio, or a 0.5:1 ratio, or a 1:1 ratio, or a 1:2 ratio, or a 1:3, or a 1:4 ratio, or a 1:5 ratio, or a 1:7 ratio, or a 1:10 ratio, or a 1:15 ratio, or a 1:20 ratio of immediate release and extended release compositions. In a further embodiment the composition provides an immediate release of a first otic structure modulating agent or innate immune system modulating agent and an extended release of a second otic structure modulating agent or innate immune system modulating agent or other therapeutic agent. In yet other embodiments, the composition provides an immediate release and extended release composition of an otic structure modulating agent or innate immune system modulating agent, and at least one therapeutic agent. In some embodiments, the composition provides a 0.25:1 ratio, or a 0.5:1 ratio, or a 1:1 ratio, or a 1:2 ratio, or a 1:3, or a 1:4 ratio, or a 1:5 ratio, or a 1:7 ratio, or a 1:10 ratio, or a 1:15 ratio, or a 1:20 ratio of immediate release and extended release compositions of a first otic structure modulating agent or innate immune system modulating agent and second therapeutic agent, respectively.

In a specific embodiment the composition provides a therapeutically effective amount of an otic structure modulating agent or innate immune system modulating agent at the site of disease with essentially no systemic exposure. In an additional embodiment the composition provides a therapeutically effective amount of an otic structure modulating agent or innate immune system modulating agent at the site of disease with essentially no detectable systemic exposure. In other embodiments, the composition provides a therapeutically effective amount of an otic structure modulating agent or innate immune system modulating agent at the site of disease with little or no detectable systemic exposure.

The combination of immediate release, delayed release and/or extended release otic structure modulating compositions or compositions may be combined with other pharmaceutical agents, as well as the excipients, diluents, stabilizers, tonicity agents and other components disclosed herein. As such, depending upon the otic structure modulating agent or innate immune system modulating agent used, the thickness or viscosity desired, or the mode of delivery chosen, alternative aspects of the embodiments disclosed herein are combined with the immediate release, delayed release and/or extended release embodiments accordingly.

In certain embodiments, the pharmacokinetics of the otic structure modulating compositions described herein are determined by injecting the composition on or near the round window membrane of a test animal (including by way of example, a guinea pig or a chinchilla). At a determined period of time (e.g., 6 hours, 12 hours, 1 day, 2 days, 3 days, 4 days, 5 days, 6 days, and 7 days for testing the pharmacokinetics of a composition over a 1 week period), the test animal is euthanized and a 5 mL sample of the perilymph fluid is tested. The inner ear removed and tested for the presence of the otic structure modulating agent or innate immune system modulating agent. As needed, the level of an otic structure modulating agent or innate immune system modulating agent is measured in other organs. In addition, the systemic level of the otic structure modulating agent or innate immune system modulating agent is measured by withdrawing a blood sample from the test animal. In order to determine whether the composition impedes hearing, the hearing of the test animal is optionally tested.

Alternatively, an inner ear is provided (as removed from a test animal) and the migration of the otic structure modulating agent or innate immune system modulating agent is measured. As yet another alternative, an in vitro model of a round window membrane is provided and the migration of the otic structure modulating agent or innate immune system modulating agent is measured.

As described herein, compositions comprising micronized otic agents provide extended release over a longer period of time compared to compositions comprising non-micronized otic agents. In some instances, the micronized otic agent provides a steady supply (e.g., +/−20%) of active agent via slow degradation and serves as a depot for the active agent; such a depot effect increases residence time of the otic agent in the ear. In specific embodiments, selection of an appropriate particle size of the active agent (e.g., micronized active agent) in combination with the amount of gelling agent in the composition provides tunable extended release characteristics that allow for release of an active agent over a period of hours, days, weeks or months.

In some embodiments, the viscosity of any formulation described herein is designed to provide a suitable rate of release from an otic compatible gel. In some embodiments, the concentration of a thickening agent (e.g., gelling components such as polyoxyethylene-polyoxypropylene copolymers) allows for a tunable mean dissolution time (MDT). The MDT is inversely proportional to the release rate of an active agent from a composition or device described herein. Experimentally, the released otic agent is optionally fitted to the Korsmeyer-Peppas equation $$\frac{Q}{Q_\alpha} = kt^n + b$$

where Q is the amount of otic agent released at time t, $Q_\alpha$ is the overall released amount of otic agent, k is a release constant of the nth order, n is a dimensionless number related to the dissolution mechanism and b is the axis intercept, characterizing the initial burst release mechanism wherein n=1 characterizes an erosion controlled mechanism. The mean dissolution time (MDT) is the sum of different periods of time the drug molecules stay in the matrix before release, divided by the total number of molecules and is optionally calculated by:

$$MDT = \frac{nk^{-1/n}}{n+1}$$

For example, a linear relationship between the mean dissolution time (MDT) of a composition or device and the concentration of the gelling agent (e.g., poloxamer) indicates that the otic agent is released due to the erosion of the polymer gel (e.g., poloxamer) and not via diffusion. In another example, a non-linear relationship indicates release of otic agent via a combination of diffusion and/or polymer gel degradation. In another example, a faster gel elimination time course of a composition or device (a faster release of active agent) indicates lower mean dissolution time (MDT). The concentration of gelling components and/or active agent in a composition are tested to determine suitable parameters for MDT. In some embodiments, injection volumes are also tested to determine suitable parameters for preclinical and clinical studies. The gel strength and concentration of the active agent affects release kinetics of an otic agent from the composition. At low poloxamer concentration, elimination rate is accelerated (MDT is lower). An increase in otic agent concentration in the composition or device prolongs residence time and/or MDT of the otic agent in the ear.

In some embodiments, the MDT for poloxamer from a composition or device described herein is at least 6 hours. In some embodiments, the MDT for poloxamer from a composition or device described herein is at least 10 hours.

In some embodiments, the MDT for an active agent from a composition or device described herein is from about 30 hours to about 48 hours. In some embodiments, the MDT for an active agent from a composition or device described herein is from about 30 hours to about 96 hours. In some embodiments, the MDT for an active agent from a composition or device described herein is from about 30 hours to about 1 week. In some embodiments, the MDT for a composition or device described herein is from about 1 week to about 6 weeks.

In some embodiments, the mean residence time (MRT) for an active agent in a composition or device described herein is from about 20 hours to about 48 hours. In some embodiments, the MRT for an active agent from a composition or device described herein is from about 20 hours to about 96 hours. In some embodiments, the MRT for an active agent from a composition or device described herein is from about 20 hours to about 1 week.

In some embodiments, the MRT for an active agent is about 20 hours. In some embodiments, the MRT for an active agent is about 30 hours. In some embodiments, the MRT for an active agent is about 40 hours. In some embodiments, the MRT for an active agent is about 50 hours. In some embodiments, the MRT for an active agent is about 60 hours. In some embodiments, the MRT for an active agent is about 70 hours. In some embodiments, the MRT for an active agent is about 80 hours. In some embodiments, the MRT for an active agent is about 90 hours. In some embodiments, the MRT for an active agent is about 1 week. In some embodiments, the MRT for an active agent is about 90 hours. In some embodiments, the MRT for a composition or device described herein is from about 1 week to about 6 weeks. In some embodiments, the MRT for an active agent is about 1 week. In some embodiments, the MRT for an active agent is about 2 weeks. In some embodiments, the MRT for an active agent is about 3 weeks. In some embodiments, the MRT for an active agent is about 4 weeks. In some embodiments, the MRT for an active agent is about 5 weeks. The half life of an otic agent and mean residence time of the otic agent are determined for each formulation by measurement of concentration of the otic agent in the perilymph using procedures described herein.

In certain embodiments, any controlled release otic formulation described herein increases the exposure of an otic agent and increases the Area Under the Curve (AUC) in otic fluids (e.g., endolymph and/or perilymph) by about 30%, about 40%, about 50%, about 60%, about 70%, about 80% or about 90% compared to a formulation that is not a controlled release otic formulation. In certain embodiments, any controlled release otic formulation described herein increases the exposure time of an otic agent and decreases the $C_{max}$ in otic fluids (e.g., endolymph and/or perilymph) by about 40%, about 30%, about 20%, or about 10%, compared to a formulation that is not a controlled release otic formulation. In certain embodiments, any controlled release otic formulation described herein alters (e.g. reduces) the ratio of $C_{max}$ to $C_{min}$ compared to a formulation that is not a controlled release otic formulation. In certain embodiments, any controlled release otic formulation described herein increases the exposure of an otic agent and increases the length of time that the concentration of an otic agent is above $C_{min}$ by about 30%, about 40%, about 50%, about 60%, about 70%, about 80% or about 90% compared to a formulation that is not a controlled release otic formulation. In certain instances, controlled release formulations described herein delay the time to $C_{max}$. In certain instances, the controlled steady release of a drug prolongs the time the concentration of the drug will stay above the $C_{min}$. In some embodiments, auris compositions described herein prolong the residence time of a drug in the inner ear and provide a stable drug exposure profile. In some instances, an increase in concentration of an active agent in the composition saturates the clearance process and allows for a more rapid and stable steady state to be reached.

In certain instances, once drug exposure (e.g., concentration in the endolymph or perilymph) of a drug reaches steady state, the concentration of the drug in the endolymph or perilymph stays at or about the therapeutic dose for an extended period of time (e.g., one day, 2 days, 3 days, 4 days, 5 days, 6 days, or 1 week, 3 weeks, 6 weeks, 2 months). In some embodiments, the steady state concentration of active agent released from a controlled release formulation described herein is about 20 to about 50 times the steady state concentration of an active agent released from a formulation that is not a controlled release formulation.

The release of an active agent from any formulation, composition or device described herein is optionally tunable to the desired release characteristics. In some embodiments, a composition described herein is a solution that is substantially free of gelling components. In such instances, the composition provides essentially immediate release of an active agent. In some of such embodiments, the composition is useful in perfusion of otic structures, e.g., during surgery.

In some embodiments, a composition described herein is a solution that is substantially free of gelling components and comprises micronized otic agent. In some of such embodiments, the composition provides intermediate release of an active agent from about 2 day to about 4 days.

In some embodiments, a composition described herein comprises a gelling agent (e.g., poloxamer 407) and provides release of an active agent over a period of from about 1 day to about 3 days. In some embodiments, a composition described herein comprises a gelling agent (e.g., poloxamer 407) and provides release of an active agent over a period of from about 1 day to about 5 days. In some embodiments, a composition described herein comprises a gelling agent (e.g., poloxamer 407) and provides release of an active agent over a period of from about 2 days to about 7 days.

In some embodiments, a composition described herein comprises a gelling agent (e.g., poloxamer 407) in combination with micronized otic agent and provides extended sustained release. In some embodiments, a composition described herein comprises (a) about 14-17% of a gelling agent (e.g., poloxamer 407) and (b) a micronized otic agent; and provides extended sustained release over a period of from about 1 week to about 3 weeks. In some embodiments, a composition described herein comprises (a) about 16% of a gelling agent (e.g., poloxamer 407) and (b) a micronized otic agent; and provides extended sustained release over a period of from about 3 weeks. In some embodiments, a composition described herein comprises (a) about 18-21% of a gelling agent (e.g., poloxamer 407) and (b) a micronized otic agent; and provides extended sustained release over a period of from about 3 weeks to about 6 weeks. In some embodiments, a composition described herein comprises (a) about 20% of a gelling agent (e.g., poloxamer 407) and (b) a micronized otic agent; and provides extended sustained release over a period of from about 6 weeks. In some embodiments, the amount of gelling agent in a composition, and the particle size of an otic agent are tunable to the desired release profile of an otic agent from the composition.

In specific embodiments, compositions comprising micronized otic agents provide extended release over a longer period of time compared to compositions comprising non-micronized otic agents. In specific embodiments, selection of an appropriate particle size of the active agent (e.g., micronized active agent) in combination with the amount of gelling agent in the composition provides tunable extended release characteristics that allow for release of an active agent over a period of hours, days, weeks or months.

Kits/Articles of Manufacture

The disclosure also provides kits for preventing, treating or ameliorating the symptoms of a disease or disorder in a mammal. Such kits generally will comprise one or more of the otic structure modulating agent or innate immune system modulating agent controlled-release compositions or devices disclosed herein, and instructions for using the kit. The disclosure also contemplates the use of one or more of the otic structure modulating agent or innate immune system modulating agent controlled-release compositions, in the manufacture of medicaments for treating, abating, reducing, or ameliorating the symptoms of a disease, dysfunction, or disorder in a mammal, such as a human that has, is suspected of having, or at risk for developing an inner ear disorder.

In some embodiments, kits include a carrier, package, or container that is compartmentalized to receive one or more containers such as vials, tubes, and the like, each of the container(s) including one of the separate elements to be used in a method described herein. Suitable containers include, for example, bottles, vials, syringes, and test tubes. In other embodiments, the containers are formed from a variety of materials such as glass or plastic.

The articles of manufacture provided herein contain packaging materials. Packaging materials for use in packaging pharmaceutical products are also presented herein. See, e.g., U.S. Pat. Nos. 5,323,907, 5,052,558 and 5,033,252. Examples of pharmaceutical packaging materials include, but are not limited to, blister packs, bottles, tubes, inhalers, pumps, bags, vials, containers, syringes, bottles, and any packaging material suitable for a selected composition and intended mode of administration and treatment. A wide array of a otic structure modulating compositions provided herein are contemplated as are a variety of treatments for any disease, disorder, or condition that would benefit by controlled-release administration of an otic structure modulating agent or innate immune system modulating agent to the inner ear.

In some embodiments, a kit includes one or more additional containers, each with one or more of various materials (such as reagents, optionally in concentrated form, and/or devices) desirable from a commercial and user standpoint for use of a composition described herein. Non-limiting examples of such materials include, but not limited to, buffers, diluents, filters, needles, syringes; carrier, package, container, vial and/or tube labels listing contents and/or instructions for use and package inserts with instructions for use. A set of instructions is optionally included. In a further embodiment, a label is on or associated with the container. In yet a further embodiment, a label is on a container when letters, numbers or other characters forming the label are attached, molded or etched into the container itself; a label is associated with a container when it is present within a receptacle or carrier that also holds the container, e.g., as a package insert. In other embodiments a label is used to indicate that the contents are to be used for a specific therapeutic application. In yet another embodiment, a label also indicates directions for use of the contents, such as in the methods described herein.

In certain embodiments, the pharmaceutical compositions are presented in a pack or dispenser device that contains one or more unit dosage forms containing a compound provided herein. In another embodiment, the pack for example contains metal or plastic foil, such as a blister pack. In a further embodiment, the pack or dispenser device is accompanied by instructions for administration. In yet a further embodiment, the pack or dispenser is also accompanied with a notice associated with the container in form prescribed by a governmental agency regulating the manufacture, use, or sale of pharmaceuticals, which notice is reflective of approval by the agency of the form of the drug for human or veterinary administration. In another embodiment, such notice, for example, is the labeling approved by the U.S. Food and Drug Administration for prescription drugs, or the approved product insert. In yet another embodiment, compositions containing a compound provided herein formulated in a compatible pharmaceutical carrier are also prepared, placed in an appropriate container, and labeled for treatment of an indicated condition.

EXAMPLES

Example 1—Preparation of a Methotrexate/Hyaluronidase Thermoreversible Gel Formulation

| Ingredient | Quantity (mg/g of formulation) |
|---|---|
| Methylparaben | 1.0 |
| HPMC | 10.0 |
| Poloxamer 407 | 180.0 |
| TRIS HCl buffer (0.1 M) | 808.0 |
| Hyaluronidase | 1.0 |
| Thimerosal | 0.1 |

A 10-g batch of gel formulation containing 0.1% of hyaluronidase is prepared by suspending 1.80 g of Poloxamer 407 (BASF Corp.) in 5.00 g of TRIS HCl buffer (0.1 M) and the components are mixed under agitation overnight at 4° C. to ensure complete dissolution. The hydroxypropylmethylcellulose (100.0 mg), methylparaben (10 mg) and additional TRIS HCl buffer (0.1 M) (3.08 g) are added and further stirring allowed until complete dissolution is observed. Methotrexate (10 mg) is added and mixed in order to solubilize. The mixture is maintained below room temperature until use.

Example 2—Preparation of a Collagen Mucoadhesive, Thermoreversible Gel Formulation

| Ingredient | Quantity (mg/g of formulation) |
|---|---|
| Collagen | 10.0 |
| Methylparaben | 1.0 |
| HPMC | 10.0 |
| Carbopol 934P | 2.0 |
| Poloxamer 407 | 180.0 |
| TRIS HCl buffer (0.1M) | 797.0 |
| Thimerosal | 0.1 |

A 10-g batch of a mucoadhesive, gel formulation containing 1.0% of collagen is prepared by suspending 20.0 mg of Carbopol 934P and 1.80 g of Poloxamer 407 (BASF Corp.) in 5.00 g of TRIS HCl buffer (0.1 M) and the components are mixed under agitation overnight at 4° C. to ensure complete dissolution. The hydroxypropylmethylcellulose (100.0 mg), methylparaben (10 mg) and additional TRIS HCl buffer (0.1 M) (2.97 g) are added and further stirring allowed until complete dissolution is observed. The mixture is maintained below room temperature until use.

Example 3—Preparation of a Thermoreversible Gel KCNQ Modulator/Hyaluronidase Formulation

| Ingredient | Quantity (mg/g of formulation) |
|---|---|
| Retigabine | 18.0 |
| Hyaluronidase | 2.0 |
| methylparaben | 1.0 |
| HPMC | 10.0 |
| Poloxamer 407 | 180.0 |
| TRIS HCl buffer (0.1M) | 789.0 |

A 10-g batch of gel formulation containing 1.8% of retigabine, 0.2% hyaluronidase is prepared by suspending 1.80 g of Poloxamer 407 (BASF Corp.) in 5.00 g of TRIS HCl buffer (0.1 M) and the components are mixed under agitation overnight at 4° C. to ensure complete dissolution. The retigabine (200.0 mg), hydroxypropylmethylcellulose (100.0 mg), methylparaben (10 mg) and additional TRIS HCl buffer (0.1 M) (2.89 g) is added and further stirring allowed until complete dissolution is observed. The mixture is maintained below room temperature until use.

Example 4—Preparation of a Hyaluronidase Mucoadhesive-Based Formulation

| Ingredient | Quantity (mg/g of formulation) |
|---|---|
| Hyaluronidase | 10.0 |
| Sodium citrate | 1.25 |
| Sodium ascorbate | 0.8 |
| Paraffin oil | 200 |
| Trihydroxystearate | 10 |
| Cetyl dimethicon copolyol | 30 |
| Water | qs ad 1000 |
| Phosphate buffer pH 7.4 | qs pH 7.4 |

The cream-type formulation is first prepared by gently mixing a hyaluronidase with a buffer. A second system is prepared by mixing paraffin oil, trihydroxystearate and cetyl dimethicon copolyol with warming to 60° C. Upon cooling to room temperature, the lipid system is mixed with the aqueous phase for 30 minutes.

Example 5—Preparation of a Collagenase Mucoadhesive, Thermoreversible Gel Formulation

| Ingredient | Quantity (mg/g of formulation) |
|---|---|
| Collagenase | 10.0 |
| Methylparaben | 1.0 |
| Poloxamer 407 | 180.0 |
| Carbopol 934P | 2.0 |
| TRIS HCl buffer (0.1M) | 316.0 |
| Thimerosal | 0.1 |

The Carbopol 934P and Poloxamer 407 (BASF Corp.) is first suspended in the TRIS HCl buffer (0.1 M) and the components are mixed under agitation overnight at 4° C. to ensure complete dissolution. The methylparaben is added and further stirring allowed until complete dissolution is observed. The collagenase is mixed in while maintaining stirring to produce a 0.2% collagenase mucoadhesive, thermoreversible gel formulation. The mixture is maintained below room temperature until use.

Viscosity determinations of the pharmaceutical compositions described herein are performed at room temperature and 37° C. and are made using a Brookfield (spindle and cup) viscometer at 20 rpm.

Example 6—Preparation of a Keratin Mucoadhesive-Based Formulation

| Ingredient | Quantity (mg/g of formulation) |
|---|---|
| Keratin | 100.0 |
| Sodium citrate | 6.75 |
| Sodium ascorbate | 4.32 |
| Paraffin oil | 500.0 |
| Trihydroxystearate | 54.0 |
| Cetyl dimethicon copolyol | 162.0 |
| Water | qs ad 1000 |
| Phosphate buffer pH 7.4 | qs pH 7.4 |

The cream-type formulation is first prepared by gently mixing a keratin with a buffer. A second system is prepared by mixing paraffin oil, trihydroxystearate and cetyl dimethicon copolyol with warming to 60° C. Upon cooling to room temperature, the lipid system is mixed with the aqueous phase for 30 minutes.

Example 7—Preparation of a Gel/Liposome Thyme Oil Formulation

| Ingredient | Quantity |
|---|---|
| Thyme oil | 20.0 mg/g |
| Liposomes | 15 umol/ml |
| Chitosan-Glycerophosphate | 100.0 mg/g |

The liposomes are prepared in the presence of the thyme oil by the reversed-phase evaporation method, where lipids in chloroform or chloroform-methanol (2:1, v/v) are deposited on the sides of a tube by evaporation of the organic solvent. The lipid film is redissolved in diethyl ether and the aqueous phase (pH 7.4 300 mOsm/kg) containing 20 mM Hepes and 144 mM NaCl is added. The mixture is sonicated to obtain a homogeneous emulsion, and then the organic solvent is removed under vacuum. The preparation is extruded to obtain the required liposome size and free components removed by size-exclusion chromatography using a Sephadex G-50 column (Amersham Pharmacia Biotech, Uppsala, Sweden).

To prepare the chitosan-glycerophosphate formulation, a 5 ml solution of acetic acid is titrated to a pH of about 4.0. The chitosan is added to achieve a pH of about 5.5. This solution is sterilized by filtration. A 5 ml aqueous solution of glycerophosphate disodium is also prepared and sterilized. The two solutions are mixed and within 2 h at 37° C., and the desired gel is formed. The chitosan-glycerophosphate solution is gently mixed with the liposomes at room temperature.

Example 8—Preparation of a Bisphosphonate Thermoreversible Gel Formulation

| Ingredient | Quantity (mg/g of formulation) |
|---|---|
| Alendronate sodium | 10.0 |
| Sodium citrate | 1.25 |
| Sodium ascorbate | 0.8 |
| Hyaluronidase PH20 | 10 |
| Poloxamer 407 | 15 |
| Water | qs ad 1000 |
| Phosphate buffer pH 7.4 | qs pH 7.4 |

The liquid formulation is prepared by mixing alendronate sodium and hyaluronidase PH20 with a buffer to form a first solution. A second system is prepared by mixing poloxamer 407, sodium citrate, and sodium ascorbate in water with warming to 60° C. The first solution is added to the second system and mixed well.

Example 9—Preparation of a Hyaluronidase Thermoreversible Gel Formulation

| Ingredient | Quantity (mg/g of formulation) |
|---|---|
| Hyaluronidase PH20 | 200 |
| Sodium chloride | 10 |
| Edetate disodium | 1.2 |
| Calcium chloride | 0.5 |
| Poloxamer 188 | 12 |
| Water | qs ad 1000 |
| Phosphate buffer pH 7.4 | qs pH 7.4 |

The liquid formulation is first prepared by gently mixing PH20 with a buffer. A second system is prepared by mixing poloxamer 188, sodium chloride, edetate disodium and calcium chloride in water with warming to 60° C. The PH20 solution is added to the second system and mixed well.

Example 10—Preparation of a Bisphosphonate Mucoadhesive-Based Formulation

| Ingredient | Quantity (mg/g of formulation) |
|---|---|
| risedronate | 10.0 |
| Sodium citrate | 1.25 |
| Sodium ascorbate | 0.8 |
| Paraffin oil | 200 |
| Hydroxypropyl methylcellulose | 10 |
| Cetyl dimethicon copolyol | 30 |
| Water | qs ad 1000 |
| Phosphate buffer pH 7.4 | qs pH 7.4 |

The cream-type formulation is first prepared by gently mixing risedronate with a buffer. A second system is prepared by mixing paraffin oil, hydroxypropyl methylcellulose and cetyl dimethicon copolyol with warming to 60° C. Upon cooling to room temperature, the lipid system is mixed with the aqueous phase for 30 minutes.

Example 11—Preparation of a Parathyroid Hormone Mucoadhesive-Based Formulation

| Ingredient | Quantity (mg/g of formulation) |
|---|---|
| Parathyroid Hormone | 100.0 |
| Sodium citrate | 6.75 |

-continued

| Ingredient | Quantity (mg/g of formulation) |
|---|---|
| Sodium ascorbate | 4.32 |
| Paraffin oil | 500.0 |
| Trihydroxystearate | 54.0 |
| Cetyl dimethicon copolyol | 162.0 |
| Water | qs ad 1000 |
| Phosphate buffer pH 7.4 | qs pH 7.4 |

The cream-type formulation is first prepared by gently mixing a parathyroid hormone with a buffer. A second system is prepared by mixing paraffin oil, trihydroxystearate and cetyl dimethicon copolyol with warming to 60° C. Upon cooling to room temperature, the lipid system is mixed with the aqueous phase for 30 minutes.

Example 12—Preparation of a FUT-175 Thermoreversible Gel Formulation

| Ingredient | Quantity (mg/g of formulation) |
|---|---|
| Methylparaben | 3.0 |
| HPMC | 30.0 |
| Poloxamer 407 | 540.0 |
| TRIS HCl buffer (0.1M) | 2424.0 |
| FUT-175 | 3.0 |

A 10-g batch of gel formulation containing 0.1% of FUT-175 is prepared by suspending 1.80 g of Poloxamer 407 (BASF Corp.) in 5.00 g of TRIS HCl buffer (0.1 M) and the components are mixed under agitation overnight at 4° C. to ensure complete dissolution. The hydroxypropylmethylcellulose (100.0 mg), methylparaben (10 mg) and additional TRIS HCl buffer (0.1 M) (3.08 g) are added and further stirring allowed until complete dissolution is observed. The mixture is maintained below room temperature until use.

Example 13—Preparation of a TKIXc Mucoadhesive, Thermoreversible Gel Formulation

| Ingredient | Quantity (mg/g of formulation) |
|---|---|
| TKIXc | 45.0 |
| Methylparaben | 4.5 |
| HPMC | 45.0 |
| Carbopol 934P | 9.0 |
| Poloxamer 407 | 810.0 |
| TRIS HCl buffer (0.1M) | 3586.5 |

A 10-g batch of a mucoadhesive, gel formulation containing 1.0% of TKIXc is prepared by suspending 20.0 mg of Carbopol 934P and 1.80 g of Poloxamer 407 (BASF Corp.) in 5.00 g of TRIS HCl buffer (0.1 M) and the components are mixed under agitation overnight at 4° C. to ensure complete dissolution. The hydroxypropylmethylcellulose (100.0 mg), methylparaben (10 mg) and additional TRIS HCl buffer (0.1 M) (2.97 g) are added and further stirring allowed until complete dissolution is observed. The mixture is maintained below room temperature until use.

Example 14—Preparation of a TKIXc Mucoadhesive-Based Formulation

| Ingredient | Quantity (mg/g of formulation) |
|---|---|
| TKIXc | 25.0 |
| Sodium citrate | 3.125 |
| Sodium ascorbate | 2.0 |
| Paraffin oil | 500.0 |
| Trihydroxystearate | 25.0 |
| Cetyl dimethicon copolyol | 75.0 |
| Water | qs ad 1000 |
| Phosphate buffer pH 7.4 | qs pH 7.4 |

The cream-type formulation is first prepared by gently mixing a TKIXc with a buffer. A second system is prepared by mixing paraffin oil, trihydroxystearate and cetyl dimethicon copolyol with warming to 60° C. Upon cooling to room temperature, the lipid system is mixed with the aqueous phase for 30 minutes.

Example 15—Preparation of a Heparin Mucoadhesive, Thermoreversible Gel Formulation

| Ingredient | Quantity (mg/g of formulation) |
|---|---|
| Heparin | 10.0 |
| Methylparaben | 1.0 |
| Poloxamer 407 | 180.0 |
| Carbopol 934P | 2.0 |
| TRIS HCl buffer (0.1M) | 316.0 |
| Thimerosal | 0.1 |

The Carbopol 934P and Poloxamer 407 (BASF Corp.) is first suspended in the TRIS HCl buffer (0.1 M) and the components are mixed under agitation overnight at 4° C. to ensure complete dissolution. The methylparaben is added and further stirring allowed until complete dissolution is observed. The heparin is mixed in while maintaining stirring to produce a 0.2% collagenase mucoadhesive, thermoreversible gel formulation. The mixture is maintained below room temperature until use.

Viscosity determinations of the pharmaceutical compositions described herein are performed at room temperature and 37° C. and are made using a Brookfield (spindle and cup) viscometer at 20 rpm.

Example 16—Application of an Enhanced Viscosity Otic Agent Formulation onto the Round Window Membrane A formulation according to Example 2 is prepared and loaded into 5 ml siliconized glass syringes attached to a 15-gauge luer lock disposable needle. Lidocaine is topically applied to the tympanic membrane, and a small incision made to allow visualization into the middle ear cavity. The needle tip is guided into place over the round window membrane, and the otic agent formulation applied directly onto the round-window membrane.

Example 17—Preparation of a Gel/Liposome sCR1-SLe$^x$ Formulation

| Ingredient | Quantity |
| --- | --- |
| sCR1-SLe$^x$ | 20.0 mg/g |
| Liposomes | 15 umol/ml |
| Chitosan-Glycerophosphate | 100.0 mg/g |

The liposomes are prepared in the presence of the sCR1-SLe$^x$ by the reversed-phase evaporation method, where lipids in chloroform or chloroform-methanol (2:1, v/v) are deposited on the sides of a tube by evaporation of the organic solvent. The lipid film is redissolved in diethyl ether and the aqueous phase (pH 7.4 300 mOsm/kg) containing 20 mM Hepes and 144 mM NaCl is added. The mixture is sonicated to obtain a homogeneous emulsion, and then the organic solvent is removed under vacuum. The preparation is extruded to obtain the required liposome size and free components removed by size-exclusion chromatography using a Sephadex G-50 column (Amersham Pharmacia Biotech, Uppsala, Sweden).

To prepare the chitosan-glycerophosphate formulation, a 5 ml solution of acetic acid is titrated to a pH of about 4.0. The chitosan is added to achieve a pH of about 5.5. This solution is sterilized by filtration. A 5 ml aqueous solution of glycerophosphate disodium is also prepared and sterilized. The two solutions are mixed and within 2 h at 37° C., and the desired gel is formed. The chitosan-glycerophosphate solution is gently mixed with the liposomes at room temperature.

Example 18—Application of an Enhanced Viscosity Otic Agent Formulation onto the Round Window Membrane A formulation according to example 2 is prepared and loaded into 5 ml siliconized glass syringes attached to a 15-gauge luer lock disposable needle. Lidocaine is topically applied to the tympanic membrane, and a small incision made to allow visualization into the middle ear cavity. The needle tip is guided into place over the round window membrane, and the otic agent formulation applied directly onto the round-window membrane.

Example 19—Effect of pH on Degradation Products for Autoclaved 17% Poloxamer 407NF/2% Otic Agent in PBS Buffer A stock solution of a 17% poloxamer 407/2% otic agent is prepared by dissolving 351.4 mg of sodium chloride (Fisher Scientific), 302.1 mg of sodium phosphate dibasic anhydrous (Fisher Scientific), 122.1 mg of sodium phosphate monobasic anhydrous (Fisher Scientific) and an appropriate amount of an otic agent with 79.3 g of sterile filtered DI water. The solution is cooled down in a ice chilled water bath and then 17.05 g of poloxamer 407NF (SPECTRUM CHEMICALS) is sprinkled into the cold solution while mixing. The mixture is further mixed until the poloxamer is completely dissolved. The pH for this solution is measured.

17% poloxamer 407/2% otic agent in PBS pH of 5.3. Take an aliquot (approximately 30 mL) of the above solution and adjust the pH to 5.3 by the addition of 1 M HCl.

17% poloxamer 407/2% otic agent in PBS pH of 8.0. Take an aliquot (approximately 30 mL) of the above stock solution and adjust the pH to 8.0 by the addition of 1 M NaOH.

A PBS buffer (pH 7.3) is prepared by dissolving 805.5 mg of sodium chloride (Fisher Scientific), 606 mg of sodium phosphate dibasic anhydrous (Fisher Scientific), 247 mg of sodium phosphate monobasic anhydrous (Fisher Scientific), then QS to 200 g with sterile filtered DI water.

A 2% solution of an otic agent in PBS pH 7.3 is prepared by dissolving an appropriate amount of the otic agent in the PBS buffer and QS to 10 g with PBS buffer.

One mL samples are individually placed in 3 mL screw cap glass vials (with rubber lining) and closed tightly. The vials are placed in a Market Forge-sterilmatic autoclave (settings, slow liquids) and sterilized at 250° F. for 15 minutes. After the autoclave the samples are left to cool down to room temperature and then placed in refrigerator. The samples are homogenized by mixing the vials while cold.

Appearance (e.g., discoloration and/or precipitation) is observed and recorded. HPLC analysis is performed using an Agilent 1200 equipped with a Luna C18(2) 3 μm, 100 Å, 250×4.6 mm column) using a 30-80 acetonitrile gradient (1-10 min) of (water-acetonitrile mixture containing 0.05% TFA), for a total run of 15 minutes. Samples are diluted by taking 30 μL of sample and dissolved with 1.5 mL of a 1:1 acetonitrile water mixture. Purity of the otic agent in the autoclaved samples is recorded.

In general the composition should not have any individual impurity (e.g., degradation product of otic agent) of more than 2% and more preferably not more than one percent. In addition, the composition should not precipitate during storage or change in color after manufacturing and storage.

Compositions comprising alprazolam, clonazepam, diazepam, or micronized diazepam, prepared according to the procedure in Example 6, are tested using the above procedure to determine the effect of pH on degradation during the autoclaving step.

Example 20—Effect of Autoclaving on the Release Profile and Viscosity of a 17% Poloxamer 407NF/2% Otic Agent in PBS An aliquot of the sample from example 6 (autoclaved and not autoclaved) is evaluated for release profile and viscosity measurement to evaluate the impact of heat sterilization on the properties of the gel.

Dissolution is performed at 37° C. in snapwells (6.5 mm diameter polycarbonate membrane with a pore size of 0.4 μm). 0.2 mL of gel is placed into snapwell and left to harden, then 0.5 mL is placed into reservoir and shaken using a Labline orbit shaker at 70 rpm. Samples are taken every hour (0.1 mL withdrawn and replace with warm buffer). Samples are analyzed for poloxamer concentration by UV at 624 nm using the cobalt thiocyanate method, against an external calibration standard curve. In brief, 20 μL of the sample is mixed with 1980 μL of a 15 mM cobalt thiocyanate solution and absorbance measured at 625 nm, using a Evolution 160 UV/Vis spectrophotometer (Thermo Scientific).

The released otic agent is fitted to the Korsmeyer-Peppas equation $$\frac{Q}{Q_\alpha} = kt^n + b$$

where Q is the amount of otic agent released at time t, $Q_\alpha$ is the overall released amount of otic agent, k is a release constant of the nth order, n is a dimensionless number related to the dissolution mechanism and b is the axis intercept, characterizing the initial burst release mechanism wherein n=1 characterizes an erosion controlled mechanism. The mean dissolution time (MDT) is the sum of different periods of time the drug molecules stay in the matrix before release, divided by the total number of molecules and is calculated by:

$$MDT = \frac{nk^{-1/n}}{n+1}$$

Viscosity measurements are performed using a Brookfield viscometer RVDV-II+P with a CPE-51 spindle rotated at 0.08 rpm (shear rate of 0.31 s$^{-1}$), equipped with a water jacketed temperature control unit (temperature ramped from 15-34° C. at 1.6° C./min). Tgel is defined as the inflection point of the curve where the increase in viscosity occurs due to the sol-gel transition.

Compositions comprising collagen, keratin, collagenase, or micronized collagen prepared according to the procedure in Example 6, are tested using the procedure described above to determine Tgel.

Example 21—Effect of Addition of a Secondary Polymer on the Degradation Products and Viscosity of a Composition Containing 2% Otic Agent and 17% Poloxamer 407NF after Heat Sterilization (Autoclaving)

Solution A. A solution of pH 7.0 comprising sodium carboxymethylcellulose (CMC) in PBS buffer is prepared by dissolving 178.35 mg of sodium chloride (Fisher Scientific), 300.5 mg of sodium phosphate dibasic anhydrous (Fisher Scientific), 126.6 mg of sodium phosphate monobasic anhydrous (Fisher Scientific) dissolved with 78.4 of sterile filtered DI water, then 1 g of Blanose 7M65 CMC (Hercules, viscosity of 5450 cP @ 2%) is sprinkled into the buffer solution and heated to aid dissolution, and the solution is then cooled down.

A solution of pH 7.0 comprising 17% poloxamer 407NF/1% CMC/2% otic agent in PBS buffer is made by cooling down 8.1 g of solution A in a ice chilled water bath and then adding an appropriate amount of an otic agent followed by mixing. 1.74 g of poloxamer 407NF (Spectrum Chemicals) is sprinkled into the cold solution while mixing. The mixture is further mixed until all the poloxamer is completely dissolved.

Two mL of the above sample is placed in a 3 mL screw cap glass vial (with rubber lining) and closed tightly. The vial is placed in a Market Forge-sterilmatic autoclave (settings, slow liquids) and sterilized at 250° F. for 25 minutes. After autoclaving the sample is left to cool down to room temperature and then placed in refrigerator. The sample is homogenized by mixing while the vials are cold.

Precipitation or discoloration are observed after autoclaving. HPLC analysis is performed using an Agilent 1200 equipped with a Luna C18(2) 3 μm, 100 Å, 250×4.6 mm column) using a 30-80 acetonitrile gradient (1-10 min) of (water-acetonitrile mixture containing 0.05% TFA), for a total run of 15 minutes. Samples are diluted by taking 30 μL of sample and dissolving with 1.5 mL of a 1:1 acetonitrile water mixture. Purity of the otic agent in the autoclaved samples is recorded.

Viscosity measurements are performed using a Brookfield viscometer RVDV-II+P with a CPE-51 spindle rotated at 0.08 rpm (shear rate of 0.31 s$^{-1}$), equipped with a water jacketed temperature control unit (temperature ramped from 15-34° C. at 1.6° C./min). Tgel is defined as the inflection point of the curve where the increase in viscosity occurs due to the sol-gel transition.

Dissolution is performed at 37° C. for the non-autoclaved sample in snapwells (6.5 mm diameter polycarbonate membrane with a pore size of 0.4 μm), 0.2 mL of gel is placed into snapwell and left to harden, then 0.5 mL is placed into reservoir and shaken using a Labline orbit shaker at 70 rpm. Samples are taken every hour (0.1 mL withdrawn and replaced with warm buffer). Samples are analyzed for otic agent concentration by UV at 245 nm, against an external calibration standard curve.

Compositions comprising collagen, keratin, collagenase, or micronized collagen are tested using the above procedure to determine the effect addition of a secondary polymer on the degradation products and viscosity of a composition containing 2% otic agent and 17% poloxamer 407NF after heat sterilization (autoclaving).

Example 22—Effect of Buffer Type on the Degradation Products for Compositions Containing Poloxamer 407NF after Heat Sterilization (Autoclaving)

A TRIS buffer is made by dissolving 377.8 mg of sodium chloride (Fisher Scientific), and 602.9 mg of Tromethamine (Sigma Chemical Co.) then QS to 100 g with sterile filtered DI water, pH is adjusted to 7.4 with 1M HCl.

Stock Solution Containing 25% Poloxamer 407 Solution in Tris Buffer:

Weigh 45 g of TRIS buffer, chill in an ice chilled bath then sprinkle into the buffer, while mixing, 15 g of poloxamer 407 NF (Spectrum Chemicals). The mixture is further mixed until all the poloxamer is completely dissolved.

A series of compositions is prepared with the above stock solution. An appropriate amount of otic agent (or salt or prodrug thereof) and/or otic agent as micronized/coated/liposomal particles (or salt or prodrug thereof) is used for all experiments.

Stock Solution (pH 7.3) Containing 25% Poloxamer 407 Solution in PBS Buffer:

PBS buffer is prepared by dissolving 704 mg of sodium chloride (Fisher Scientific), 601.2 mg of sodium phosphate dibasic anhydrous (Fisher Scientific), 242.7 mg of sodium phosphate monobasic anhydrous (Fisher Scientific) with 140.4 g of sterile filtered DI water. The solution is cooled down in an ice chilled water bath and then 50 g of poloxamer 407NF (SPECTRUM CHEMICALS) is sprinkled into the cold solution while mixing. The mixture is further mixed until the poloxamer is completely dissolved.

A series of compositions is prepared with the above stock solution. An appropriate amount of otic agent (or salt or prodrug thereof) and/or otic agent as micronized/coated/liposomal particles (or salt or prodrug thereof) is used for all experiments.

Tables 2 and 3 list samples prepared using the procedures described above. An appropriate amount of otic agent is added to each sample to provide a final concentration of 2% otic agent in the sample.

TABLE 2

Preparation of samples containing TRIS buffer

| Sample | pH | 25% Stock Solution (g) | TRIS Buffer (g) |
|---|---|---|---|
| 20% P407/2% otic agent/TRIS | 7.45 | 8.01 | 1.82 |
| 18% P407/2% otic agent/TRIS | 7.45 | 7.22 | 2.61 |
| 16% P407/2% otic agent/TRIS | 7.45 | 6.47 | 3.42 |
| 18% P4072% otic agent/TRIS | 7.4 | 7.18 | 2.64 |
| 4% otic agent/TRIS | 7.5 | — | 9.7 |
| 2% otic agent/TRIS | 7.43 | — | 5 |
| 1% otic agent/TRIS | 7.35 | — | 5 |
| 2% otic agent/TRIS (suspension) | 7.4 | — | 4.9 |

TABLE 3

Preparation of samples containing PBS buffer (pH of 7.3)

| Sample | 25% Stock Solution in PBS (g) | PBS Buffer (g) |
|---|---|---|
| 20% P407/2% otic agent/PBS | 8.03 | 1.82 |
| 18% P407/2% otic agent/PBS | 7.1 | 2.63 |
| 16% P407/2% otic agent/PBS | 6.45 | 3.44 |
| 18% P407/2% otic agent/PBS | — | 2.63 |
| 2% otic agent/PBS | — | 4.9 |

One mL samples are individually placed in 3 mL screw cap glass vials (with rubber lining) and closed tightly. The vials are placed in a Market Forge-sterilmatic autoclave (setting, slow liquids) and sterilized at 250° F. for 25 minutes. After the autoclaving the samples are left to cool down to room temperature. The vials are placed in the refrigerator and mixed while cold to homogenize the samples.

HPLC analysis is performed using an Agilent 1200 equipped with a Luna C18(2) 3 µm, 100 Å, 250×4.6 mm column) using a 30-80 acetonitrile gradient (1-10 min) of (water-acetonitrile mixture containing 0.05% TFA), for a total run of 15 minutes. Samples are diluted by taking 30 µL of sample and dissolving with 1.5 mL of a 1:1 acetonitrile water mixture. Purity of the otic agent in the autoclaved samples is recorded. The stability of compositions in TRIS and PBS buffers is compared.

Viscosity measurements are performed using a Brookfield viscometer RVDV-II+P with a CPE-51 spindle rotated at 0.08 rpm (shear rate of 0.31 s$^{-1}$), equipped with a water jacketed temperature control unit (temperature ramped from 15-34° C. at 1.6° C./min). Tgel is defined as the inflection point of the curve where the increase in viscosity occurs due to the sol-gel transition. Only compositions that show no change after autoclaving are analyzed.

Compositions comprising Compositions comprising collagen, keratin, collagenase, or micronized collagen are tested using the above procedure to determine the effect addition of a secondary polymer on the degradation products and viscosity of a composition containing 2% otic agent and 17% poloxamer 407NF after heat sterilization (autoclaving). Stability of compositions containing micronized otic agent is compared to non-micronized otic agent composition counterparts.

Example 23—Pulsed Release Otic Compositions

Diazepam is used to prepare a pulsed release otic agent composition using the procedures described herein. A 17% poloxamer solution is prepared by dissolving 351.4 mg of sodium chloride (Fisher Scientific), 302.1 mg of sodium phosphate dibasic anhydrous (Fisher Scientific), 122.1 mg of sodium phosphate monobasic anhydrous (Fisher Scientific) and an appropriate amount of an otic agent with 79.3 g of sterile filtered DI water. The solution is cooled down in a ice chilled water bath and then 17.05 g of poloxamer 407NF (SPECTRUM CHEMICALS) is sprinkled into the cold solution while mixing. The mixture is further mixed until the poloxamer is completely dissolved. The pH for this solution is measured. 20% of the delivered dose of diazepam is solubilized in the 17% poloxamer solution with the aid of beta-cyclodextrins. The remaining 80% of the otic agent is then added to the mixture and the final composition is prepared using any procedure described herein.

Pulsed release compositions comprising Compositions comprising collagen, keratin, collagenase, or micronized collagen prepared according to the procedures and examples described herein, are tested using procedures described herein to determine pulse release profiles.

Example 24—Preparation of a 17% Poloxamer 407/2% Otic Agent/78 Ppm Evans Blue in PBS A Stock solution of Evans Blue (5.9 mg/mL) in PBS buffer is prepared by dissolving 5.9 mg of Evans Blue (Sigma Chemical Co) with 1 mL of PBS buffer. PBS buffer is prepared by dissolving 704 mg of sodium chloride (Fisher Scientific), 601.2 mg of sodium phosphate dibasic anhydrous (Fisher Scientific), 242.7 mg of sodium phosphate monobasic anhydrous (Fisher Scientific) with 140.4 g of sterile filtered DI water.

A Stock solution containing 25% Poloxamer 407 solution in PBS buffer (as in Example 9) is used in this study. An appropriate amount of an otic agent is added to the 25% Poloxamer 407 solution stock solution to prepare compositions comprising 2% of an otic agent (Table 4).

TABLE 4

Preparation of poloxamer 407 samples containing Evans Blue

| Sample ID | 25% P407 in PBS (g) | PBS Buffer (g) | Evans Blue Solution (µL) |
|---|---|---|---|
| 17% P407/2% otic agent/EB | 13.6 | 6 | 265 |
| 20% P407/2% otic agent/EB | 16.019 | 3.62 | 265 |
| 25% P407/2% otic agent/EB | 19.63 | — | 265 |

Compositions comprising collagen, keratin, collagenase, or micronized collagen are prepared according to the procedures in Example 12 and are sterile filtered through 0.22 µm PVDF syringe filters (Millipore corporation), and autoclaved.

The above compositions are dosed to guinea pigs in the middle ear by procedures described herein and the ability of compositions to gel upon contact and the location of the gel is identified after dosing and at 24 hours after dosing.

Example 25—Terminal Sterilization of Poloxamer 407 Compositions with and without a Visualization Dye 17% poloxamer 407/2% otic agent/in phosphate buffer, pH 7.3: Dissolve 709 mg of sodium chloride (Fisher Scientific), 742 mg of sodium phosphate dibasic dehydrate USP (Fisher Scientific), 251.1 mg of sodium phosphate monobasic monohydrate USP (Fisher Scientific) and an appropriate amount of an otic agent with 158.1 g of sterile filtered DI water. The solution is cooled down in an ice chilled water bath and then 34.13 g of poloxamer 407NF (Spectrum chemicals) is sprinkled into the cold solution while mixing. The mixture is further mixed until the poloxamer is completely dissolved.

17% poloxamer 407/2% otic agent/59 ppm Evans blue in phosphate buffer: Take two mL of the 17% poloxamer 407/2% otic agent/in phosphate buffer solution and add 2 mL of a 5.9 mg/mL Evans blue (Sigma-Aldrich chemical Co) solution in PBS buffer.

25% poloxamer 407/2% otic agent/in phosphate buffer: Dissolve 330.5 mg of sodium chloride (Fisher Scientific), 334.5 mg of sodium phosphate dibasic dehydrate USP (Fisher Scientific), 125.9 mg of sodium phosphate monobasic monohydrate USP (Fisher Scientific) and an appropriate amount of an otic agent with 70.5 g of sterile filtered DI water.

The solution is cooled down in an ice chilled water bath and then 25.1 g of poloxamer 407NF (Spectrum chemicals) is sprinkled into the cold solution while mixing. The mixture is further mixed until the poloxamer is completely dissolved.

25% poloxamer 407/2% otic agent/59 ppm Evans blue in phosphate buffer: Take two mL of the 25% poloxamer 407/2% otic agent/in phosphate buffer solution and add 2 mL of a 5.9 mg/mL Evans blue (Sigma-Aldrich chemical Co) solution in PBS buffer.

Place 2 mL of composition into a 2 mL glass vial (Wheaton serum glass vial) and seal with 13 mm butyl str (kimble stoppers) and crimp with a 13 mm aluminum seal. The vials are placed in a Market Forge-sterilmatic autoclave (settings, slow liquids) and sterilized at 250° F. for 25 minutes. After the autoclaving the samples are left to cool down to room temperature and then placed in refrigeration. The vials are placed in the refrigerator and mixed while cold to homogenize the samples. Sample discoloration or precipitation after autoclaving is recorded.

HPLC analysis is performed using an Agilent 1200 equipped with a Luna C18(2) 3 μm, 100 Å, 250×4.6 mm column) using a 30-95 methanol:acetate buffer pH 4 gradient (1-6 min), then isocratic for 11 minutes, for a total run of 22 minutes. Samples are diluted by taking 30 μL of sample and dissolved with 0.97 mL of water. The main peaks are recorded in the table below. Purity before autoclaving is always greater than 99% using this method.

Viscosity measurements are performed using a Brookfield viscometer RVDV-II+P with a CPE-51 spindle rotated at 0.08 rpm (shear rate of 0.31 $s^{-1}$), equipped with a water jacketed temperature control unit (temperature ramped from 15-34° C. at 1.6° C./min). Tgel is defined as the inflection point of the curve where the increase in viscosity occurs due to the sol-gel transition.

Compositions comprising collagen, keratin, collagenase, or micronized collagen prepared according to the procedure in Example 11, are tested using the above procedures to determine stability of the compositions.

Example 26—In Vitro Comparison of Release Profile

Dissolution is performed at 37° C. in snapwells (6.5 mm diameter polycarbonate membrane with a pore size of 0.4 μm), 0.2 mL of a gel composition described herein is placed into snapwell and left to harden, then 0.5 mL buffer is placed into reservoir and shaken using a Labline orbit shaker at 70 rpm. Samples are taken every hour (0.1 mL withdrawn and replace with warm buffer). Samples are analyzed for otic agent concentration by UV at 245 nm against an external calibration standard curve. Pluronic concentration is analyzed at 624 nm using the cobalt thiocyanate method. Relative rank-order of mean dissolution time (MDT) as a function of % P407 is determined. A linear relationship between the compositions mean dissolution time (MDT) and the P407 concentration indicates that the otic agent is released due to the erosion of the polymer gel (poloxamer) and not via diffusion. A non-linear relationship indicates release of otic agent via a combination of diffusion and/or polymer gel degradation.

Alternatively, samples are analyzed using the method described by Li Xin-Yu paper [Acta Pharmaceutica Sinica 2008, 43(2):208-203] and Rank-order of mean dissolution time (MDT) as a function of % P407 is determined.

Compositions comprising collagen, keratin, collagenase, or micronized collagen prepared according to the procedures described herein, are tested using the above procedure to determine the release profile of the otic agents.

Example 27—In Vitro Comparison of Gelation Temperature

The effect of Poloxamer 188 and an otic agent on the gelation temperature and viscosity of Poloxamer 407 compositions is evaluated with the purpose of manipulating the gelation temperature.

A 25% Poloxamer 407 stock solution in PBS buffer (as in Example 9) and a PBS solution (as in Example 11) are used. Poloxamer 188NF from BASF is used. An appropriate amount of otic agent is added to the solutions described in Table 5 to provide a 2% composition of the otic agent.

TABLE 5

Preparation of samples containing poloxamer 407/poloxamer 188

| Sample | 25% P407 Stock Solution (g) | Poloxamer 188 (mg) | PBS Buffer (g) |
|---|---|---|---|
| 16% P407/10% P188 | 3.207 | 501 | 1.3036 |
| 17% P407/10% P188 | 3.4089 | 500 | 1.1056 |
| 18% P407/10% P188 | 3.6156 | 502 | 0.9072 |
| 19% P407/10% P188 | 3.8183 | 500 | 0.7050 |
| 20% P407/10% P188 | 4.008 | 501 | 0.5032 |
| 20% P407/5% P188 | 4.01 | 256 | 0.770 |

Mean dissolution time, viscosity and gel temperature of the above compositions are measured using procedures described herein.

An equation is fitted to the data obtained and can be utilized to estimate the gelation temperature of F127/F68 mixtures (for 17-20% F127 and 0-10% F68).

$T_{gel} = -1.8(\% F127) + 1.3(\% F68) + 53$

An equation is fitted to the data obtained and can be utilized to estimate the Mean Dissolution Time (hr) based on the gelation temperature of F127/F68 mixtures (for 17-25% F127 and 0-10% F68), using results obtained in example 13 and 15.

$MDT = -0.2(T_{gel}) + 8$

Compositions comprising collagen, keratin, collagenase, or micronized collagen are prepared by addition of an appropriate amount of otic agents to the solutions described in Table 5. The gel temperature of the compositions is determined using the procedure described above.

Example 28—Determination of Temperature Range for Sterile Filtration

The viscosity at low temperatures is measured to help guide the temperature range at that the sterile filtration needs to occur to reduce the possibility of clogging.

Viscosity measurements are performed using a Brookfield viscometer RVDV-II+P with a CPE-40 spindle rotated at 1, 5 and 10 rpm (shear rate of 7.5, 37.5 and 75 s$^{-1}$), equipped with a water jacketed temperature control unit (temperature ramped from 10-25° C. at 1.6° C./min).

The Tgel of a 17% Pluronic P407 is determined as a function of increasing concentration of otic agent. The increase in Tgel for a 17% pluronic composition is estimated by:

$$\Delta T_{gel} = 0.93[\% \text{ otic agent}]$$

Compositions comprising collagen, keratin, collagenase, or micronized collagen prepared according to procedures described herein, are tested using the above procedure to determine the temperature range for sterile filtration. The effect of addition of increased amounts of otic agent on the Tgel, and the apparent viscosity of the compositions is recorded.

Example 29—Determination of Manufacturing Conditions

TABLE 6

Viscosity of potential compositions at manufacturing/filtration conditions.

| Sample | Apparent Viscosity$^a$ (cP) | | Temperature @ |
|---|---|---|---|
| | 5° C. below Tgel | 20° C. | 100 cP |
| Placebo | 52 cP @ 17° C. | 120 cP | 19° C. |
| 17% P407/20 otic agent | 90 cP @ 18° C. | 147 cP | 18.5° C. |
| 17% P407/6% otic agent | 142 cP @ 22° C. | 105 cP | 19.7° C. |

$^a$Viscosity measured at a shear rate of 37.5 s$^{-1}$

An 8 liter batch of a 17% P407 placebo is manufactured to evaluate the manufacturing/filtration conditions. The placebo is manufactured by placing 6.4 liters of DI water in a 3 gallon SS pressure vessel, and left to cool down in the refrigerator overnight. The following morning the tank was taken out (water temperature 5° C., RT 18° C.) and 48 g of sodium chloride, 29.6 g of sodium phosphate dibasic dehydrate and 10 g of sodium phosphate monobasic monohydrate is added and dissolved with an overhead mixer (IKA RW20 @ 1720 rpm). Half hour later, once the buffer is dissolved (solution temperature 8° C., RT 18° C.), 1.36 kg of poloxamer 407 NF (spectrum chemicals) is slowly sprinkled into the buffer solution in a 15 minute interval (solution temperature 12° C., RT 18° C.), then speed is increased to 2430 rpm. After an additional one hour mixing, mixing speed is reduced to 1062 rpm (complete dissolution).

The temperature of the room is maintained below 25° C. to retain the temperature of the solution at below 19° C. The temperature of the solution is maintained at below 19° C. up to 3 hours of the initiation of the manufacturing, without the need to chill/cool the container.

Three different Sartoscale (Sartorius Stedim) filters with a surface area of 17.3 cm$^2$ are evaluated at 20 psi and 14° C. of solution 1) Sartopore 2, 0.2 µm 5445307HS-FF (PES), flow rate of 16 mL/min
2) Sartobran P, 0.2 µm 5235307HS-FF (cellulose ester), flow rate of 12 mL/min
3) Sartopore 2 XLI, 0.2 µm 5445307IS-FF (PES), flow rate of 15 mL/min Sartopore 2 filter 5441307H4-SS is used, filtration is carried out at the solution temperature using a 0.45, 0.2 µm Sartopore 2 150 sterile capsule (Sartorius Stedim) with a surface area of 0.015 m$^2$ at a pressure of 16 psi. Flow rate is measured at approximately 100 mL/min at 16 psi, with no change in flow rate while the temperature is maintained in the 6.5-14° C. range. Decreasing pressure and increasing temperature of the solution causes a decrease in flow rate due to an increase in the viscosity of the solution. Discoloration of the solution is monitored during the process.

TABLE 7

Predicted filtration time for a 17% poloxamer 407 placebo at a solution temperature range of 6.5-14° C. using Sartopore 2, 0.2 µm filters at a pressure of 16 psi of pressure.

| Filter | Size (m$^2$) | Estimated flow rate (mL/min) | Time to filter 8 L (estimated) |
|---|---|---|---|
| Sartopore 2, size 4 | 0.015 | 100 mL/min | 80 min |
| Sartopore 2, size 7 | 0.05 | 330 mL/min | 24 min |
| Sartopore 2, size 8 | 0.1 | 670 mL/min | 12 min |

Viscosity, Tgel and UV/Vis absorption is check before filtration evaluation. Pluronic UV/Vis spectra are obtained by a Evolution 160 UV/Vis (Thermo Scientific). A peak in the range of 250-300 nm is attributed to BHT stabilizer present in the raw material (poloxamer). Table 8 lists physicochemical properties of the above solutions before and after filtration.

TABLE 8

Physicochemical properties of 17% poloxamer 407 placebo solution before and after filtration

| Sample | Tgel (° C.) | Viscosity$^a$ @ 19° C. (cP) | Absorbance @ 274 nm |
|---|---|---|---|
| Before filtration | 22 | 100 | 0.3181 |
| After filtration | 22 | 100 | 0.3081 |

$^a$Viscosity measured at a shear rate of 37.5 s$^{-1}$

The above process is applicable for manufacture of 17% P407 compositions, and includes temperature analysis of the room conditions. Preferably, a maximum temperature of 19° C. reduces cost of cooling the container during manufacturing. In some instances, a jacketed container is used to further control the temperature of the solution to ease manufacturing concerns.

Example 30—In Vitro Release of Otic Agent from an Autoclaved Micronized Sample 17% poloxamer 407/1.5% otic agent in TRIS buffer: 250.8 mg of sodium chloride (Fisher Scientific), and 302.4 mg of Tromethamine (Sigma Chemical Co.) is dissolved in 39.3 g of sterile filtered DI water, pH is adjusted to 7.4 with 1M HCl. 4.9 g of the above solution is used and an appropriate amount of micronized otic agent is suspended and dispersed well. 2 mL of the composition is transferred into a 2 mL glass vial (Wheaton serum glass vial) and sealed with 13 mm butyl styrene (kimble stoppers) and crimped with a 13 mm aluminum seal. The vial is placed in a Market Forge-sterilmatic autoclave (settings, slow liquids) and sterilized at 250° F. for 25 minutes. After the autoclaving the sample is left to cool down to room temperature. The vial is placed in the refrigerator and mixed while cold to homogenize the sample. Sample discoloration or precipitation after autoclaving is recorded.

Dissolution is performed at 37° C. in snapwells (6.5 mm diameter polycarbonate membrane with a pore size of 0.4 µm), 0.2 mL of gel is placed into snapwell and left to harden, then 0.5 mL PBS buffer is placed into reservoir and shaken using a Labline orbit shaker at 70 rpm. Samples are taken every hour [0.1 mL withdrawn and replaced with warm PBS buffer containing 2% PEG-40 hydrogenated castor oil (BASF) to enhance otic agent solubility]. Samples are analyzed for otic agent concentration by UV at 245 nm against an external calibration standard curve. The release rate is compared to other compositions disclosed herein. MDT time is calculated for each sample.

Solubilization of otic agent in the 17% poloxamer system is evaluated by measuring the concentration of the otic agent in the supernatant after centrifuging samples at 15,000 rpm for 10 minutes using an eppendorf centrifuge 5424. otic agent concentration in the supernatant is measured by UV at 245 nm against an external calibration standard curve.

Compositions comprising collagen, keratin, collagenase, or micronized collagen prepared according to the procedures described herein, are tested using the above procedures to determine release rate of the otic agent from each composition.

Example 31—Release Rate or MDT and Viscosity of Composition Containing Sodium Carboxymethyl Cellulose 17% poloxamer 407/2% otic agent/1% CMC (Hercules Blanose 7M): A sodium carboxymethylcellulose (CMC) solution (pH 7.0) in PBS buffer is prepared by dissolving 205.6 mg of sodium chloride (Fisher Scientific), 372.1 mg of sodium phosphate dibasic dihydrate (Fisher Scientific), 106.2 mg of sodium phosphate monobasic monohydrate (Fisher Scientific) in 78.1 g of sterile filtered DI water. 1 g of Blanose 7M CMC (Hercules, viscosity of 533 cP @ 2%) is sprinkled into the buffer solution and heated to ease solution, solution is then cooled down and 17.08 g poloxamer 407NF (Spectrum Chemicals) is sprinkled into the cold solution while mixing. A composition comprising 17% poloxamer 407NF/1% CMC/2% otic agent in PBS buffer is made adding/dissolving an appropriate amount of otic agent to 9.8 g of the above solution, and mixing until all the otic agent is completely dissolved.

17% poloxamer 407/2% otic agent/0.5% CMC (Blanose 7M65): A sodium carboxymethylcellulose (CMC) solution (pH 7.2) in PBS buffer is prepared by dissolving 257 mg of sodium chloride (Fisher Scientific), 375 mg of sodium phosphate dibasic dihydrate (Fisher Scientific), 108 mg of sodium phosphate monobasic monohydrate (Fisher Scientific) in 78.7 g of sterile filtered DI water. 0.502 g of Blanose 7M65 CMC (Hercules, viscosity of 5450 cP @ 2%) is sprinkled into the buffer solution and heated to ease solution, solution is then cooled down and 17.06 g poloxamer 407NF (Spectrum Chemicals) is sprinkled into the cold solution while mixing. A 17% poloxamer 407NF/1% CMC/2% otic agent solution in PBS buffer is made adding/dissolving an appropriate amount of otic agent to 9.8 g of the above solution, and mixing until the otic agent is completely dissolved.

17% poloxamer 407/2% otic agent/0.5% CMC (Blanose 7H9): A sodium carboxymethylcellulose (CMC) solution (pH 7.3) in PBS buffer is prepared by dissolving 256.5 mg of sodium chloride (Fisher Scientific), 374 mg of sodium phosphate dibasic dihydrate (Fisher Scientific), 107 mg of sodium phosphate monobasic monohydrate (Fisher Scientific) in 78.6 g of sterile filtered DI water, then 0.502 g of Blanose 7H9 CMC (Hercules, viscosity of 5600 cP @ 1%) is sprinkled to the buffer solution and heated to ease solution, solution is then cooled down and 17.03 g poloxamer 407NF (Spectrum Chemicals) is sprinkled into the cold solution while mixing. A 17% poloxamer 407NF/1% CMC/2% otic agent solution in PBS buffer is made adding/dissolving an appropriate amount of otic agent to 9.8 of the above solution, and mixing until the otic agent is completely dissolved.

Viscosity measurements are performed using a Brookfield viscometer RVDV-II+P with a CPE-40 spindle rotated at 0.08 rpm (shear rate of 0.6 s$^{-1}$), equipped with a water jacketed temperature control unit (temperature ramped from 10-34° C. at 1.6° C./min). Tgel is defined as the inflection point of the curve where the increase in viscosity occurs due to the sol-gel transition.

Dissolution is performed at 37° C. in snapwells (6.5 mm diameter polycarbonate membrane with a pore size of 0.4 µm). 0.2 mL of gel is placed into snapwell and left to harden, then 0.5 mL PBS buffer is placed into reservoir and shaken using a Labline orbit shaker at 70 rpm. Samples are taken every hour, 0.1 mL withdrawn and replaced with warm PBS buffer. Samples are analyzed for otic agent concentration by UV at 245 nm against an external calibration standard curve. MDT time is calculated for each of the above compositions.

Compositions comprising collagen, keratin, collagenase, or micronized collagen prepared according to procedures described above, are tested using the above procedures to determine relationship between release rate and/or mean dissolution time and viscosity of composition containing sodium carboxymethyl cellulose. Any correlation between the mean dissolution time (MDT) and the apparent viscosity (measured at 2° C. below the gelation temperature) is recorded.

Example 32—Application of an Enhanced Viscosity Otic Structure Modulating Agent or Innate Immune System Modulating Agent Composition onto the Round Window Membrane A composition according to Example 2 is prepared and loaded into 5 ml siliconized glass syringes attached to a 15-gauge luer lock disposable needle. Lidocaine is topically applied to the tympanic membrane, and a small incision made to allow visualization into the middle ear cavity. The needle tip is guided into place over the round window membrane, and the composition applied directly onto the round-window membrane.

Example 33—In Vivo Testing of Intratympanic Injection of a Otic Structure Modulating Composition in a Guinea Pig A cohort of 21 guinea pigs (Charles River, females weighing 200-300 g) is intratympanically injected with 50 µL of different P407-DSP compositions described herein, containing 0 to 6% of an otic agent. The gel elimination time course for each composition is determined. A faster gel elimination time course of a composition indicates lower mean dissolution time (MDT). Thus the injection volume and the concentration of an otic structure modulating agent or innate immune system modulating agent in a composition are tested to determine optimal parameters for preclinical and clinical studies.

Example 34—In Vivo Extended Release Kinetics

A cohort of 21 guinea pigs (Charles River, females weighing 200-300 g) is intratympanically injected with 50

μL 17% Pluronic F-127 composition buffered at 280 mOsm/kg and containing 1.5% to 4.5% of an otic structure modulating agent or innate immune system modulating agent by weight of the composition. Animals are dosed on day 1. The release profile for the compositions is determined based on analysis of the perilymph.

Example 35—Effect of Poloxamer Concentration and Active Agent Concentration on Release Kinetics A series of compositions comprising varying concentrations of a gelling agent and micronized dexamethasone was prepared using procedures described above. The mean dissolution time (MDT) for each composition in Table 9 was determined using procedures described above.

TABLE 9

Preparation of poloxamer/otic agent compositions

| Sample | pH | MDT |
|---|---|---|
| 15.5% P407/1.5% dexamethasone/PBS | 7.4 | 46 h |
| 16% P407/1.5% dexamethasone/PBS | 7.4 | 40 h |
| 17% P407/1.5% dexamethasone/PBS | 7.4 | 39 h |
| 15.5% P407/4.5% dexamethasone/PBS | 7.4 | >7 days |
| 16% P407/4.5% dexamethasone/PBS | 7.4 | >7 days |
| 17% P407/4.5% dexamethasone/PBS | 7.4 | >7 days |

The effect of gel strength and otic agent concentration on release kinetics of an otic agent from the composition or device was determined by measurement of the MDT for poloxamer, and measurement of MDT for otic agent. The half life of the otic agent and mean residence time of the otic agent was also determined for each formulation by measurement of concentration of the otic agent in the perilymph.

The apparent viscosity of each composition was measured as described above. A thermoreversible polymer gel concentration of about 15.5% in a composition or device described above provided an apparent viscosity of about 270,000 cP. A thermoreversible polymer gel concentration of about 16% in a composition or device described above provided an apparent viscosity of about 360,000 cP. A thermoreversible polymer gel concentration of about 17% in a composition or device described above provided an apparent viscosity of about 480,000 cP.

Compositions comprising collagen, keratin, collagenase, or micronized collagen, prepared according to the procedures described herein, are tested using the above procedure to determine release rate of the otic agent from each composition.

Example 36—Evaluation of Otic Agent Formulations in an Otitis Media Animal Model Induction of Otitis Media Healthy adult chinchillas weight 400 to 600 g with normal middle ears, ascertained by otoscopy and tympanometry are used for these studies. Eustachian tube obstruction is performed 24 hours before inoculation to prevent the inoculum from flowing out of the eustachian tube. One milliliter of type 3 *S. pneumoniae* strain at 4-h-log phase (containing approximately 40 colony forming units (CFU)) is placed directly into both middle ear hypotympanic bullae of the chinhillas. Control mice are inoculated with one milliliter sterile PBS.

Treatment

*S. pneumoniae* inoculated and control mice are sorted into two groups (n=10 in each group). Otic agent formulation of Example 3 containing hyaluronidase is applied to the walls of the tympanic cavity of one group of animals. Control formulation containing no hyaluronidase is applied to the second group. The hyaluronidase and control formulations are reapplied three days after the initial application. The animals are sacrificed after the seventh day of treatment.

Analysis of Results

The amount of auris media ear fluid (MEF) is measured at 12, 24, 48, 72, 96, 120, and 148 hours after pneumoccal inocualtion. Hearing analysis is also performed at 12, 24, 48, 72, 96, 120, and 148 hours after pneumoccal inocualtion. Finally, balance analysis is performed at 12, 24, 48, 72, 96, 120, and 148 hours after pneumoccal inocualtion.

Example 37—Evaluation of Otic Agent Formulations in Tympanic Membrane Perforation Animal Model Otic agent formulations of Example 3 are tested in a tympanic membrane perforation animal model described in Amoils, C. P., et al. *Otolaryngol Head Neck Surg.* (1992), 106, 47-55. A cohort of 20 Chinchillas is divided into control/untreated and test/treated groups for comparison of the effect of the otic agent formulation on tympanic membrane healing. The animals are subjected to thermal myringectomy followed by medial infolding of tympanic membrane microflaps, resulting in permanent subtotal chronic tympanic membrane perforations. The animals are kept under observation for 6-8 weeks to ensure chronicity of tympanic membrane perforations. Any animal demonstrating otitis externa, or otitis media are discarded. Any animal with spontaneous closure of the perforation is excluded from the study. At the end of the observation period, the animals are treated with the composition of Example 1 once a day for three weeks. The animals are examined by visual otologic exam weekly for closure of the perforation. Progression of healing is also recorded.

Example 38—Evaluation of Otic Agent Formulations in an Otosclerosis Animal Model Otic agent formulations of Example 8 are tested in an otosclerosis animal model described in ARO abstracts, 2008, abstract 352, Bisphosphonates Inhibit Bone Remodeling in the Otic Capsule of Osteoprotegerin Deficient Mouse, an Animal Model of Otosclerosis. Three week old OPG knockout mice are treated with the formulation of Example 8 (100 microgram/kg/day, 6 days, or 500 microgram/kg/day, 6 days) and sacrificed 9 and 18 weeks later. Prior to sacrifice, hearing is evaluated with auditory brainstem evoked response and distortion product otoacoustic emissions. Bone remodeling is evaluated as follows: temporal bones are processed for histological analysis and stained with Azure or tartrate resistant acid phosphatase stain, which evaluates osteoclast activity.

Example 39—Clinical Trials of Hyaluronidase in Otitis Media with Effusion Patients Study Objective The primary objective of this study will be to assess the safety and efficacy of hyaluronidase compared with that of placebo in ameliorating otitis media with effusion symptoms in afflicted patients.

Methods

Study Design

This will be a phase 3, multicentre, double-blind, randomised, placebo-controlled, three-arm study comparing TKIXc (100 mg and 200 mg) to placebo in the treatment of otitis media with effusion symptoms. Approximately 150 subjects will be enrolled in this study, and randomised (1:1)

to 1 of 3 treatment groups based on a randomisation sequence prepared by sponsor. Each group will receive 200 mg controlled release hyaluronidase, 400 mg controlled release hyaluronidase, or controlled release placebo formulation.

After a 1-week baseline phase, patients from each group will be randomized to a 16 week double treatment period (8-week treatment followed by an 8-week maintenance period). Primary efficacy will be measured as a percentage change in the amount of fluids (i.e. effusions) seen in the ears of the subjects.

Example 40—Clinical Trials of Bisphosphonates in Patients Suffering from Otosclerosis Study Objective The primary objective of this study will be to assess the safety and efficacy of bisphosphonates compared with that of placebo in improving hearing in afflicted patients.
Methods
Study Design This will be a phase 3, multicentre, double-blind, randomised, placebo-controlled, three-arm study comparing the efficacy of risendronate (100 mg and 200 mg) to placebo in the treatment of otosclerosis. Approximately 150 subjects will be enrolled in this study, and randomised (1:1) to 1 of 3 treatment groups based on a randomisation sequence prepared by sponsor. Each group will receive 200 mg of risendronate mucoadhesive formulation, 400 mg of risendronate mucoadhesive formulation, or mucoadhesive placebo formulation. Inclusion criteria include otosclerosis where surgery is planned, air/bone gap larger than 20 dB and normal middle ear status. Exclusion criteria are pregnancy, deafness on other ear or stapedectomy previously performed on ear.

After a 1-week baseline phase, patients from each group will be randomized to a 16 week double treatment period (8-week treatment followed by an 8-week maintenance period). Primary efficacy will be measured as a change in hearing thresholds.

Example 41—Evaluation of Otic Agent Formulations in an Otitis Media Animal Model Induction of Otitis Media Healthy adult chinchillas weight 400 to 600 g with normal middle ears, ascertained by otoscopy and tympanometry are used for these studies. Eustachian tube obstruction is performed 24 hours before inoculation to prevent the inoculum from flowing out of the eustachian tube. One milliliter of type 3 *S. pneumoniae* strain at 4-h-log phase (containing approximately 40 colony forming units (CFU)) is placed directly into both middle ear hypotympanic bullae of the chinhillas. Control mice are inoculated with one milliliter sterile PBS.

Treatment

*S. pneumoniae* inoculated and control mice are sorted into two groups (n=10 in each group). Otic agent formulation of Example 3 is applied to the walls of the tympanic cavity of one group of animals. A control formulation containing no active agent is applied to the second group. The formulations are reapplied three days after the initial application. The animals are sacrificed after the seventh day of treatment.

Analysis of Results

The amount of auris media ear fluid (MEF) is measured at 12, 24, 48, 72, 96, 120, and 148 hours after pneumoccal inocualtion. Hearing analysis is also performed at 12, 24, 48, 72, 96, 120, and 148 hours after pneumoccal inocualtion. Finally, balance analysis is performed at 12, 24, 48, 72, 96, 120, and 148 hours after pneumoccal inocualtion.

Example 42—Clinical Trials of TKIXc in Otitis Media Patients

Study Objective

The primary objective of this study will be to assess the safety and efficacy of TKIXc compared with that of placebo in ameliorating otitis media with effusion symptoms in afflicted patients.
Methods
Study Design This will be a phase 3, multicentre, double-blind, randomised, placebo-controlled, three-arm study comparing TKIXc (100 mg and 200 mg) to placebo in the treatment of otitis media with effusion symptoms. Approximately 150 subjects will be enrolled in this study, and randomised (1:1) to 1 of 3 treatment groups based on a randomisation sequence prepared by sponsor. Each group will receive 200 mg controlled release TKIXc, 400 mg controlled release TKIXc, or controlled release placebo formulation.

After a 1-week baseline phase, patients from each group will be randomized to a 16 week double treatment period (8-week treatment followed by an 8-week maintenance period). Primary efficacy will be measured as a percentage change in the amount of fluids (i.e. effusions) seen in the ears of the subjects.

While preferred embodiments of the present disclosure have been shown and described herein, such embodiments are provided by way of example only. Various alternatives to the embodiments described herein are optionally employed in practicing the inventions. It is intended that the following claims define the scope of the invention and that methods and structures within the scope of these claims and their equivalents be covered thereby.

We claim:

1. A sterile otic composition comprising
   (i) a thermoreversible gel comprising from about 14% to about 17% of a copolymer of polyoxyethylene and polyoxypropylene by weight of the composition; and
   (ii) from about 0.01% to about 20% of a multiparticulate non-microencapsulated bisphosphonate by weight of the composition;
   wherein the average diameter of the multiparticulate non-microencapsulated bisphosphonate is from about 3 µm to about 50 µm; and
   wherein the composition provides a sustained release of the bisphosphonate across the round window membrane into the cochlea for a period of at least 5 days after a single administration, and wherein the composition is aqueous and substantially free of co-solvent.

2. The composition of claim 1, wherein the composition comprises Poloxamer 407.

3. The composition of claim 1, wherein the bisphosphonate is selected from Etidronate; Clodronate; Tiludronate; Pamidronate; Neridronate; Olpadronate; Alendronate; Ibandronate; Risedronate; and Zoledronate.

* * * * *

UNITED STATES PATENT AND TRADEMARK OFFICE
CERTIFICATE OF CORRECTION

PATENT NO. : 10,092,580 B2
APPLICATION NO. : 12/506091
DATED : October 9, 2018
INVENTOR(S) : Jay Lichter et al.

Page 1 of 1

It is certified that error appears in the above-identified patent and that said Letters Patent is hereby corrected as shown below:

On the Title Page

(60) "provisional application No. 61/156,771, filed on Mar. 2, 2008," should read -- provisional application No. 61/156,771, filed on Mar. 2, 2009, --

Signed and Sealed this
Fourth Day of December, 2018

Andrei Iancu
*Director of the United States Patent and Trademark Office*